(12) United States Patent
Bakaher et al.

(10) Patent No.: US 10,287,599 B2
(45) Date of Patent: May 14, 2019

(54) **ISOPROPYLMALATE SYNTHASE FROM *NICOTIANA TABACUM* AND METHODS AND USES THEREOF**

(75) Inventors: Nicholas Bakaher, Villers-le-Lac (FR); Gregor Nicholas Bindler, Chabrey (CH); Michel Philippe Blanc, Corcelles NE (CH); Simon Goepfert, Lausanne (CH); Florian Martin, Peseux (CH)

(73) Assignee: Philip Morris Products S.A., Neuchatel (CH)

( * ) Notice: Subject to any disclaimer, the term of this patent is extended or adjusted under 35 U.S.C. 154(b) by 1119 days.

(21) Appl. No.: 14/241,185

(22) PCT Filed: Aug. 31, 2012

(86) PCT No.: PCT/EP2012/003662
§ 371 (c)(1),
(2), (4) Date: May 6, 2014

(87) PCT Pub. No.: WO2013/029799
PCT Pub. Date: Mar. 7, 2013

(65) Prior Publication Data
US 2014/0352706 A1    Dec. 4, 2014

(30) Foreign Application Priority Data
Sep. 2, 2011   (EP) .................................... 11179882

(51) Int. Cl.
| C12N 15/82 | (2006.01) |
| C12N 9/10 | (2006.01) |
| A24B 15/20 | (2006.01) |
| C12P 7/40 | (2006.01) |
| C07H 13/04 | (2006.01) |

(52) U.S. Cl.
CPC .......... *C12N 15/8246* (2013.01); *A24B 15/20* (2013.01); *C07H 13/04* (2013.01); *C12N 9/1025* (2013.01); *C12N 9/1029* (2013.01); *C12N 15/8218* (2013.01); *C12N 15/8245* (2013.01); *C12P 7/40* (2013.01); *C12Y 203/03013* (2013.01)

(58) Field of Classification Search
CPC ....... C07K 14/415; A24B 15/10; A24B 13/00; A24B 15/18; A24B 3/12; C12N 15/8243; C12N 15/8218; C12N 15/8253; C12N 5/04; A01H 1/00; A01H 1/06; C12Y 203/03013
See application file for complete search history.

(56) References Cited

U.S. PATENT DOCUMENTS

| 2,766,145 A * | 10/1956 | O'Brien | ............... A24B 15/30 131/276 |
| 3,927,682 A * | 12/1975 | Matsuyama | ........... A24B 3/12 131/290 |
| 5,260,281 A | 11/1993 | Pittarelli | |
| 6,605,598 B1 | 8/2003 | Chortyk | |
| 7,025,066 B2 | 4/2006 | Lawson | |
| 2004/0084056 A1 | 5/2004 | Lawson | |
| 2007/0137663 A1 | 6/2007 | Taylor | |

FOREIGN PATENT DOCUMENTS

| EA | 000634 | 12/1999 |
| EA | 004652 | 6/2004 |
| EA | 009898 | 4/2008 |
| EP | 2090662 A2 | 8/2009 |
| KZ | 5543 | 12/1997 |
| RU | 2143496 | 12/1999 |
| RU | 2324736 | 5/2008 |
| WO | WO 2008/034648 | 3/2008 |
| WO | WO 2010042575 | 4/2010 |

OTHER PUBLICATIONS

Suzuki, Kenji, Ichiro Yamashita, and Nobukazu Tanaka. "Tobacco plants were transformed by Agrobacterium rhizogenes infection during their evolution." The Plant Journal 32.5 (2002): 775-787.*
Ning, Jing, et al. "A feedback-insensitive isopropylmalate synthase affects acylsugar composition in cultivated and wild tomato." Plant physiology 169.3 (2015): 1821-1835.*
Kandra, Lili, Ray Severson, and George Joseph Wagner. "Modified branched-chain amino acid pathways give rise to acyl acids of sucrose esters exuded from tobacco leaf trichomes." European Journal of Biochemistry 188.2 (1990): 385-391.*
Danehower, D. A., S. M. Reed, and E. A. Wernsman. "Identification of the chromosome carrying the gene for production of β-methylvaleryl sucrose esters in Nicotiana tabacum." Agricultural and biological chemistry 53.10 (1989): 2813-2815.*
Matsuzaki, Toshiake, Koushi Koseki, and Akira Koiwai. "Germination and growth inhibition of surface lipids from Nicotiana species and identification of sucrose esters." Agricultural and biological chemistry 52.8 (1988): 1889-1897.*

(Continued)

*Primary Examiner* — Weihua Fan
(74) *Attorney, Agent, or Firm* — Mueting, Raasch & Gebhardt, P.A.

(57) ABSTRACT

The present invention relates to a mutant, non-naturally occurring or transgenic plant cell comprising: (i) at least one polynucleotide comprising, consisting or consisting essentially of a sequence encoding an isopropylmalate synthase and having at least 60% sequence identity to SEQ ID NO:1 or SEQ ID NO:10 or SEQ ID NO: 12 or SEQ ID NO:14; or (ii) a polypeptide encoded by said polynucleotide(s); or (iii) a polypeptide having at least 60% sequence identity to SEQ ID NO:2 or SEQ ID NO:11 or SEQ ID NO:13 or SEQ ID NO:15; or (iv) a construct, vector or expression vector comprising said polynucleotide sequence(s), optionally wherein said construct, vector or expression vector additionally comprises a promoter comprising, consisting or consisting essentially of the sequence set forth in SEQ ID NO:8 or a variant thereof with at least about 60% identity thereto or a trichome promoter.

10 Claims, 7 Drawing Sheets

Specification includes a Sequence Listing.

(56) References Cited

OTHER PUBLICATIONS

Friedberg, Iddo. "Automated protein function prediction—the genomic challenge." Briefings in bioinformatics 7.3 (2006): 225-242.*
Michalecka, Agnieszka M., et al. "Identification of a mitochondrial external NADPH dehydrogenase by overexpression in transgenic Nicotiana sylvestris." The Plant Journal 37.3 (2004): 415-425.*
NCBI Reference Sequence XP_009800501.1, published on Oct. 21, 2014, retrieved from www.ncbi.nlm.nih.gov/protein/XP_009800501.1.*
Wang, Erming, Susheng Gan, and George J. Wagner. "Isolation and characterization of the CYP71D16 trichome-specific promoter from Nicotiana tabacum L." Journal of experimental botany 53.376 (2002): 1891-1897 (Year: 2002).*
Matsuzaki, T., et al, 1988, Agricultural and Biological Chemistry, 52:8, 1889-1897 (Year: 1988).*
Friedberg, I. (2006). Automated protein function prediction—the genomic challenge. Briefings in bioinformatics, 7(3), 225-242. (Year : 2006).*
Ning, J., Moghe, G. D., Leong, B., Kim, J., Ofner, I., Wang, Z., . . . & Last, R. L. (2015). A feedback-insensitive isopropylmalate synthase affects acylsugar composition in cultivated and wild tomato. Plant physiology, 169(3), 1821-1835. (Year: 2015).*
Kroumova, A. B., & Wagner, G. J. (2009). Pathways for synthesis, and possibilities for genetic modification of sugar ester acyl groups produced by trichomes of solanaceous species. General and Applied Plant Physiology, 35(3-4), 95. (Year: 2009).*
Severson, R. F., Arrendale, R. F., Chortyk, O. T., Green, C. R., Thome, F. A., Stewart, J. L., & Johnson, A. W. (1985). Isolation and characterization of the sucrose esters of the cuticular waxes of green tobacco leaf. Journal of agricultural and food chemistry, 33(5), 870-875. (Year: 1985).*
Slocombe, S. P., Schauvinhold, I., McQuinn, R. P., Besser, K., Welsby, N. A., Harper, A., . . . & Dixon, R. A. (2008). Transcriptomic and reverse genetic analysesof branched-chain fatty acid and acyl sugar production in Solanum pennellii and Nicotiana benthamiana. Plant physiology, 148(4), 1830-1846. (Year: 2008).*
Ennajdaoui, Hanane, et al. "Trichome specific expression of the tobacco (*Nicotiana sylvestris*) cembratrien-ol synthase genes is controlled by both activating and repressing cis-regions." Plant molecular biology 73.6 (2010): 673-685. (Year: 2010).*
Vontimitta, V., Danehower, D. A., Steede, T., Moon, H. S., & Lewis, R. S. (2009). Analysis of a Nicotiana tabacum L. genomic region controlling two leaf surface chemistry traits. Journal of agricultural and food chemistry, 58(1), 294-300. (Year: 2009).*
Kroumova, Antoaneta B., and George J. Wagner. "Pathways for synthesis, and possibilities for genetic modification of sugar ester acyl groups produced by trichomes of solanaceous species." General and Applied Plant Physiology 35.3-4 (2009): 95. (Year: 2009).*
Ennajdaoui, Hanane, et al. "Trichonne specific expression of the tobacco (*Nicotiana sylvestris*) cembratrien-ol synthase genes is controlled by both activating and repressing cis-regions." Plant molecular biology 73.6 (2010): 673-685. (Year: 2010).*
PCT International Search Report and Written Opinion dated Dec. 5, 2012 for PCT/EP2012/003662.
Kroumova et al., "Pathways for Synthesis, and Possibilities for Genetic Modification of Sugar Ester Acyl Groups Produced by Trichomes of Solanaceous Species," *General and Applied Plant Physiology*, vol. 35, No. 3-4, 2009, pp. 95-110.
Field et al., "Expression of a Brassica Isopropylmalate Synthase Gene in *Arabidopsis* Perturbs Both Glucosinolate and Amino Acid Metabolism", *Plant Molecular Biology*, Klumer Acadamic Publishers, Dordrecht, NL, vol. 60, No. 5, Mar. 1, 2006, pp. 717-727.
Mazourek et al., "A Dynamic Interface for Capsaicinoid Systems Biology", *Plant Physiology*, No. 150, No. 4, Aug. 1, 2009, pp. 1806-1821.
Vontimitta et al., "Analysis of a Nicotiana Tabacum L. Genomic Region Controlling Two Leaf Surface Chemistry Traits", *Journal of Agricultural and Food Chemistry*, vol. 58, No. 1, Jan. 13, 2010, pp. 294-300.
PCT International Preliminary Report on Patentability dated Mar. 4, 2014 for PCT/EP2012/003662 (6 pages).
EP Search Report for EP Application No. 11179882 dated Jan. 16, 2012 (4 pages).
Gwynn, et al., "Inheritance of Sucrose Esters Containing Beta-Methylvaleric Acid in Tobacco," *Tobacco Science*, 29:79-81 (1985).
Slocombe, et al., "Transcriptomic and Reverse Genetic Analyses of Branched-Chain Fatty Acid and Acyl Sugar Production in Solanum Pennellii and Nicotiana Benthamiana," *Plant Physiol.*, 148(4):1830-46 (2008).
Schilmiller, et al., "Mass Spectrometry Screening Reveals Widespread Diversity in Trichome Specialized Metabolites of Tomato Chromosomal Substitution Lines," *The Plant Journal*, 62(3):391-403 (2010).
Office Action issued in Singapore for Application No. 11201400209U dated Oct. 31, 2014 (7 pages).
Office Action issued in Australian for Application No. 20122301349 dated Feb. 26, 2015 (3 pages).
Office Action issued in Kazakhstan for Application No. 2014/1548.1 (11 pages) dated Dec. 29, 2015. English translation included.
Office Action issued in Israel for Application No. 231101 dated May 16, 2016 (2 pages). English translation attached.
Office Action issued in Japan for Application No. 2014-527530 dated Apr. 27, 2016 (15 pages). English translation included.
Office Action issued in Singapore for Application No. 11201400209U dated Jul. 18, 2016 (10 pages).
Severson et al., "Isolation and Characterization of the Sucrose Esters of the Cuticular Waxes of Green Tobacco Leaf," *J. Agric. Food Chem.*, 1965, 33, pp. 870-875.
Examination Report issued in Europe for Application No. 12758404.3 dated Dec. 9, 2016 (3 pages).
Office Action issued in China for Application No. 2016112901855150 dated Dec. 2, 2016 (10 pages). English translation included.
Examination Report issued in Russia for Application No. 2014112234/10 dated Mar. 29, 2017 (19 pages). English translation included.
Examination Report issued in Japan for Application No. 2014-527530 dated Apr. 3, 2017 (14 pages). English translation included.
Database GenBank: ACF 17660.1 of Aug. 12, 2009.
Database: EMBL-EBI:EU616568 of Sep. 4, 2008.
Capsicum Annum Putative Isopropylmalate Synthase mRNA, Complete Eds. GenBank [online], Accession No. EU616568, 2009, Aug. 2009 [retrieved on Mar. 23, 2017], URL https://www.ncbi.nlm.nih.gov/nuccore/EU616568.
Alpha-Isopropylmalate Synthase A., Protein Database [online], Accession No. 004973, May 31, 2011, [retrieved on Mar. 23, 2017], url: https://www.ncbi.nlm.nih.gov/protein/7387848?sat=14&satkey=10929401.
Examination Report issued in Ukraine for Application No. a201403274 dated Feb. 2, 2017 (10 pages).
Examination Report issued in the Philippines for Application No. 1/2014/500455 dated Feb. 28, 2018.
Kandra, L., Severson, R. & Wagner, G.J. "Modified Branched-Chain Amino Acid Pathways Give Rise to Acyl Acids of Sucrose Esters Exuded from Tobacco Leaf Trichomes", *Eur. J. Biochem.* 188, 385-391 (1990).
Office Action issued in India for Application No. 1706/CHENP/2014 dated Feb. 27, 2018 (6 pages). English translation included.
Office Action issued in Mexico for Application No. MS/a/2014/002497 dated Apr. 19, 2018 (5 pages).
Ennajdaoui et al., "Trichome Specific Expression of the Tobaco (*Nicotiana sylvestris*) Cembratrien-ol Synthase Genes is Controlled by Both Activating and Repressing Cis-Regions", *Plant Mol. Bio* (2010), 73:673-685.

* cited by examiner

| MW(Da) | Description | Acyl composition | Presence in *bmvse* tobacco varieties | Presence in BMVSE in tobacco varieties |
|---|---|---|---|---|
| 594 | C15:0 | C5C5C5 |  | + |
|  |  | C6C5C4 |  | + |
|  | C2C12:0 | C2C3C4C5 | + | + |
|  |  | C2C2C5C5 | + | + |
| 608 | C16:0 | C6C5C5 |  | + |
|  | C2C13:0 | C2C4C4C5 | + | + |
|  |  | C2C3C4C6 |  | + |
|  |  | C2C3C5C5 | + | + |
| 622 | C17:0 | C6C6C5 |  | + |
|  | C2C14:0 | C2C4C4C6 |  | + |
|  |  | C2C4C5C5 | + | + |
|  |  | C2C3C5C6 |  | + |
| 636 | C18:0 | C6C6C6 |  | + |
|  | C2C15:0 | C2C4C5C6 | + | + |
|  |  | C2C5C5C5 |  | + |
|  |  | C2C3C6C6 |  | + |
| 650 | C2C16:0 | C2C5C5C6 |  | + |
|  |  | C2C4C6C6 |  | + |
| 664 | C2C17:0 | C2C5C6C6 |  | + |
| 678 | C2C18:0 | C2C6C6C6 |  | + |
| 692 | C2C19:0 | C2C6C6C7 |  | + |

FIG. 2

SEQUENCE LISTING

<160> NUMBER OF SEQ ID NOS: 15

<210> SEQ ID NO 1
<211> LENGTH: 1809
<212> TYPE: DNA
<213> ORGANISM: Nicotiana tabacum

<400> SEQUENCE: 1

```
atggcttctc tctctgtaaa ttctataatt tccctgagca cttcccttc attacattct      60
aaaaacccac ttattcacag tgtcttcagt ttcacgcctt caaccacaag gcattcagct     120
atatgctgct caaatattcg tcggcggccg gagtataaac atggaaaatt ctctgaccct     180
gattatgttg gtattttga caccagtctt cgcgatggcg aacaggccgc tggtgctacc     240
atgactagta aagaaaaact ggacattgca cgtcagttgg ctaagcttgg tgttgatgtt     300
attgaggccg gttttcctt tgcctctgaa gctgagttcg agcttgtaaa gttgatagca     360
caggaaattg gtaataacgt agacaaagaa ggatacgtgc cgatgatatg tgccttagct     420
aggtctagta agaaggatat tgaaagagct tgggatgctt taaagtatgc aaagaaacca     480
atgcttcata tgtttattgc gacgagtgat atacatatga agtacaagtt aaagatgagt     540
agagaagaaa ttgtggagac agctaggagt acggtggctt atgcaaaaac cctatttgag     600
gatgttcggt ttagcgctga agatgctgca agatctgata gggagttcct ttatcatatt     660
attggagaag ttatcaaagc tggtgcaaca gtgattggcc tccctgatac agttggatgc     720
aatttgccca gtgaatatgc acaactgatt tctgatataa aagccaatac cccaggaata     780
caagatgcaa acatttcaac acactgtcac aacgatcttg gcttgctac tgccaactcc     840
ttagctggaa tttgcgcagg cgcaagacta gtagatgtta ccatcaatgg aattggtgaa     900
agagctggaa atgcttctct ggaggagatt gtaatggcct taaaatatcg tggagagcaa     960
gtactaggtg gtatctatac tgggattaat acaaagcata tattcatgac gagcaaaatg    1020
gtagaagagt acagtgggct taagctgcag ccacataagg ccattgttgg agctaatgca    1080
ttttctcatg agagtggcat ccatcaggat ggagtgttaa agaacagaga tacatatgag    1140
tttgtatctc atgaagatgt tgggtatcgt cgtgctaatg aaaacggtat tagtctggga    1200
aagctcagtg gccgccatgc attgaaagcc aaaatgctg agcttggata tgactttgat    1260
ggaaaagaac ttgatgacct ctttcgtcga ttcaagtcac tagctgagag gaaaagaaa    1320
attacagatg atgacttgag agcacttgta tcagatgacg ttttccagcc tcaagtttcc    1380
tggcaacttg gagatgtaca gattacttgt ggaaatgttg gccgctctac agcaaatgtt    1440
aagcttattg acagcgatgg tcaagagcac actgcctttt ctgttggaac aggacctgtt    1500
gatgcagctt acaaggcagt tgacctcatt gtaaaggtac ctgtaacact cgttgaatat    1560
tcggttaatg caatcacaaa acgtataaat tccacagctt caaccagagt gttagttcgt    1620
```

-continued

```
gggaatgatg actatgcatc gtttaatact tcaaacgggc aaactgttaa tcgtacagtt    1680
agtggaacag agcgcatat ggacattgtc gtttcaagtg tccaagccta tgttgaggcg     1740
ttgaacaaaa tattcagtta caaaaaaaca ggtctcgtga acaaatttga aggcagtgcg    1800
caatcgtaa                                                             1809
```

<210> SEQ ID NO 2
<211> LENGTH: 602
<212> TYPE: PRT
<213> ORGANISM: Nicotiana tabacum

<400> SEQUENCE: 2

```
Met Ala Ser Leu Ser Val Asn Ser Ile Ile Ser Leu Ser Thr Ser Leu
1               5                   10                  15

Ser Leu His Ser Lys Asn Pro Leu Ile His Ser Val Phe Ser Phe Thr
            20                  25                  30

Pro Ser Thr Thr Arg His Ser Ala Ile Cys Cys Ser Asn Ile Arg Arg
        35                  40                  45

Arg Pro Glu Tyr Lys His Gly Lys Phe Ser Asp Pro Asp Tyr Val Gly
    50                  55                  60

Ile Phe Asp Thr Ser Leu Arg Asp Gly Glu Gln Ala Ala Gly Ala Thr
65                  70                  75                  80

Met Thr Ser Lys Glu Lys Leu Asp Ile Ala Arg Gln Leu Ala Lys Leu
                85                  90                  95

Gly Val Asp Val Ile Glu Ala Gly Phe Pro Phe Ala Ser Glu Ala Glu
            100                 105                 110

Phe Glu Leu Val Lys Leu Ile Ala Gln Glu Ile Gly Asn Asn Val Asp
        115                 120                 125

Lys Glu Gly Tyr Val Pro Met Ile Cys Ala Leu Ala Arg Ser Ser Lys
    130                 135                 140

Lys Asp Ile Glu Arg Ala Trp Asp Ala Leu Lys Tyr Ala Lys Lys Pro
145                 150                 155                 160

Met Leu His Met Phe Ile Ala Thr Ser Asp Ile His Met Lys Tyr Lys
                165                 170                 175

Leu Lys Met Ser Arg Glu Glu Ile Val Glu Thr Ala Arg Ser Thr Val
            180                 185                 190

Ala Tyr Ala Lys Thr Leu Phe Glu Asp Val Arg Phe Ser Ala Glu Asp
        195                 200                 205

Ala Ala Arg Ser Asp Arg Glu Phe Leu Tyr His Ile Ile Gly Glu Val
    210                 215                 220

Ile Lys Ala Gly Ala Thr Val Ile Gly Leu Pro Asp Thr Val Gly Cys
225                 230                 235                 240

Asn Leu Pro Ser Glu Tyr Ala Gln Leu Ile Ser Asp Ile Lys Ala Asn
                245                 250                 255

Thr Pro Gly Ile Gln Asp Ala Asn Ile Ser Thr His Cys His Asn Asp
            260                 265                 270

Leu Gly Leu Ala Thr Ala Asn Ser Leu Ala Gly Ile Cys Ala Gly Ala
        275                 280                 285

Arg Leu Val Asp Val Thr Ile Asn Gly Ile Gly Glu Arg Ala Gly Asn
    290                 295                 300

Ala Ser Leu Glu Glu Ile Val Met Ala Leu Lys Tyr Arg Gly Glu Gln
305                 310                 315                 320

Val Leu Gly Gly Ile Tyr Thr Gly Ile Asn Thr Lys His Ile Phe Met
                325                 330                 335
```

```
Thr Ser Lys Met Val Glu Glu Tyr Ser Gly Leu Lys Leu Gln Pro His
            340                 345                 350

Lys Ala Ile Val Gly Ala Asn Ala Phe Ser His Glu Ser Gly Ile His
            355                 360                 365

Gln Asp Gly Val Leu Lys Asn Arg Asp Thr Tyr Glu Phe Val Ser His
            370                 375                 380

Glu Asp Val Gly Tyr Arg Arg Ala Asn Glu Asn Gly Ile Ser Leu Gly
385                 390                 395                 400

Lys Leu Ser Gly Arg His Ala Leu Lys Ala Lys Met Ala Glu Leu Gly
            405                 410                 415

Tyr Asp Phe Asp Gly Lys Glu Leu Asp Asp Leu Phe Arg Arg Phe Lys
            420                 425                 430

Ser Leu Ala Glu Arg Lys Lys Lys Ile Thr Asp Asp Leu Arg Ala
            435                 440                 445

Leu Val Ser Asp Asp Val Phe Gln Pro Gln Val Ser Trp Gln Leu Gly
            450                 455                 460

Asp Val Gln Ile Thr Cys Gly Asn Val Gly Arg Ser Thr Ala Asn Val
465                 470                 475                 480

Lys Leu Ile Asp Ser Asp Gly Gln Glu His Thr Ala Phe Ser Val Gly
            485                 490                 495

Thr Gly Pro Val Asp Ala Ala Tyr Lys Ala Val Asp Leu Ile Val Lys
            500                 505                 510

Val Pro Val Thr Leu Val Glu Tyr Ser Val Asn Ala Ile Thr Lys Arg
            515                 520                 525

Ile Asn Ser Thr Ala Ser Thr Arg Val Leu Val Arg Gly Asn Asp Asp
530                 535                 540

Tyr Ala Ser Phe Asn Thr Ser Asn Gly Gln Thr Val Asn Arg Thr Val
545                 550                 555                 560

Ser Gly Thr Gly Ala His Met Asp Ile Val Val Ser Ser Val Gln Ala
            565                 570                 575

Tyr Val Glu Ala Leu Asn Lys Ile Phe Ser Tyr Lys Lys Thr Gly Leu
            580                 585                 590

Val Asn Lys Phe Glu Gly Ser Ala Gln Ser
            595                 600
```

<210> SEQ ID NO 3
<211> LENGTH: 2036
<212> TYPE: DNA
<213> ORGANISM: Nicotiana tabacum

<400> SEQUENCE: 3

```
ctcttttctt agggaaaaga ataatggctt ctctctctgt aaattctata atttccctga      60
gcacttccct ttcattacat tctaaaaacc cacttattca cagtgtcttc agtttcacgc     120
cttcaaccac aaggcattca gctatatgct gctcaaatat tcgtcggcgg ccggagtata     180
aacatggaaa attctctgac cctgattatg ttggtatttt tgacaccagt cttcgcgatg     240
gcgaacaggc cgctggtgct accatgacta gtaaagaaaa actggacatt gcacgtcagt     300
tggctaagct tggtgttgat gttattgagg ccggttttcc ttttgcctct gaagctgagt     360
tcgagcttgt aaagttgata gcacaggaaa ttggtaataa cgtagacaaa gaaggatacg     420
tgccgatgat atgtgcctta ctaggtctag taagaagga tattgaaaga gcttgggatg      480
ctttaaagta tgcaaagaaa ccaatgcttc atatgtttat tgcgacgagt gatatacata     540
tgaagtacaa gttaaagatg agtagagaag aaattgtgga gacagctagg agtacggtgg     600
```

```
cttatgcaaa aaccctattt gaggatgttc ggtttagcgc tgaagatgct gcaagatctg    660
atagggagtt cctttatcat attattggag aagttatcaa agctggtgca acagtgattg    720
gcctccctga tacagttgga tgcaatttgc ccagtgaata tgcacaactg atttctgata    780
taaaagccaa tacccagga atacaagatg caaacatttc aacacactgt cacaacgatc    840
ttgggcttgc tactgccaac tccttagctg gaatttgcgc aggcgcaaga ctagtagatg    900
ttaccatcaa tggaattggt gaaagagctg gaaatgcttc tctggaggag attgtaatgg    960
ccttaaaata tcgtggagag caagtactag gtggtatcta tactgggatt aatacaaagc   1020
atatattcat gacgagcaaa atggtagaag agtacagtgg gcttaagctg cagccacata   1080
aggccattgt tggagctaat gcattttctc atgagagtgg catccatcag gatggagtgt   1140
taaagaacag agatacatat gagtttgtat ctcatgaaga tgttgggtat cgtcgtgcta   1200
atgaaaacgg tattagtctg ggaaagctca gtggccgcca tgcattgaaa gccaaaatgg   1260
ctgagcttgg atatgacttt gatggaaaag aacttgatga cctctttcgt cgattcaagt   1320
cactagctga gaggaaaaag aaaattacag atgatgactt gagagcactt gtatcagatg   1380
acgttttcca gcctcaagtt tcctggcaac ttggagatgt acagattact tgtggaaatg   1440
ttggccgctc tacagcaaat gttaagctta ttgacagcga tggtcaagag cacactgcct   1500
tttctgttgg aacaggacct gttgatgcag cttacaaggc agttgacctc attgtaaagg   1560
tacctgtaac actcgttgaa tattcggtta atgcaatcac aaaacgtata aattccacag   1620
cttcaaccag agtgttagtt cgtgggaatg atgactatgc atcgtttaat acttcaaacg   1680
ggcaaactgt taatcgtaca gttagtggaa caggagcgca tatggacatt gtcgtttcaa   1740
gtgtccaagc ctatgttgag gcgttgaaca aaatattcag ttacaaaaaa acaggtctcg   1800
tgaacaaatt tgaaggcagt gcgcaatcgt aaaagtgatg gtgtgtgctc cagaaacaaa   1860
agcttaaatg ctgcttagtg ctcgatgatc ataaatttat gctctattca tgcatgcatt   1920
actgaagtta attaagaagt aatcttaatt gtataagatg taaacatgtt tctattcatg   1980
cattactatg aaattaatta caatttctga gccaaaaaaa aaaaaaaaa aaaaaa        2036
```

<210> SEQ ID NO 4
<211> LENGTH: 1585
<212> TYPE: DNA
<213> ORGANISM: Nicotiana tabacum
<220> FEATURE:
<221> NAME/KEY: misc_feature
<222> LOCATION: (1520)..(1520)
<223> OTHER INFORMATION: n is a, c, g, or t
<220> FEATURE:
<221> NAME/KEY: misc_feature
<222> LOCATION: (1575)..(1575)
<223> OTHER INFORMATION: n is a, c, g, or t
<220> FEATURE:
<221> NAME/KEY: misc_feature
<222> LOCATION: (1577)..(1578)
<223> OTHER INFORMATION: n is a, c, g, or t
<220> FEATURE:
<221> NAME/KEY: misc_feature
<222> LOCATION: (1582)..(1582)
<223> OTHER INFORMATION: n is a, c, g, or t

<400> SEQUENCE: 4

```
agcaagatgt caagaagcac acttgccttt tcctgttgga acaggacctg ttgatgcagc     60
ttacaaggca gttgacctca ttgtaaaggt ttataatgaa actgaaaact ctcataatgt    120
ttgtatcttg tcacactagt aggataggta atttaggttt tatatacgct gaaggtataa    180
aaatatttac tcaatcagag cgcttacaag acaattgcag gtaactctat gagtagctta    240
```

```
gactaaaaga taaacgtagt aatttcaatg taaatagttt aggagacatg cgaatctttc    300
cttgacaaag aaactaaaaa acttgcgaag cacgcacctc aatcacccg tctgtgtgaa     360 ttgaacgaac ttaaaagtac aaccagctta aactgatttt ttacctattt tttagtgttc    420
agacggatct gcagcaacca tgatttgatt caccggtcga caaatatcct caccgtgcat    480
tcgaactccc tttctccaca tcctaaaaat cctcttctaa gatgtctttg tttgcaaact    540
ctagccgtca tatcttggtg gaaaacatgt ctcttctaat atgtgtattt atatgttata    600
aatagtattt aggagaatgg caagttaaca gactaattaa cacctattat gaatggatcc    660
aaccgaatag aaatattcca acatttagct aagtaagctg ccaagtcaaa taagactgat    720
agagtaaaaa ctctttcata tagcaatgaa tataacctaa atcctttagt tactgctagc    780
aattttgtag gtataattgc tttgtttggt aaaaacatct atgtaacttt tgttttataa    840
gtaatgttct ttgtcattat gcaggtacct gtaacactcg ttgaatattc ggttaatgca    900
atcacaaaac gtataaattc cacagcttca accagagtgt tagttcgtgg gaatgatgac    960
tatgcatccg tttaatactt caaacgggca aactgttaat cgtacagtta ggtatgaaat   1020
atacatgaag tactgtttcc ctttaatta tccttatttc ccttaataat attctttcat    1080
gcataatgtg ggaacatgaa gatgacagag aagaattaaa acgattttt cctaaaggag    1140 aaaataatat gtgatagggaa tgaaatgttg tcagttttat atagttctca aatttatgg    1200 tactacgggt atctagagcc aacctgagaa tagaaagtat catataagaa atatacacag    1260
cagttagata gagtacattt ttaattattt aattatattt atgcatgcct caacacgttt    1320
actcacctct tagcctaatt tttgttacat gggatcgttc tacattttga gtagctgaga    1380
gatttgaact taggaccttt attttctcta acactatgtt atattgccag tggaacagga    1440
gcgcatatgg acattgtcgt ttcaagtgtc caagcctatg ttgaggcgtt gaacaaaata   1500
ttcagttaca aaaaacagn tctcgtgaac aaatttgaag gcagtgcgca atcgtaaaag    1560
tgatggtgtg tgctncnnct anaag                                        1585
```

<210> SEQ ID NO 5
<211> LENGTH: 551
<212> TYPE: DNA
<213> ORGANISM: Nicotiana tabacum
<220> FEATURE:
<221> NAME/KEY: misc_feature
<222> LOCATION: (541)..(541)
<223> OTHER INFORMATION: n is a, c, g, or t

<400> SEQUENCE: 5

```
gtcaagagca cactgccttt tctgttggaa caggacctgt tgatgcagct tacaaggcag     60
ttgacctcat tgtaaaggtt tataatgaaa ctgaaaactc tcataatgtt tgtatcttgt    120
cacactagta ggataggtaa tttaagtttt atatacgctg aaggtataaa aatatttact    180
caatcagagc gcttacaaga caattgcagg taactctatg agtagcttag actaaaagtt    240
ttaattattt aattatattt atgcatgcct caacacgttt actcacctct tagcctaatt    300
tttgttacat gggatcgttc tacattttga gtagctgaga gatttgaact taggaccttt    360
attttctcta acactatgtt atattgccag tggaacagga gcgcatatgg acattgtcgt    420
ttcaagtgtc caagcctatg ttgaggcgtt gaacaaaata ttcagttaca aaaaacagg     480 tctcgtgaac aaatttgaag gcagtgcgca atcgtaaaag tgatggtgtg tgctatctgc    540
naaaaactcg a                                                        551
```

<210> SEQ ID NO 6
<211> LENGTH: 14232
<212> TYPE: DNA
<213> ORGANISM: Artificial sequence
<220> FEATURE:
<221> NAME/KEY: source
<222> LOCATION: 1..14232
<223> OTHER INFORMATION: /note="Description of artificial sequence:
    NtIPMS2 corresponding BAC contig sequence (total BAC length is
    76832bp. Only 14232bp are shown)"

<400> SEQUENCE: 6

```
tgatgatttc tcattataat tgtaactagt ggtggcaaaa tggtaaaaag aaaacagtta      60
tccatccata ttattcatta aaaaatgggt tgtataatga acttttaaa aaaggatcaa     120
ttatggataa gaaccatatt atccgcttag aaaatggata accaataagt taacttctac    180
acttgtaaag cttcaaattg ggggttcctc aagtttgtga gaagaagaat tctcccaaag    240
tgatcatatt caagaagtct tggataaatg aatatccata ttatccgccg attatctcgt    300
tttaatccgt attaaatatg agtcggttcg aataattat ctgttttgt attatctact      360
ttggacatgt ccatacccga cccgaccccg ctcgtttgtc accctagtt gtaacatata     420
ctgtttgctt acctaacggg ttgagttaag taccatcacg acttggtggg attttggctc    480
ttacaaaact acaattgagc ctgattataa tattttatta taaaattgag gttcggtata    540
attatttttg ctgatcaaat cttggtgatt caaagttcaa ctgaaatatg caatactaaa    600
ttattttctt atttaataaa tttatgatg agctaatatt tataatttga ataaaaaaaa    660
attcataata ctagtatttt tgagttgaat agaaattgtc agtacagttg aatataacaa    720
ctgtaattat tcataaaata ttttagtttg atataataat aatctttcaa aaaacattct    780
tacagaactt gactgaaacc ataataaagt atctcactac ttttgtgcga caaggtttct   840
tcctaaatga gatcaacaat cattctttta aggattttta tttttatttt tatcacaaat    900
atattactca atatctaagt aatctttaaa aatctgtata ctcattacta taaagcatac    960
atgcaaaacg cgtacaataa aaactaattt ttaaaaaata ggggggaagga gaagggatga   1020
acagaaccct cattaataaa gcaaaaattt aaatatccaa caaattgaac tgttaagatt   1080
ataaaaaaaa agaaaaaaga acttcattgt cgaagtaagt caaagtatca ctagccgtaa   1140
aaatttcggc acctttttaaa agaatgataa atatactagg gaaagcctaa aacctcttgg   1200
tattaataac tatagtttag aaattaggca aagccgctac tagggtagtt aattattggt    1260
tctgttttata tttatatcat tcgttttgtt gataatgatg agcaacgttc cattacatga   1320
agaaaccacg tcaatgttta ttccctcatt cgttttctaa atttattcga gatgtgagta   1380
aacctccccc caccccaca caccccttt tttttttgct gttaaagttt cgacaataag    1440
aacgttcaga gtttcttgaa cttctgtttt atctgcagaa attataaatt ggagtcaacc   1500
actgcatccc aaattgatgc agactttatc tgaataatta atcagtatat aattataata   1560
tctattttct atgtttctaa tttatgtgac acatttctta tccgttagtt taaaaaaaat   1620
gataaattta tatatttcag aataatttaa ctttaaattt ttttatttta tccattttac   1680
ctttaatgag aaacttttgt aaccatacaa atgttataga atatatttag aacaacaagt   1740
ttcaaatatt ttatagtcac ataaatttaa cacacaaata ttagagcaaa tttcaaacta   1800
cttcacataa attgaaacag agggaaaat aatactcct ccgttccctt ttacttggca     1860
cgttttgact tttacgcccc cttaagaaat aataaatgaa gtgcataatt taccatgata   1920
cccatattaa ttgatgtata ttttattgga tttgaaaaat gatttgaaat gagtaataaa   1980
```

-continued

```
tatcgtgggt ataacaaaaa aaaaattatc ttctcttgat atgcgtaaag tgacaagcaa      2040
aaatgaaaat ctattttag tatacatgcc aaataaaagt gaacggtaaa aatgaacgga       2100
gggagtatat attattacta ctaaaacggg aaactgggca tgctaagttt ttcattgcta      2160
tttcaagttc cgattaatag ccataatata atgttttcta gaaacaaaga acaacgccaa      2220
gataaatttt cccaaaaagt agcacaaatg taacaaattc ttacctcaaa ttttaatcta     2280
aacacataaa ttttctttat aattgtttct taaaaactta aactaaattc aaatgccaac     2340
aagtttaaat gagcaaggaa gtattttcag tttctatttc ttgaatttaa taagaatgga    2400
aatattttcc gtttgtttac tgggttctgt ctagtctagc ttaagacgaa aattgtcttg    2460
ttttaagttt tacaaaccgt aaggggtggt aattcaattt tcaattgtag tatgagcaat   2520
taattccaac acaaaatctc acgtgaaata atatactcta gtgtttgttt ggcgtacgaa    2580
aaagaaagtc tacataatta atgcagcgtt ccatagttga tattaaaata atacccgtaa    2640
taaattatat aaaactttat gtgttattct tttgataaaa cagcaaccag acacaccagg    2700
ggctactttg gtcatttct ctccaataaa aacccttgtt tcaccagctt tgtaggtgtt     2760
cgaattcacc aaagcgaaca ttccattaac tccgatccac tctcttttct tagggaaaag    2820
aataatggct tctctctctg taaattctat aatttccctg agcacttccc tttcattaca    2880
ttctaaaaac ccacttattc acagtgtctt cagtttcacg ccttcaacca caaggcattc    2940
agctatatgc tgctcaaata ttcgtcggcg gccggagtat aaacatggaa aattctctga    3000
ccctgattat gttggtattt ttgacaccag tcttcgcgat ggcgaacagg ccgctggtgc    3060
taccatgact agtaaagaaa aactggacat tgcacgtcag ttggctaagc ttggtgttga    3120
tgttattgag gccggttttc cttttgcctc tgaagctgag ttcgagcttg taaagttgat    3180
agcacaggaa attggtaacc tttaatgttt aaccgttcac atttctaata tttacttatt   3240
tgtaacatgt cgtcacgtgt tagtttcatt cttttatga accaaacatg catgcaaaga    3300
tatttttaga tatttggacg gcgagtgaga tttgaaacta ggaccgtttg cctgatacaa    3360
tattaaaata tgtaaccatt ttatgtacaa gtttaaactg ttgatagtag catatttttt     3420
actttatttt aagtatacta tattccaaca ggtaataacg tagacaaaga aggatacgtg    3480
ccgatgatat gtgccttagc taggtctagt aagaaggata ttgaaagagc ttgggatgct    3540
ttaaagtatg caaagaaacc aatgcttcat agtaagaaaa tatttcaaga tcgaattagg    3600
tcaaaagtgt aatcgtaaaa agtaaaagag agaatctaaa ggtacttatt tgttctggtc    3660
tttttctttt ttaatataag cggccttgag attataggag gtttgatata gacctctacc    3720
atgtaaattc ttatttattt gcttttgtt tagctttaa cctttccct gtactgaaat       3780 agattgtaat ggcctaaaa tatcgtggag agcaagtact aggtggtatc tatactggga    3840
ttaatacaaa gcatatattc atgacgagca aaatggtact ctcatcttaa tcttctagtt   3900
agagatatat tttaccagtt ttaaagctgc ttaatttttt gtgcctttct gttgacacaa    3960
ttgttgctat gtaggtagaa gagtacagtg ggcttaagct gcagccacat aaggccattg   4020
tcggagctaa tgcatttct catgagagtg gcatccatca ggttttgcgt tattttctc      4080 taaaagtttt acttctacat acactagatt tgttgaaaga ttactgaatt ggcgaccttc    4140
tacactaggt taaattgcaa taaacatttc ataccactac cggttgatat aaaataaatc    4200
ctttctcgtt aagataagat gggtaaaatg aagaattcaa agttgaatta ttttcaatta    4260
tagaaatgta tcattctttt tgtaacagac taataaggaa attgtgtcat ctaaataaca    4320
```

```
catgaagtat ttggattcag cccattgccc cttcctcttt cattatcgcc ttaatcagga    4380
ttctctactt ccatagtatc attcagtttt cattcttcct tttaaatttt ttttaatgt    4440 ggtttaggat ggagtgttaa agaacagaga tacatatgaa tttgtatctc ttgaagatgt    4500
tgggtatcgt cgtgctaatg aaaacggtat tagtctggga aagctcaggt atgatttgat    4560
tttcagagtg atcgatttgt tatgttgatg gtttgataga gattattgtt tcaaattctt    4620
tggtctttcc cccatatttt tggatgagtc aaaataattc gactaatata tagtcctacc    4680
aatttggtgt caacatatgt acgaattgaa tatagtcatc aatcaactat gtccaactat    4740
ccatactgta aggtatactc cctttacatt aaaaaataca agtgaactga aaaaaaaaag    4800 acattttta attaaagtgt gctatctcta accgtttaaa tttttagatt agattatcat    4860
acagttcaaa cactttaaaa ctcgtactat cccctagaat ttcagtacct ccgttgtatt    4920
gaatcaaccc caaccttca tttttctcat ttacattagg cacattgatg tacctctttc    4980
ctttaaggaa tacattttgt aacatggtag aatattttgt gcagtggccg ccatgcattg    5040
aaagccaaaa tggctgaggt aagatacata atctatagta cgatatacta caaatattat    5100
agtatatgga aatggatcaa atcatttat ttttgttaca gcttggatat gactttgatg    5160
gaaaagaact tgatgacctc tttcgtcgat tcaagtcact ggctgagagg aaaaaggtga    5220
ttacgttgct gatatttcat agtgcaacag tcaaatttgt gatcgcacct tttcgttcct    5280
agtgtttgtc catatttttt gagttaattt caaatatgat cactaatttc tactataaca    5340
ataaaattta aatttttta ttcgcattaa agtgactgaa ctaacaatta aaaatatttg    5400
aaaaatatat gaaaaattac ggccaaagaa aaactctttt gactctcgac atccgagcat    5460
caccacatag taataaatga gaaaattatt ttttatcaaa ttaaagtaac tgaattttac    5520
ttattattca taataaaaga aaatcactaa actatacgca ctatagtggc aaaacctatc    5580
catattcaag gtgactttaa gtaccggtct agtaggtaga ttttgtgat tttactgtta    5640 tagtggataa aattaaagtc acttttttg ataaattgga agaatagcct gacagacatc    5700
tcacttattc ggctttgaca tcccggtccc cctactccat ataatttcaa ccaaacactt    5760
aaacttgtat aaaacattag tcttaaacac ctctgatact gtgtgtgttg ttcactcgtg    5820
ctgatataaa ggacacatca gatccacctc agatatatta atgccacatc attatctatt    5880
tttacaaaaa atatttttta ataaaaatat caaactcatc cctttcttct ccaaaaaaaa    5940
aaacaaacct tattcctctc tccaccattc catctctgcc tcttccaccc gtcaccgcca    6000
ctaccaaaca ctgcacccctt cctcttccat gagaaaacac tcaatcaaac ctacttcatc    6060
ttttattttt gtcctaaact tctccattac tacaatctat tcaaccaccc atggtagtct    6120
tgttgccacc atcgccagca accactccaa aaccaccact atatctcctc ttctcttcat    6180
attcatgtca ctcttcaaa acctagacat tgaacgagtt taataaaatc tatccttaaa    6240
ttttctttct agccaaatac ccaaagcaaa accaaaaaaa ttgaaaaaga aagagaagaa    6300
atttttactc aaaattctta ttgaccccctc cagcaacgat aaaatttata aaactaacaa    6360
aatcaagctt cggcgttttc aacaaccgat gacgatccaa tttctggctt aaacactatt    6420
ttcaagcttc aatgtctctt aattctccgg cgtcttcatt gtcttcttca gttatttga    6480 gaaaacaaa aattaaataa ctttgttcct tgactagctg ctctgctaaa ctctattagt    6540
ttggtcttgt tatactgctt cttttttat tttatcata gtccagttga ttgctaaaat    6600
tgtaagagaa ataatgtaat gctgtttgag aaaactctac ttgagaaaca aaatttaat    6660 atagagggtg tggagcgtgt caatttcaat ggcgttttta agagatttgg gggtaagaag    6720
```

-continued

```
aagcggctgg gatagagagg ggcgagataa tggctagcat tgttttaat ttttttttct    6780
tttcatttttt ctcttttatt attttctaat caaattttgt atagttactc gcttttagga    6840
gcgtgcaatc acttattttg tttgactcac aaaacaaagg ctacataagt ttggtcaatg    6900
gttagatgag tttaaaacta atgtcttata caagttcaag tgcctgattg aaactatgtg    6960
gagtagggtg atcggaatgt caaagccgaa taagtcgagg cagtggcgaa gccaagaaat    7020
tcaacaaggg tattcaaacc tttgccagtg ggctatgtaa gggtgttcaa agcctatttt    7080
taatcaataa caagtaatat tttaccttat acggagtata attttctggc gaagggtagt    7140
cagttgacca cccttgattg cacgtagctt cgcccctgag tcgaggtgtc tcttaggcta    7200
aaatagcgtg ataaatttta taataaaatt tattttatat gagtaaagtt aataaaattt    7260
attttatatg agtaaagtta agtaaattat aatacttaaa gaaaattgaa agcttacata    7320
tgcagaggtc cggtcctcga cccacttatc ttgatccccc tctttcttct tcttcacaat    7380
atgcgtctcc ttgaatagct catcatgact cattggacgc ccatacttct tttcctgaaa    7440
ataaattaat ttagttaata aataaaatag atatacttag aaaagtaaaa taatttaagc    7500
aattacgtac caatcttctt tttattgtcc ctaggctgat cgcacctcta gtgtgcaagg    7560
agcctccctt ctcggatgcg cgagctttct ttcctttttc gctcctctct aagaactttg    7620
cggtaagcca ttgccttttgc aaatcattcc acaaattctc aagtaaccag ccaggcctct    7680
tgttcttctt tctagcatcc gagaaagcat ccgccaatct cttactagct ttgtgatgaa    7740
aatttgcagc cacttccgcg ctatagcggt ctttccatac acacttgctc tgtatttaa    7800
aatttaatta ttagatggaa acatcataaa tataaattat taaactgttt aaaaaaatat    7860
ttataccta aattgattga aaatttgctc tttcagtgag aatggacaat cagtccaagt    7920
cgtataaggg ccatcataaa gctttctgat ggcattagtg attatcttcg tagtcttatt    7980
acccggcctg aacctacaat ttaataataa aaacacatta atatcttagt aaaaatgtta    8040
caaatcaata gacggaaaaa taatgaataa cacttaccca tcacccttag ggactatgat    8100
gatcctgcca tatcgatcat aatgcactac ctcgtcatca ctattcgaag catgtgtatc    8160
agaggcatgt gaagacggtg taggcgggtc agagctactg cctcgtaggc gaaggcctgc    8220
aatagatgga gtcgataatg aagatggttg tgatccctgt gactacaaca tagctggatg    8280
tgacccaagt ggatgtgata atgctggctg tgacccgagt ggctgtgaca tggatggatg    8340
cgatccatgt ggctgtgata tgtagggatg tgatccatat ggatgtgatg tagatggctg    8400
cgatgcagat ggctgtgagg cagctggact gtatgtcgaa catatagtcc tatggccctg    8460
tgatggaaga cctggtgtct gaacgaaggt gtatgattcg tgatgctgtg gaaactcagt    8520
atagccgtgt ggtggaggat aagacatagg catctctgaa aagggtggac aagagggact    8580
attattttct acccctcctct ttcccttcct acccttttct cgaccctgag aactagtagg    8640
gtcattgtta ccttgacccct tgcctgccat ctgtatgata taatgcacat ttagattgaa    8700
acatataaga aactagctat aaaacaagag tgctttaaaa aaccaacttt ttaatcctca    8760
tcgacgtatt gttcctcgtc cgagaattct tcgtcctcat ttgtttgagc ttcatcagtt    8820
gattcttcgt cctcatttc tttaattgtt acttcattta tatcaccttc ttccaatatg    8880
cattcaggat gttccaaatc attttctaac tgatcgtcca ctatttggtg aatattagaa    8940
atatcatttt gatatgcaat atttaacaca ttctcgactt ccaccctacc tacatgctta    9000
gtttttatta caacccacca atcggactta ttccgccgca atggataagg agcataatac    9060
```

```
acttgcctaa cgttatgtgc aattatgaaa ggatcatagc gatcatactc cctcgtatga    9120
ttaacctcaa ttatgttgta ttggtggtgt acacttgtac ctcttgttgg atttgggtca    9180
aaccacttgc atataaagag tatcaatttc ttatatggcc aacctgtata ttctagttgt    9240
aatatttctt tgaccacacc ataataatca atatctccaa cttggttgcc atcaccacct    9300
tgaacccaca ccccgctgtt gttactattt ttatttttag agccatcctt tgtatgaaac    9360
ttataaccat tcactacgta cttagacatt gttgtgacct gaagcccagg tccccaagat    9420
atatctttca aaaattgatt tacaccatta tttggattat ttacctacat agtgttaaaa    9480
atattcataa gttagcataa cttataaatc aattttata cattcattac atatatatat    9540
atatatatat ataactagtg tatatatata tacaaactgt ttgaacacgt atcaaatctc    9600
gtatatacaa catcatggcc aaattgacct acgaagtgac tgtgacacat caaatatttt    9660
tagtagttgc atcaatatgt agtcacagta aatttttacat tttgataact aataaatcaa   9720
tacttacttg agaaatggta caacttcgga acaatttagc aacacatgaa gtgtagctga    9780
cttgtactcc atatcactca aacttctctt tctaacatcc ttagaacatc ggcctggttg    9840
attgaatata gatattggtg gatataatgg atcattcaca tattcgaccg tgtgcctatt    9900
gggcctattc ctagaacatg gcacgttatt ctcaaaataa taagaacaaa aatatgcagt    9960
tttctttgca agataggctt cgcatataga tccttcaatc ctattccctg cttaacaaat   10020
tgtttgcatt tgccaattgt cctacataat gtcatgttag ccaagaacat tcaaataaaa   10080
tagaatatta catcaaactt ataatattac ctctcaaagg gatacatcca tctgcattga   10140
acatgccctc caagtcgtgc ctcgtgtaca aggtgtattg gaaggtgttc cattacatca   10200
aagaaaccac atgggaatat tttttccatc ttactagaaa ttacacgaat gttctggtcc   10260
atccgaagta ggttttcttc ccttaatgtg gtagaacaca agcctttgaa aaacaaatta   10320
atctttatga tgggtttcca gattcttttca ggcaaaccac aaaatgcaat aggtactaag   10380
gtctccatga aaacatggca gtcatgactt tcaaatggc tcaacttccc tacctccata    10440
tctatttttt tcaagattcg acgcataacc ctcaggcatc ttcaatttcg taacccaatc   10500
acaaatttgt cgtctttcct ccaaaatgaa tgtgtaactt gctttggact tgaacacctt   10560
accattgttt gctgtctgca agtataattc aggccgcctg caatattctt gtaagtccat   10620
tctagccttc ggggtatctt ttgtcttacc tttaacatcc atcactatgt tgaacaaatt   10680
gtcaaaataa ttcttctcta tatgcatgac atcaaggttg tgtcggagaa gattatcctt   10740
ccaataaggc aactcccaaa atatactttg tttcgtccaa ttatgattaa caccatatcc   10800
gaggaatcta aaggtggag cctcagtaac tttactgaag ttctggaccc tctcccaaat    10860
tttctcacct gaaagtatcg gaggtggaga atcatattcc actttattct ttttgaatgc   10920
attttttcatc cttctaaact catgatcatc aggcaagaat tgacggtgac aatcaaacca   10980
tgattacttt cggccatgtt tcaaagtgaa cgctttacta tttttcatac agtaaggata   11040
agctagctt ccagcagtca tccacccaga caacattcca tacgcaggaa aatcgttaat   11100
agtccacatt aaattaggac gcaaattgaa attctgcttg gttgatatgt catatgtttc   11160
aacaccatca taccacaatt gttttagctc atcaatcaaa ggttacaaat ataaataaat   11220
caaacctttt ggattacgtg gactgaggat aatataattt cagaatatat atggactagt   11280
catatacaac taaggtggta gattataagg tataagaaag acaggctaac atgagtatgg   11340
tgtcgcagat atagaaaaag gcgtgaagcc atccgcacac agacctaacc gaatgttcct   11400
tgattcacta gcaaaatctg gatatgtcct atcaaagtgt ttccaagctt ctccatctga   11460
```

```
aagatgacac ataacaccgg gtggtcttct attttcaaag tgccatctca tatgaggagc   11520
agaactcatc gacgcatata acctttttaa cctaggtata agaagtaaat aatgcatcgc   11580
cttgacaacg gccatattcc cactggaaag cctcttgaaa cgaggatttt cgcaaaattt   11640
acaactgtct aaagttgcat catctttata atataacatg caaccatctt cacaacaatc   11700
aattctcatt gacgaaagtc ctaacttaga aaccaatctc tttgcctcat agaaatcacc   11760
aggtaagttg atattagggt caactagttc actcataagg tcaatgaaag agtccatggc   11820
tgcttgagaa atattccaat cagatttgat acttagtaat ctaactgcaa cagacagctc   11880
agagtgcaga cttccttcac gtagtagatg actagcttcc tctagtgttc ataaaaacat   11940
tttgcgtctt cattaggagt ttgttcaata ttttcattgg gctcacccc gaagtgcatc   12000 ccaaaagcat ccgcaaccat atcctgaatt ctagaatcaa gatttgtatt ctccaccgac   12060
ctactacttt caccaacaac catgttacga aatatcccac ggctaccatc gatctctcca   12120
tgattagtcc acacaaagta attctctata aaccccttcc tataaagatg aagcttaatt   12180
tcctccgatt ttttaaattt catacaatcg cacctgatac aaggtcacca aattactcct   12240
tcactttggt atggtggaag tgacattgca tgtctaataa agtcatcaac cccttctaca   12300
aaatcctccc gcaatccccg ccgattagga taattcctat tgtacatcca agtacatgtt   12360
ccatctatac aaataaaaca agaacaaatt aatttattct acaattataa attaattata   12420 tctttttag ttaattcaag ataattattg tttcctaatt ataccaattt atatcctaaa   12480
agttcaattc acacccaaaa ggtccaattc atatcttaaa agtttaattc atatcctaaa   12540
agtttaattc acaagaacaa atcctaaaaa ctaaaatttc aattcatatc ctacgagttt   12600
aaccataaac gaactaaact aaagaaattc aacccatacc ctaaaagttc gattcacaag   12660
aacaaattaa tttattctac aattataaat taattatatt tttttagtt aattcaagat   12720 aattattttt ttctaattac accaatttat atcctaaaag ttcaattcat atccaaaagg   12780
tccaattcat atcttaaaag ttcaattcat atcctaaaag ttcaattcac tagaacaaat   12840
cctaaaaact aaaatttcaa ttcatatcct acgagtttaa acataaacta actaaactaa   12900
aaaatttcaa cccatacct aaaagtttga ttcacaagaa caaatcataa acctagatt   12960 ctaactaaac tattcaagaa aatacaaagt taataattca attctaacta gactattcaa   13020
gacaatacaa actcaaaatt gaaatactca tcaattaaaa ctaattcata actaattgac   13080
taactaacaa aactaattag ttaataaaac taattaacaa aactaattaa aacaagacct   13140
aaaccctaat cctcaataaa atgcaatgtt caaataattg aaatactaat caattgaaac   13200
taattcataa ctaattaaca aaacctagaa ataataaata aatgggttgt aattcaaacg   13260
tagaattttt aggagatgga gaaggagagg ggcggcagtg gcagtggcag tggcagtggc   13320
agcggcgatg gcgatggcga cggcgcggcg acggtgatgg ctgggcagtg gcgacgcggg   13380
gtggggaatg agatttatgt gagggaaata tagaaggaga gggaaggtt ttgagtgaga   13440 aaaatagaga aggagagggg aagataagag agaaatgggg gttccccgt ttttcaattc   13500 tgatttcaga attaccgacc aaagttggtc agtaattttg gtcggtacat taagtgttga   13560
ccgtttgacc aaaaaccgac caacttcggt cggtttttt ttttaaaatt aaactttttt   13620
ttttggtgtg tttttttctt aaaatattat aaactataaa aatatatta taaactacaa   13680 gcatttattt tatttaacaa tacaattatt ataataatt ataaactata agtataatat   13740
ttacaaataa ttatattaac tatttaattt taataaatta taatagcatc tatctaagta   13800
```

```
aattttctaa gttataatta agtatgtgag taatttctca catacacaca tacactatat    13860
tgtaattgat gctaattact tcttttttca ttcgttcatc actaataatg catgacatag    13920
attaatcgat ataggtcg agacgttttg atgaatcatc gattaatatt catcgataca    13980
tctaagtaag ttataagtcg atgaatcaat ttacaaatag atatatttga tgataaagta    14040
tatatactaa ttagtatctt cccaagtcta tccctaaaag aacccgaccc tatggtccta    14100
gcgcttcgtg ttcttatata tatacggcta tacctatata tatatacaca cacacacaca    14160
cacacaaata cacttcactg taatacttta actatatata tatatatata tatatatata    14220
tatatatata ta                                                        14232
```

<210> SEQ ID NO 7
<211> LENGTH: 10082
<212> TYPE: DNA
<213> ORGANISM: Artificial sequence
<220> FEATURE:
<221> NAME/KEY: source
<222> LOCATION: 1..10082
<223> OTHER INFORMATION: /note="Description of artificial sequence: NtIPMS2 corresponding BAC contig sequence (total BAC length is 10082bp)"

<400> SEQUENCE: 7

```
taaaacacgc ttcgttgtac tactttaact acatatatag catattatat atagtatatg      60
ttagtgtatt cattatttgt attacaaaag tgttaacgaa ttcatttat attatttaga     120 tagtaaatat aaaagtaatt cgaaagtttg accaatgttg acgtaataac cgaccaactt     180
tggtcggtta ttttacagaa aatatcaatt accgaccaaa gttggtcggt aaatactttc     240
cctgcattaa ccgaccaacg ttggtcgata atttaaata taaattctta aatattataa     300
aatattttaa ataataaaat aattattaaa atttaaaaa ttgggtccag attaccgacc     360
aacgttggtc ggtaatccaa aattttcttg tctgaccagc taggtcaatt cgttgaccaa     420
ttttgccgac caacgttggt cggtatttag ttcaaaaaaa atgtaaaatt ttttgtttcc     480
agttttcgtc caagctggac ggttttggt cgcttttttt tttaccgacc aacgttggtc     540
ggaaatattt ggtcagtttt tatcagattt ttagtagtgt caaacacttt aaaactcgtt     600
ttatccctta gaatttcagt acctccattg tattgaatca accccaaccc tccattttc    660 tcatttacat taggcgcatt gatgtacctc tttcctttta aggaatatat tttgtaacat     720
ggtgaatatt ttgtgcagtg gccaccatgc attgaaagcc aaaatggctg aggtaagata     780
cataatctat agtacgatat actacaaata ttatagtata tggacttgga tcaaatcatt     840
ttatttttgt tacagcttgg atatgacttt gatggaaaag aacttgatga cctctttcgt     900
cgattcaagt cactggctga gaggaaaaag gtgattaagt tgctgatctt tcatagtgca     960
atggtcaaac ttgtgatcgc accttttcgt tcctagtgtt tgttcatatt ttttgagtta    1020
attttaagta tgatcactaa tttctattat aataataaaa tttaatttta tttattcaca    1080
ttaaaatgac tgaactaaca attaaaaata tttgaaaaac atatgaaaaa ttacggccaa    1140
agaaaaattt ctttgactct caaacatcca agcatcacca catagtaata aatgaaaaaa    1200
ttatttttta tcacattaaa gtaactgaat tttacttact attcataata aaagaaaacc    1260
actaaacttt acgcactata gtgggaaaac ctatccatat tcaaggtgac tttaagtact    1320
ggtctaatag gtagattttt gtgattttac tgttatagtg gataaaatta agtaactttt    1380
tttgataaat tagcagaata gcctgagtga catctcacta attcggcttt gacatctcgg    1440
tccccttact ccacagtttc aaccaaacac ttgaacttgt ataaaatatt agttttaaac    1500
```

```
acctctgata ctgtgtgttg tccactcgcg ctgatataaa tgacacatca gagtcacctc   1560
agatacattt aatgccacgt cattatctat ttttacaaaa aatatttttt taataaaaat   1620
atcaaactca tccctttttc tccaaaaaaa gaaaacaaac cttagttctc tctccaccgt   1680
tccatatctg cctcttccac ccatcaccgc cactaccaaa cactgcaccc ttcctcttcc   1740
atgagaaaac actcaatcaa accactttat ctttttttt gtcctaaatt tctccattac    1800
tacaatctat tcaaccaccc atggaagttc tgttgccacc atcgccagca accactccaa   1860
aaccaccact atatctcctc ttctcttcat attcatgtca cccttcaaa acctagacat    1920 tgaacgagtt taagaaaatt tatccttcaa ttttctttct agccaaacac ccaaagaaaa   1980
acccaaaaat tgaaaagaa agagaagaaa ttttactta atatttggta cctcaaaatt    2040
cttattaacc cctctagcta cggcaaaatt tataaaacta acaaaatcaa gcttcgacgt   2100
cttcaacaac cgatgacgac ccaattttg gcttaaacac tattttcaag cttcaatgtc    2160
tcttaattct ccgacgtctt tattgtcttc ttcagttatt ttgagaaaaa acaaaaatta   2220
aacaactttg ttccttgact agctgctctg ctaagctcta ttagtttgat gttgttatgc   2280
tacacctttt tgttttttat catagtccag ttgattgcta agattgtaag agaaataatg   2340
taatgttatt tgagaaaact ctacttgaga aacaaaaatt taatattaga gggtgtggag   2400
cgtgccaatt tcaatggcgt ttttaaggga tttgggggta agaagaagcg gatgggatag   2460
aggggcgaga taatggctag cattgttttt aatttttaa tttttttattt ttctcttata   2520 ttattttcta atcaaatttt gtatagttac ttgcttttag gagtgtgcaa tcacttattt   2580
tgcttgactc aacaaaacaa aggccgtata agcttggtca atggtcatat gggtttaaaa   2640
ctaatgtctt atacaagttc aagtacctga ttgaaactat gtggagtagg gggatcgtaa   2700
tagcaaagcc gaataagtcg aggtgtctct tagtctaaag tagccttatt ttatagtgag   2760
taaagttatg tcattatatt tatatatgaa attaaccta taggtttcc agttctttgg     2820 tgaagcttac ctaattaaaa ttttacctgt gtcggtataa tgaatatgta tgtccgccta   2880
tttatcttcc ctacatctat ttttcagaaa attacagatg atgacttgag agcacttgta   2940
tcagatgacg ttttccagcc tcaagtttcc tggcaacttg gagatgtaca ggtacatgta   3000
aatactattt catgtgtttt tgcctaagtt gctctgacac ggcagtttag gtgacacgcc   3060
cgtgtcggca agacactagt atgagtgtgg atgtgagatc cgtaccggat ctggtcaaat   3120
aattttgggt actttgaccg cagcgtacga aaaaattaga gataagatac aatttgattc   3180
ccgaaatcag aaccaaagct agggtgaatt tgaacaaaat agcatacatt atctaggaaa   3240
tcaatccttt acttatctac aactcgagaa taaaaaataa atccacacat tacaagttat   3300
acgtaagtat tccacaaaat ttctcgtaat ttagatatat ttttatattt ttatttaatt   3360
gaattatttt tagtcggatc cccgcacccg tatccgtatt aggatcagta tcccaaaatc   3420
ttagaattta catctcgaag gatccgacct ctagatctgc acctgtatcg gatacccgta   3480
cccgtatctg agcaacttag gttttttgcta gtctcactta gttgtggatt gaaaaggaat   3540
taatgttcac ctaaatctaa tgatttgctg tttattgtac agattacttg tggaaatgtt   3600
ggccgctcta cagcaaatgt taagcttatt gacagcgatg gtcaagagca cactgccttt   3660
tctgttggaa caggacctgt tgatgcagct tacaaggcag ttgacctcat tgtaaaggtt   3720
tataatgaaa ctgaaaactc tcataatgtt tgtatcttgt cacactagta ggataggtaa   3780 tttaagttttt atatacgctg aaggtataaa aatatttact caatcagagc gcttacaaga   3840
```

-continued

```
caattgcagg taactctatg agtagcttag actaaaagtt ttaattattt aattatattt      3900
atgcatgcct caacacgttt actcacctct tagcctaatt tttgttacat gggatcgttc      3960
tacattttga gtagctgaga gatttgaact taggaccttt attttctcta acactatgtt      4020
atattgccag tggaacagga gcgcatatgg acattgtcgt ttcaagtgtc caagcctatg      4080
ttgaggcgtt gaacaaaata ttcagttaca aaaaaacagg tctcgtgaac aaatttgaag      4140
gcagtgcgca atcgtaaaag tgatggtgtg tgctccagaa acaaaagctt aaatgctgct      4200
tagtgctcga tgatcataaa tttatgctct attcatgcat gcattactga agttaattaa      4260
gaagtaatct taattgtata agatgtaaac atgtttctat tcatgcatta ctatgaaatt      4320
aattacaatt tctgagccaa ttttttttatt tggttcttaa aatttataca aatctcttta      4380
tttgtatttg actaacagat tttcgggaat tagggcaagt agtccaatca gaatcacatt      4440
aagcttggag agtaaaatca aaatctgcac tcctgaacaa accttgactc aaagtacctt      4500
taacatattt taaaacatga aaaggagcag ccatatgaga agcagccata tgagaagcag      4560
ccatgtgcgg tcctcacatt gcttgagcct gcaggtattc tgtagctgca caatttgatc      4620
tgcagctgca cttcagcttc tacgatcgca caattcatgt gcagtccgca cttctggcaa      4680
ggcttcagtc ttgttcattt tgcacgctct ctgaactttt tgtattcttt tcagtgcaac      4740
tatgttctgc ggccacacaa attgtgtgcg gtctgcaatt ctcttcaatc acttctaggc      4800
ttctacatta gatctatggc cgtagagaga attatatggt ccgcactttc ctctacggcc      4860
acagaaatac ttttgcggac cgcacttctg ctctactgcg ctccttcttg ccttgtgagc      4920
cggaacactc ctttttgagt tgaatttctt cattagagta caaatttcca acattcctgt      4980
aatttgcaga cttttattag ttttgggaac ataaatcaat acttttggac taaaactaaa      5040
gcaagaaggt actaataagt ggtcaaaatc cacacttatc accaatccat acccaaaata      5100
acatcaaaat ctaccatatt aagtaacaaa agattaaccc tagtctcgta gccccaatag      5160
tgacaaaaca agaacaatag acacagtcta ccacaataga atcccaacg gggtgtagaca      5220
cataagtagg agtattgaga gaatcatgag acatatccaa atatgaagaa agtaggatg      5280
acacatacga atatgtagaa cccagatcaa atcaaactaa tgcctctcta tgacagatca      5340
gaatgatacc tgtgataact gcatctgaag caactgcctc agtcctacca aggaaagaat      5400
aacaacgagc tcggcctcct cctctatgat gacctctacc cgcctgtcct ccacctccag      5460
ctagctgtgc aggtgaagta gcaactggag cgggaactgt agccttagta ccttgctgag      5520
gtccatccat cttaagtctg ggacaatctc tcaccttgtc cctagtatca tcacactcta      5580
aataacctct atgcgagcgt tgctgctggt actgagtttg cccgtgacga ttggaatgac      5640
cactctagga acctcatgca gaaggcacac tgaaatatgt ccggtacgag tgctctaaga      5700
tccatggcta gctggagcac cacaggaaat gtgaggtgca tactgaacta gtcgactgac      5760
aaagcctctg ccataaaggg tctaagctgt atagtaaaaa ccactaaatc ctccagaacc      5820
acgaggcttc ttatcctccc tatcctccct ctcctgacag cggatacgct ctaacatcct      5880
agcaatctcc acaacctgat gaaatgcaat ctcagtctct aactcccgtg ccataccata      5940
tctgaggcta aaggcgagtc cctcaataaa tctacgaact ctctctctat cagtggaaac      6000
caaggaaggt gcatgacgag ataactccgt aaacctcata gcatactcgg acacagtcat      6060
gctcccctgg cgcaactgct caaactcatt gcacaactca tccctgcagg tctaagctcc      6120
atcaagaaaa gatcagagaa tagggaccat gtaaatggtg ttgcgccaac tatcatactc      6180
gcctcataaa tctaccacca tatgtatgcc gaacccgtca actggaaaag tagtaaggtt      6240
```

```
gaccccctc gactccacca aacctatggt acgtagaatg cgatgatact aatccaataa    6300
actttgtgca tcctcagaag tccctccact aaactaggga ggatgaaact tcagtaacct    6360
ctccaaacac ctctgtccct cagccgagac aactggccct acctcgggct gaactgccgt    6420
tattggctgc accaacacaa cacccagtgt ctggtaagca tgagtcggct actctggtgt    6480
gcgggctgcg tgagtttgag ctcctccccc agtatatgaa gtagctggtg caaccagaat    6540
caactcttcc tcggccaaac tcacaaacat actcatgaag tatgccaagg tctcctagag    6600
cgccagtgta ggaataggct gctcaggtgc acgctcaacc tgctcgggct cctaatcctc    6660
aactggatct gttggagatc caccgttgct actctagcta tagcatgtgc ccctcctcgg    6720
cctctacctc ggccctggcc tcttgcgact ctaatagcgg gcacttgtgc ctgcttagct    6780
aatttggtag agcgtgtctt cgccatctat gggagaatag aagagtaaag gttcaaactt    6840
tggaataaca aatcgacatg ataaagaatg aaggaaggtg atgtttccta acagttcggt    6900
agcctctcaa agataagtac aaatgtcttt gtaccgatcg gcaagattat actaaacctg    6960
ctcatgacaa ctcgtagaac ttatgaacct agagctataa taccaacttg tcatgatcca    7020
aatctcacca taggggtctt gatggaacct agtctataaa actaggtaag tcgaccactt    7080
aacaatattt aaatcagcaa aacatgatat aataaggcag agtttaatat gaaagcagaa    7140
aatagagtta acatcagcca aaatggcaat actcaaatat ttccccagaa ttaggtagta    7200
caaagtcatg agctctgata gaatacataa ggatgtctta aattacaata ctgtttgaat    7260
atgaaaataa caatataaat atagggaagg gactccaagg gaatgcgccg gtcatgcagg    7320
tctaccttga atccttgcgg tcaatgtaag cctcactgcc taggtccgct gcctccaaca    7380
cctaaatcta cacaaaatat gtagaattat agtatgagta cactactatc gataccagta    7440
agtatcaaga ctaacctcgg tgaagtagtg atgaggttca agtcatttga tactcactag    7500
tcaaataagc tgtacaatat atcaaagact agaaatagaa tgtataatag aaaataatat    7560
caacaatctc tttggaacat atgataacaa ctcaatgcaa gtaaaggttc atcttgacaa    7620
aaagttatca aatagaaaca caaacgtatg atacctcgta acacaataac aatatccatc    7680
tgcatcactc agccctgaca aaataacaat acctaaactt atctcttcgt cctgacacaa    7740
taacaatatc catctgtatc gctctgccct gatataataa caatatccat ctgtattact    7800
ccgccctgac ataacaacaa tatccacccg tgtcgttcca ccctgacaca ataacaatat    7860
ccatctgttt cgctcggcct tgacacaata acaatatcca tatgtatcgc tcagaactgt    7920
cacaataaca atcacaatcg tacgacagaa acctcgtgcc aacacccaaa caatccgcca    7980
acatgtccat atgtgtcaca attataacaa aacaataatg tcaagtttca tcaaatacta    8040
gctcacaatt tatcaacaag gtgcacaagg acatgataac aataaaaatg tggatgggta    8100
ttcaacatat aaagcatgac tacgactaat tcaattgaaa agattatgtt catgtagtca    8160
caaagtgatt aagtatgttt catgtagagg acatttccaa attaaggcat attaatagcc    8220
taaggtctaa tctagtcata agccgtatat aacgcccatg tacacgctcg tcacctcatg    8280
tacacgtcgc ttttcacata acacgaataa taattaagga caaatcataa ggggtattcc    8340
cccaccccac aagattaggc aagatactta cctcaaataa ggcaaatcaa tactttaaaa    8400
agcccttgcc tatcgaatcg gcctccgaaa gggtcaaata tagcctaaaa acaactcaat    8460
aatatcaaat acgactatag aaattgattt caagtaagaa agctctgatc tttatcaaat    8520
atcaaaaatt cactccgaac tcgcctcccg gaacccgata aaatttacaa atctcgagta    8580
```

| | |
|---|---|
| cccattcgaa tacgagttca aatgtgcaag ttttatccaa attggactcc gaatcgggt | 8640 |
| tcaaatctct attttttatt ttagaatagt tttttccaaa attcccaatt ttctcacttt | 8700 |
| gattaaccaa taaaaagcca aattcaagat ggaatcatga acaataatca atccgagta | 8760 |
| aagaacactt acccaatcca agtgggtgaa atcgcctaa aggatttcct caattcgagc | 8820 |
| tttaaatctc aaaatatgat aaaataagtc aaaccttcaa ttaaaatact ctactcagtg | 8880 |
| attttcgctt ctgcgtacca tcccatcgca tctgcaatgc cgcttttgtg agcccactct | 8940 |
| cgcatatgcg aagttcagtg ctccccgat cctctgcttc tctgatacta ttctcgcttc | 9000 |
| tacggagtcg cttctgcacc caaactagca tacctgcgcc caagttccg tacctacgga | 9060 |
| caatgctgcc ttcctcttcc cttcgcatct gtagcccttt tgtctgcatc tgcagactca | 9120 |
| aactcgctag tgcgagaaca ctagaatctg aagtgctacc ataatatcaa ataatccaa | 9180 |
| aacacacccg aggcctcggg accccatgta atcataccaa tcaatccaaa aatataacac | 9240 |
| ggacctactc gagtccgcaa atcacataga ataacatcaa aaccataaat cacacatcaa | 9300 |
| ttcaagttta atgaactaac taacttccaa actttcaaca ctcacgccaa aacatatcta | 9360 |
| aactacttag aatgaccta aatttcacac acaagtctca aattacataa ttaacctatt | 9420 |
| ccaactttca gaataacaat ccagacccga cagcctcaat gtcaactccc ggtaaaacct | 9480 |
| atgaaccttc caaacctta aatttccaac attcgccaaa tagagccaaa taaacctagg | 9540 |
| aacctccaaa tctaaatccg gacatacgcc taagtctaaa atcacaatac aaatctattg | 9600 |
| gaaccatcaa ataccattc cagaatcatt ttatataaaa gtcaaacatc ggtcaactcc | 9660 |
| tataacttaa gcttgcatgc ctgcaggtcg actctagagg atccccgggt accgagctcg | 9720 |
| aattcgccct atagtgagtc gtattacaat tcactggccg tcgttttaca acgtcgtgac | 9780 |
| tgggaaaacc ctggcgttac ccaacttaat cgccttgcag cacatcccc tttcgccagc | 9840 |
| tggcgtaata gcgaagaggc ccgcaccgat cgcccttccc aacagttgcg cagctgaatg | 9900 |
| gcgaatggcg cctgatgcgg tattttctcc ttacgcatct gtgtggtatt tcacaccgca | 9960 |
| tatggtgcac tctcagtaca atctgctctg atgccgcata gttaagccag ccccgacac | 10020 |
| cccgccaaca cccgctgacg cgaaccccctt gcggccgcat cgaatataac ttcgtataat | 10080 |
| gt | 10082 |

<210> SEQ ID NO 8
<211> LENGTH: 1456
<212> TYPE: DNA
<213> ORGANISM: Nicotiana tabacum

<400> SEQUENCE: 8

| | |
|---|---|
| agcttctgca aatctcccaa cattatcacc ttctgccgcc tctgaaagca agtagctaag | 60 |
| cattaattaa gaatgaccac acaaaataaa tagtagtagt aaagtagccg aactacatat | 120 |
| aattagaccc atcatatagg ttttctagcc aatactttc caattaagat taggtttcct | 180 |
| ttttaaaaat ttgcacaatt cttagagaga tatctaatag tgcaaaacac agaaatatat | 240 |
| atccaaacta cctttctct ctccttaaac attttattta actaacacgg cactagttga | 300 |
| aacaatcagg ggatatttgt aaaggtaata aatgactggt tgattttaa acgttagata | 360 |
| tgttgaaata aattcaattt gaaaaaacga ctaataatta aagctggaac gctacgtatt | 420 |
| caacactaag aaaatataat gtgctatttg acaatatatg aagtcaagaa ataagaactg | 480 |
| gcattatata tgttttcaag taggtttagg ctatggcaaa atactaataa gcaagcactt | 540 |
| aattttgcgg tacaaaataa agtttttgtat tgttaaataa gaagatatat cacgtaacaa | 600 |

-continued

```
aatagagagt attgcctata gttaatttgc atcgctcgtc ctttgtgagc atttcaatag      660
gcttatgatc acacataaat ttgtgtgtga attgctttag aaaaattaca taatttgaat      720
ttgaggtctt aatatgtgtt caatccagag gagtaggcac cttagctcga gcgatatcgc      780
gtgacaccgc ttcgacaaca tatttcataa atatgtatgt ataaatatta agaaaaataa      840
aaatattgag tataaatata aaagatgaca ttgcacttct ttaaatattg ataccgctta      900
caaaacttct ttgcgcgcac gccattgatt caatctatca tagttcttgt aaatgttatt      960
tcagatcttt aatttaaaat attttaataa agtcaatcat ttttaacatc tagatttctc     1020
gtttttactt tttgtttatt atatcacatt ttggacatag cactaagtcg gtataactaa     1080
ttgtgacttg tgcaagttaa gaaaatacaa tgcaatgctg ctgaaacaac agagcaactc     1140
gtttccagta aaaatctaaa gtttactact ttcacaaaaa ctaataaaag ttttagagtg     1200
cgtttgacaa tttatttcat gcaaagattc gagaacaatc aacacagaat taggctgaag     1260
tgtctaagag aatttaatat ttgcccttca tcaagaggca atatataaat aagcctgcgc     1320
cattgcaaca actcaaacca tttccaatat tgcctcacaa gtcagtagtg cctttcctct     1380
ctcaaacgtt cattgtcttt atctcccttc cccaattctc attggaagaa taaaacaaaa     1440
attaaattag aaaatg                                                     1456
```

<210> SEQ ID NO 9
<211> LENGTH: 713
<212> TYPE: DNA
<213> ORGANISM: Artificial sequence
<220> FEATURE:
<221> NAME/KEY: source
<222> LOCATION: 1..713
<223> OTHER INFORMATION: /note="Description of artificial sequence:
      Synthetic construct used to trigger the suppression of NtIPMS2
      gene expression via the RNAi mechanism."

<400> SEQUENCE: 9

```
gctaagcttg tcgaccatgg aaattctctg accctgatta tgttggtatt tttgacacca       60
gtcttcgcga tggcgaacag gccgctggtg ctaccatgac tagtaaagaa aaactggaca      120
ttgcacgtca gttggctaag cttggtgttg atgttattga ggccggtttt ccttttgcct      180
ctgaagctga gttcgagctt gtaaagttga tagcacagga aattggtaac ctttaatgtt      240
taaccgttca catttctaat atttacttat ttgtaacatg tcgtcacgtg ttagtttcat      300 tcttttttatg aaccaaacat gcatgcaaag atattttttag atatttggac ggcgagtgag      360
atttgaaact aggaccgttt gcctgataca atattaaaat atgtaaccat tttatgtaca      420
agtttaaact gttgatagta gcatattttt tactttattt taagtatact atattccaac      480
aggtaagtta accaatttcc tgtgctatca actttacaag ctcgaactca gcttcagagg      540
caaaaggaaa accggcctca ataacatcaa caccaagctt agccaactga cgtgcaatgt      600
ccagtttttc tttactagtc atggtagcac cagcggcctg ttcgccatcg cgaagactgg      660
tgtcaaaaat accaacataa tcagggtcag agaatttggc gcgccaattg acc            713
```

<210> SEQ ID NO 10
<211> LENGTH: 1824
<212> TYPE: DNA
<213> ORGANISM: Nicotiana tabacum

<400> SEQUENCE: 10

```
atgtcttctc tctgttcaaa ctctgcaact tctcttagtt gtaataactc cttccaatcc       60
```

| | | |
|---|---|---|
| aaaaatcctc ttcttcacac catctttaac ttctttcctt caatcaaacc acactcttgt | 120 | |
| ttcccatata cagttatccg gtgctcaatt caaaagcgac ctgaatatat accgagtaaa | 180 | |
| atctccgacc acaaatacgt acgcattttc gacacgactc tccgcgatgg agagcaatcc | 240 | |
| ccgggcgcta cgatgactac gaaagaaaaa ttagatgttg cccgtaaatt agcgaaactc | 300 | |
| ggagttgaca taatcgaagc tgggtttcca gcttcatctg aagctgattt tgaagctgtg | 360 | |
| agattaatag cagaggaaat tggtaataat agcgacggtg attatgtgcc ggtgatttgt | 420 | |
| ggattagcga ggtgcaataa gagggatatt gataaagcgt gggaagctgt gaagtgtgcg | 480 | |
| aagagaccta gggttcatac gtttatagcg acgagtgaga tacatatgaa gtataagttg | 540 | |
| aagatgagta agaagaagt agtggagaaa gcgcggagta tggttgctta tgcgaggagt | 600 | |
| ttgggatgtg aggatgttga atttagccct gaagatgctg gaaggtctga gcgtgagttc | 660 | |
| ctttaccata tccttggaga agttatcaaa gctggtgcaa caaccctaa catacctgat | 720 | |
| actgttggat acactgtgcc cactgaattt ggacaattaa ttgctgacat aaaagccaat | 780 | |
| accccaggaa ttgaaaatgt gatcattcct acacactgcc agaatgatct tggacttcct | 840 | |
| actgccaaca ctttagctgg agcttgtgca ggggcaagac aagtagaagt gaccatcaat | 900 | |
| ggcattggtg aaagagctgg aaatgcttct ctggaggagg ttgtaatggc cttaaaatgt | 960 | |
| cgtggagagc aagtactagg tggcctgtat acaggaatta atacacaaca tatactcatg | 1020 | |
| tcaagcaaga tggtagagga gtacaccggg cttcatgtgc agccacacaa ggccattgtt | 1080 | |
| ggagctaatg ctttgctca tgaaagtggc atccatcagg atggaatgtt aaaacacaaa | 1140 | |
| gatacatatg agattatatc tcctgaagat attgggctta gtcgtgctaa tgaagccggt | 1200 | |
| attgtccttg ggaagctcag tgggcgccat gcattgaaat ccaaaatgct tgagcttgga | 1260 | |
| tatgacattg agggaaaaga actggaggac ctcttctggc gatttaagtc ggtggctgag | 1320 | |
| aagaaaaaga aaattacaga tgatgacata atagcactga tgtcagatga agttttccag | 1380 | |
| cctcaagttg tttggcaact tgcagatgta cagattgcct gtggaagtct tggcctctct | 1440 | |
| acagcaactg ttaagcttat tgacagtgat ggtcaagagc atgttgcttg ttctgttgga | 1500 | |
| accggaccag ttgatgcagc ttataaggca gttgacctca ttgtaaaggt acctataaca | 1560 | |
| ctcctcgagt attccatgaa tgcagtcaca gaaggtatag atgccatagc ctcaaccaga | 1620 | |
| gtattaatcc gcggggagga tgaccatgct ataaccaatg gttcaattgg accgactcat | 1680 | |
| caccgtatat ttagtggaac tggagctgat atggacgttg tcatctctag tgtccgagcc | 1740 | |
| tatattggtg cattgaacaa aatgttgagt ttcgggaagc tggtttcgag gtacaagaag | 1800 | |
| cctgaaggta gtgtggtagt ataa | 1824 | |

<210> SEQ ID NO 11
<211> LENGTH: 607
<212> TYPE: PRT
<213> ORGANISM: Nicotiana tabacum

<400> SEQUENCE: 11

```
Met Ser Ser Leu Cys Ser Asn Ser Ala Thr Ser Leu Ser Cys Asn Asn
1               5                   10                  15

Ser Phe Gln Ser Lys Asn Pro Leu Leu His Thr Ile Phe Asn Phe Phe
            20                  25                  30

Pro Ser Ile Lys Pro His Ser Cys Phe Pro Tyr Thr Val Ile Arg Cys
        35                  40                  45

Ser Ile Gln Lys Arg Pro Glu Tyr Ile Pro Ser Lys Ile Ser Asp His
    50                  55                  60
```

```
Lys Tyr Val Arg Ile Phe Asp Thr Thr Leu Arg Asp Gly Glu Gln Ser
 65                  70                  75                  80

Pro Gly Ala Thr Met Thr Thr Lys Glu Lys Leu Asp Val Ala Arg Lys
                 85                  90                  95

Leu Ala Lys Leu Gly Val Asp Ile Ile Glu Ala Gly Phe Pro Ala Ser
            100                 105                 110

Ser Glu Ala Asp Phe Glu Ala Val Arg Leu Ile Ala Glu Glu Ile Gly
        115                 120                 125

Asn Asn Ser Asp Gly Asp Tyr Val Pro Val Ile Cys Gly Leu Ala Arg
130                 135                 140

Cys Asn Lys Arg Asp Ile Asp Lys Ala Trp Glu Ala Val Lys Cys Ala
145                 150                 155                 160

Lys Arg Pro Arg Val His Thr Phe Ile Ala Thr Ser Glu Ile His Met
                165                 170                 175

Lys Tyr Lys Leu Lys Met Ser Lys Glu Val Val Glu Lys Ala Arg
            180                 185                 190

Ser Met Val Ala Tyr Ala Arg Ser Leu Gly Cys Glu Asp Val Glu Phe
        195                 200                 205

Ser Pro Glu Asp Ala Gly Arg Ser Glu Arg Glu Phe Leu Tyr His Ile
210                 215                 220

Leu Gly Glu Val Ile Lys Ala Gly Ala Thr Thr Leu Asn Ile Pro Asp
225                 230                 235                 240

Thr Val Gly Tyr Thr Val Pro Thr Glu Phe Gly Gln Leu Ile Ala Asp
                245                 250                 255

Ile Lys Ala Asn Thr Pro Gly Ile Glu Asn Val Ile Ile Ser Thr His
            260                 265                 270

Cys Gln Asn Asp Leu Gly Leu Ser Thr Ala Asn Thr Leu Ala Gly Ala
        275                 280                 285

Cys Ala Gly Ala Arg Gln Val Glu Val Thr Ile Asn Gly Ile Gly Glu
290                 295                 300

Arg Ala Gly Asn Ala Ser Leu Glu Glu Val Val Met Ala Leu Lys Cys
305                 310                 315                 320

Arg Gly Glu Gln Val Leu Gly Gly Leu Tyr Thr Gly Ile Asn Thr Gln
                325                 330                 335

His Ile Leu Met Ser Ser Lys Met Val Glu Glu Tyr Thr Gly Leu His
            340                 345                 350

Val Gln Pro His Lys Ala Ile Val Gly Ala Asn Ala Phe Ala His Glu
        355                 360                 365

Ser Gly Ile His Gln Asp Gly Met Leu Lys His Lys Asp Thr Tyr Glu
370                 375                 380

Ile Ile Ser Pro Glu Asp Ile Gly Leu Ser Arg Ala Asn Glu Ala Gly
385                 390                 395                 400

Ile Val Leu Gly Lys Leu Ser Gly Arg His Ala Leu Lys Ser Lys Met
                405                 410                 415

Leu Glu Leu Gly Tyr Asp Ile Glu Gly Lys Glu Leu Glu Asp Leu Phe
            420                 425                 430

Trp Arg Phe Lys Ser Val Ala Glu Lys Lys Lys Ile Thr Asp Asp
        435                 440                 445

Asp Ile Ile Ala Leu Met Ser Asp Glu Val Phe Gln Pro Gln Val Val
450                 455                 460

Trp Gln Leu Ala Asp Val Gln Ile Ala Cys Gly Ser Leu Gly Leu Ser
465                 470                 475                 480
```

```
Thr Ala Thr Val Lys Leu Ile Asp Ser Asp Gly Gln Glu His Val Ala
                485                 490                 495

Cys Ser Val Gly Thr Gly Pro Val Asp Ala Ala Tyr Lys Ala Val Asp
            500                 505                 510

Leu Ile Val Lys Val Pro Ile Thr Leu Leu Glu Tyr Ser Met Asn Ala
            515                 520                 525

Val Thr Glu Gly Ile Asp Ala Ile Ala Ser Thr Arg Val Leu Ile Arg
        530                 535                 540

Gly Glu Asp Asp His Ala Ile Thr Asn Gly Ser Ile Gly Pro Thr His
545                 550                 555                 560

His Arg Ile Phe Ser Gly Thr Gly Ala Asp Met Asp Val Val Ile Ser
                565                 570                 575

Ser Val Arg Ala Tyr Ile Gly Ala Leu Asn Lys Met Leu Ser Phe Gly
            580                 585                 590

Lys Leu Val Ser Arg Tyr Lys Lys Pro Glu Gly Ser Val Val Val
            595                 600                 605
```

<210> SEQ ID NO 12
<211> LENGTH: 1821
<212> TYPE: DNA
<213> ORGANISM: Nicotiana tabacum

<400> SEQUENCE: 12

```
atggcgtcta tcaccataaa ccattcattt tcccgtaacc ctaacatctc attccatccc      60
caaaatcctc tcattcaaac ccaagctctc ttcaatttca aaccatcaat ctccaaatgt     120
tcccctatta tccactgcgc aatccgccgt cgacccgaat ataccccgag ccacattccc     180
gacccgaact acattcgcat cttcgacacc actctccgcg acggcgaaca atccccaggc     240
gccacaatga ccacaaaaga aaaactcgac gttgcgcgtc agttagctaa gcttggtgtt     300
gacataattg aagccggttt tcctgcttct tctgaagctg atctcgaagc tgtgaaatta     360
atagcgaagg aagttggaaa tggtgtgaat gaagagggac atgttccggt aatttgtgga     420
cttgcgaggt gtaataagag ggatattgat aaggcttggg aggctgtgaa gtatgcgaaa     480
aaaccgagga ttcatacgtt tattgcgact agtgagatac atatgaagtt taagttgaag     540
atgagtagag atgaagttgt ggagaaagct aggagtatgg ttgcttatgc taggagtatt     600
ggttgtgagg atgttgaatt tagcccagaa gatgctggaa gatccgatcc agagttcctc     660
tatcatatcc ttggagaggt catcaaagct ggggcaacaa cccttaacat ccctgatact     720
gttggataca ctgttcccag cgaatttgga aaattgattg ctgatataaa ggccaatacc     780
ccaggaattg gagatgtgat catctcaaca cactgccaga acgatcttgg gctttctact     840
gccaacacct agctggagc atgcgcaggt gcaagacaag tagaagtgac catcaacgga     900
atcggtgaaa gagctggaaa tgcttctttg gaggaggttg taatggcctt aaaatgtcgt     960
ggagagcaag tactaggtgg cctgtataca ggaattaata cacaacatat actcatgtca    1020
agcaagatgg tagaggagta caccgggctt catgtgcagc cacacaaggc cattgttgga    1080
gctaatgcgt ttgctcatga agtggcatc catcaggatg gaatgttaaa acacaaagat    1140
acatatgaga ttatatctcc tgaagatatt gggcttaacc gagttaatga atctggcatc    1200
gtccttggga aactcagtgg gcgtcatgct ttgcaagcca aaatgctcga gcttggatac    1260
gatattgagg gaaagaaact tgaggacctc ttttggcgat tcaaatctgt ggccgagaag    1320
aaaaagaaaa ttcagatgga tgacctgata gcattaatgt cagatgaagt tttccagcct    1380
caatttgttt ggcaacttga aaatgtacag gttacatgtg gaagtcttgg cctttctacg    1440
```

```
gcaactgtta agctcattga cgctgatggt caagagcatg tttcttgttc tgttggaacg    1500
gggccagttg atgcggctta taaggcagtt gatctcattg taaaggtacc tgtagcactc    1560
cttgaatatt ccttgaatgc agtcacggaa ggtatagatg ccatagcttc aaccagagtt    1620
ttaattcgtg gggagaatgg ccatacatca acccatgctt taactggaga gactgtacac    1680
cgttctttta gtggaaccgg agcagatatg gatattgtta ctccagtgt ccgagcctat     1740 attggtgcat tgaataagat gttgagtttc agaaagctgg tatcgaaaca cagcaaacct    1800
gaaggcagtg cagtcgtata g                                              1821
```

<210> SEQ ID NO 13
<211> LENGTH: 606
<212> TYPE: PRT
<213> ORGANISM: Nicotiana tabacum

<400> SEQUENCE: 13

```
Met Ala Ser Ile Thr Ile Asn His Ser Phe Ser Arg Asn Pro Asn Ile
1               5                   10                  15

Ser Phe His Pro Gln Asn Pro Leu Ile Gln Thr Gln Ala Leu Phe Asn
            20                  25                  30

Phe Lys Pro Ser Ile Ser Lys Cys Ser Pro Ile Ile His Cys Ala Ile
        35                  40                  45

Arg Arg Arg Pro Glu Tyr Thr Pro Ser His Ile Pro Asp Pro Asn Tyr
    50                  55                  60

Ile Arg Ile Phe Asp Thr Thr Leu Arg Asp Gly Glu Gln Ser Pro Gly
65                  70                  75                  80

Ala Thr Met Thr Thr Lys Glu Lys Leu Asp Val Ala Arg Gln Leu Ala
                85                  90                  95

Lys Leu Gly Val Asp Ile Ile Glu Ala Gly Phe Pro Ala Ser Ser Glu
            100                 105                 110

Ala Asp Leu Glu Ala Val Lys Leu Ile Ala Lys Glu Val Gly Asn Gly
        115                 120                 125

Val Asn Glu Glu Gly His Val Pro Val Ile Cys Gly Leu Ala Arg Cys
    130                 135                 140

Asn Lys Arg Asp Ile Asp Lys Ala Trp Glu Ala Val Lys Tyr Ala Lys
145                 150                 155                 160

Lys Pro Arg Ile His Thr Phe Ile Ala Thr Ser Glu Ile His Met Lys
                165                 170                 175

Phe Lys Leu Lys Met Ser Arg Asp Glu Val Val Glu Lys Ala Arg Ser
            180                 185                 190

Met Val Ala Tyr Ala Arg Ser Ile Gly Cys Glu Asp Val Glu Phe Ser
        195                 200                 205

Pro Glu Asp Ala Gly Arg Ser Asp Pro Glu Phe Leu Tyr His Ile Leu
    210                 215                 220

Gly Glu Val Ile Lys Ala Gly Ala Thr Thr Leu Asn Ile Pro Asp Thr
225                 230                 235                 240

Val Gly Tyr Thr Val Pro Ser Glu Phe Gly Lys Leu Ile Ala Asp Ile
                245                 250                 255

Lys Ala Asn Thr Pro Gly Ile Gly Asp Val Ile Ile Ser Thr His Cys
            260                 265                 270

Gln Asn Asp Leu Gly Leu Ser Thr Ala Asn Thr Leu Ala Gly Ala Cys
        275                 280                 285

Ala Gly Ala Arg Gln Val Glu Val Thr Ile Asn Gly Ile Gly Glu Arg
    290                 295                 300
```

```
Ala Gly Asn Ala Ser Leu Glu Glu Val Val Met Ala Leu Lys Cys Arg
305                 310                 315                 320

Gly Glu Gln Val Leu Gly Gly Leu Tyr Thr Gly Ile Asn Thr Gln His
            325                 330                 335

Ile Leu Met Ser Ser Lys Met Val Glu Glu Tyr Thr Gly Leu His Val
        340                 345                 350

Gln Pro His Lys Ala Ile Val Gly Ala Asn Ala Phe Ala His Glu Ser
    355                 360                 365

Gly Ile His Gln Asp Gly Met Leu Lys His Lys Asp Thr Tyr Glu Ile
370                 375                 380

Ile Ser Pro Glu Asp Ile Gly Leu Asn Arg Val Asn Glu Ser Gly Ile
385                 390                 395                 400

Val Leu Gly Lys Leu Ser Gly Arg His Ala Leu Gln Ala Lys Met Leu
                405                 410                 415

Glu Leu Gly Tyr Asp Ile Glu Gly Lys Glu Leu Glu Asp Leu Phe Trp
            420                 425                 430

Arg Phe Lys Ser Val Ala Glu Lys Lys Lys Ile Thr Asp Asp Asp
        435                 440                 445

Leu Ile Ala Leu Met Ser Asp Glu Val Phe Gln Pro Gln Phe Val Trp
450                 455                 460

Gln Leu Glu Asn Val Gln Val Thr Cys Gly Ser Leu Gly Leu Ser Thr
465                 470                 475                 480

Ala Thr Val Lys Leu Ile Asp Ala Asp Gly Gln Glu His Val Ser Cys
                485                 490                 495

Ser Val Gly Thr Gly Pro Val Asp Ala Ala Tyr Lys Ala Val Asp Leu
            500                 505                 510

Ile Val Lys Val Pro Val Ala Leu Leu Glu Tyr Ser Leu Asn Ala Val
        515                 520                 525

Thr Glu Gly Ile Asp Ala Ile Ala Ser Thr Arg Val Leu Ile Arg Gly
    530                 535                 540

Glu Asn Gly His Thr Ser Thr His Ala Leu Thr Gly Glu Thr Val His
545                 550                 555                 560

Arg Ser Phe Ser Gly Thr Gly Ala Asp Met Asp Ile Val Ile Ser Ser
                565                 570                 575

Val Arg Ala Tyr Ile Gly Ala Leu Asn Lys Met Leu Ser Phe Arg Lys
            580                 585                 590

Leu Val Ser Lys His Ser Lys Pro Glu Gly Ser Ala Val Val
        595                 600                 605

<210> SEQ ID NO 14
<211> LENGTH: 1821
<212> TYPE: DNA
<213> ORGANISM: Nicotiana tabacum

<400> SEQUENCE: 14
atggcgtcta tcaccgcaaa ccatacattt tcccgtaacc ctaacatctc attgcatccc      60
caaaatcctc tcattcaaac ccaagctctc ttcaacttca atcatcaat  ccccaaatgt     120 tcccctatta tctgctgcgc aatccgccgt cgacccgact ataccccgag ccacattccc     180
gacccgaaat acatccgcat cttcgacacc actctccgcg acggcgaaca atctccaggc     240
gccacaatga ccacaaaaga aaaactcgac gttgcgcgtc agttagctaa gcttggtgtt     300
gacataattg aagccggttt tcctgcttct tctgaagctg atctcgaagc tgtgaaatta     360
atagcgaagg aagttggaaa tggtgtgtat gaagagggac atgttccggt aatctgtgga     420
```

```
cttgcgaggt gtaataagag ggatattgat aaggcttggg aggctgtgaa gtatgcgaaa    480
aaaccgagga ttcatacgtt tattgcgact agtgagatac atatgaagtt taagttgaag    540
atgagtagag atgaagttgt ggagaaagct agaagtatgg ttgcttatgc taggagtatt    600
ggttgtgagg atgttgaatt tagccctgaa gatgctggaa gatctgatcc tgagttcctc    660
tatcatatcc ttggagaggt catcaaagct ggggcaacaa cccttaacat ccctgatact    720
gttggataca ctgttcccag tgaatttgga aaattgatcg ctgatataaa ggccaatacc    780
ccaggaattg agatgtgat catctcaacg cactgccaga acgatcttgg ctttctact     840 gccaacacct tagctggagc atgtgcaggt gcaagacaag tagaagtgac catcaatgga    900
atcggtgaaa gagctggaaa tgcttctttg gaggaggttg taatggcctt aaaatgtcgt    960
ggagagcaag tactaggtgg cctgtataca ggaattaata cacaacatat actcatgtca   1020
agcaagatgg tagaggagta caccgggctt catgtgcagc cacacaaggc cattgttgga   1080
gctaatgctt ttgctcatga aagtggcatc catcaggatg gaatgttaaa acacaaagat   1140
acatatgaga ttatatctcc tgaagatatt gggcttaacc gagctaatga atctggtatc   1200
gtcctcggga aactcagtgg gcgtcatgct ttgcaagcca aaatgctcga gcttggatac   1260
gatattgagg gaaaagaact tgaggacctc ttttggcgat tcaaatctgt ggctgagaag   1320
aaaaagaaaa ttacagatga tgacctgata gcattgatgt cagatgaagt tttccagcct   1380
caatttgttt ggcaactcga aaatgtacag gttacatgtg gaagtcttgg cctttctacg   1440
gcaactgtta agctcattga cgctgatggt caagagcatg tttcttgttc tgttggaacg   1500
gggccagttg atgcggctta caaggcagtt gatctcattg taaaggtacc tgtagcacta   1560
cttgaatatt ccttgaatgc agtcacggaa ggtatagatg ccatagcttc aaccagagtt   1620
ttaattcgtg gggagaatgg acatacatca acccatgctt taactggaga gactgtacac   1680
cgttcgttta gtggaaccgg agcagatatg gatattgtta tctctagtgt ccgagcctat   1740
attggagcat tgaataagat gctgagtttc agaaagctgg tgtcgaaaca cagcagacct   1800
gaaggcagtg cagtcgtata g                                              1821
```

<210> SEQ ID NO 15
<211> LENGTH: 606
<212> TYPE: PRT
<213> ORGANISM: Nicotiana tabacum

<400> SEQUENCE: 15

```
Met Ala Ser Ile Thr Ala Asn His Thr Phe Ser Arg Asn Pro Asn Ile
1               5                   10                  15

Ser Leu His Pro Gln Asn Pro Leu Ile Gln Thr Gln Ala Leu Phe Asn
            20                  25                  30

Phe Lys Ser Ser Ile Pro Lys Cys Ser Pro Ile Ile Cys Cys Ala Ile
        35                  40                  45

Arg Arg Arg Pro Asp Tyr Thr Pro Ser His Ile Pro Asp Pro Lys Tyr
    50                  55                  60

Ile Arg Ile Phe Asp Thr Thr Leu Arg Asp Gly Glu Gln Ser Pro Gly
65                  70                  75                  80

Ala Thr Met Thr Thr Lys Glu Lys Leu Asp Val Ala Arg Gln Leu Ala
                85                  90                  95

Lys Leu Gly Val Asp Ile Ile Glu Ala Gly Phe Pro Ala Ser Ser Glu
            100                 105                 110

Ala Asp Leu Glu Ala Val Lys Leu Ile Ala Lys Glu Val Gly Asn Gly
```

```
                    115                 120                 125
Val Tyr Glu Gly His Val Pro Val Ile Cys Gly Leu Ala Arg Cys
        130                 135                 140

Asn Lys Arg Asp Ile Asp Lys Ala Trp Glu Ala Val Lys Tyr Ala Lys
145                 150                 155                 160

Lys Pro Arg Ile His Thr Phe Ile Ala Thr Ser Glu Ile His Met Lys
                165                 170                 175

Phe Lys Leu Lys Met Ser Arg Asp Glu Val Val Glu Lys Ala Arg Ser
            180                 185                 190

Met Val Ala Tyr Ala Arg Ser Ile Gly Cys Glu Asp Val Glu Phe Ser
        195                 200                 205

Pro Glu Asp Ala Gly Arg Ser Asp Pro Glu Phe Leu Tyr His Ile Leu
    210                 215                 220

Gly Glu Val Ile Lys Ala Gly Ala Thr Thr Leu Asn Ile Pro Asp Thr
225                 230                 235                 240

Val Gly Tyr Thr Val Pro Ser Glu Phe Gly Lys Leu Ile Ala Asp Ile
                245                 250                 255

Lys Ala Asn Thr Pro Gly Ile Gly Asp Val Ile Ile Ser Thr His Cys
            260                 265                 270

Gln Asn Asp Leu Gly Leu Ser Thr Ala Asn Thr Leu Ala Gly Ala Cys
        275                 280                 285

Ala Gly Ala Arg Gln Val Glu Val Thr Ile Asn Gly Ile Gly Glu Arg
    290                 295                 300

Ala Gly Asn Ala Ser Leu Glu Glu Val Val Met Ala Leu Lys Cys Arg
305                 310                 315                 320

Gly Glu Gln Val Leu Gly Gly Leu Tyr Thr Gly Ile Asn Thr Gln His
                325                 330                 335

Ile Leu Met Ser Ser Lys Met Val Glu Glu Tyr Thr Gly Leu His Val
            340                 345                 350

Gln Pro His Lys Ala Ile Val Gly Ala Asn Ala Phe Ala His Glu Ser
        355                 360                 365

Gly Ile His Gln Asp Gly Met Leu Lys His Lys Asp Thr Tyr Glu Ile
    370                 375                 380

Ile Ser Pro Glu Asp Ile Gly Leu Asn Arg Ala Asn Glu Ser Gly Ile
385                 390                 395                 400

Val Leu Gly Lys Leu Ser Gly Arg His Ala Leu Gln Ala Lys Met Leu
                405                 410                 415

Glu Leu Gly Tyr Asp Ile Glu Gly Lys Glu Leu Glu Asp Leu Phe Trp
            420                 425                 430

Arg Phe Lys Ser Val Ala Glu Lys Lys Lys Ile Thr Asp Asp Asp
        435                 440                 445

Leu Ile Ala Leu Met Ser Asp Glu Val Phe Gln Pro Gln Phe Val Trp
    450                 455                 460

Gln Leu Glu Asn Val Gln Val Thr Cys Gly Ser Leu Gly Leu Ser Thr
465                 470                 475                 480

Ala Thr Val Lys Leu Ile Asp Ala Asp Gly Gln Glu His Val Ser Cys
                485                 490                 495

Ser Val Gly Thr Gly Pro Val Asp Ala Ala Tyr Lys Ala Val Asp Leu
            500                 505                 510

Ile Val Lys Val Pro Val Ala Leu Leu Glu Tyr Ser Leu Asn Ala Val
        515                 520                 525

Thr Glu Gly Ile Asp Ala Ile Ala Ser Thr Arg Val Leu Ile Arg Gly
    530                 535                 540
```

```
Glu Asn Gly His Thr Ser Thr His Ala Leu Thr Gly Glu Thr Val His
545                 550                 555                 560

Arg Ser Phe Ser Gly Thr Gly Ala Asp Met Asp Ile Val Ile Ser Ser
                565                 570                 575

Val Arg Ala Tyr Ile Gly Ala Leu Asn Lys Met Leu Ser Phe Arg Lys
            580                 585                 590

Leu Val Ser Lys His Ser Arg Pro Glu Gly Ser Ala Val Val
        595                 600                 605
```

ISOPROPYLMALATE SYNTHASE FROM *NICOTIANA TABACUM* AND METHODS AND USES THEREOF

This application is a U.S. National Stage Application of International Application No. PCT/EP2012/003662 filed Aug. 31, 2012, which was published in English on Mar. 7, 2013 as International Patent Publication WO 2013/029799 A1 and which claims priority to European Application No. 11179882.3, filed Sep. 2, 2011.

FIELD OF THE INVENTION

The present invention discloses the isopropylmalate synthase gene from *Nicotiana tabacum* and variants, homologues and fragments thereof. In particular, there is described the modification of the expression of this gene or the activity of the protein encoded thereby in order to alter the sucrose ester composition of a plant—such as a tobacco plant.

BACKGROUND OF THE INVENTION

Sucrose esters are widely recognized as having insecticidal properties in plants and have shown toxicity toward soft-bodied insects, including aphids, mites, pear psylla, and whiteflies, as well as antibiotic activity. Sucrose esters are also considered as flavour precursors and are accumulated on the leaf surface during the life of the plant. They are stable compounds that can be identified in cured and smoking material. Esterified small carboxylic acids are released from sucrose esters upon heating. These small carboxylic acids are very potent flavour molecules and are considered to be responsible in part for the oriental flavour of tobacco. Sucrose esters are produced in the glandular trichome cells of plants. The glandular trichome cells are also the place for synthesis of other leaf exudates—such as proteins (phylloplanins) and diterpenoids (cembrenoids and labdenoids). The sucrose and the small carboxylic acids that are esterified to the sucrose to give rise to the sucrose esters are produced via two distinct metabolic blocks. Tobacco varieties differ in their quantities and qualities of the sucrose ester present on the surface of the leaf. As a general rule, flue cured, burley and Maryland varieties accumulate low amounts of sucrose esters with acyl groups up to five carbon chain length whereas most oriental varieties and many cigar tobacco types accumulate high amounts of sucrose esters having acyl groups up to six carbon chain length, and to a lesser extent, esters having acyl groups with a seven carbon chain length can be observed. The dichotomy observed in the sucrose ester produced among tobacco varieties is linked to a single dominant locus called BMVSE (beta-methylvaleryl containing sucrose esters) for its functional allele and bmvse for its non functional allele. The BMVSE genomic locus has been positioned to chromosome A of tobacco.

Kroumova and Wagner (2009) *General and Applied Plant Physiology* 35, 3-4, p 95-110 describe attempts to change sucrose ester acyl group content in various plants using a reverse genetics approach to knock down the expression of isopropylmalate synthase expression using double stranded interfering RNA. In this study, the isopropylmalate synthase gene from *Solanum pennellii* was used to amplify part of the genes from cDNA. They were then introduced in the sense and antisense orientation into a double stranded interfering RNA construct and transformed via *Agrobacterium* into *Nicotiana tabacum* T.I. 1068, *Nicotiana glutinosa* cv. 24a and *S. pennellii*. The results obtained using *N. tabacum* plants showed some changes in the acyl group abundance of sugar esters through reduced beta-methlyvaleryl and increased 2-methylbutyryl-acylation compared to non-transformed controls. However, the *N. tabacum* plants that were obtained were phenotypically impaired since they were chlorotic and some had curly leaves. Likewise, the transformed *N. glutinosa* and *S. pennellii* plants were phenotypically impaired. The authors conclude that isopropylmalate synthase is a critical enzyme and that its impairment probably would lead to an unhealthy plant.

There is a need in the art for plants in which the sucrose ester composition is modulated and whilst minimising undesirable effects on the plant. It is an object of the present invention to satisfy this need.

SUMMARY OF THE INVENTION

The present invention is based, at least in part, on the surprising finding that modulating the activity or expression of the isopropylmalate synthase gene from *Nicotiana tabacum* results in a change in sucrose ester composition with fewer undesirable effects on the overall metabolism of the plant. Most of the effects are concentrated in the trichomes of the plant and to secondary metabolism. Thus, modulating the activity or expression of the isopropylmalate synthase gene from *Nicotiana tabacum* does not substantially result in alterations in the visual appearance of the plant as compared to a control plant. This is advantageous because plants can be used for the commercial production of various products where alterations in visual appearance would either not be acceptable to the industry or could result in unacceptably reduced production yields. Advantageously, the flavour profile of the aerosol generated from tobacco can be modified such that new flavour profiles can be created. Moreover, the pest resistance of the plants in which the sucrose ester profile has been modified can be changed. Compositions of sucrose esters can be extracted from the plants for various uses—such as in drugs, food additives, smoking flavourants and as components of organic pesticides and the like.

ASPECTS AND EMBODIMENTS OF THE INVENTION

Aspect and embodiments of the present invention are set forth in the accompanying claims. In a first aspect, there is provided an isolated polynucleotide comprising, consisting or consisting essentially of a sequence encoding an isopropylmalate synthase and having at least 60% sequence identity to SEQ ID NO:1 or SEQ ID NO:10 or SEQ ID NO: 12 or SEQ ID NO:14. In another aspect, there is provided an isolated polypeptide encoded by the polynucleotide. In another aspect, there is provided an isolated polypeptide having at least 60% sequence identity to SEQ ID NO:2 or SEQ ID NO:11 or SEQ ID NO:13 or SEQ ID NO:15.

A construct, vector or expression vector comprising the isolated polynucleotide sequence, optionally wherein said construct, vector or expression vector additionally comprises a promoter comprising, consisting or consisting essentially of the sequence set forth in SEQ ID NO:8 or a variant thereof with at least about 60% identity thereto or a trichome promoter or the natural isopropylmalate synthase promoter.

In another aspect, there is provided an isolated polynucleotide comprising, consisting or consisting essentially of SEQ ID NO:8 or a variant thereof with at least about 60% identity thereto.

In another aspect, there is provided a mutant, non-naturally occurring or transgenic plant cell comprising at least one of the polynucleotides, at least one of the polypeptides or the construct, vector or expression vector of the present invention. Suitably, the expression of isopropylmalate synthase or the activity of the protein encoded thereby is modulated and at least a part of the plant has a change in the composition of sucrose esters as compared to a control plant in which the expression or the activity of isopropylmalate synthase has not been modulated. Suitably, the visual appearance of the plant is substantially the same as the control plant.

In another aspect, there is provided a mutant, non-naturally occurring or transgenic plant comprising the plant cell of the present invention.

In another aspect, there is provided a method for modulating the quantity of sucrose esters in a part of a plant, comprising the steps of: (i) modulating the expression or activity of isopropylmalate synthase in the plant, preferably, wherein the isopropylmalate synthase comprises the polynucleotide sequence or the polypeptide sequence described herein; (ii) measuring the quantity of sucrose esters in at least a part of the mutant, non-naturally occurring or transgenic plant obtained in step (i); and (iii) identifying a mutant, non-naturally occurring or transgenic plant in which the quantity of sucrose esters therein has changed in comparison to a control plant in which the expression or activity of isopropylmalate synthase has not been modulated and, preferably, wherein the visual appearance of said mutant, non-naturally occurring or transgenic plant is substantially the same as the control plant.

In another aspect, there is provided a mutant, non-naturally occurring or transgenic plant that is obtained or obtainable by this method.

In another aspect, there is provided a mutant, non-naturally occurring or transgenic plant, wherein expression of isopropylmalate synthase or the activity of the protein encoded thereby is modulated and at least a part of the plant has a change in the composition of sucrose esters as compared to a control plant in which the expression or the activity of isopropylmalate synthase has not been modulated and wherein the visual appearance of said plant is substantially the same as the control plant.

In another aspect, there is provided plant material including biomass, seed or leaves comprising cells or tissue from the plant.

In another aspect, there is provided a tobacco product comprising a part of the plant or plant material according to the present invention.

In another aspect, there is provided a method for producing a composition of sucrose esters comprising the steps of: (i) providing at least part of a mutant, non-naturally occurring or transgenic plant, plant material or the tobacco product according to the present invention; (ii) extracting the (for example, one or more) sucrose esters therefrom; and (iii) optionally, purifying the extracted sucrose esters.

A composition of sucrose esters obtained or obtainable by said method is also provided.

Suitably, the one or more sucrose esters have the structure as shown in FIG. 5 and wherein R3 is acetyl or hydrogen, preferably acetyl; one or more of R1, R2 and R4 comprise at least one acyl chain with 6 carbons, preferably beta-methylvaleryl; and R5 is an acetyl or hydrogen, preferably, hydrogen.

Suitably, the one or more sucrose esters are selected from the group consisting of a sucrose ester as shown in FIG. 5 wherein R3=acetyl, R1=propionyl or an isomer thereof, R2=propionyl or an isomer thereof, R4=hexanoyl or an isomer thereof and R5 is hydrogen or acetyl; or a sucrose ester as shown in FIG. 5 wherein R3=acetyl, R1=propionyl or an isomer thereof, R2=valeryl or an isomer thereof, R4=valeryl or an isomer thereof and R5 is hydrogen or acetyl; or a sucrose ester as shown in FIG. 5 wherein R3=acetyl, R1=butyryl, R2=valeryl or an isomer thereof, R4=hexanoyl or an isomer thereof and R5 is hydrogen or acetyl (C2C14:0); a sucrose ester as shown in FIG. 5 wherein R3=acetyl, R1=propionyl or an isomer thereof, R2=valeryl or an isomer thereof, R4=hexanoyl or an isomer thereof and R5 is hydrogen or acetyl; or a sucrose ester as shown in FIG. 5 wherein R3=acetyl, R1=valeryl or an isomer thereof, R2=valeryl or an isomer thereof, R4=valeryl or an isomer thereof and R5 is hydrogen or acetyl; or a sucrose ester as shown in FIG. 5 wherein R3=acetyl, R1=butyrl, R2=hexanoyl or an isomer thereof, R4=hexanoyl or an isomer thereof and R5 is hydrogen or acetyl (C2C15:0); a sucrose ester that has the general structure shown in FIG. 5 and wherein R3 is acetyl, R1 is valeryl or an isomer thereof, R2 is valeryl or an isomer thereof, R4 is hexanoyl or an isomer thereof and R5 is either a hydrogen atom or an acetyl moiety (C2C16:0); or a sucrose ester that has the general structure shown in FIG. 5 and wherein R3 is acetyl, R1 is propionyl or an isomer thereof, R2 is hexanoyl or an isomer thereof, R4 is hexanoyl or an isomer thereof and R5 is either a hydrogen atom or an acetyl moiety (C2C16:0); a sucrose ester that has the general structure shown in FIG. 5 and wherein R3 is acetyl, R1 is valeryl or an isomer thereof, R2 is hexanoyl, R4 is hexanoyl and R5 is either a hydrogen atom or an acetyl moiety (C2C17:0); or a sucrose ester that has the general structure shown in FIG. 5 and wherein R3 is acetyl, R1 is hexanoyl, R2 is hexanoyl, R4 is hexanoyl and R5 is either a hydrogen atom or an acetyl moiety (C2C18:0) or a combination thereof.

Suitably, the one or more sucrose esters are selected from the group consisting of a sucrose ester as shown in FIG. 5 wherein R3=acetyl, R1=propionyl or an isomer thereof, R2=valeryl or an isomer thereof, R4=hexanoyl or an isomer thereof and R5 is hydrogen or acetyl; or a sucrose ester as shown in FIG. 5 wherein R3=acetyl, R1=valeryl or an isomer thereof, R2=valeryl or an isomer thereof, R4=valeryl or an isomer thereof and R5 is hydrogen or acetyl; or a sucrose ester as shown in FIG. 5 wherein R3=acetyl, R1=butyrl, R2=hexanoyl or an isomer thereof, R4=hexanoyl or an isomer thereof and R5 is hydrogen or acetyl (C2C15:0); a sucrose ester that has the general structure shown in FIG. 5 and wherein R3 is acetyl, R1 is valeryl or an isomer thereof, R2 is valeryl or an isomer thereof, R4 is hexanoyl or an isomer thereof and R5 is either a hydrogen atom or an acetyl moiety (C2C16:0); or a sucrose ester that has the general structure shown in FIG. 5 and wherein R3 is acetyl, R1 is propionyl or an isomer thereof, R2 is hexanoyl or an isomer thereof, R4 is hexanoyl or an isomer thereof and R5 is either a hydrogen atom or an acetyl moiety (C2C16:0); a sucrose ester that has the general structure shown in FIG. 5 and wherein R3 is acetyl, R1 is valeryl or an isomer thereof, R2 is hexanoyl, R4 is hexanoyl and R5 is either a hydrogen atom or an acetyl moiety (C2C17:0); or a sucrose ester that has the general structure shown in FIG. 5 and wherein R3 is acetyl, R1 is hexanoyl, R2 is hexanoyl, R4 is hexanoyl and R5 is either a hydrogen atom or an acetyl moiety (C2C18:0) or a combination thereof.

In a further aspect, there is provided a method for modulating the flavour of tobacco or a tobacco product comprising: (i) adding to tobacco or a tobacco product, part of a plant, preferably leaves, from a mutant, non-naturally occurring or transgenic plant or plant material as described herein, preferably, wherein said mutant, non-naturally occurring or transgenic plant or plant material belongs to the genus Nicotinia; or (ii) adding to tobacco or a tobacco product a composition comprising beta-methylvaleryl containing sucrose esters obtained or obtainable by the method described herein.

In a further aspect, there is provided a method for producing beta-methylvaleric acid comprising the steps of: (i) providing at least part of the mutant, non-naturally occurring or transgenic plant, the plant material or the tobacco product; (ii) hydrolysing the material provided in step (i) or an extract thereof; and (iii) optionally isolating or purifying the beta-methylvaleric acid. Suitably, the plant is a tobacco plant—such as a plant of the genus Nicotiana or of the species Nicotiana tabacum.

Suitably, the visual appearance of the plant is substantially the same as the control plant. Suitably, the visual appearance of the plant is substantially the same as the control plant three months after field transplant or 36 days after topping, preferably, wherein the stalk height of the mutant, non-naturally occurring or transgenic plants is substantially the same as the stalk height of the control plants three months after field transplant or 36 days after topping and/or the chlorophyll content of the mutant, non-naturally occurring or transgenic plants is substantially the same as the chlorophyll content of the control plants three months after field transplant or 36 days after topping. In other embodiments, any one or more of the following characteristics: degree of maturity, number of leaves per plant, stalk height, leaf insertion angle, leaf size (width and length), internode distance, lamina-midrib ratio, and colouration of the leaves of the mutant, non-naturally occurring or transgenic plants is substantially the same as the control plants at three months after field transplant or 36 days after topping.

A further aspect relates to biomass, seed or leaves comprising cells or tissue from the plant(s) described herein as is a tobacco product comprising a part of the plant or biomass, seed or leaves.

Tobacco material identified or identifiable by this method is also provided in a further aspect of the disclosure.

The pest resistance of the plant may be modulated.

Still further aspects of the present invention are set forth below.

A chimeric gene comprising the isolated polynucleotide operably linked to one or more regulatory sequences.

An isopropylmalate synthase polynucleotide construct comprising, consisting or consisting essentially of at least 15-30 nucleotides, 30-50 nucleotides, 50-100 nucleotides, 100-150 nucleotides, 150-200 nucleotides, 200-300 nucleotides, 300-400 nucleotides, 400-500 nucleotides, 500-600 nucleotides, 600-700 nucleotides, 700-1000 nucleotides, 1000-1300 nucleotides, 1300-1500 nucleotides or 1500-1900 nucleotides.

A consumable product incorporating or utilising plant material, biomass, seed or leaves according to the present invention.

A cell or cell line comprising the isolated polynucleotide, the chimeric gene, the polynucleotide construct, the double-stranded RNA, the conjugate or the expression vector and the like according to the present invention.

A method for modulating the expression of isopropylmalate synthase or the activity of the protein encoded thereby in a cell, said method comprising administering the chimeric gene, the polynucleotide construct, the double-stranded RNA, the conjugate or the expression vector described herein.

A method for detecting, isolating, amplifying or analysing an isopropylmalate synthase polynucleotide, the method comprising the step of providing a sample comprising a polynucleotide and hybridising said polynucleotide to a polynucleotide molecule comprising a nucleotide sequence of at least 10 contiguous nucleotides from the isolated nucleotide sequence according to the present invention.

Use of an agent that modulates the expression of isopropylmalate synthase or the activity of the protein encoded thereby for modulating the sucrose ester content in at least a part of a plant—such as the leaves.

In one embodiment, the agent is or is derived from isopropylmalate synthase nucleic acid, a chimeric isopropylmalate synthase gene, a polynucleotide construct comprising an isopropylmalate synthase polynucleotide, an antisense RNA, a double-stranded RNA, a cDNA, a conjugate comprising an isopropylmalate synthase polynucleotide and at least one non-nucleotide or non-polynucleotide moiety covalently attached thereto, a ribozyme, a mutagen, a zinc finger, a small molecule or a meganuclease.

In another embodiment, the polynucleotide fragment(s) encodes an antisense nucleic acid, a ribozyme, an RNA that effects spliceosome-mediated trans-splicing, an interfering RNA (RNAi), a guide RNA, or other non-translated RNA and the like. In another embodiment, the polynucleotide fragment(s) encodes an RNAi.

A further aspect relates to a method of producing a tobacco product comprising the steps of: (a) obtaining seed from the transgenic, mutant or non-naturally occurring plant described herein; (b) planting and growing the seed into a plant; (c) harvesting the plant; and (d) preparing a tobacco product from the harvested plant.

The above-mentioned embodiments are disclosed as embodiments of each of the aspects described above.

Figure 5:
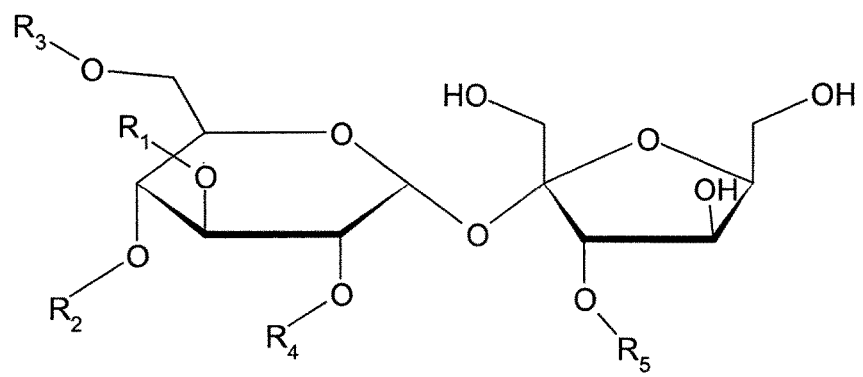

5 wherein R3=acetyl, R1=butyryl, R2=valeryl or an isomer thereof, R4=hexanoyl or an isomer thereof and R5 is hydrogen or acetyl. C2C15:0 includes a (saturated) sucrose ester as shown in FIG. 5 wherein R3=acetyl, R1=propionyl or an isomer thereof, R2=valeryl or an isomer thereof, R4=hexanoyl or an isomer thereof and R5 is hydrogen or acetyl; or a sucrose ester as shown in FIG. 5 wherein R3=acetyl, R1=valeryl or an isomer thereof, R2=valeryl or an isomer thereof, R4=valeryl or an isomer thereof and R5 is hydrogen or acetyl; or a sucrose ester as shown in FIG. 5 wherein R3=acetyl, R1=butyryl, R2=hexanoyl or an isomer thereof, R4=hexanoyl or an isomer thereof and R5 is hydrogen or acetyl; C2C16:0 includes a (saturated) sucrose ester that has the general structure shown in FIG. 5 and wherein R3 is acetyl, R1 is valeryl or an isomer thereof, R2 is valeryl or an isomer thereof, R4 is hexanoyl or an isomer thereof and R5 is either a hydrogen atom or an acetyl moiety; or wherein the sucrose ester has the general structure shown in FIG. 5 and wherein R3 is acetyl, R1 is propionyl or an isomer thereof, R2 is hexanoyl or an isomer thereof, R4 is hexanoyl or an isomer thereof and R5 is either a hydrogen atom or an acetyl moiety. C2C17:0 includes a (saturated) sucrose ester as shown in FIG. 5 wherein R3 is acetyl, R1 is valeryl or an isomer thereof, R2 is hexanoyl, R4 is hexanoyl and R5 is either a hydrogen atom or an acetyl moiety. C2C18:0 includes a (saturated) sucrose ester as shown in FIG. 5 wherein R3 is acetyl, R1 is hexanoyl, R2 is hexanoyl, R4 is hexanoyl and R5 is either a hydrogen atom or an acetyl moiety.

FIG. 2 shows the major sucrose ester isomers sorted by molecular mass and their occurrence in tobacco varieties producing or not producing sucrose esters containing beta-methylvaleryl esters. No distinction is made between 2 and 3-methylbutyryl or 3 and 4 methylvaleryl esters listed as C5 and C6 respectively. The following nomenclature is used to define the acyl composition. Referring for example to C2C4C4C5 this refers to the number of carbons in the acyl group at R3, R1, R2 and R4, respectively. C2 may be acetyl; C3 may be butyrl; C4 may be propionyl or an isomer thereof or isobutyrl; C5 may be valeryl (pentanoyl) or an isomer thereof or 2-methyl-butyry or isovaleryl or isopentenoyl or pentenoyl; C6 may be hexanoyl or an isomer thereof or 2-methylvaleryl or beta-methylvaleryl or 4-methylvaleryl. An acetyl or hydrogen may be present at R5 (not shown), suitably hydrogen.

Figure 3:
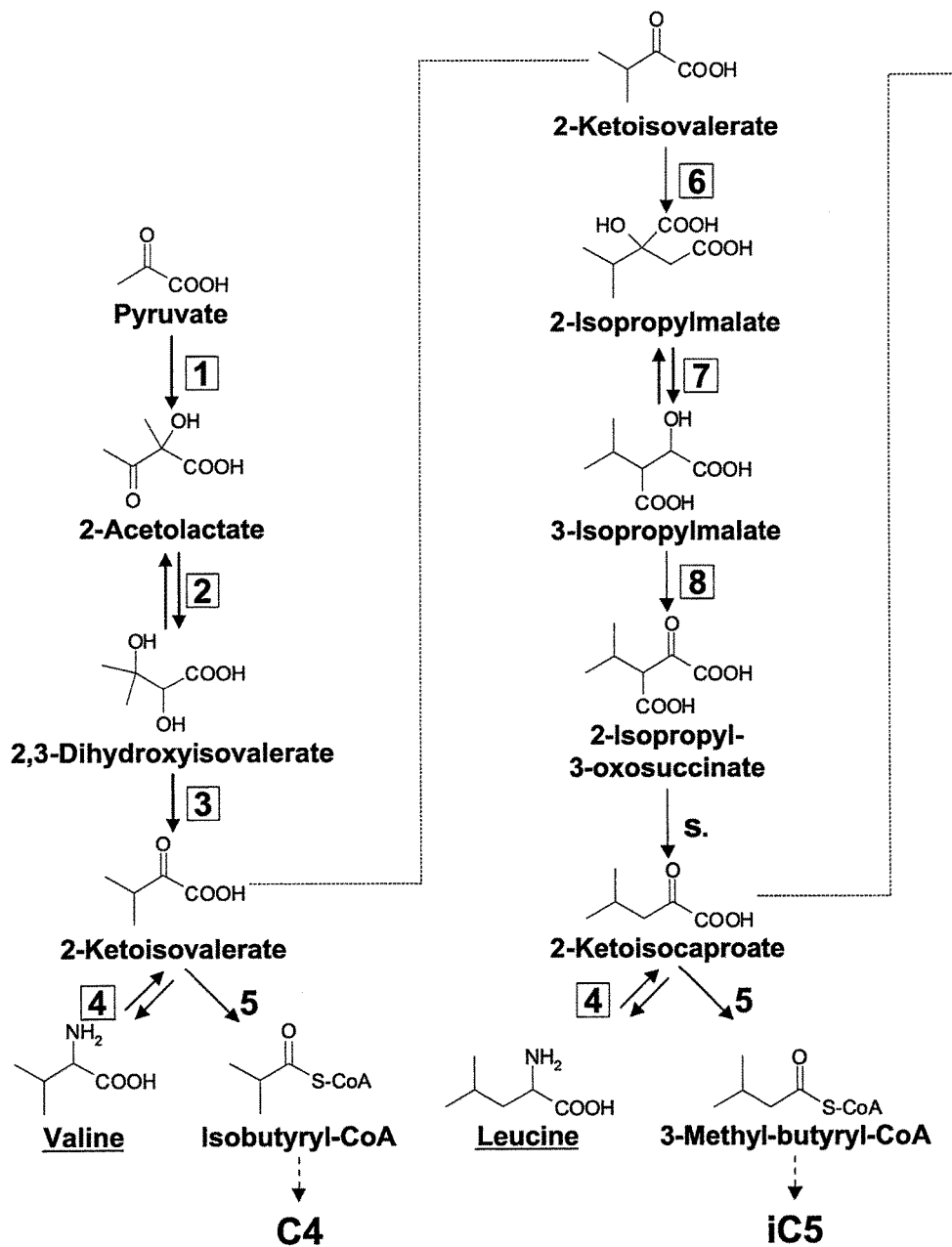
Figure 3:
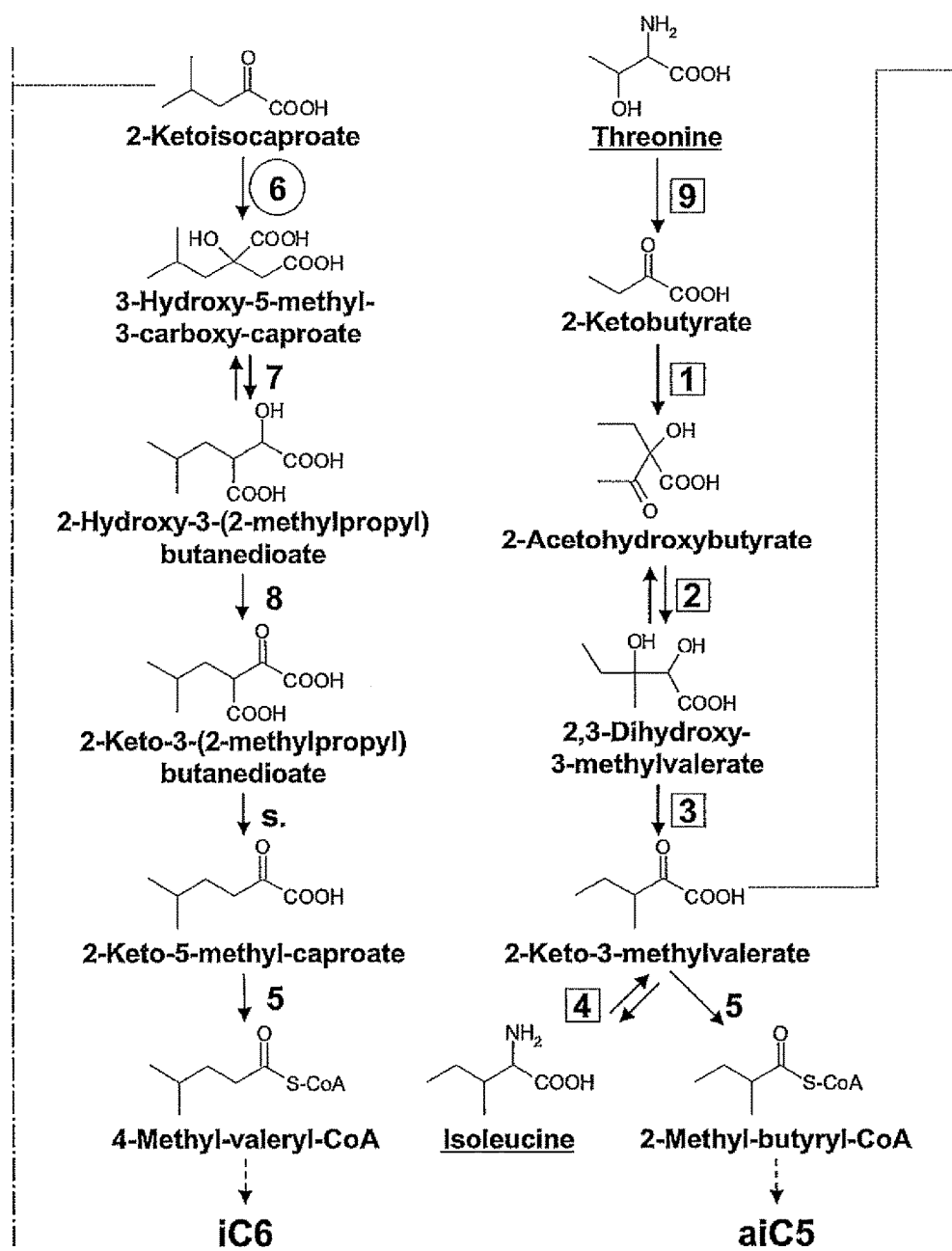
Figure 3:
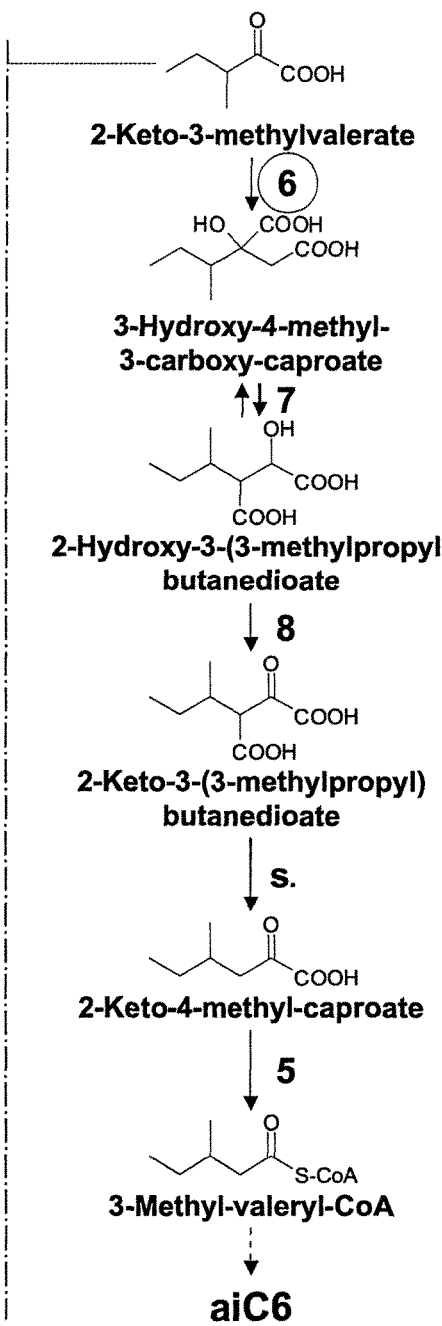

FIG. 3 illustrates the branched chain amino acid synthesis pathway and generation of the acyl chains that are esterified on sucrose. Boxed steps represent the core branched chain amino acid synthesis pathway where carbon chains are extended by one carbon per cycle of condensation isomerization and decarboxylation. 1: Acetolactate synthase [2.2.1.6]; 2: Acetohydroxy acid isomeroreductase [1.1.1.86]; 3: 3,4-Dihydroxy acid dehydratase [4.2.1.9]; 4: Branched-chain amino acid aminotransferase [2.6.1.42]; 5: Branched-chain keto acid dehydrogenase complex (BCKD) ([1.2.4.4] [2.3.1.168] [1.8.1.4]); 6: Isopropylmalate synthase [2.3.3.13]; 7: Isopropylmalate isomerase [4.2.1.33]; 8: Isopropylmalate dehydrogenase [1.1.1.85]; 9: Threonine deaminase [4.3.1.19]. C4: isobutanoyl ester; iC5: 3-methyl-butyryl ester (isovaleryl ester); aiC5: 2-methyl-butyryl ester (anteiso-valeryl ester); iC6: 4-methyl-valeryl ester (iso-caproyl ester); aiC6: 3-methyl-valeryl ester (anteiso-caproyl ester), β-methylvaleryl ester, BMV). Carboxylic acids are presented in neutral form although names reflect soluble forms. The proposed IPMS2 catalyzed steps are circled.

Figure 4:
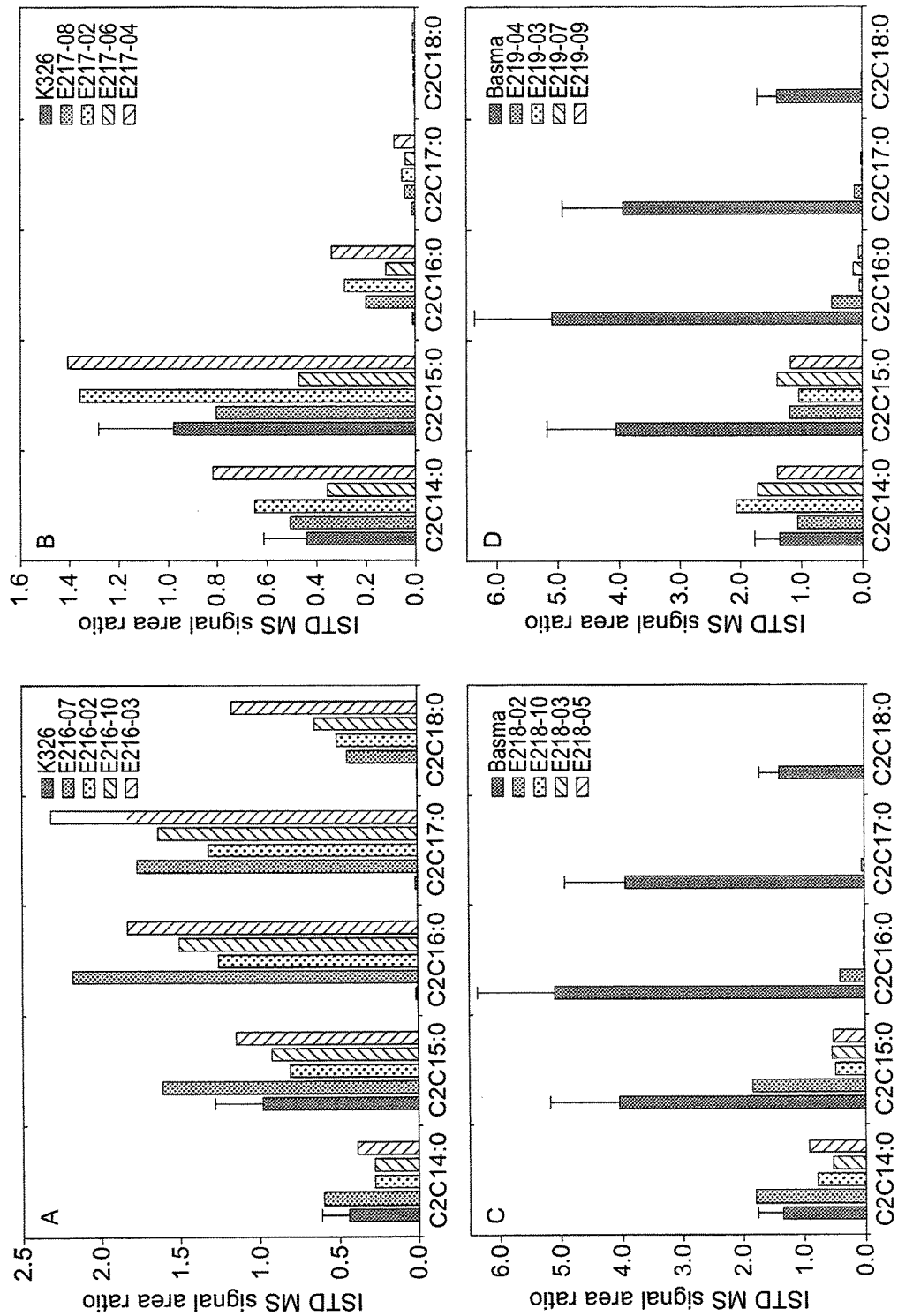

FIG. 4 shows the estimation of sucrose tetraester abundance in surface leaf exudate of transformant plants. Leaves are collected from one month old regenerating plants resulting from independent transformation events. Internal standard (sucrose octaacetate) is added at the rate of 2.5 ng/mg fresh weight. The area of the signal recorded for the ion specific to each sucrose ester is measured and plotted as ratio of internal standard area. The ratio to internal standard signal area allows the normalisation of signals on leaf fresh weight. The sucrose ester nomenclature presented here is described in FIG. 2. A: composition of leaf exudates of the parental variety K326 (Flue cured, n=3) and the transformants expressing SEQ ID NO:1 under a trichome specific promoter; B: composition of leaf exudates of the parental variety K326 and the transformants expressing SEQ ID NO:1 under the control of a viral promoter; C: composition of leaf exudates of the parental variety Basma (Oriental, n=4) and the transformants expressing the RNAi construct of SEQ ID NO: 9 under a trichome specific promoter; and D: composition of leaf exudates of the parental variety Basma and transformants expressing the RNAi construct of SEQ ID NO: 9 under a viral promoter. C2C14:0 includes a (saturated) sucrose ester as shown in FIG. 5 wherein R3=acetyl, R1=propionyl or an isomer thereof, R2=propionyl or an isomer thereof, R4=hexanoyl or an isomer thereof and R5 is hydrogen or acetyl; or a sucrose ester as shown in FIG. 5 wherein R3=acetyl, R1=propionyl or an isomer thereof, R2=valeryl or an isomer thereof, R4=valeryl or an isomer thereof and R5 is hydrogen or acetyl; or a sucrose ester as shown in FIG. 5 wherein R3=acetyl, R1=butyryl, R2=valeryl or an isomer thereof, R4=hexanoyl or an isomer thereof and R5 is hydrogen or acetyl. C2C15:0 includes a (saturated) sucrose ester as shown in FIG. 5 wherein R3=acetyl, R1=propionyl or an isomer thereof, R2=valeryl or an isomer thereof, R4=hexanoyl or an isomer thereof and R5 is hydrogen or acetyl; or a sucrose ester as shown in FIG. 5 wherein R3=acetyl, R1=valeryl or an isomer thereof, R2=valeryl or an isomer thereof, R4=valeryl or an isomer thereof and R5 is hydrogen or acetyl; or a sucrose ester as shown in FIG. 5 wherein R3=acetyl, R1=butyryl, R2=hexanoyl or an isomer thereof, R4=hexanoyl or an isomer thereof and R5 is hydrogen or acetyl; C2C16:0 includes a (saturated) sucrose ester that has the general structure shown in FIG. 5 and wherein R3 is acetyl, R1 is valeryl or an isomer thereof, R2 is valeryl or an isomer thereof, R4 is hexanoyl or an isomer thereof and R5 is either a hydrogen atom or an acetyl moiety; or wherein the sucrose ester has the general structure shown in FIG. 5 and wherein R3 is acetyl, R1 is propionyl or an isomer thereof, R2 is hexanoyl or an isomer thereof, R4 is hexanoyl or an isomer thereof and R5 is either a hydrogen atom or an acetyl moiety. C2C17:0 includes a (saturated) sucrose ester as shown in FIG. 5 wherein R3 is acetyl, R1 is valeryl or an isomer thereof, R2 is hexanoyl, R4 is hexanoyl and R5 is either a hydrogen atom or an acetyl moiety. C2C18:0 includes a (saturated) sucrose ester as shown in FIG. 5 wherein R3 is acetyl, R1 is hexanoyl, R2 is hexanoyl, R4 is hexanoyl and R5 is either a hydrogen atom or an acetyl moiety.

FIG. 5 illustrates the structure of the sucrose ester scaffold. R1 to R5 are either hydrogen atoms or acyl moieties linked by an ester bond.

Figure 6:
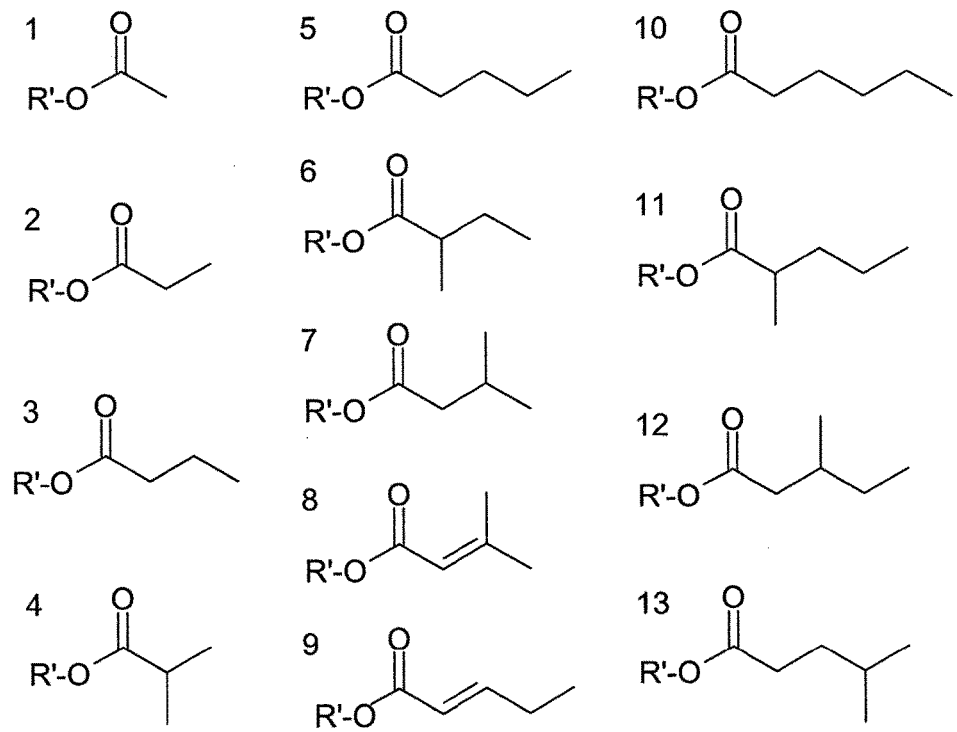

FIG. 6 illustrates the acyl chains esterified in sucrose esters. R' represents the sucrose molecule. 1. acetyl, 2. butyryl, 3. propionyl, 4. isobutyryl, 5. valeryl (pentanoyl), 6. 2-methyl-butyryl, 7. isovaleryl, 8. isopentenoyl, 9. pentenoyl, 10. hexanoyl or an isomer thereof 11. 2-methylvaleryl, 12. beta-methylvaleryl, 13. 4-methylvaleryl. Isomers and derivatives thereof are also contemplated. Thus, by way of example, the isomer may be an isomer of propionyl—such as isobutyryl. By way of further example, the isomer may be an isomer of valeryl (pentanoyl)—such as 2-methylbutyryl or isovaleryl; or an isomer of valeryl (pentanoyl) with a double bond—such as isopentenoyl or pentenoyl. By way of further example, the isomer may be an isomer of hexanoyl—such as 2-methylvaleryl, beta-methylvaleryl or 4-methylvaleryl. The isomer may or may not comprise one or more double bonds.

DEFINITIONS

The technical terms and expressions used within the scope of this application are generally to be given the meaning commonly applied to them in the pertinent art of plant and molecular biology. All of the following term definitions apply to the complete content of this application. The word "comprising" does not exclude other elements or steps, and the indefinite article "a" or "an" does not exclude a plurality. A single step may fulfil the functions of several features recited in the claims. The terms "about", "essentially" and "approximately" in the context of a given numerate value or range refers to a value or range that is within 20%, within 10%, or within 5%, 4%, 3%, 2% or 1% of the given value or range.

The term "isolated" refers to any entity that is taken from its natural milieu, but the term does not connote any degree of purification.

A "vector" refers to a nucleic acid vehicle that comprises a combination of nucleic acid components for enabling the transport of nucleic acid, nucleic acid constructs and nucleic acid conjugates and the like. Suitable vectors include episomes capable of extra-chromosomal replication such as circular, double-stranded nucleic acid plasmids; linearized double-stranded nucleic acid plasmids; and other vectors of any origin.

An "expression vector" is a nucleic acid vehicle that comprises a combination of nucleic acid components for enabling the expression of nucleic acid, nucleic acid constructs and nucleic acid conjugates and the like. Suitable expression vectors include episomes capable of extra-chromosomal replication such as circular, double-stranded nucleic acid plasmids; linearized double-stranded nucleic acid plasmids; and other functionally equivalent expression vectors of any origin. An expression vector comprises at least a promoter positioned upstream and operably-linked to a nucleic acid, nucleic acid constructs or nucleic acid conjugate, as defined below.

The term "construct" refers to a double-stranded, recombinant nucleic acid fragment comprising one or more polynucleotides. The construct comprises a "template strand" base-paired with a complementary "sense or coding strand." A given construct can be inserted into a vector in two possible orientations, either in the same (or sense) orientation or in the reverse (or anti-sense) orientation with respect to the orientation of a promoter positioned within a vector—such as an expression vector. An exemplary construct is set forth in SEQ ID NO: 9.

A "promoter" refers to a nucleic acid element/sequence, typically positioned upstream and operably-linked to a double-stranded nucleic acid fragment. Promoters can be derived entirely from regions proximate to a native gene of interest, or can be composed of different elements derived from different native promoters or synthetic nucleic acid segments. An exemplary promoter is set forth in SEQ ID NO: 8.

The terms "homology, identity or similarity" refer to the degree of sequence similarity between two polypeptides or between two nucleic acid molecules compared by sequence alignment. The degree of homology between two discrete nucleic acid sequences being compared is a function of the number of identical, or matching, nucleotides at comparable positions. The percent identity may be determined by visual inspection and mathematical calculation. Alternatively, the percent identity of two nucleic acid sequences may be determined by comparing sequence information using a computer program such as—ClustalW, ClustalX, BLAST, FASTA or Smith-Waterman.

The term "plant" refers to any plant at any stage of its life cycle or development, and its progenies. In one embodiment, the plant is a tobacco plant, which refers to a plant belonging to the genus Nicotiana. Preferred species, cultivars, hybrids and varieties of tobacco plant are described herein.

A "plant cell" refers to a structural and physiological unit of a plant. The plant cell may be in the form of a protoplast without a cell wall, an isolated single cell or a cultured cell, or as a part of higher organized unit such as but not limited to, plant tissue, a plant organ, or a whole plant.

The term "plant material" refers to any solid, liquid or gaseous composition, or a combination thereof, obtainable from a plant, including biomass, leaves, leaf lamina, midrib, stems, roots, flowers or flower parts, fruits, pollen, egg cells, zygotes, seeds, cuttings, secretions, extracts, cell or tissue cultures, or any other parts or products of a plant. In one embodiment, the plant material comprises or consists of biomass, seed or leaves. In another embodiment, the plant material comprises or consists of leaves.

The term "variety" refers to a population of plants that share constant characteristics which separate them from other plants of the same species. While possessing one or more distinctive traits, a variety is further characterized by a very small overall variation between individuals within that variety. A variety is often sold commercially.

The term "line" or "breeding line" as used herein denotes a group of plants that are used during plant breeding. A line is distinguishable from a variety as it displays little variation between individuals for one or more traits of interest, although there may be some variation between individuals for other traits.

The term "modulating" may refer to reducing, inhibiting, increasing or otherwise affecting the activity of a polypeptide. The term may also refer to reducing, inhibiting, increasing or otherwise affecting the activity of a gene encoding a polypeptide which can include, but is not limited to, modulating transcriptional activity.

The term "reduce" or "reduced" as used herein, refers to a reduction of from about 10% to about 99%, or a reduction of at least 10%, at least 20%, at least 25%, at least 30%, at least 40%, at least 50%, at least 60%, at least 70%, at least 75%, at least 80%, at least 90%, at least 95%, at least 98%, at least 99%, or at least 100% or more of a quantity or an activity, such as but not limited to polypeptide activity, transcriptional activity, and/or protein expression.

The term "inhibit" or "inhibited" as used herein, refers to a reduction of from about 98% to about 100%, or a reduction of at least 98%, at least 99%, but particularly of 100%, of a quantity or an activity, such as but not limited to polypeptide activity, transcriptional activity, and/or protein expression.

The term "increase" or "increased" as used herein, refers to an increase of from about 10% to about 99%, or an increase of at least 10%, at least 20%, at least 25%, at least 30%, at least 40%, at least 50%, at least 60%, at least 70%, at least 75%, at least 80%, at least 90%, at least 95%, at least 98%, at least 99%, at least 100%, at least 150%, or at least 200% or more or more of a quantity or an activity, such as but not limited to polypeptide activity, transcriptional activity, and/or protein expression.

The term "control" in the context of a control plant or control plant cells means a plant or plant cells in which the expression or activity of isopropylmalate synthase has not been modified (for example, increased or reduced) and so it can provide a comparison with a plant in which the expression or activity of isopropylmalate synthase has been modified. The control plant may comprise an empty vector. The control plant may correspond to a wild-type plant.

DETAILED DESCRIPTION

In one aspect, there is provided an isolated polynucleotide comprising, consisting or consisting essentially of a polynucleotide sequence and having at least 60% sequence identity to any of the sequences described herein, including any of polynucleotides shown in the sequence listing. Suitably, the isolated polynucleotides comprise, consist or consist essentially of a sequence having at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity thereto.

In one aspect, there is provided an isolated polynucleotide comprising, consisting or consisting essentially of a polynucleotide sequence encoding an isopropylmalate synthase and having at least 60% sequence identity to SEQ ID NO:1. Suitably, the isolated polynucleotides comprise, consist or consist essentially of a sequence having at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity to SEQ ID NO:1.

In another aspect, there is provided an isolated polynucleotide comprising, consisting or consisting essentially of a polynucleotide sequence encoding an isopropylmalate synthase and having at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity to SEQ ID NO:10.

In another aspect, there is provided an isolated polynucleotide comprising, consisting or consisting essentially of a polynucleotide sequence encoding an isopropylmalate synthase and having at least 60%, 61%, 62%, 63%, 64%, 65%, 70%, 75%, 80%, 85%, 87%, 88%, 89%, 90%, 91%, 92%, 93%, 94%, 95% 96%, 97%, 98%, 99% or 100% sequence identity to SEQ ID NO:12.

In another aspect, there is provided an isolated polynucleotide comprising, consisting or consisting essentially of a polynucleotide sequence encoding an isopropylmalate synthase and having at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity to SEQ ID NO:14.

In another aspect, there is provided an isolated polynucleotide comprising, consisting or consisting essentially of a polynucleotide sequence having at least 60%, 61%, 62%, 63%, 64%, 65%, 70%, 75%, 80%, 85%, 87%, 88%, 89%, 90%, 91%, 92%, 93%, 94%, 95% 96%, 97%, 98%, 99% or 100% sequence identity to SEQ ID NO: 8. SEQ ID NO: 8 encodes a preferred promoter. The term "polynucleotide" refers to a polymer of nucleotides, which may be unmodified or modified deoxyribonucleic acid (DNA) or ribonucleic acid (RNA). Accordingly, a polynucleotide can be, without limitation, a genomic DNA, complementary DNA (cDNA), mRNA, or antisense RNA or a fragment(s) thereof. Moreover, a polynucleotide can be single-stranded or double-stranded, nucleic acid that is a mixture of single-stranded and double-stranded regions, a hybrid molecule comprising DNA and RNA, or a hybrid molecule with a mixture of single-stranded and double-stranded regions or a fragment(s) thereof. In addition, the polynucleotide can be composed of triple-stranded regions comprising DNA, RNA, or both or a fragment(s) thereof. A polynucleotide can contain one or more modified bases, such as phosphothioates, and can be a peptide nucleic acid (PNA). Generally, polynucleotides can be assembled from isolated or cloned fragments of cDNA, genomic DNA, oligonucleotides, or individual nucleotides, or a combination of the foregoing. Although the polynucleotide sequences described herein are shown as DNA sequences, the sequences include their corresponding RNA sequences, and their complementary (for example, completely complementary) DNA or RNA sequences, including the reverse complements thereof.

The term "isopropylmalate synthase polynucleotide" includes polynucleotides encoding isopropylmalate synthase (IMPS) from *Nicotiana tabacum* and includes polynucleotides comprising, consisting or consisting essentially of polynucleotides with substantial homology (that is, sequence similarity) or substantial identity to SEQ ID NO:1, SEQ ID NO: 10, SEQ ID NO: 12 or SEQ ID NO: 14; polynucleotide variants that have at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98% or 99% sequence identity to the sequence of SEQ ID NO:1, SEQ ID NO: 10, SEQ ID NO: 12 or SEQ ID NO: 14; fragments of the polynucleotides including fragments of SEQ ID NO:1, SEQ ID NO: 10, SEQ ID NO: 12 or SEQ ID NO: 14; and fragments of SEQ ID NO:1, SEQ ID NO: 10, SEQ ID NO: 12 or SEQ ID NO: 14 with substantial homology (that is, sequence similarity) or substantial identity thereto that have at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity to the corresponding fragments of SEQ ID NO:1, SEQ ID NO: 10, SEQ ID NO: 12 or SEQ ID NO: 14. The isopropylmalate synthase polynucleotide also includes sequences comprising a sufficient or substantial degree of identity or similarity to SEQ ID NO:1, SEQ ID NO: 10, SEQ ID NO: 12 or SEQ ID NO: 14 to encode a polypeptide that functions as an isopropylmalate synthase. In one embodiment, the term "isopropylmalate synthase polynucleotide" refers to a polymer of nucleotides which comprises, consists or consists essentially of a polynucleotide designated herein as SEQ ID NO:1, SEQ ID NO: 10, SEQ ID NO: 12 or SEQ ID NO: 14.

A polynucleotide as described herein will generally contain phosphodiester bonds, although in some cases, polynucleotide analogs are included that may have alternate backbones, comprising, for example, phosphoramidate, phosphorothioate, phosphorodithioate, or O-methylphosphoroamidite linkages; and peptide polynucleotide backbones and linkages. Other analog polynucleotides include those with positive backbones; non-ionic backbones, and non-ribose backbones. Modifications of the ribose-phosphate backbone may be done for a variety of reasons, for example, to increase the stability and half-life of such molecules in physiological environments or as probes on a biochip. Mixtures of naturally occurring polynucleotides and analogs can be made; alternatively, mixtures of different polynucleotide analogs, and mixtures of naturally occurring polynucleotides and analogs may be made.

A variety of polynucleotide analogs are known, including, for example, phosphoramidate, phosphorothioate, phosphorodithioate, O-methylphosphoroamidite linkages and peptide polynucleotide backbones and linkages. Other analog polynucleotides include those with positive backbones, non-ionic backbones and non-ribose backbones. Polynucleotides containing one or more carbocyclic sugars are also included.

Other analogs include peptide nucleic acids which are peptide polynucleotide analogs. These backbones are substantially non-ionic under neutral conditions, in contrast to the highly charged phosphodiester backbone of naturally occurring polynucleotides. This may result in advantages. First, the peptide polynucleotide backbone may exhibit improved hybridization kinetics. Peptide nucleic acids have larger changes in the melting temperature for mismatched versus perfectly matched basepairs. DNA and RNA typically exhibit a 2-4° C. drop in melting temperature for an internal mismatch. With the non-ionic peptide polynucleotide backbone, the drop is closer to 7-9° C. Similarly, due to their non-ionic nature, hybridization of the bases attached to these backbones is relatively insensitive to salt concentration. In addition, peptide nucleic acids may not be degraded or degraded to a lesser extent by cellular enzymes, and thus may be more stable.

Among the uses of the disclosed polynucleotides, and combinations of fragments thereof, is the use of fragments as probes in nucleic acid hybridisation assays or primers in nucleic acid amplification assays. Such fragments generally comprise at least about 10, 11, 12, 13, 14, 15, 16, 17, 18, 19 or 20 or more contiguous nucleotides of a DNA sequence. In other embodiments, a DNA fragment comprises at least about 10, 15, 20, 30, 40, 50 or 60 or more contiguous nucleotides of a DNA sequence. These techniques can also be used to identify BMVSE and bmvse plants since a functional isopropylmalate synthase gene is shown herein to be necessary for the formation of sucrose esters. The close by genetic markers and the alleles of the isopropylmalate synthase gene can be used as predictors of sucrose ester production by a plant. Such a test could be used to track plant varieties or to predict smoking quality or batch type homogeneity. Thus, in one aspect, there is also provided a method for detecting an isopropylmalate synthase polynucleotide as described herein comprising the use of probes or primers capable of specifically detecting or specifically amplifying said polynucleotide or specifically detecting and specifically amplifying said polynucleotide. In a further aspect, there is provided a method for identifying a plant that is capable of producing sucrose esters comprising the steps of: (a) providing a sample comprising nucleic acid from a plant of interest; and (b) determining the presence of an isopropylmalate synthase polynucleotide as described herein, wherein the presence of said polynucleotide in said plant is indicative that said plant is capable of producing the sucrose esters. Kits for detecting at least a portion of the isopropylmalate synthase polynucleotide are also provided which comprise one of more primers or probes for specifically detecting at least a portion of isopropylmalate synthase polynucleotide. The kit may comprise reagents for polynucleotide amplification—such as polymerase chain reaction (PCR)—or reagents for nucleic acid probe hybridization-detection technology—such as Southern Blots, Northern Blots, in-situ hybridization, or microarray. The kit may comprise reagents for antibody binding-detection technology such as Western Blots, ELISAs, SELDI mass spectrometry or test strips. The kit may comprise reagents for DNA sequencing. The kit may comprise reagents and/or instructions for determining sucrose ester content. In some embodiments, a kit may comprise instructions for one or more of the methods described. The kits described may be useful for genetic identity determination, phylogenetic studies, genotyping, haplotyping, pedigree analysis or plant breeding particularly with co-dominant scoring. The methods and kits may be of use in a breeding approach relying on a cross between a BMVSE and a bmvse variety and a sequence-based selection of the plants in the offspring. Typically, plants showing the functional isopropylmalate synthase genetic region that was present in the BMVSE producing variety or plants showing the dysfunctional isopropylmalate synthase genetic region the was present in the bmvse non producing variety will be selected.

The basic parameters affecting the choice of hybridization conditions and guidance for devising suitable conditions are described by Sambrook, J., E. F. Fritsch, and T. Maniatis (1989, Molecular Cloning: A Laboratory Manual, Cold Spring Harbor Laboratory Press, Cold Spring Harbor, N.Y.). Using knowledge of the genetic code in combination with the amino acid sequences described herein, sets of degenerate oligonucleotides can be prepared. Such oligonucleotides are useful as primers, for example, in PCR, whereby DNA fragments are isolated and amplified. In certain embodiments, degenerate primers can be used as probes for genetic libraries. Such libraries would include but are not limited to cDNA libraries, genomic libraries, and even electronic express sequence tag or DNA libraries. Homologous sequences identified by this method would then be used as probes to identify homologues of the sequences identified herein.

Also of potential use are polynucleotides and oligonucleotides (for example, primers or probes) that hybridize under reduced stringency conditions, typically moderately stringent conditions, and commonly highly stringent conditions to the polynucleotide(s) as described herein. The basic parameters affecting the choice of hybridization conditions and guidance for devising suitable conditions are set forth by Sambrook, J., E. F. Fritsch, and T. Maniatis (1989, Molecular Cloning: A Laboratory Manual, Cold Spring Harbor Laboratory Press, Cold Spring Harbor, N.Y.) and can be readily determined by those having ordinary skill in the art based on, for example, the length or base composition of the polynucleotide.

One way of achieving moderately stringent conditions involves the use of a prewashing solution containing 5× Standard Sodium Citrate, 0.5% Sodium Dodecyl Sulphate, 1.0 mM Ethylenediaminetetraacetic acid (pH 8.0), hybridization buffer of about 50% formamide, 6× Standard Sodium Citrate, and a hybridization temperature of about 55° C. (or other similar hybridization solutions, such as one containing about 50% formamide, with a hybridization temperature of about 42° C.), and washing conditions of about 60° C., in 0.5× Standard Sodium Citrate, 0.1% Sodium Dodecyl Sulphate. Generally, highly stringent conditions are defined as hybridization conditions as above, but with washing at approximately 68° C., 0.2× Standard Sodium Citrate, 0.1% Sodium Dodecyl Sulphate. SSPE (1×SSPE is 0.15M sodium chloride, 10 mM sodium phosphate, and 1.25 mM Ethylenediaminetetraacetic acid, pH 7.4) can be substituted for Standard Sodium Citrate (1× Standard Sodium Citrate is 0.15M sodium chloride and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, for example, Sambrook, J., E. F. Fritsch, and T. Maniatis (1989, Molecular Cloning: A Laboratory Manual, Cold Spring Harbor Laboratory Press, Cold Spring Harbor, N.Y.). When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity. The hybridization temperature for hybrids anticipated to be less than 50 base pairs in length should be 5 to 10° C. less than the melting temperature of the hybrid, where melting temperature is determined according to the following equations. For hybrids less than 18 base pairs in length, melting temperature (° C.)=2(number of A+T bases)+4(number of G+C bases). For hybrids above 18 base pairs in length, melting temperature (° C.)=81.5+16.6(log 10 [Na+])+0.41(% G+C)−(600/N), where N is the number of bases in the hybrid, and [Na+] is the concentration of sodium ions in the hybridization buffer ([Na+] for 1× Standard Sodium Citrate=0.165M). Typically, each such hybridizing polynucleotide has a length that is at least 25% (commonly at least 50%, 60%, or 70%, and most commonly at least 80%) of the length of a polynucleotide to which it hybridizes, and has at least 60% sequence identity (for example, at least 65%, 70%, 75%, 80%, 85%, 90%, 95%, 96%, 97%, 98%, 99% or 100%) with a polynucleotide to which it hybridizes. As will be understood by the person skilled in the art, a linear DNA has two possible orientations: the 5-to-3' direction and the 3'-to-5' direction. For example, if a reference sequence is positioned in the 5-to-3' direction, and if a second sequence is positioned in the 5'-to-3' direction within the same polynucleotide molecule/strand, then the reference sequence and the second sequence are orientated in the same direction, or have the same orientation. Typically, a promoter sequence and a gene of interest under the regulation of the given promoter are positioned in the same orientation. However, with respect to the reference sequence positioned in the 5'-to-3' direction, if a second sequence is positioned in the 3'-to-5' direction within the same polynucleotide molecule/strand, then the reference sequence and the second sequence are orientated in anti-sense direction, or have anti-sense orientation. Two sequences having anti-sense orientations with respect to each other can be alternatively described as having the same orientation, if the reference sequence (5'-to-3' direction) and the reverse complementary sequence of the reference sequence (reference sequence positioned in the 5'-to-3') are positioned within the same polynucleotide molecule/strand. The sequences set forth herein are shown in the 5'-to-3' direction.

Recombinant constructs provided herein can be used to transform plants or plant cells in order to modulate isopropylmalate synthase protein expression levels. A recombinant polynucleotide construct can comprise a polynucleotide encoding an isopropylmalate synthase polynucleotide as described herein, operably linked to a regulatory region suitable for expressing the isopropylmalate synthase polypeptide in the plant or cell. Thus, a polynucleotide can comprise a coding sequence that encodes the isopropylmalate synthase polypeptide as described herein. The isopropylmalate synthase polypeptide encoded by a recombinant polynucleotide can be a native isopropylmalate synthase polypeptide, or can be heterologous to the cell. In some cases, the recombinant construct contains a polynucleotide that reduces or inhibits expression of a isopropylmalate synthase-modulating polypeptide, operably linked to a regulatory region. Examples of suitable regulatory regions are described herein.

Vectors containing recombinant polynucleotide constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available.

The vectors can also include, for example, origins of replication, scaffold attachment regions or markers. A marker gene can confer a selectable phenotype on a plant cell. For example, a marker can confer biocide resistance, such as resistance to an antibiotic (for example, kanamycin, G418, bleomycin, or hygromycin), or an herbicide (for example, glyphosate, chlorsulfuron or phosphinothricin). In addition, an expression vector may include a tag sequence designed to facilitate manipulation or detection (for example, purification or localization) of the expressed polypeptide. Tag sequences, such as luciferase, beta-glucuronidase (GUS), green fluorescent protein (GFP), glutathione S-transferase (GST), polyhistidine, c-myc or hemagglutinin sequences typically are expressed as a fusion with the encoded polypeptide. Such tags can be inserted anywhere within the polypeptide, including at either the carboxyl or amino terminus.

A plant or plant cell can be transformed by having the recombinant polynucleotide integrated into its genome to become stably transformed. Stably transformed cells typically retain the introduced polynucleotide with each cell division. A plant or plant cell may also be transiently transformed such that the recombinant polynucleotide is not integrated into its genome.

Transiently transformed cells typically lose all or some portion of the introduced recombinant polynucleotide with each cell division such that the introduced recombinant polynucleotide cannot be detected in daughter cells after a sufficient number of cell divisions.

A number of methods are available in the art for transforming a plant cell which are all encompassed herein, including biolistics, gene gun techniques, *Agrobacterium*-mediated transformation, viral vector-mediated transformation and electroporation. The *Agrobacterium* system for integration of foreign nucleic acid into plant chromosomes has been extensively studied, modified, and exploited for plant genetic engineering. Naked recombinant nucleic acid molecules comprising nucleic acid sequences corresponding to the subject purified tobacco protein operably linked, in the sense or antisense orientation, to regulatory sequences are joined to appropriate T-DNA sequences by conventional methods. These are introduced into tobacco protoplasts by polyethylene glycol techniques or by electroporation techniques, both of which are standard. Alternatively, such vectors comprising recombinant nucleic acid molecules encoding the subject purified protein are introduced into live *Agrobacterium* cells, which then transfer the nucleic acid into the plant cells. Transformation by naked DNA without accompanying T-DNA vector sequences can be accomplished via fusion of tobacco protoplasts with nucleic acid-containing liposomes or via electroporation. Naked DNA unaccompanied by T-DNA vector sequences can also be used to transform tobacco cells via inert, high velocity microprojectiles.

If a cell or cultured tissue is used as the recipient tissue for transformation, plants can be regenerated from transformed cultures if desired, by techniques known to those skilled in the art.

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a polynucleotide can be modulated in a similar manner. Some suitable regulatory regions initiate transcription only, or predominantly, in certain cell types. Methods for identifying and characterizing regulatory regions in plant genomic DNA are known in the art.

Suitable promoters include tissue-specific promoters recognized by tissue-specific factors present in different tissues or cell types (for example, root-specific promoters, shoot-specific promoters, xylem-specific promoters), or present during different developmental stages, or present in response to different environmental conditions. Suitable promoters include constitutive promoters that can be activated in most cell types without requiring specific inducers. Examples of suitable promoters for controlling isopropylmalate synthase RNAi polypeptide production include the cauliflower mosaic virus 35S (CaMV/35S), SSU, OCS, lib4, usp, STLS1, B33, nos or ubiquitin- or phaseolin-promoters. Persons skilled in the art are capable of generating multiple variations of recombinant promoters.

Tissue-specific promoters are transcriptional control elements that are only active in particular cells or tissues at specific times during plant development, such as in vegetative tissues or reproductive tissues. Tissue-specific expression can be advantageous, for example, when the expression of polynucleotides in certain tissues is preferred. Examples of tissue-specific promoters under developmental control include promoters that can initiate transcription only (or primarily only) in certain tissues, such as vegetative tissues, for example, roots or leaves, or reproductive tissues, such as fruit, ovules, seeds, pollen, pistils, flowers, or any embryonic to tissue. Reproductive tissue-specific promoters may be, for example, anther-specific, ovule-specific, embryo-specific, endosperm-specific, integument-specific, seed and seed coat-specific, pollen-specific, petal-specific, sepal-specific, or combinations thereof.

Suitable leaf-specific promoters include pyruvate, orthophosphate dikinase (PPDK) promoter from C4 plant (maize), cab-m1Ca+2 promoter from maize, the *Arabidopsis thaliana* myb-related gene promoter (Atmyb5), the ribulose biphosphate carboxylase (RBCS) promoters (for example, the tomato RBCS 1, RBCS2 and RBCS3A genes expressed in leaves and light-grown seedlings, RBCS1 and RBCS2 expressed in developing tomato fruits or ribulose bisphosphate carboxylase promoter expressed almost exclusively in mesophyll cells in leaf blades and leaf sheaths at high levels).

Suitable senescence-specific promoters include a tomato promoter active during fruit ripening, senescence and abscission of leaves, a maize promoter of gene encoding a cysteine protease. Suitable anther-specific promoters can be used. Suitable root-preferred promoters known to persons skilled in the art may be selected. Suitable seed-preferred promoters include both seed-specific promoters (those promoters active during seed development such as promoters of seed storage proteins) and seed-germinating promoters (those promoters active during seed germination). Such seed-preferred promoters include, but are not limited to, Cim1 (cytokinin-induced message); cZ19B1 (maize 19 kDa zein); milps (myo-inositol-1-phosphate synthase); mZE40-2, also known as Zm-40; nucic; and celA (cellulose synthase). Gamma-zein is an endosperm-specific promoter. Glob-1 is an embryo-specific promoter. For dicots, seed-specific promoters include, but are not limited to, bean beta-phaseolin, napin, 3-conglycinin, soybean lectin, cruciferin, and the like. For monocots, seed-specific promoters include, but are not limited to, a maize 15 kDa zein promoter, a 22 kDa zein promoter, a 27 kDa zein promoter, a gamma-zein promoter, a 27 kDa γ-zein promoter (such as gzw64A promoter, see Genbank Accession number S78780), a waxy promoter, a shrunken 1 promoter, a shrunken 2 promoter, a globulin 1 promoter (see Genbank Accession number L22344), an ltp2 promoter, cim1 promoter, maize end1 and end2 promoters, nuc1 promoter, Zm40 promoter, eep1 and eep2; lec1, thioredoxin H promoter; mlip15 promoter, PCNA2 promoter; and the shrunken-2 promoter.

Examples of inducible promoters include promoters responsive to pathogen attack, anaerobic conditions, elevated temperature, light, drought, cold temperature, or high salt concentration. Pathogen-inducible promoters include those from pathogenesis-related proteins (PR proteins), which are induced following infection by a pathogen (for example, PR proteins, SAR proteins, beta-1,3-glucanase, chitinase).

In addition to plant promoters, other suitable promoters may be derived from bacterial origin for example, the octopine synthase promoter, the nopaline synthase promoter and other promoters derived from Ti plasmids), or may be derived from viral promoters (for example, 35S and 19S RNA promoters of cauliflower mosaic virus (CaMV), constitutive promoters of tobacco mosaic virus, cauliflower mosaic virus (CaMV) 19S and 35S promoters, or figwort mosaic virus 35S promoter).

The term "isopropylmalate synthase polypeptide" refers to a polypeptide encoding isopropylmalate synthase (IPMS) from *Nicotiana tabacum* and includes polypeptide variants comprising, consisting or consisting essentially of an amino acid sequence encoded by a polynucleotide variant with at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98% or 99% sequence identity to SEQ ID NO:2, SEQ ID NO:11, SEQ ID NO:13 or SEQ ID NO: 15; fragments of the isopropylmalate synthase polypeptide(s); and fragments of SEQ ID NO:2, SEQ ID NO:11, SEQ ID NO:13 or SEQ ID NO: 15 that have at least about 60%, 65%, 70%, 75%, 80%, 85%, 87%, 88%, 89%, 90%, 91%, 92%, 93%, 94%, 95% 96%, 97%, 98%, 99% or 100% sequence identity to the corresponding fragments of SEQ ID NO:2, SEQ ID NO:11, SEQ ID NO:13 and SEQ ID NO: 15. The isopropylmalate synthase polypeptide also includes sequences comprising a sufficient or substantial degree of identity or similarity to SEQ ID NO:2, SEQ ID NO:11, SEQ ID NO:13 and SEQ ID NO: 15 to function as an isopropylmalate synthase. The fragments of the isopropylmalate synthase polypeptide typically retain isopropylmalate synthase activity. Isopropylmalate synthase polypeptides also include mutants produced by introducing any type of alterations (for example, insertions, deletions, or substitutions of amino acids; changes in glycosylation states;

changes that affect refolding or isomerizations, three-dimensional structures, or self-association states), which can be deliberately engineered or isolated naturally provided that they still function as an isopropylmalate synthase. Isopropylmalate synthase polypeptides may be in linear form or cyclized using known methods. The term "isopropylmalate synthase polypeptide" can also refer to a polypeptide encoded by SEQ ID NO:1, SEQ ID NO:10, SEQ ID NO:12 or SEQ ID NO: 14 that has 60%, 65%, 70%, 75%, 80%, 85%, 87%, 88%, 89%, 90%, 91%, 92%, 93%, 94%, 95% 96%, 97%, 98%, 99% or 100% sequence identity thereto or a polypeptide comprising, consisting or consisting essentially of the sequence set forth in SEQ ID NO:2, SEQ ID NO:11, SEQ ID NO:13 or SEQ ID NO:15 that has 100% sequence identity thereto.

In another aspect, there is provided an isolated polypeptide comprising, consisting or consisting essentially of a polypeptide sequence having at least 60% sequence identity to any of the sequences described herein, including any of polypeptides shown in the sequence listing. Suitably, the isolated polypeptides comprise, consist or consist essentially of a sequence having at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity thereto.

Polypeptides include variants produced by introducing any type of alterations (for example, insertions, deletions, or substitutions of amino acids; changes in glycosylation states; changes that affect refolding or isomerizations, three-dimensional structures, or self-association states), which can be deliberately engineered or isolated naturally. The variant may have alterations which produce a silent change and result in a functionally equivalent protein. Deliberate amino acid substitutions may be made on the basis of similarity in polarity, charge, solubility, hydrophobicity, hydrophilicity and the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine. Conservative substitutions may be made, for example according to the Table below. Amino acids in the same block in the second column and preferably in the same line in the third column may be substituted for each other:

| ALIPHATIC | Non-polar | Gly Ala Pro Ile Leu Val |
|---|---|---|
| | Polar-uncharged | Cys Ser Thr Met Asn Gly |
| | Polar-charged | Asp Glu Lys Arg |
| AROMATIC | | His Phe Trp Tyr |

The polypeptide may be a mature protein or an immature protein or a protein derived from an immature protein. Polypeptides may be in linear form or cyclized using known methods. Polypeptides typically comprise at least 10, at least 20, at least 30, or at least 40 contiguous amino acids.

In another aspect, there is provided an isolated isopropylmalate synthase polypeptide comprising, consisting or consisting essentially of a sequence encoding an isopropylmalate synthase and having at least about 60%, 65%, 70%, 75%, 80%, 85%, 87%, 88%, 89%, 90%, 91%, 92%, 93%, 94%, 95% 96%, 97%, 98%, 99% or 100% sequence identity to SEQ ID NO:2.

In another aspect, there is provided an isolated isopropylmalate synthase polypeptide comprising, consisting or consisting essentially of a sequence encoding an isopropylmalate synthase and having at least about 60%, 65%, 70%, 75%, 80%, 85%, 87%, 88%, 89%, 90%, 91%, 92%, 93%, 94%, 95% 96%, 97%, 98%, 99% or 100% sequence identity to SEQ ID NO:11. In another aspect, there is provided an isolated isopropylmalate synthase polypeptide comprising, consisting or consisting essentially of a sequence encoding an isopropylmalate synthase and having at least about 60%, 65%, 70%, 75%, 80%, 85%, 87%, 88%, 89%, 90%, 91%, 92%, 93%, 94%, 95% 96%, 97%, 98%, 99% or 100% sequence identity to SEQ ID NO:13. In another aspect, there is provided an isolated isopropylmalate synthase polypeptide comprising, consisting or consisting essentially of a sequence encoding an isopropylmalate synthase and having at least about 60%, 65%, 70%, 75%, 80%, 85%, 87%, 88%, 89%, 90%, 91%, 92%, 93%, 94%, 95% 96%, 97%, 98%, 99% or 100% sequence identity to SEQ ID NO:15. Fragments of the polypeptide sequences are also disclosed herein, suitably, such fragments retain the activity of the full length sequence.

Mutant polypeptides can be used to create mutant plants, non-naturally occurring plants or transgenic plants comprising the mutant polypeptide. Suitably, the mutant polypeptide retains the activity of the unmutated polypeptide. The activity of the mutant polypeptide may be higher, lower or about the same as the unmutated polypeptide.

A polypeptide may be prepared by culturing transformed or recombinant host cells under culture conditions suitable to express a polypeptide. The resulting expressed polypeptide may then be purified from such culture using known purification processes. The purification of the polypeptide may include an affinity column containing agents which will bind to the polypeptide; one or more column steps over such affinity resins; one or more steps involving hydrophobic interaction chromatography; or immunoaffinity chromatography. Alternatively, the polypeptide may also be expressed in a form that will facilitate purification. For example, it may be expressed as a fusion polypeptide, such as those of maltose binding polypeptide, glutathione-5-transferase or thioredoxin. Kits for expression and purification of fusion polypeptides are commercially available. The polypeptide may be tagged with an epitope and subsequently purified by using a specific antibody directed to such epitope. One or more liquid chromatography steps—such as reverse-phase high performance liquid chromatography can be employed to further purify the polypeptide. Some or all of the foregoing purification steps, in various combinations, can be employed to provide a substantially homogeneous recombinant polypeptide. The polypeptide thus purified may be substantially free of other polypeptides and is defined herein as an "substantially purified polypeptide"; such purified polypeptides include polypeptides, fragments, variants, and the like. Expression, isolation, and purification of the polypeptides and fragments can be accomplished by any suitable technique, including but not limited to the methods described herein.

It is also possible to utilise an affinity column such as a monoclonal antibody generated against polypeptides, to affinity-purify expressed polypeptides. These polypeptides can be removed from an affinity column using conventional techniques, for example, in a high salt elution buffer and then dialyzed into a lower salt buffer for use or by changing pH or other components depending on the affinity matrix utilized, or be competitively removed using the naturally occurring substrate of the affinity moiety.

A polypeptide may also be produced by known conventional chemical synthesis. Methods for constructing the polypeptides or fragments thereof by synthetic means are known to those skilled in the art. The synthetically-constructed polypeptide sequences, by virtue of sharing primary, secondary or tertiary structural or conformational characteristics with a native polypeptides may possess biological properties in common therewith, including biological activity.

The term 'non-naturally occurring' as used herein describes an entity (for example, a polynucleotide, a genetic mutation, a polypeptide, a plant, a plant cell and plant material) that is not formed by nature or that does not exist in nature. Such non-naturally occurring entities or artificial entities may be made, synthesized, initiated, modified, intervened, or manipulated by methods described herein or that are known in the art. Thus, by way of example, a non-naturally occurring plant, a non-naturally occurring plant cell or non-naturally occurring plant material may be made using traditional plant breeding techniques—such as back-crossing—or by genetic manipulation technologies—such as antisense RNA, interfering RNA, meganuclease and the like. By way of further example, a non-naturally occurring plant, a non-naturally occurring plant cell or non-naturally occurring plant material may be made by introgression of or by transferring one or more genetic mutations (for example one or more polymorphisms) from a first plant or plant cell into a second plant or plant cell (which may itself be naturally occurring), such that the resulting plant, plant cell or plant material or the progeny thereof comprises a genetic constitution (for example, a genome, a chromosome or a segment thereof) that is not formed by nature or that does not exist in nature. The resulting plant, plant cell or plant material is thus artificial or non-naturally occurring. Accordingly, an artificial or non-naturally occurring plant or plant cell may be made by modifying a genetic sequence in a first artificial or naturally occurring plant or plant cell, resulting in a modified genetic sequence (i) that is artificial; or (ii) that occurs naturally in a second plant or plant cell, provided that the second plant or plant cell comprises a different genetic background from the first plant or plant cell. Differences in genetic background of a plant or plant cell can be detected by phenotypic differences or by molecular biology techniques known in the art—such as nucleic acid sequencing, presence or absence of genetic markers (for example, microsatellite RNA markers).

A number of polynucleotide based methods can be used to increase gene expression in plants. By way of example, a construct, vector or expression vector that is compatible with the plant to be transformed can be prepared which comprises the gene of interest together with an upstream promoter that is capable of overexpressing the gene in the plant. Exemplary promoters are described herein. Following transformation and when grown under suitable conditions, the promoter can drive expression in order to modulate (for example, increase) the levels of this enzyme in the plant, or in a specific tissue thereof. In one exemplary embodiment, a vector carrying isopropylmalate synthase is generated to overexpress the gene in a plant. The vector carries a suitable promoter upstream of the isopropylmalate synthase gene driving its expression in all tissues of the plant. The vector may also carry an antibiotic resistance gene in order to confer selection of the transformed calli and cell lines. In one embodiment, the promoter promotes transcriptional activity in the trichomes of a plant. In one embodiment, the promoter has transcriptional activity in the trichomes of a plant. In another embodiment, the promoter has transcriptional activity specifically in the trichomes of a plant with no or substantially no activity in any other parts of a plant. Suitably, the promoter comprises, consists or consists essentially of the sequence set forth in SEQ ID NO: 8 or a trichome promoter or a natural isopropylmalate synthase promoter. The natural isopropylmalate synthase promoter will be located at the 5' end of the isopropylmalate synthase gene. In SEQ ID NO:6 for example, the endogenous isopropylmalate synthase promoter will be positioned before nucleotide 2826. Accordingly, the isopropylmalate synthase gene may be over expressed in the trichome of a plant. Surprisingly, the inventors have discovered that constitutive expression does not result in as high an accumulation of sucrose esters as compared to the levels achieved using trichome specific expression (see FIG. 4 and the description thereof).

According to one embodiment, the expression or activity of isopropylmalate synthase is increased in a plant already capable of producing beta-methylvaleryl containing sucrose esters thereby resulting in the increased accumulation of isopropylmalate synthase therein and thus increased beta-methylvaleryl containing sucrose ester production. According to another embodiment, the expression or activity of isopropylmalate synthase is increased in a plant that is not already capable of producing beta-methylvaleryl containing sucrose esters thereby resulting in the accumulation of isopropylmalate synthase therein and thus beta-methylvaleryl containing sucrose ester production.

A number of polynucleotide based methods, including antisense RNA, ribozyme directed RNA cleavage, post-transcriptional gene silencing, for example, RNA interference and transcriptional gene silencing, can be used to modulate gene expression in plants. Whilst such approaches are classically used to reduce or inhibit gene expression, they can also be used to increase gene expression by increasing cellular productivity and the quality of proteins that are expressed. Such approaches can include the silencing of apoptosis-associated gene expression, protein glycosylation-associated gene expression, lactate dehydrogenase involved in cellular metabolism, and dihydrofolate reductase used for gene amplification. Other approaches can be extended to reducing or inhibiting multiple targets involved in different cellular pathways for changing gene regulation in plant cells.

In some embodiments, a complement of the full-length polynucleotide or a fragment thereof can be used. Typically, a fragment is at least 10 contiguous nucleotides, for example, at least 10, 11, 12, 13, 14, 15, 16, 17, 18, 19, 20, 21, 22, 23, 24, 25, 26, 27, 30, 35, 40, 50, 80, 100, 200, 500 contiguous nucleotides or more. In one embodiment, the polynucleotide fragment(s) is able to decrease expression or activity and may encode, for example, an antisense nucleic acid, a ribozyme, an RNA that effects spliceosome-mediated trans-splicing, an interfering RNA, a guide RNA, or other non-translated RNA and the like as described herein. In another embodiment, the polynucleotide fragment(s) encodes an interfering RNA.

Compositions that can reduce the expression or the activity of isopropylmalate synthase include, but are not limited to, sequence-specific polynucleotides that can interfere with the transcription of one or more endogenous isopropylmalate synthase gene(s); sequence-specific polynucleotides that can interfere with the translation of isopropylmalate synthase RNA transcripts (for example, double-stranded RNAs, siRNAs, ribozymes); sequence-specific polypeptides that can interfere with the stability of isopropylmalate synthase proteins; sequence-specific polynucleotides that can interfere with the enzymatic activity of isopropylmalate synthase protein or the binding activity of isopropylmalate synthase protein with respect to substrates or regulatory proteins; antibodies that exhibit specificity for isopropylmalate synthase protein; small molecule compounds that can interfere with the stability of isopropylmalate synthase protein or the enzymatic activity of isopropylmalate synthase protein or the binding activity of isopropylmalate synthase protein; zinc finger proteins that bind isopropylmalate synthase polynucleotide; and meganucleases that have activity towards isopropylmalate synthase polynucleotide.

Antisense technology is one well-known method that can be used to modulate (for example, reduce or inhibit) the expression of a polypeptide. A polynucleotide to be repressed is cloned and operably linked to a regulatory region and a transcription termination sequence so that the antisense strand of RNA is transcribed. The recombinant construct is then transformed into plants and the antisense strand of RNA is produced. The polynucleotide need not be the entire sequence of the gene to be repressed, but typically will be substantially complementary to at least a portion of the sense strand of the gene to be repressed.

A polynucleotide may be transcribed into a ribozyme, or catalytic RNA, that affects expression of an mRNA. Ribozymes can be designed to specifically pair with virtually any target RNA and cleave the phosphodiester backbone at a specific location, thereby functionally inactivating the target RNA. Heterologous polynucleotides can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. Hammerhead ribozyme sequences can be embedded in a stable RNA such as a transfer RNA to increase cleavage efficiency in vivo.

In one embodiment, the sequence-specific polynucleotides that can interfere with the translation of RNA transcripts is interfering RNA. RNA interference or RNA silencing is an evolutionarily conserved process by which specific mRNAs can be targeted for enzymatic degradation. A double-stranded RNA must be introduced or produced by a cell (for example, double-stranded RNA virus, or interfering RNA polynucleotides) to initiate the interfering RNA pathway. The double-stranded RNA can be converted into multiple small interfering RNA duplexes of 21-23 bp length by RNases III, which are double-stranded RNA-specific endonucleases. The small interfering RNAs can be subsequently recognized by RNA-induced silencing complexes that promote the unwinding of small interfering RNA through an ATP-dependent process. The unwound antisense strand of the small interfering RNA guides the activated RNA-induced silencing complexes to the targeted mRNA comprising a sequence complementary to the small interfering RNA anti-sense strand. The targeted mRNA and the anti-sense strand can form an A-form helix, and the major groove of the A-form helix can be recognized by the activated RNA-induced silencing complexes. The target mRNA can be cleaved by activated RNA-induced silencing complexes at a single site defined by the binding site of the 5'-end of the small interfering RNA strand. The activated RNA-induced silencing complexes can be recycled to catalyze another cleavage event.

Interfering RNA expression vectors may comprise interfering RNA constructs encoding interfering RNA polynucleotides that exhibit RNA interference activity by reducing the expression level of mRNAs, pre-mRNAs, or related RNA variants. The expression vectors may comprise a promoter positioned upstream and operably-linked to a interfering RNA construct, as further described herein. Interfering RNA expression vectors may comprise a suitable minimal core promoter, an interfering RNA construct of interest, an upstream (5') regulatory region, a downstream (3') regulatory region, including transcription termination and polyadenylation signals, and other sequences known to persons skilled in the art, such as various selection markers.

The polynucleotides can be produced in various forms, including as double stranded structures (that is, a double-stranded RNA molecule comprising an antisense strand and a complementary sense strand), double-stranded hairpin-like structures, or single-stranded structures (that is, a single-stranded RNA molecule comprising just an antisense strand). The structures may comprise a duplex, asymmetric duplex, hairpin or asymmetric hairpin secondary structure, having self-complementary sense and antisense strands. The double stranded interfering RNA can be enzymatically converted to double-stranded small interfering RNAs. One of the strands of the small interfering RNA duplex can anneal to a complementary sequence within the target mRNA and related RNA variants. The small interfering RNA/mRNA duplexes are recognized by RNA-induced silencing complexes that can cleave RNAs at multiple sites in a sequence-dependent manner, resulting in the degradation of the target mRNA and related RNA variants. The double-stranded RNA molecules may include small interfering RNA molecules assembled from a single oligonucleotide in a stem-loop structure, wherein self-complementary sense and antisense regions of the small interfering RNA molecule are linked by means of a polynucleotide based or non-polynucleotide-based linker(s), as well as circular single-stranded RNA having two or more loop structures and a stem comprising self-complementary sense and antisense strands, wherein the circular RNA can be processed either in vivo or in vitro to generate an active small interfering RNA molecule capable of mediating interfering RNA.

The use of small hairpin RNA molecules is also contemplated herein and comprise a specific antisense sequence in addition to the reverse complement (sense) sequence, typically separated by a spacer or loop sequence. Cleavage of the spacer or loop provides a single-stranded RNA molecule and its reverse complement, such that they may anneal to form a double-stranded RNA molecule (optionally with additional processing steps that may result in addition or removal of one, two, three or more nucleotides from the 3' end or the 5 end of either or both strands). The spacer can be of a sufficient length to permit the antisense and sense sequences to anneal and form a double-stranded structure (or stem) prior to cleavage of the spacer (and, optionally, subsequent processing steps that may result in addition or removal of one, two, three, four, or more nucleotides from the 3' end or the 5 end of either or both strands). The spacer sequence is typically an unrelated nucleotide sequence that is situated between two complementary nucleotide sequence regions which, when annealed into a double-stranded polynucleotide, comprise a small hairpin RNA. The spacer sequence generally comprises between about 3 and about 100 nucleotides.

Any RNA polynucleotide of interest can be produced by selecting a suitable sequence composition, loop size, and stem length for producing the hairpin duplex. A suitable range for designing stem lengths of a hairpin duplex, includes stem lengths of at least about 10, 11, 12, 13, 14, 15, 16, 17, 18, 19 or 20 nucleotides—such as about 14-30 nucleotides, about 30-50 nucleotides, about 50-100 nucleotides, about 100-150 nucleotides, about 150-200 nucleotides, about 200-300 nucleotides, about 300-400 nucleotides, about 400-500 nucleotides, about 500-600 nucleotides, and about 600-700 nucleotides. A suitable range for designing loop lengths of a hairpin duplex, includes loop lengths of about 4-25 nucleotides, about 25-50 nucleotides, or longer if the stem length of the hair duplex is substantial. A double-stranded RNA or single-stranded RNA molecule is between about 15 and about 40 nucleotides in length. The small interfering RNA molecule may be a double-stranded RNA or single-stranded RNA molecule between about 15 and about 35 nucleotides in length. The small interfering RNA molecule may be a double-stranded RNA or single-stranded RNA molecule between about 17 and about 30 nucleotides in length. The small interfering RNA molecule may be a double-stranded RNA or single-stranded RNA molecule between about 19 and about 25 nucleotides in length. The small interfering RNA molecule is a double-stranded RNA or single-stranded RNA molecule between about 21 to about 23 nucleotides in length. Hairpin structures with duplexed regions longer than 21 nucleotides may promote effective small interfering RNA-directed silencing, regardless of loop sequence and length.

The target mRNA sequence may be between about 14 to about 50 nucleotides in length. The target mRNA can, therefore, be scanned for regions between about 14 and about 50 nucleotides in length that preferably meet one or more of the following criteria for a target sequence: an A+T/G+C ratio of between about 2:1 and about 1:2; an AA dinucleotide or a CA dinucleotide at the 5' end of the target sequence; a sequence of at least 10 consecutive nucleotides unique to the target mRNA (that is, the sequence is not present in other mRNA sequences from the same plant); and no "runs" of more than three consecutive guanine (G) nucleotides or more than three consecutive cytosine (C) nucleotides. These criteria can be assessed using various techniques known in the art, for example, computer programs such as BLAST can be used to search publicly available databases to determine whether the selected target sequence is unique to the target mRNA. Alternatively, a target sequence can be selected (and a small interfering RNA sequence designed) using computer software available commercially (for example, OligoEngine, Target Finder and the small interfering RNA Design Tool which are commercially available.

Target mRNA sequences may be selected that are between about 14 and about 30 nucleotides in length that meet one or more of the above criteria, or target sequences may be selected that are between about 16 and about 30 nucleotides in length that meet one or more of the above criteria. Target sequences may be selected that are between about 19 and about 30 nucleotides in length that meet one or more of the above criteria. Target sequences are selected that are between about 19 and about 25 nucleotides in length that meet one or more of the above criteria.

The small interfering RNA molecules may comprise a specific antisense sequence that is complementary to at least 12, 13, 14, 15, 16, 17, 18, 19, 20, 21, 22, 23, 24, 25, 26, 27, 28, 29, 30, or more contiguous nucleotides of any one of the polynucleotide sequences described herein.

The specific antisense sequence comprised by the small interfering RNA molecule may be identical or substantially identical to the complement of the target sequence. The specific antisense sequence comprised by the small interfering RNA molecule may be at least about 75%, 80%, 85%, 90%, 95%, 96%, 97%, 98%, 99% or 100% identical to the complement of the target mRNA sequence. Methods of determining sequence identity are known in the art and can be determined, for example, by using the BLASTN program of the University of Wisconsin Computer Group (GCG) software or provided on the NCBI website.

The specific antisense sequence of the small interfering RNA molecules may exhibit variability by differing (for example, by nucleotide substitution, including transition or transversion) at one, two, three, four or more nucleotides from the sequence of the target mRNA. When such nucleotide substitutions are present in the antisense strand of a double-stranded RNA molecule, the complementary nucleotide in the sense strand with which the substitute nucleotide would typically form hydrogen bond base-pairing may or may not be correspondingly substituted. double-stranded RNA molecules in which one or more nucleotide substitution occurs in the sense sequence, but not in the antisense strand, are also contemplated. When the antisense sequence of an small interfering RNA molecule comprises one or more mismatches between the nucleotide sequence of the small interfering RNA and the target nucleotide sequence, as described above, the mismatches may be found at the 3' terminus, the 5' terminus or in the central portion of the antisense sequence.

The small interfering RNA molecules may comprise a specific antisense sequence that is capable of selectively hybridizing under stringent conditions to a portion of a naturally occurring target gene or target mRNA. As known to those of ordinary skill in the art, variations in stringency of hybridization conditions may be achieved by altering the time, temperature or concentration of the solutions used for the hybridization and wash steps. Suitable conditions can also depend in part on the particular nucleotide sequences used, for example the sequence of the target mRNA or gene.

One method for inducing double stranded RNA-silencing in plants is transformation with a gene construct producing hairpin RNA (see Smith et al. (2000) *Nature*, 407, 319-320). Such constructs comprise inverted regions of the target gene sequence, separated by an appropriate spacer. The insertion of a functional plant intron region as a spacer fragment additionally increases the efficiency of the gene silencing induction, due to generation of an intron spliced hairpin RNA (Wesley et al. (2001) *Plant J.*, 27, 581-590). Suitably, the stem length is about 50 nucleotides to about 1 kilo bases in length. Methods for producing intron spliced hairpin RNA are well described in the art (see for example, *Bioscience, Biotechnology, and Biochemistry* (2008) 72, 2, 615-617).

Interfering RNA molecules having a duplex or double-stranded structure, for example double-stranded RNA or small hairpin RNA, can have blunt ends, or can have 3' or 5' overhangs. As used herein, "overhang" refers to the unpaired nucleotide or nucleotides that protrude from a duplex structure when a 5-terminus of one RNA strand extends beyond the 5-terminus of the other strand (3' overhang), or vice versa (5' overhang). The nucleotides comprising the overhang can be ribonucleotides, deoxyribonucleotides or modified versions thereof. In one embodiment, at least one strand of the interfering RNA molecule has a 3' overhang from about 1 to about 6 nucleotides in length. In other embodiments, the 3' overhang is from about 1 to about 5 nucleotides, from about 1 to about 3 nucleotides and from about 2 to about 4 nucleotides in length.

When the interfering RNA molecule comprises a 3' overhang at one end of the molecule, the other end can be blunt-ended or have also an overhang (5' or 3'). When the interfering RNA molecule comprises an overhang at both ends of the molecule, the length of the overhangs may be the same or different. In one embodiment, the interfering RNA molecule comprises 3' overhangs of about 1 to about 3 nucleotides on both ends of the molecule. In a further embodiment, the interfering RNA molecule is a double-stranded RNA having a 3' overhang of 2 nucleotides at both ends of the molecule. In yet another embodiment, the nucleotides comprising the overhang of the interfering RNA are TT dinucleotides or UU dinucleotides.

When determining the percentage identity of the interfering RNA molecule comprising one or more overhangs to the target mRNA sequence, the overhang(s) may or may not be taken into account. For example, the nucleotides from a 3' overhang and up to 2 nucleotides from the 5'- or 3'-terminus of the double strand may be modified without significant loss of activity of the small interfering RNA molecule.

The interfering RNA molecules can comprise one or more 5' or 3'-cap structures. The interfering RNA molecule can comprise a cap structure at the 3'-end of the sense strand, the antisense strand, or both the sense and antisense strands; or at the 5'-end of the sense strand, the antisense strand, or both the sense and antisense strands of the interfering RNA molecule. Alternatively, the interfering RNA molecule can comprise a cap structure at both the 3'-end and 5'-end of the interfering RNA molecule. The term "cap structure" refers to a chemical modification incorporated at either terminus of an oligonucleotide, which protects the molecule from exonuclease degradation, and may also facilitate delivery or localisation within a cell. Another modification applicable to interfering RNA molecules is the chemical linkage to the interfering RNA molecule of one or more moieties or conjugates which enhance the activity, cellular distribution, cellular uptake, bioavailability or stability of the interfering RNA molecule. The polynucleotides may be synthesized or modified by methods well established in the art. Chemical modifications may include, but are not limited to 2' modifications, introduction of non-natural bases, covalent attachment to a ligand, and replacement of phosphate linkages with thiophosphate linkages. In this embodiment, the integrity of the duplex structure is strengthened by at least one, and typically two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues.

In yet another embodiment, the nucleotides at one or both of the two single strands may be modified to reduce or inhibit the activation of cellular enzymes, such as, for example, without limitation, certain nucleases. Techniques for reducing or inhibiting the activation of cellular enzymes are known in the art including, but not limited to, 2'-amino modifications, 2'-fluoro modifications, 2'-alkyl modifications, uncharged backbone modifications, morpholino modifications, 2'-O-methyl modifications, and phosphoramidate. Thus, at least one 2'-hydroxyl group of the nucleotides on a double-stranded RNA is replaced by a chemical group. Also, at least one nucleotide may be modified to form a locked nucleotide. Such locked nucleotide contains a methylene or ethylene bridge that connects the 7-oxygen of ribose with the 4'-carbon of ribose. Introduction of a locked nucleotide into an oligonucleotide improves the affinity for complementary sequences and increases the melting temperature by several degrees.

Ligands may be conjugated to a interfering RNA molecule, for example, to enhance its cellular absorption. In certain embodiments, a hydrophobic ligand is conjugated to the molecule to facilitate direct permeation of the cellular membrane. These approaches have been used to facilitate cell permeation of antisense oligonucleotides. In certain instances, conjugation of a cationic ligand to oligonucleotides often results in improved resistance to nucleases. Representative examples of cationic ligands include propylammonium and dimethylpropylammonium. Anti-sense oligonucleotides can retain their high binding affinity to mRNA when the cationic ligand is dispersed throughout the oligonucleotide.

According to one embodiment, the expression or activity of isopropylmalate synthase is decreased in a plant already capable of producing beta-methylvaleryl containing sucrose esters thereby resulting in the decreased accumulation of isopropylmalate synthase therein and thus decreased beta-methylvaleryl containing sucrose ester production.

The molecules and nucleotides described herein may be prepared using well-known techniques of solid-phase synthesis. Any other means for such synthesis known in the art may additionally or alternatively be employed.

Various embodiments are directed to expression vectors comprising one or more of the polynucleotides described herein or interfering RNA constructs that comprise one or more polynucleotides.

Various embodiments are directed to expression vectors comprising one or more polynucleotides or one or more interfering RNA constructs.

Various embodiments are directed to expression vectors comprising one or more polynucleotides or one or more interfering RNA constructs encoding one or more interfering RNA polynucleotides capable of self-annealing to form a hairpin structure, in which the construct comprises (a) one or more of the polynucleotides described herein; (b) a second sequence encoding a spacer element that includes an intron, which when spliced, forms a loop of the hairpin structure; and (c) a third sequence comprising a reverse complementary sequence of the first sequence, positioned in the same orientation as the first sequence, wherein the second sequence is positioned between the first sequence and the third sequence, and the second sequence is operably-linked to the first sequence and to the third sequence.

The disclosed sequences can be utilized for constructing various polynucleotides that do not form hairpin structures. For example, a double-stranded RNA can be formed by (1) transcribing a first strand of the DNA by operably-linking to a first promoter, and (2) transcribing the reverse complementary sequence of the first strand of the DNA fragment by operably-linking to a second promoter. Each strand of the polynucleotide can be transcribed from the same expression vector, or from different expression vectors. The RNA duplex having RNA interference activity can be enzymatically converted to small interfering RNAs to reduce RNA levels.

Thus, various embodiments are directed to expression vectors comprising polynucleotide or interfering RNA constructs encoding interfering RNA polynucleotides capable of self-annealing, in which the construct comprises (a) one or more of the polynucleotides described herein; and (b) a second sequence comprising a complementary (for example, reverse complementary) sequence of the first sequence, positioned in the same orientation as the first sequence.

Various compositions and methods are provided for reducing the endogenous expression levels of isopropylmalate synthase by promoting co-suppression of gene expression. The phenomenon of co-suppression occurs as a result of introducing multiple copies of a transgene into a plant cell host. Integration of multiple copies of a transgene can result in reduced expression of the transgene and the targeted endogenous gene. The degree of co-suppression is dependent on the degree of sequence identity between the transgene and the targeted endogenous gene. The silencing of both the endogenous gene and the transgene can occur by extensive methylation of the silenced loci (that is, the endogenous promoter and endogenous gene of interest) that can preclude transcription. Alternatively, in some cases, co-suppression of the endogenous gene and the transgene can occur by post transcriptional gene silencing, in which transcripts can be produced but enhanced rates of degradation preclude accumulation of transcripts. The mechanism for co-suppression by post-transcriptional gene silencing is thought to resemble RNA interference, in that RNA seems to be both an important initiator and a target in these processes, and may be mediated at least in part by the same molecular machinery, possibly through RNA-guided degradation of mRNAs.

Co-suppression of nucleic acids can be achieved by integrating multiple copies of the nucleic acid or fragments thereof, as transgenes, into the genome of a plant of interest. The host plant can be transformed with an expression vector comprising a promoter operably-linked to the nucleic acid or fragments thereof. Various embodiments are directed to expression vectors for promoting co-suppression of endogenous genes comprising a promoter operably-linked to a polynucleotide.

Methods for obtaining conservative mutant polynucleotides and polypeptides are also described. Any plant of interest, including a plant cell or plant material, can be genetically modified by various methods known to induce mutagenesis, including site-directed mutagenesis, oligonucleotide-directed mutagenesis, chemically-induced mutagenesis, irradiation-induced mutagenesis, mutagenesis utilizing modified bases, mutagenesis utilizing gapped duplex DNA, double-strand break mutagenesis, mutagenesis utilizing repair-deficient host strains, mutagenesis by total gene synthesis, DNA shuffling and other equivalent methods. Alternatively, genes can be targeted for inactivation by introducing transposons (for example, IS elements) into the genomes of plants of interest. These mobile genetic elements can be introduced by sexual cross-fertilization and insertion mutants can be screened for loss in protein activity. The disrupted gene in a parent plant can be introduced into other plants by crossing the parent plant with plant not subjected to transposon-induced mutagenesis by, for example, sexual cross-fertilization. Any standard breeding techniques known to persons skilled in the art can be utilized. In one embodiment, one or more genes can be inactivated by the insertion of one or more transposons. Mutations can result in homozygous disruption of one or more genes, in heterozygous disruption of one or more genes, or a combination of both homozygous and heterozygous disruptions if more than one gene is disrupted. Suitable transposable elements include retrotransposons, retroposons, and SINE-like elements. Such methods are known to persons skilled in the art.

Alternatively, genes can be targeted for inactivation by introducing ribozymes derived from a number of small circular RNAs that are capable of self-cleavage and replication in plants. These RNAs can replicate either alone (viroid RNAs) or with a helper virus (satellite RNAs). Examples of suitable RNAs include those derived from avocado sunblotch viroid and satellite RNAs derived from tobacco ringspot virus, lucerne transient streak virus, velvet tobacco mottle virus, *solanum nodiflorum* mottle virus, and subterranean clover mottle virus. Various target RNA-specific ribozymes are known to persons skilled in the art.

In some embodiments, the expression of an isopropylmalate synthase polypeptide can be modulated by non-transgenic means, such as creating a mutation in a gene. Methods that introduce a mutation randomly in a gene sequence can include chemical mutagenesis, EMS mutagenesis and radiation mutagenesis. Methods that introduce one or more targeted mutations into a cell include but are not limited to genome editing technology, particularly zinc finger nuclease-mediated mutagenesis, tilling (targeting induced local lesions in genomes), homologous recombination, oligonucleotide-directed mutagenesis, and meganuclease-mediated mutagenesis.

Some non-limiting examples of mutations are deletions, insertions and missense mutations of at least one nucleotide, single nucleotide polymorphisms and a simple sequence repeat. After mutation, screening can be performed to identify mutations that create premature stop codons or otherwise non-functional genes. After mutation, screening can be performed to identify mutations that create functional genes that are capable of being expressed at elevated levels. Screening of mutants can be carried out by sequencing, or by the use of probes or primers specific to the gene or protein. Specific mutations in polynucleotides can also be created that can result in reduced or increased gene expression, reduced or increased stability of mRNA, or reduced or increased stability of protein. Such plants are referred to herein as mutant plants. The mutant plants can have any combination of one or more mutations which results in modulated polypeptide levels. For example, the mutant plants may have a single mutation in a single gene; multiple mutations in a single gene; a single mutation in two or more or three or more genes; or multiple mutations in two or more or three or more genes. Accordingly, mutant plants comprising the mutant polypeptide variants are disclosed.

In one embodiment, seeds from plants are mutagenised and then grown into first generation mutant plants. The first generation plants are then allowed to self-pollinate and seeds from the first generation plant are grown into second generation plants, which are then screened for mutations in their loci. Though the mutagenized plant material can be screened for mutations, an advantage of screening the second generation plants is that all somatic mutations correspond to germline mutations. One of skill in the art would understand that a variety of plant materials, including but not limited to, seeds, pollen, plant tissue or plant cells, may be mutagenised in order to create the mutant plants. However, the type of plant material mutagenised may affect when the plant nucleic acid is screened for mutations. For example, when pollen is subjected to mutagenesis prior to pollination of a non-mutagenized plant, the seeds resulting from that pollination are grown into first generation plants. Every cell of the first generation plants will contain mutations created in the pollen; thus these first generation plants may then be screened for mutations instead of waiting until the second generation.

Mutagens that create point mutations, short deletions, insertions, transversions, or transitions, including chemical mutagens or radiation, may be used to create the mutations. Mutagens include, but are not limited to, ethyl methanesulfonate, methylmethane sulfonate, N-ethyl-N-nitrosurea, triethylmelamine, N-methyl-N-nitrosourea, procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine, nitrosoguanidine, 2-aminopurine, 7,12 dimethyl-benz(a)anthracene, ethylene oxide, hexamethylphosphoramide, bisulfan, diepoxyalkanes (diepoxyoctane, diepoxybutane, and the like), 2-methoxy-6-chloro-9[3-(ethyl-2-chloro-ethyl)aminopropylamino]acridine dihydrochloride and formaldehyde. Spontaneous mutations in the locus that may not have been directly caused by the mutagen are also contemplated provided that they result in the desired phenotype. Suitable mutagenic agents also include, for example, ionising radiation—such as X-rays, gamma rays, fast neutron irradiation and UV radiation.

Any method of plant nucleic acid preparation known to those of skill in the art may be used to prepare the plant nucleic acid for mutation screening.

Prepared nucleic acid from individual plants, plant cells, or plant material can optionally be pooled in order to expedite screening for mutations in the isopropylmalate synthase gene of the population of plants originating from the mutagenized plant tissue, cells or material. One or more subsequent generations of plants, plant cells or plant material can be screened. The size of the optionally pooled group is dependent upon the sensitivity of the screening method used. After the nucleic acid samples are optionally pooled, they can be subjected to polynucleotide-specific amplification techniques, such as Polymerase Chain Reaction (PCR). Any one or more primers or probes specific to the isopropylmalate synthase gene or the sequences immediately adjacent thereto may be utilized to amplify the sequences within the optionally pooled nucleic acid sample. Preferably, the one or more primers are designed to amplify the regions of the isopropylmalate synthase locus where useful mutations are most likely to arise. Most preferably, the primer is designed to detect mutations within regions of the isopropylmalate synthase polynucleotide. Additionally, it is preferable for the primer(s) to avoid known polymorphic sites in order to ease screening for point mutations. To facilitate detection of amplification products, the one or more primers or probes may be labelled using any conventional labelling method. Primer(s) or probes can be designed based upon the sequences described herein using methods that are well understood in the art. Polymorphisms may be identified by means known in the art, In a further aspect there is provided a method of preparing a mutant plant. The method involves providing at least one cell of a plant comprising a gene encoding a functional isopropylmalate synthase polypeptide. Next, the at least one cell of the plant is treated under conditions effective to modulate the activity of the isopropylmalate synthase gene. The at least one mutant plant cell is then propagated into a mutant plant, where the mutant plant has a modulated level of isopropylmalate synthase polypeptide as compared to that of a control plant. In one embodiment of this method of making a mutant plant, the treating step involves subjecting the at least one cell to a chemical mutagenising agent as described above and under conditions effective to yield at least one mutant plant cell. In another embodiment of this method, the treating step involves subjecting the at least one cell to a radiation source under conditions effective to yield at least one mutant plant cell. The term "mutant plant" includes mutant plants in which the genotype is modified as compared to a control plant, suitably by means other than genetic engineering or genetic modification.

In certain embodiments, the mutant plant, mutant plant cell or mutant plant material may comprise one or more mutations that have occurred naturally in another plant, plant cell or plant material and confer a desired trait. This mutation can be incorporated (for example, introgressed) into another plant, plant cell or plant material (for example, a plant, plant cell or plant material with a different genetic background to the plant from which the mutation was derived) to confer the trait thereto. Thus by way of example, a mutation that occurred naturally in a first plant may be introduced into a second plant—such as a second plant with a different genetic background to the first plant. The skilled person is therefore able to search for and identify a plant carrying naturally in its genome one or more mutant alleles of the isopropylmalate synthase gene which confer a desired trait. The mutant allele(s) that occurs naturally can be transferred to the second plant by various methods including breeding, backcrossing and introgression to produce a lines, varieties or hybrids that have one or more mutations in the isopropylmalate synthase gene. Plants showing a desired trait may be screened out of a pool of mutant plants. Suitably, the selection is carried out utilising the knowledge of the isopropylmalate synthase nucleotide sequences as described herein. Consequently, it is possible to screen for a genetic trait being indicative of changes in sucrose ester composition as compared to a control. Such a screening approach may involve the application of conventional nucleic acid amplification and/or hybridization techniques as discussed herein. Thus, a further aspect of the present invention relates to a method for identifying a mutant plant comprising the steps of: (a) providing a sample comprising a isopropylmalate synthase polynucleotide from a plant; and (b) determining the nucleic acid sequence of the isopropylmalate synthase polynucleotide, wherein a difference in the sequence of the isopropylmalate synthase polynucleotide as compared to the isopropylmalate synthase polynucleotide of a control plant is indicative that said plant is an isopropylmalate synthase mutant plant. In another aspect there is provided a method for identifying a mutant plant which has a change in the composition of sucrose esters as compared to a control plant comprising the steps of: (a) providing a sample from a plant to be screened; (b) determining if said sample comprises one or more mutations in the isopropylmalate synthase polynucleotide; and (c) determining the composition of the sucrose esters in said plant; wherein if said sample comprises one or more mutations in the isopropylmalate synthase polynucleotide that modulate the expression or the activity of the protein encoded as compared to a control plant and a part of the plant has a change in the composition of sucrose esters as compared to a control plant in which the expression or the activity of isopropylmalate synthase has not been reduced is indicative of a mutant plant which has a change in the composition of sucrose esters. In another aspect there is provided a method for preparing a mutant plant which has a change in the composition of sucrose esters as compared to a control plant comprising the steps of: (a) providing a sample from a first plant; (b) determining if said sample comprises one or more mutations in the isopropylmalate synthase polynucleotide that result in a change in the composition of sucrose esters therein; and (c) transferring the one or more mutations into a second plant. The mutation(s) can be transferred into the second plant using various methods that are known in the art—such as by genetic engineering, genetic manipulation, introgression, plant breeding, backcrossing and the like. In one embodiment, the first plant is a naturally occurring plant. In one embodiment, the second plant has a different genetic background to the first plant. In another aspect there is provided a method for preparing a mutant plant which has a change in the composition of sucrose esters as compared to a control plant comprising the steps of: (a) providing a sample from a first plant; (b) determining if said sample comprises one or more mutations in the isopropylmalate synthase polynucleotide that results in a change in the composition of sucrose esters therein; and (c) introgressing the one or more mutations from the first plant into a second plant. In one embodiment, the step of introgressing comprises plant breeding, optionally including backcrossing and the like. In one embodiment, the first plant is a naturally occurring plant. In one embodiment, the second plant has a different genetic background to the first plant. In one embodiment, the first plant is not a cultivar or an elite cultivar. In one embodiment, the second plant is a cultivar or an elite cultivar. A further aspect relates to a mutant plant (including a cultivar or elite cultivar mutant plant) obtained or obtainable by the methods described herein. In certain embodiments, the mutant plants may have one or more mutations localised only to a specific region of the plant—such as within the sequence of the isopropylmalate synthase polynucleotide. According to this embodiment, the remaining genomic sequence of the mutant plant will be the same or substantially the same as the plant prior to the mutagenesis.

In certain embodiments, the mutant plant may have one or more mutations localised in more than one region of the plant—such as within the sequence of the isopropylmalate synthase polynucleotide—and in one or more further regions of the genome. According to this embodiment, the remaining genomic sequence of the mutant plant will not be the same or will not be substantially the same as the plant prior to the mutagenesis. In certain embodiments, the mutant plant does not have one or more mutations in one or more, two or more, three or more, four or more or five or more exons of the isopropylmalate synthase polynucleotide; or in one or more, two or more, three or more, four or more or five or more introns of the isopropylmalate synthase polynucleotide; in a promoter of the isopropylmalate synthase polynucleotide; in the 3' untranslated region of the isopropylmalate synthase polynucleotide; in the 5' untranslated region of the isopropylmalate synthase polynucleotide; in the coding region of the isopropylmalate synthase polynucleotide; or in the non-coding region of the isopropylmalate synthase polynucleotide; or any combination of two or more, three or more, four or more, five or more; or six or more thereof parts thereof. In a further aspect there is provided a method of identifying a plant, a plant cell or plant material comprising a mutation in a gene encoding isopropylmalate synthase comprising: (a) subjecting a plant, a plant cell or plant material to mutagenesis; (b) obtaining a nucleic acid sample from said plant, plant cell or plant material or descendants thereof; and (c) determining the nucleic acid sequence of the gene encoding isopropylmalate synthase or a variant or a fragment thereof, wherein a difference in said sequence is indicative of one or more mutations therein.

Zinc finger proteins can be used to modulate expression or the activity of isopropylmalate synthase. In various embodiments, a genomic DNA sequence comprising a part of or all of the coding sequence of a polynucleotide is modified by zinc finger nuclease mediated mutagenesis. The genomic DNA sequence is searched for a unique site for zinc finger protein binding. Alternatively, the genomic DNA sequence is searched for two unique sites for zinc finger protein binding wherein both sites are on opposite strands and close together, for example, 1, 2, 3, 4, 5, 6 or more basepairs apart. Accordingly, zinc finger proteins that bind to the polynucleotides described herein are provided.

A zinc finger protein may be engineered to recognize a selected target site in the isopropylmalate synthase gene. A zinc finger protein can comprise any combination of motifs derived from natural zinc finger DNA-binding domains and non-natural zinc finger DNA-binding domains by truncation or expansion or a process of site-directed mutagenesis coupled to a selection method such as, but not limited to, phage display selection, bacterial two-hybrid selection or bacterial one-hybrid selection. The term "non-natural zinc finger DNA-binding domain" refers to a zinc finger DNA-binding domain that binds a three-basepair sequence within the target DNA and that does not occur in the cell or organism comprising the DNA which is to be modified. Methods for the design of zinc finger protein which binds specific nucleotide sequences which are unique to a target gene are known in the art.

A zinc finger nuclease may be constructed by making a fusion of a first polynucleotide coding for a zinc finger protein that binds to a polynucleotide, and a second polynucleotide coding for a non-specific endonuclease such as, but not limited to, those of a Type IIS endonuclease. A fusion protein between a zinc finger protein and the nuclease may comprise a spacer consisting of two basepairs or alternatively, the spacer can consist of three, four, five, six or seven or more basepairs. In various embodiments, a zinc finger nuclease introduces a double stranded break in a regulatory region, a coding region, or a non-coding region of a genomic DNA sequence of a polynucleotide and leads to a reduction of the level of expression of a polynucleotide, or a reduction in the activity of the protein encoded thereby. Cleavage by zinc finger nuclease frequently results in the deletion of DNA at the cleavage site following DNA repair by non-homologous end joining.

In other embodiments, a zinc finger protein may be selected to bind to a regulatory sequence of a isopropylmalate synthase polynucleotide. More specifically, the regulatory sequence may comprise a transcription initiation site, a start codon, a region of an exon, a boundary of an exon-intron, a terminator, or a stop codon. Accordingly, the disclosure provides a mutant, non-naturally occurring or transgenic plant or plant cells, produced by zinc finger nuclease-mediated mutagenesis in the vicinity of or within the isopropylmalate synthase gene, nd methods for making such a plant or plant cell by zinc finger nuclease-mediated mutagenesis. Methods for delivering zinc finger protein and zinc finger nuclease to a plant are similar to those described below for delivery of meganuclease.

In another aspect, methods for producing recombinant, mutant, non-naturally occurring or transgenic or otherwise genetically-modified plants using meganucleases—such as meganuclease I-Crel—are provided. Naturally occurring meganucleases as well as recombinant meganucleases may be used to specifically cause a double-stranded break at a single site or at relatively few sites in the genomic DNA of a plant to allow for the disruption of a isopropylmalate synthase polynucleotide. The meganuclease may be an engineered meganuclease with altered DNA-recognition properties. Meganuclease proteins can be delivered into plant cells by a variety of different mechanisms known in the art.

The disclosure encompasses the use of meganucleases to inactivate one or more of the polynucleotides described herein in a plant cell or plant. Aspects also relate to a method for inactivating a polynucleotide in a plant using a meganuclease comprising: (a) providing a plant cell comprising one or more polynucleotides described herein; (b) introducing a meganuclease or a construct encoding a meganuclease into said plant cell; and (c) allowing the meganuclease to substantially inactivate the polynucleotide.

Meganucleases can be used to cleave meganuclease recognition sites within the coding regions of a polynucleotide. Such cleavage frequently results in the deletion of DNA at the meganuclease recognition site following mutagenic DNA repair by non-homologous end joining. Such mutations in the gene coding sequence are typically sufficient to inactivate the gene. This method to modify a plant cell involves, first, the delivery of a meganuclease expression cassette to a plant cell using a suitable transformation method. For highest efficiency, it is desirable to link the meganuclease expression cassette to a selectable marker and select for successfully transformed cells in the presence of a selection agent. This approach will result in the integration of the meganuclease expression cassette into the genome, however, which may not be desirable if the plant is likely to require regulatory approval. In such cases, the meganuclease expression cassette (and linked selectable marker gene) may be segregated away in subsequent plant generations using conventional breeding techniques. Alternatively, plant cells may be initially be transformed with a meganuclease expression cassette lacking a selectable marker and may be grown on media lacking a selection agent. Under such conditions, a fraction of the treated cells will acquire the meganuclease expression cassette and will express the engineered meganuclease transiently without integrating the meganuclease expression cassette into the genome. Because it does not account for transformation efficiency, this latter transformation procedure requires that a greater number of treated cells be screened to obtain the desired genome modification. The above approach can also be applied to modify a plant cell when using a zinc finger protein or zinc finger nuclease.

Following delivery of the meganuclease expression cassette, plant cells are grown, initially, under conditions that are typical for the particular transformation procedure that was used. This may mean growing transformed cells on media at temperatures below 26.degree.C., frequently in the dark. Such standard conditions can be used for a period of time, preferably 1-4 days, to allow the plant cell to recover from the transformation process. At any point following this initial recovery period, growth temperature may be raised to stimulate the activity of the engineered meganuclease to cleave and mutate the meganuclease recognition site.

For certain applications, it may be desirable to precisely remove the polynucleotide from the genome of the plant. Such applications are possible using a pair of engineered meganucleases, each of which cleaves a meganuclease recognition site on either side of the intended deletion.

Meganucleases and other DNA-repair strategies may also be used to trigger a heterologous recombination between a DNA contained in a plant cell and the target DNA. The target DNA typically comprises at least one, preferably two regions that are homologous to the DNA contained in the plant cell. Following DNA repair by the cell, homologous ends are joined resulting in the introduction of the target DNA into the cell.

In a further embodiment, expression levels of isopropylmalate synthase in a plant may be increased by inserting the gene directly into the chloroplast genome since isopropylmalate synthase is a chloroplastic protein encoded in the plant cell nucleus. Likewise, increasing the transport or the import of isopropylmalate synthase protein into chloroplasts can also modulate the activity pattern.

One object is to provide mutant, transgenic or non-naturally occurring plants that exhibit modulated sucrose ester levels whilst maintaining substantially the same visual appearance as compared to a control plant. Accordingly, there is described herein mutant, transgenic or non-naturally occurring plants or cells that have modulated levels of sucrose esters as compared to control cells or control plants. The mutant, transgenic or non-naturally occurring plants or cells have been modified to modulate the synthesis or activity of isopropylmalate synthase described herein by modulating the expression of one or more polypeptides encoding the polynucleotide sequences described herein.

A further aspect, relates to a mutant, non-naturally occurring or transgenic plant or cell, wherein the expression of or the activity of isopropylmalate synthase is modulated and a part of the plant has an increase or a decrease in sucrose ester levels of at least 5% as compared to a control plant in which the expression or the activity said enzyme has not been modulated. A still further aspect, relates to a mutant, non-naturally occurring or transgenic plant or cell, wherein expression of isopropylmalate synthase or the activity of the protein encoded thereby is modulated and wherein the sucrose ester levels in aerosol is increased or decreased by at least 5% as compared to the aerosol from the control plant.

The change in the sucrose ester content as compared to the control plant may be at least about 5%, at least about 10%, at least about 20%, at least about 25%, at least about 30%, at least about 40%, at least about 50%, at least about 60%, at least about 70%, at least about 75%, at least about 80%, at least about 90%, at least about 95%, at least about 96%, at least about 97%, at least about 98%, at least about 99%, or about 100% or more.

The plant may be heated to 100° C. or above—such as at least 125° C., at least 150° C., at least 175° C. or at least 200° C.—to release the aerosol.

Plants suitable for use in genetic modification include monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genera *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis*, and *Zea*.

Suitable species may include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed), *Secale cereale* (rye), *Salix* spp. (willow), *Eucalyptus* spp. (eucalyptus), *Triticosecale*, bamboo, *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), *Brassica juncea*, *Beta vulgaris* (sugarbeet), *Manihot esculenta* (cassaya), *Lycopersicon esculentum* (tomato), *Lactuca sativa* (lettuce), *Musa paradisiaca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Rosa* spp. (rose), *Dianthus caryophyllus* (carnation), *Petunia* spp. (petunia), *Poinsettia pulcherrima* (poinsettia), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy), *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

Various embodiments are directed to mutant plants, non-naturally occurring plants or transgenic plants modified to reduce isopropylmalate synthase gene expression levels thereby, producing plants—such as tobacco plants—in which the expression level of isopropylmalate synthase are reduced within plant tissues of interest as compared to a control plant. The disclosed compositions and methods can be applied to any species of the genus *Nicotiana*, including *N. rustica* and *N. tabacum* (for example, LA B21, LN KY171, TI 1406, Basma, Galpao, Perique, Beinhart 1000-1, K326, Hicks Broadleaf and Petico). Other species include *N. acaulis, N. acuminata, N. acuminata* var. *multiflora, N. africana, N. alata, N. amplexicaulis, N. arentsii, N. attenuate, N. benavidesii, N. benthamiana, N. bigelovii, N. bonariensis, N. cavicola, N. clevelandii, N. cordifolia, N. corymbosa, N. debneyi, N. excelsior, N. forgetiana, N. fragrans, N. glauca, N. glutinosa, N. goodspeedii, N. gossei, N. hybrid, N. ingulba, N. kawakamii, N. knightiana, N. langsdorffii, N. linearis, N. longiflora, N. maritima, N. megalosiphon, N. miersii, N. noctiflora, N. nudicaulis, N. obtusifolia, N. occidentalis, N. occidentalis* subsp. *hesperis, N. otophora, N. paniculata, N. pauciflora, N. petunioides, N. plumbaginifolia, N. quadrivalvis, N. raimondii, N. repanda, N. rosulata, N. rosulata* subsp. *ingulba, N. rotundifolia, N. setchellii, N. simulans, N. solanifolia, N. spegazzinii, N. stocktonii, N. suaveolens, N. sylvestris, N. thyrsiflora, N. tomentosa, N. tomentosiformis, N. trigonophylla, N. umbratica, N. undulate, N. velutina, N. wigandioides*, and *N. x sanderae*. In a highly preferred embodiment, the plant is a tobacco plant—such as a plant of the genus *Nicotiana* or the species *Nicotiana tabacum*.

The use of tobacco cultivars and elite tobacco cultivars is also contemplated herein. The transgenic, non-naturally occurring or mutant plant may therefore be a tobacco variety or elite tobacco cultivar that comprises one or more transgenes, or one or more genetic mutations or a combination thereof. The genetic mutation(s) (for example, one or more polymorphisms) can be mutations that do not exist naturally in the individual tobacco variety or tobacco cultivar (for example, elite tobacco cultivar) or can be genetic mutation(s) that do occur naturally provided that the mutation does not occur naturally in the individual tobacco variety or tobacco cultivar (for example, elite tobacco cultivar). Particularly useful *Nicotiana tabacum* varieties include Burley type, dark type, flue-cured type, and Oriental type tobaccos. Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF911, DT 538 LC Galpao tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KTY14xL8 LC, Little Crittenden, McNair 373, McNair 944, msKY 14xL8, Narrow Leaf Madole, Narrow Leaf Madole LC, NBH 98, N-126, N-777LC, N-7371LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC, 'Perique' tobacco, PVH03, PVH09, PVH19, PVHSO, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, VA359, M 37-1, B 13P, Xanthi (Mitchell-Mor), Bel-W3, 79-615, Samsun Holmes NN, KTRDC number 2 Hybrid 49, Burley 21, KY 8959, KY 9, MD 609, PG 01, PG 04, PO1, PO2, PO3, RG 11, RG 8, VA 509, AS44, Banket A1, Basma Drama B84/31, Basma I Zichna ZP4/B, *Basma Xanthi* BX 2A, Batek, Besuki Jember, C104, Coker 347, Criollo Misionero, Delcrest, Djebel 81, DVH 405, Galpão Comum, HBO4P, Hicks Broadleaf, Kabakulak Elassona, Kutsage E1, LA BU 21, NC 2326, NC 297, PVH 2110, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, TI-1070, TW136, Basma, TKF 4028, L8, TKF 2002, GR141, *Basma xanthi*, GR149, GR153, Petit Havana. Low converter subvarieties of the above, even if not specifically identified herein, are also contemplated. Cultivars and elite cultivars are preferred in certain embodiments. The species *Nicotiana tabacum* can be used in certain other embodiments. *Nicotiana tabacum* Burley type can be used.

Embodiments are also directed to compositions and methods for producing mutant, non-naturally occurring or transgenic plants that have been modified to modulate isopropylmalate synthase expression or activity which can result in plants or plant components with modulated levels of sucrose esters as compared to a control. Modulating the levels of sucrose esters in plants may be used to generate plants in which the flavour profile of the aerosol generated therefrom is changed. The present invention may therefore provide new blending opportunities to generate desirable tobacco flavours. Thus, by way of example, the sucrose ester content of the plant may be increased by increasing the expression or activity of isopropylmalate synthase which may result in a plant capable of releasing elevated levels of flavour molecules that are more similar to oriental tobacco. Thus, by way of further example, the sucrose ester content of the plant may be decreased by decreasing the expression or activity of isopropylmalate synthase which may result in a plant capable of releasing lower levels of flavour molecules, that are more similar to flue cured tobacco.

In a further aspect there is provided a method for blending tobacco comprising the step of, replacing or adding to the one or more types of tobacco in a tobacco blend, tobacco (for example, tobacco leaves or a composition derived or derivable from tobacco leaves) derived from a transgenic, mutant or non-naturally occurring plant in which the sucrose ester content of the plant has been modulated (for example, increased or decreased) by modulating (preferably, increasing) the expression or activity of isopropylmalate synthase as described herein. In another aspect there is provided a method for blending tobacco comprising the step of replacing, reducing or omitting the Oriental type tobacco in a tobacco blend and adding tobacco (for example, tobacco leaves or a composition derived or derivable from tobacco leaves) derived from a transgenic, mutant or non-naturally occurring plant in which the sucrose ester content of the plant has been modulated (preferably, increased) by modulating (preferably, increasing) the expression or activity of isopropylmalate synthase as described herein. The replacement, reduction or addition of tobacco—such as Oriental tobacco—may correspond to about 10%, 20%, 30%, 40%, 50%, 60%, 70%, 80%, 90% or 100% of the tobacco that is replaced, reduced or added.

A further aspect relates to a method for modulating the flavour of tobacco or a tobacco product comprising, adding to the tobacco (for example, tobacco leaves or a composition derived or derivable from tobacco leaves) or the tobacco product, tobacco derived or derivable from a transgenic, mutant or non-naturally occurring plant in which the sucrose ester content of the plant has been modulated as described herein.

A further aspect relates to the use of agent that modulates the expression or activity of isopropylmalate synthase for modulating the flavour of tobacco or a tobacco product. Modulating the levels of sucrose esters in plants may also be used to generate plants in which the pest resistance of the plant is altered. The pest resistance of the plant may be increased by increasing the levels of sucrose ester production as described herein. The pest resistance of the plant may be decreased by decreasing-the-levels of sucrose ester production as described herein.

Compositions of the sucrose esters that are produced in the plants described herein may be extracted and optionally purified therefrom for various further uses—such as in drugs, food additives, smoking flavourants and as components of organic pesticides and the like. In one embodiment, the sucrose esters are extracted from leaves or the surface of leaves. Accordingly, products—such as drugs, food additives, smoking flavourants and organic pesticides comprising the sucrose esters—are a further aspect of this disclosure.

Sucrose esters according to the present disclosure have the general structure shown in FIG. 5, wherein R1, R2, R3, R4 and R5 are either hydrogen atoms or acyl chains. The acyl chains that can be esterified in sucrose esters are set forth in FIG. 6. Some examples of specific sucrose esters are set forth in Table 1 and FIG. 2.

The total number of carbons in the acyl chains at R1, R2 and R4 in each of the one or more sucrose esters can be, for example, 12, 13, 14, 15, 16, 17 or 18; suitably, 14, 15, 16, 17 or 18; suitably, 16, 17 or 18; or suitably 14 or 15. Provided that this total number of carbons is present in each of the sucrose esters then the constituent acyl chains may be selected from any of those set forth in FIG. 6. Suitably, the sucrose ester has an acetyl at R3 and an acetyl or hydrogen at R5. Suitably, the sucrose ester has an acetyl at R3 and a hydrogen at R5. Suitably, one or more, two or more or three of more of the acyl chains will be beta-methylvaleryl, especially when a 6 carbon acyl chain is present.

In one embodiment, the sucrose ester is a sucrose ester that has an acetyl or a hydrogen at R3 and R5 and an acyl chain with 3, 4, 5 or 6 carbons at any of positions R1, R2 and R4. Suitably, the sucrose ester has an acetyl at R3 and an acetyl or hydrogen at R5. Suitably, the sucrose ester has an acetyl at R3 and a hydrogen at R5. In another embodiment, the sucrose ester has an acetyl or a hydrogen at R3 and R5 and an acyl chain with 4, 5 or 6 carbons at any of positions R1, R2 and R4. Suitably, the sucrose ester has an acetyl at R3 and an acetyl or hydrogen at R5. Suitably, the sucrose ester has an acetyl at R3 and a hydrogen at R5. In another embodiment, the sucrose ester has an acetyl or a hydrogen at R3 and R5 and an acyl chain with 5 or 6 carbons at any of positions R1, R2 and R4. Suitably, the sucrose ester has an acetyl at R3 and an acetyl or hydrogen at R5. Suitably, the sucrose ester has an acetyl at R3 and a hydrogen at R5. In another embodiment, the sucrose ester has an acetyl or a hydrogen at R3 and R5 and an acyl chain with 6 carbons at positions R1, R2 and R4. Suitably, the sucrose ester has an acetyl at R3 and an acetyl or hydrogen at R5. Suitably, the sucrose ester has an acetyl at R3 and a hydrogen at R5.

In one embodiment, the sucrose ester has an acetyl or a hydrogen at R3 and R5 and an acyl chain with 3, 4, 5 or 6 carbons at position R1, an acyl chain with 3, 4, 5 or 6 carbons at position R2 and an acyl chain with 3, 4, 5 or 6 carbons at position R4. Suitably, the sucrose ester has an acetyl at R3 and an acetyl or hydrogen at R5. Suitably, the sucrose ester has an acetyl at R3 and a hydrogen at R5. In another embodiment, the sucrose ester has an acetyl or a hydrogen at R3 and R5 and an acyl chain with 4, 5 or 6 carbons at position R1, an acyl chain with 4, 5 or 6 carbons at position R2 and an acyl chain with 4, 5 or 6 carbons at position R4. Suitably, the sucrose ester has an acetyl at R3 and an acetyl or hydrogen at R5. Suitably, the sucrose ester has an acetyl at R3 and a hydrogen at R5. In another embodiment, the sucrose ester has an acetyl or a hydrogen at R3 and R5 and an acyl chain with 5 or 6 carbons at position R1, an acyl chain with 5 or 6 carbons at position R2 and an acyl chain with 5 or 6 carbons at position R4. Suitably, the sucrose ester has an acetyl at R3 and an acetyl or hydrogen at R5. Suitably, the sucrose ester has an acetyl at R3 and a hydrogen at R5.

In one embodiment, the sucrose ester has an acetyl or a hydrogen at R3 and R5 and an acyl chain with 6 carbons at least at one of positions R1, R2 and R4. Suitably, the sucrose ester has an acetyl at R3 and an acetyl or hydrogen at R5. Suitably, the sucrose ester has an acetyl at R3 and a hydrogen at R5.

In one embodiment, the sucrose ester has an acetyl or a hydrogen at R3 and R5 and an acyl chain with 6 carbons at position R1, an acyl chain with 6 carbons at position R2 and an acyl chain with 6 carbons at position R4. Suitably, the sucrose ester has an acetyl at R3 and an acetyl or hydrogen at R5. Suitably, the sucrose ester has an acetyl at R3 and a hydrogen at R5. In one embodiment, the sucrose ester is a (branched chain) beta-methylvaleryl containing sucrose ester.

In one embodiment, the sucrose ester has the general structure shown in FIG. 5 and wherein each of R1 to R5 is any one of the acyl chains selected from the group consisting of acetyl, butyryl, propionyl or an isomer thereof, isobutyryl, valeryl (pentanoyl), 2-methyl-butyryl, isovaleryl, isopentenoyl, pentenoyl, hexanoyl or an isomer thereof 2-methylvaleryl, beta-methylvaleryl and 4-methylvaleryl. In another embodiment, the sucrose ester has the general structure shown in FIG. 5 and wherein R3 is acetyl and each of R1, R2, R4 and R5 is any one of the acyl chains selected from the group consisting of acetyl, butyryl, propionyl or an isomer thereof, isobutyryl, valeryl (pentanoyl), 2-methyl-butyryl, isovaleryl, isopentenoyl, pentenoyl, hexanoyl or an isomer thereof 2-methylvaleryl, beta-methylvaleryl and 4-methylvaleryl. In one embodiment, it is preferred that the acyl chain with 6 carbons is a branched chain. In another embodiment, it is preferred that the acyl chain with 6 carbons is beta-methylvaleryl.

In another embodiment, the sucrose ester has the general structure shown in FIG. 5 and wherein R3 is hydrogen or acetyl, R5 is hydrogen or acetyl and each of R1, R2 and R4 is any one of the acyl chains selected from the group consisting of acetyl, butyryl, propionyl or an isomer thereof, isobutyryl, valeryl (pentanoyl) or an isomer thereof, 2-methyl-butyryl, isovaleryl, isopentenoyl, pentenoyl, hexanoyl or an isomer thereof 2-methylvaleryl, beta-methylvaleryl and 4-methylvaleryl. Individual sucrose esters are disclosed in Table 1 and FIG. 2.

In another embodiment, the sucrose ester has the general structure shown in FIG. 5 and wherein R3 is acetyl, R5 is hydrogen or acetyl and each of R1, R2 and R4 is any one of the acyl chains selected from the group consisting of acetyl, butyryl, propionyl or an isomer thereof, isobutyryl, valeryl (pentanoyl) or an isomer thereof, 2-methyl-butyryl, isovaleryl, isopentenoyl, pentenoyl, hexanoyl or an isomer thereof 2-methylvaleryl, beta-methylvaleryl and 4-methylvaleryl.

In another embodiment, the sucrose ester has the general structure shown in FIG. 5 and wherein R3 is acetyl, R5 is hydrogen or acetyl; R1 is butyryl, propionyl or an isomer thereof, valeryl (pentanoyl) or an isomer thereof, or hexanoyl or an isomer thereof; R2 is propionyl or an isomer thereof, valeryl (pentanoyl) or an isomer thereof, or hexanoyl or an isomer thereof; and R4 is valeryl (pentanoyl) or an isomer thereof or hexanoyl or an isomer thereof.

In another embodiment, the sucrose ester has the general structure shown in FIG. 5 and wherein R3 is acetyl, R5 is hydrogen or acetyl; R1 is propionyl or an isomer thereof, valeryl (pentanoyl) or an isomer thereof, or hexanoyl or an isomer thereof; R2 is valeryl (pentanoyl) or an isomer thereof, or hexanoyl or an isomer thereof; and R4 is hexanoyl or an isomer thereof.

In one embodiment, the sucrose ester that is modulated has the general structure shown in FIG. 5 wherein R3=acetyl, R1=propionyl or an isomer thereof, R2=propionyl or an isomer thereof, R4=hexanoyl or an isomer thereof and R5 is hydrogen or acetyl; or a sucrose ester as shown in FIG. 5 wherein R3=acetyl, R1=propionyl or an isomer thereof, R2=valeryl or an isomer thereof, R4=valeryl or an isomer thereof and R5 is hydrogen or acetyl; or a sucrose ester as shown in FIG. 5 wherein R3=acetyl, R1=butyryl, R2=valeryl or an isomer thereof, R4=hexanoyl or an isomer thereof and R5 is hydrogen or acetyl (C2C14:0).

In one embodiment, the sucrose ester has the general structure shown in FIG. 5 wherein R3=acetyl, R1=propionyl or an isomer thereof, R2=valeryl or an isomer thereof, R4=hexanoyl or an isomer thereof and R5 is hydrogen or acetyl; or a sucrose ester as shown in FIG. 5 wherein R3=acetyl, R1=valeryl or an isomer thereof, R2=valeryl or an isomer thereof, R4=valeryl or an isomer thereof and R5 is hydrogen or acetyl; or a sucrose ester as shown in FIG. 5 wherein R3=acetyl, R1=butyrl, R2=hexanoyl or an isomer thereof, R4=hexanoyl or an isomer thereof and R5 is hydrogen or acetyl (C12C15:0).

In one embodiment, the sucrose ester has the general structure shown in FIG. 5 and wherein R3 is acetyl, R1 is valeryl or an isomer thereof, R2 is valeryl or an isomer thereof, R4 is hexanoyl or an isomer thereof and R5 is either a hydrogen atom or an acetyl moiety (C2C16:0) In one embodiment, the sucrose ester that is modulated has the general structure shown in FIG. 5 and wherein R3 is acetyl, R1 is propionyl or an isomer thereof, R2 is hexanoyl or an isomer thereof, R4 is hexanoyl or an isomer thereof and R5 is either a hydrogen atom or an acetyl moiety (C2C16:0).

In one embodiment, the sucrose ester has the general structure shown in FIG. 5 and wherein R3 is acetyl, R1 is valeryl or an isomer thereof, R2 is hexanoyl or an isomer thereof, R4 is hexanoyl or an isomer thereof and R5 is either a hydrogen atom or an acetyl moiety (C2C17:0).

In one embodiment, the sucrose ester that is modulated has the general structure shown in FIG. 5 and wherein R3 is acetyl, R1 is hexanoyl or an isomer thereof, R2 is hexanoyl or an isomer thereof, R4 is hexanoyl or an isomer thereof and R5 is either a hydrogen atom or an acetyl moiety (C2C18:0).

In another embodiment the sucrose ester has a molecular weight of from about 594 Daltons to 692 Daltons. In one embodiment, the sucrose ester has a molecular weight of from about 608 Daltons to 692 Daltons. In one embodiment, the sucrose ester has a molecular weight of from about 622 Daltons to 692 Daltons. In one embodiment, the sucrose ester has a molecular weight of from about 636 Daltons to 692 Daltons. In one embodiment, the sucrose ester has a molecular weight of from about 650 Daltons to 692 Daltons. In one embodiment, the sucrose ester has a molecular weight of from about 650 Daltons to 678 Daltons. In another embodiment the sucrose ester has a molecular weight of from about 594 Daltons to 678 Daltons. In one embodiment, the sucrose ester has a molecular weight of from about 608 Daltons to 678 Daltons. In one embodiment, the sucrose ester has a molecular weight of from about 622 Daltons to 678 Daltons. In one embodiment, the sucrose ester has a molecular weight of from about 636 Daltons to 678 Daltons. In one embodiment, the sucrose ester has a molecular weight of from about 650 Daltons to 678 Daltons. In one embodiment, the sucrose ester has a molecular weight of from about 664 Daltons to 678 Daltons.

A further aspect relates to a method for modulating the flavour of tobacco or a tobacco product comprising adding compositions of sucrose esters described herein thereto.

In another embodiment, the concentration, levels or production of the sucrose esters in a plant are increased. In another embodiment, the concentration, levels or production of the sucrose esters in a plant are decreased.

In one specific embodiment, compositions and methods for producing mutant, non-naturally occurring or transgenic plants that have been modified to increase isopropylmalate synthase expression or activity are provided which can result in plants or plant material in which the concentration, levels or production of sucrose esters are increased. Specifically, the levels or the production of the sucrose esters described herein are increased or induced.

In another specific embodiment, compositions and methods for producing mutant, non-naturally occurring or transgenic plants that have been modified to reduce or inhibit isopropylmalate synthase expression or activity are provided which can result in plants or plant material in which the concentration, levels or production of sucrose esters are reduced. Specifically, the levels of the sucrose esters described herein are decreased or abolished.

Advantageously, the mutant, non-naturally occurring or transgenic plants that are obtained according to the methods described herein are similar or substantially the same in visual appearance to the control plants. In one embodiment, the stalk height of the mutant, non-naturally occurring or transgenic plants is substantially the same as the control plants at, for example, one, two or three or more months after field transplant or 10, 20, 30 or 36 or more days after topping. For example, the stalk height of the mutant, non-naturally occurring or transgenic plants is not less than the stalk height of the control plants. In another embodiment, the chlorophyll content of the mutant, non-naturally occurring or transgenic plants is substantially the same as the control plants. In another embodiment, the stalk height of the mutant, non-naturally occurring or transgenic plants is substantially the same as the control plants and the chlorophyll content of the mutant, non-naturally occurring or transgenic plants is substantially the same as the control plants. In other embodiments, the size or form or number or colouration of the leaves of the mutant, non-naturally occurring or transgenic plants is substantially the same as the control plants. Suitably, the plant is a tobacco plant.

In another aspect, there is provided a method for modulating the sucrose ester content—such as the beta-methylvaleryl sucrose ester content—in at least a part of a plant, comprising the steps of: (i) modulating the expression or activity of isopropylmalate synthase in the plant, preferably, wherein the isopropylmalate synthase comprises the polynucleotide sequence described herein or the polypeptide sequence described herein; (ii) optionally measuring the sucrose ester content in at least a part of the mutant, non-naturally occurring or transgenic plant obtained in step (i); and (iii) identifying a mutant, non-naturally occurring or transgenic plant in which the sucrose ester content therein has been modulated in comparison to a control plant. Suitably, the visual appearance of said mutant, non-naturally occurring or transgenic plant is substantially the same as the control plant. Suitably, the plant is a tobacco plant.

In another aspect, there is provided a method for increasing the sucrose ester content—such as the beta-methylvaleryl sucrose ester content—in at least a part of a plant (for example, the leaves), comprising the steps of: (i) increasing the expression or activity of isopropylmalate synthase in the plant, preferably, wherein the isopropylmalate synthase comprises the polynucleotide sequence described herein or the polypeptide sequence described herein; (ii) optionally measuring the sucrose ester content in at least a part of the mutant, non-naturally occurring or transgenic plant obtained in step (i); and (iii) identifying a mutant, non-naturally occurring or transgenic plant in which the sucrose ester content therein has been increased in comparison to a control plant.

In another aspect, there is provided a method for decreasing the sucrose ester content—such as the beta-methylvaleryl sucrose ester content—in at least a part of a plant, comprising the steps of: (i) reducing the expression or activity of isopropylmalate synthase in the plant, preferably, wherein the isopropylmalate synthase comprises the polynucleotide sequence described herein or the polypeptide sequence described herein; (ii) optionally measuring the sucrose ester content in at least a part of the mutant, non-naturally occurring or transgenic plant obtained in step (i); and (iii) identifying a mutant, non-naturally occurring or transgenic plant in which the sucrose ester content therein has been decreased in comparison to a control plant.

Advantageously, the methods described herein can also be used to generate plants which have oriental traits by increasing the expression or activity of isopropylmalate synthase. Thus, according to this embodiment, a non-oriental plant variety such as a flue cured or a burley variety plant—can be engineered such that the expression or activity of isopropylmalate synthase is increased therein. The may impart oriental traits into plants which can be advantageous since this may change (for example, increase or enhance) the oriental flavour thereof, thereby producing new aromatic plant lines, varieties or hybrids.

The methods described herein can also be used to generate plants in which the oriental traits are reduced, inhibited or abolished by decreasing the expression or activity of isopropylmalate synthase. Thus, according to this embodiment, an oriental plant variety can be engineered such that the expression or activity of isopropylmalate synthase is decreased therein. The reduction or abolishment of oriental traits into plants can be advantageous since this may change or reduce the oriental flavour thereof, thereby producing new aromatic plant lines, varieties or hybrids.

The increase in expression of isopropylmalate synthase as compared to the control plant may be from about 5% to about 100% or more, or an increase of at least 10%, at least 20%, at least 25%, at least 30%, at least 40%, at least 50%, at least 60%, at least 70%, at least 75%, at least 80%, at least 90%, at least 95%, at least 98%, 100%, 150%, or 200% or more which includes an increase in transcriptional activity or protein expression or both.

The increase in the activity of isopropylmalate synthase as compared to a control plant may be from about 5% to about 100% or more, or an increase of at least 10%, at least 20%, at least 25%, at least 30%, at least 40%, at least 50%, at least 60%, at least 70%, at least 75%, at least 80%, at least 90%, at least 95%, at least 98%, 100%, 150%, or 200% or more or more.

The reduction in expression of isopropylmalate synthase as compared to the control plant may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100%, which includes a reduction in transcriptional activity or protein expression or both.

The reduction in activity of isopropylmalate synthase as compared to a control plant may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100% or more.

The increase in sucrose ester content as compared to a control plant may be from about 5% to about 100%, or an increase of at least 10%, at least 20%, at least 25%, at least 30%, at least 40%, at least 50%, at least 60%, at least 70%, at least 75%, at least 80%, at least 90%, at least 95%, at least 98%, or up to 100%.

The decrease in sucrose ester content as compared to a control plant may be from about 5% to about 100%, or a decrease of at least 10%, at least 20%, at least 25%, at least 30%, at least 40%, at least 50%, at least 60%, at least 70° A), at least 75%, at least 80%, at least 90%, at least 95° A), at least 98%, or up to 100%.

Polynucleotides and recombinant constructs described herein can be used to modulate the expression of isopropylmalate synthase described herein in a plant species of interest, suitably tobacco.

One aspect is a seed of a mutant plant, a non-naturally occurring plant, a hybrid plant, a transgenic plant of the disclosure. Preferably, the seed is a tobacco seed. A further aspect is pollen or an ovule of a mutant plant, a non-naturally occurring plant, a hybrid plant, a transgenic plant of the disclosure. In addition, the present invention provides a mutant plant, a non-naturally occurring plant, a hybrid plant, a transgenic plant as described which further comprises a nucleic acid conferring male sterility.

The disclosure also provides a tissue culture of regenerable cells of the mutant plant, non-naturally occurring plant, hybrid plant, or transgenic plant or a part thereof, of the present invention, which culture regenerates plants capable of expressing all the morphological and physiological characteristics of the parent. The regenerable cells include but are not limited to cells from leaves, pollen, embryos, cotyledons, hypocotyls, roots, root tips, anthers, flowers and a part thereof, ovules, shoots, stems, stalks, pith and capsules or callus or protoplasts derived therefrom.

According to the disclosure, a plant carrying a mutant isopropylmalate synthase allele can be used in a plant breeding program to create useful lines, varieties and hybrids. In particular, the mutant isopropylmalate synthase allele may be introgressed into the commercially important varieties described above. Thus, methods for breeding plants are provided, that comprise crossing, breeding or introgressing a mutant plant, a non-naturally occurring plant or a transgenic plant as described herein with another plant— such as a plant with a different genetic identity, a different genetic background, a different variety, a different line or a different hybrid. One method comprises crossing, breeding or introgressing a mutant plant, a non-naturally occurring plant or a transgenic plant as described herein with a cultivar or elite cultivar or a plant of the genus *Nicotiana*—such as *Nicotiana tabacum* (for example, Burley type). The method may further comprise crossing the progeny plant with another plant, and optionally repeating the crossing until a progeny with the desirable genetic traits or genetic background is obtained. The method may further comprise the step of identifying a plant in which the expression or activity of isopropylmalate synthase is modulated. The method may further comprise the step of selecting a plant in which the expression or activity of isopropylmalate synthase is modulated as compared to a control plant. One purpose served by such breeding methods is to introduce a desirable genetic trait into other varieties, breeding lines, hybrids or cultivars, particularly those that are of commercial interest. Another purpose is to facilitate stacking of genetic modifications of different genes in a single plant variety, lines, hybrids or cultivars. Intraspecific as well as interspecific matings are contemplated. The progeny plants that arise from such crosses, also referred to as breeding lines, are examples of non-naturally occurring plants of the disclosure.

In one embodiment, a method is provided for producing a non-naturally occurring plant comprising: (a) crossing a mutant or transgenic plant with a second plant to yield progeny tobacco seed; (b) growing the progeny tobacco seed, under plant growth conditions, to yield the non-naturally occurring plant. The method may further comprise the optional step of identifying a plant in which the expression or activity of isopropylmalate synthase is modulated. The method may further comprise the optional step of selecting a plant in which the expression or activity of isopropylmalate synthase is modulated as compared to a control plant. The method may further comprise: (c) crossing the previous generation of non-naturally occurring plant with itself or another plant to yield progeny tobacco seed; (d) growing the progeny tobacco seed of step (c) under plant growth conditions, to yield additional non-naturally occurring plants; and (e) repeating the crossing and growing steps of (c) and (d) multiple times to generate further generations of non-naturally occurring plants. The method may optionally comprises prior to step (a), a step of providing a parent plant which comprises a genetic identity that is characterized and that is not identical to the mutant or transgenic plant. In some embodiments, depending on the breeding program, the crossing and growing steps are repeated from 0 to 2 times, from 0 to 3 times, from 0 to 4 times, 0 to 5 times, from 0 to 6 times, from 0 to 7 times, from 0 to 8 times, from 0 to 9 times or from 0 to 10 times, in order to generate generations of non-naturally occurring plants. Backcrossing is an example of such a method wherein a progeny is crossed with one of its parents or another plant genetically similar to its parent, in order to obtain a progeny plant in the next generation that has a genetic identity which is closer to that of one of the parents. Techniques for plant breeding, particularly tobacco plant breeding, are well known and can be used in the methods described. The disclosure further provides non-naturally occurring plants produced, obtained or obtainable by these methods.

In some embodiments of methods described herein, lines resulting from breeding and screening for variant isopropylmalate synthase genes are evaluated in the field using standard field procedures. Control genotypes including the original unmutagenised parent are included and entries are arranged in the field in a randomised complete block design or other appropriate field design. For tobacco, standard agronomic practices are used, for example, the tobacco is harvested, weighed, and sampled for chemical and other common testing before and during curing. Statistical analyses of the data are performed to confirm the similarity of the selected lines to the parental line. Cytogenetic analyses of the selected plants are optionally performed to confirm the chromosome complement and chromosome pairing relationships.

In one embodiment, the plants that are obtained or obtainable by the breeding, crossing or introgressing methods described above will not produce cis-abienol, will not substantially produce cis-abienol or will not produce detectable levels of cis-abienol. In another embodiment, the sucrose ester compositions and the sucrose ester compositions obtained or obtainable by the methods described herein will not comprise or contain cis-abienol, will not comprise or contain substantial levels of cis-abienol or will not comprise or contain detectable levels of cis-abienol. Thus, the cis-abienol trait may be present or it may be absent.

DNA fingerprinting, single nucleotide polymorphism, microsatellite markers, or similar technologies may be used in a marker-assisted selection (MAS) breeding program to transfer or to breed mutant alleles of the isopropylmalate synthase gene into other tobaccos, as described herein. For example, a breeder can create segregating populations from hybridizations of a genotype containing a mutant allele with an agronomically desirable genotype. Plants in the F2 or backcross generations can be screened using a marker developed from an isopropylmalate synthase genomic sequence or a fragment thereof, using one of the techniques listed herein. Plants identified as possessing the mutant allele can be backcrossed or self-pollinated to create a second population to be screened. Depending on the expected inheritance pattern or the MAS technology used, it may be necessary to self-pollinate the selected plants before each cycle of backcrossing to aid identification of the desired individual plants. Backcrossing or other breeding procedure can be repeated until the desired phenotype of the recurrent parent is recovered.

According to the disclosure, in a breeding program, successful crosses yield F1 plants that are fertile. Selected F1 plants can be crossed with one of the parents, and the first backcross generation plants are self-pollinated to produce a population that is again screened for variant isopropylmalate synthase gene expression (for example, the null version of the isopropylmalate synthase gene). The process of backcrossing, self-pollination, and screening is repeated, for example, at least 4 times until the final screening produces a plant that is fertile and reasonably similar to the recurrent parent. This plant, if desired, is self-pollinated and the progeny are subsequently screened again to confirm that the plant exhibits variant isopropylmalate synthase gene expression. In some embodiments, a plant population in the F2 generation is screened for variant isopropylmalate synthase gene expression, for example, a plant is identified that fails to express isopropylmalate synthase due to the absence of a isopropylmalate synthase gene according to standard methods, for example, by using a PCR method with primers based upon the nucleotide sequence information for isopropylmalate synthase described herein.

Hybrid tobacco varieties can be produced by preventing self-pollination of female parent plants (that is, seed parents) of a first variety, permitting pollen from male parent plants of a second variety to fertilize the female parent plants, and allowing F1 hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), or transgenic male sterility wherein a transgene inhibits microsporogenesis and/or pollen formation, or self-incompatibility. Female parent plants containing CMS are particularly useful. In embodiments in which the female parent plants are CMS, pollen is harvested from male fertile plants and applied manually to the stigmas of CMS female parent plants, and the resulting F1 seed is harvested.

Varieties and lines described herein can be used to form single-cross tobacco F1 hybrids. In such embodiments, the plants of the parent varieties can be grown as substantially homogeneous adjoining populations to facilitate natural cross-pollination from the male parent plants to the female parent plants. The F1 seed formed on the female parent plants is selectively harvested by conventional means. One also can grow the two parent plant varieties in bulk and harvest a blend of F1 hybrid seed formed on the female parent and seed formed upon the male parent as the result of self-pollination. Alternatively, three-way crosses can be carried out wherein a single-cross F1 hybrid is used as a female parent and is crossed with a different male parent. As another alternative, double-cross hybrids can be created wherein the F1 progeny of two different single-crosses are themselves crossed.

A population of mutant, non-naturally occurring or transgenic plants can be screened or selected for those members of the population that have a desired trait or phenotype. For example, a population of progeny of a single transformation event can be screened for those plants having a desired level of expression of a polypeptide or polynucleotide. Physical and biochemical methods can be used to identify expression levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides or polynucleotides.

Mutant, non-naturally occurring or transgenic plant cells and plants are described herein comprising one or more recombinant polynucleotides—such as one or more isolated polynucleotides described herein, one or more polynucleotide constructs, one or more double-stranded RNAs, one or more conjugates or one or more vectors/expression vectors.

Gene expression can be evaluated using methods including, for example, RT-PCR, Northern blots, RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, for example, at a particular time in development or upon induction, expression can be evaluated selectively at a desired time period.

Without limitation, the plants described herein may be modified for other purposes either before or after the expression or activity has been modulated. One or more of the following genetic modifications can be present in the mutant, non-naturally occurring or transgenic plants of the disclosure. In one embodiment, one or more genes that are involved in heavy metal uptake or heavy metal transport is modified resulting in plants or parts of plants (such as leaves) having a lower heavy metal content than control plants or parts thereof without the modification(s). Non-limiting examples include genes in the family of cation diffusion facilitators (CDF), the family of Zrt-, Irt-like proteins (ZIP), the family of cation exchangers (CAX), the family of copper transporters (COPT), the family of heavy-metal P-type ATPases (HMAs, as described in WO2009074325), the family of homologs of natural resistance-associated macrophage proteins (NRAMP), and the family of ATP-binding cassette (ABC) transporters, which participate in transport of heavy metals, such as cadmium. The term heavy metal as used herein includes transition metals. In another embodiment, one or more genes that are involved in the conversion of nitrogenous metabolic intermediates is modified resulting in plants or parts of plants (such as leaves) that when heated, produces lower levels of at least one tobacco-specific nitrosamine (for example, 4-(methylnitrosamino)-1-(3-pyridyl)-1-butanone, N-nitrosonornicotine, N-nitrosoanatabine, and N-nitrosoanabasine) than control plants or parts thereof. Non-limiting examples of genes that can be modified include genes encoding a nicotine demethylase, such as CYP82E4, CYP82E5 and CYP82E10 which participate in the conversion of nicotine to nornicotine and are described in WO2006091194, WO2008070274, WO2009064771 and PCT/US2011/021088.

Examples of other modifications include herbicide tolerance, for example, glyphosate is an active ingredient of many broad spectrum herbicides. Glyphosate resistant transgenic plants have been developed by transferring the aroA gene (a glyphosate EPSP synthetase from *Salmonella typhimurium* and *E. coli*). Sulphonylurea resistant plants have been produced by transforming the mutant ALS (acetolactate synthetase) gene from *Arabidopsis*. OB protein of photosystem II from mutant *Amaranthus hybridus* has been transferred in to plants to produce atrazine resistant transgenic plants; and bromoxynil resistant transgenic plants have been produced by incorporating the bxn gene from the bacterium *Klebsiella pneumoniae*. Another exemplary modification results in plants that are resistant to insects. *Bacillus thuringiensis* (Bt) toxins can provide an effective way of delaying the emergence of Bt-resistant pests, as recently illustrated in broccoli where pyramided cry1Ac and cry1C Bt genes controlled diamondback moths resistant to either single protein and significantly delayed the evolution of resistant insects. Another exemplary modification results in plants that are resistant to diseases caused by pathogens (for example, viruses, bacteria, fungi). Plants expressing the Xa21 gene (resistance to bacterial blight) with plants expressing both a Bt fusion gene and a chitinase gene (resistance to yellow stem borer and tolerance to sheath) have been engineered. Another exemplary modification results in altered reproductive capability, such as male sterility. Another exemplary modification results in plants that are tolerant to abiotic stress (for example, drought, temperature, salinity), and tolerant transgenic plants have been produced by transferring acyl glycerol phosphate enzyme from *Arabidopsis*; genes coding mannitol dehydrogenase and sorbitol dehydrogenase which are involved in synthesis of mannitol and sorbitol improve drought resistance. Another exemplary modification results in plants that produce proteins which have favourable immunogenic properties for use in humans. For example, plants capable of producing proteins which substantially lack alpha-1,3-linked fucose residues, beta-1,2-linked xylose residues, or both, in its N-glycan may be of use. Other exemplary modifications can result in plants with improved storage proteins and oils, plants with enhanced photosynthetic efficiency, plants with prolonged shelf life, plants with enhanced carbohydrate content, and plants resistant to fungi; plants encoding an enzyme involved in the biosynthesis of alkaloids. Transgenic plants in which the expression of S-adenosyl-L-methionine (SAM) and/or cystathionine gamma-synthase (CGS) has been modulated are also contemplated.

One or more such traits may be introgressed into the mutant, non-naturally occurring or transgenic plants from another plant or tobacco cultivar or may be directly transformed into it. The introgression of the trait(s) into the mutant, non-naturally occurring or transgenic plants may be achieved by any method of plant breeding known in the art, for example, pedigree breeding, backcrossing, doubled-haploid breeding, and the like (see, Wernsman, E. A, and Rufty, R. C. 1987. Chapter Seventeen. Tobacco. Pages 669-698 In: *Cultivar Development. Crop Species*. W. H. Fehr (ed.), MacMillan Publishing Co, Inc., New York, N.Y. 761 pp.). Molecular biology-based techniques described above, in particular RFLP and microsatelite markers, can be used in such backcrosses to identify the progenies having the highest degree of genetic identity with the recurrent parent. This permits one to accelerate the production of tobacco varieties having at least 90%, preferably at least 95%, more preferably at least 99% genetic identity with the recurrent parent, yet more preferably genetically identical to the recurrent parent, and further comprising the trait(s) introgressed from the donor parent. Such determination of genetic identity can be based on molecular markers known in the art.

The last backcross generation can be selfed to give pure breeding progeny for the nucleic acid(s) being transferred. The resulting plants generally have essentially all of the morphological and physiological characteristics of the mutant, non-naturally occurring or transgenic plants of the disclosure, in addition to the transferred trait(s) (for example, one or more single gene traits). The exact backcrossing protocol will depend on the trait being altered to determine an appropriate testing protocol. Although backcrossing methods are simplified when the trait being transferred is a dominant allele, a recessive allele may also be transferred. In this instance, it may be necessary to introduce a test of the progeny to determine if the desired trait has been successfully transferred.

A plant or plant cell can be transformed by having the recombinant polynucleotide integrated into its genome to become stably transformed. Stably transformed cells typically retain the introduced polynucleotide with each cell division. A plant or plant cell may also be transiently transformed such that the recombinant polynucleotide is not integrated into its genome. Transiently transformed cells typically lose all or some portion of the introduced recombinant polynucleotide with each cell division such that the introduced recombinant polynucleotide cannot be detected in daughter cells after a sufficient number of cell divisions.

Conjugated moieties including macromolecular compounds such as proteins (for example, antibodies), fatty acid chains, sugar residues, glycoproteins, polymers (for example, polyethylene glycol), or combinations thereof are disclosed. An oligonucleotide may be conjugated to a moiety that increases cellular uptake of the oligonucleotide. Non-limiting examples of moieties include, but are not limited to, antibodies, polypeptides, lipid moieties such as a cholesterol moiety, cholic acid, a thioether, for example, hexyl-s-tritylthiol, a thiocholesterol, an aliphatic chain, for example, dodecandiol or undecyl residues, a phospholipid, a polyamine or a polyethylene glycol chain, an adamantane acetic acid, a palmityl moiety, an octadecylamine or a hexylamino-carbonyl-oxycholesterol moiety. The moiety may be a positively charged polymer—such as a positively charged peptide that is, for example, about 1 to 50 amino acid residues in length or polyalkylene oxide such as polyethylene glycol (PEG) or polypropylene glycol. Suitably the positively charged polymer, such as a polyalkylene oxide may be attached to the oligomer via a linker such as a releasable linker.

When polypeptide expression is being measured, detecting the amount of mRNA encoding a polypeptide in the cell can be quantified by, for example, PCR or Northern blot. Where a change in the amount of a polypeptide in the sample is being measured, detecting it by use of antibodies can be used to quantify the amount of polypeptide in the cell using known techniques. Alternatively the biological activity of the enzyme can be measured using methods that are well known in the art.

In another embodiment, antibodies that are immunoreactive with the polypeptides are provided herein. The polypeptides, fragments, variants, fusion polypeptides, and the like, as set forth herein, can be employed as "immunogens" in producing antibodies immunoreactive therewith. Such antibodies may specifically bind to the polypeptide via the antigen-binding sites of the antibody. Specifically binding antibodies are those that will specifically recognize and bind with a polypeptide, homologues, and variants, but not with other molecules. In one embodiment, the antibodies are specific for polypeptides having an amino acid sequence as set forth herein and do not cross-react with other polypeptides.

More specifically, the polypeptides, fragment, variants, fusion polypeptides, and the like contain antigenic determinants or epitopes that elicit the formation of antibodies. These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon polypeptide folding. Epitopes can be identified by any of the methods known in the art. Additionally, epitopes from the polypeptides can be used as research reagents, in assays, and to purify specific binding antibodies from substances such as polyclonal sera or supernatants from cultured hybridomas. Such epitopes or variants thereof can be produced using techniques known in the art such as solid-phase synthesis, chemical or enzymatic cleavage of a polypeptide, or using recombinant DNA technology.

Both polyclonal and monoclonal antibodies to the polypeptides can be prepared by conventional techniques. Hybridoma cell lines that produce monoclonal antibodies specific for the polypeptides are also contemplated herein. Such hybridomas can be produced and identified by conventional techniques. For the production of antibodies, various host animals may be immunized by injection with a polypeptide, fragment, variant, or mutants thereof. Such host animals may include, but are not limited to, rabbits, mice, and rats, to name a few. Various adjutants may be used to increase the immunological response. Depending on the host species, such adjutants include, but are not limited to, Freund's (complete and incomplete), mineral gels such as aluminium hydroxide, surface active substances such as lysolecithin, pluronic polyols, polyanions, peptides, oil emulsions, keyhole limpet hemocyanin, dinitrophenol, and potentially useful human adjutants such as BCG (bacille Calmette-Guerin) and *Corynebacterium parvum*. The monoclonal antibodies can be recovered by conventional techniques. Such monoclonal antibodies may be of any immunoglobulin class including IgG, IgM, IgE, IgA, IgD, and any subclass thereof.

The antibodies can also be used in assays to detect the presence of the polypeptides or fragments, either in vitro or in vivo. The antibodies also can be employed in purifying polypeptides or fragments by immunoaffinity chromatography.

Various embodiments provide mutant plants, non-naturally occurring plants or transgenic plants, as well as biomass in which the expression level of isopropylmalate synthase polynucleotide is modulated.

Parts of the such plants, particularly tobacco plants, and more particularly the leaf lamina and midrib of tobacco plants, can be incorporated into or used in making various consumable products including but not limited to aerosol forming materials, aerosol forming devices, smoking articles, smokable articles, smokeless products, and tobacco products. Examples of aerosol forming materials include but are not limited to tobacco compositions, tobaccos, tobacco extract, cut tobacco, cut filler, cured tobacco, expanded tobacco, homogenized tobacco, reconstituted tobacco, and pipe tobaccos. Smoking articles and smokable articles are types of aerosol forming devices. Examples of smoking articles or smokable articles include but are not limited to cigarettes, cigarillos, and cigars. Examples of smokeless products comprise chewing tobaccos, and snuffs. In certain aerosol forming devices, rather than combustion, a tobacco composition or another aerosol forming material is heated by one or more electrical heating elements to produce an aerosol. In another type of heated aerosol forming device, an aerosol is produced by the transfer of heat from a combustible fuel element or heat source to a physically separate aerosol forming material, which may be located within, around or downstream of the heat source. Smokeless tobacco products and various tobacco-containing aerosol forming materials may contain tobacco in any form, including as dried particles, shreds, granules, powders, or a slurry, deposited on, mixed in, surrounded by, or otherwise combined with other ingredients in any format, such as flakes, films, tabs, foams, or beads. As used herein, the term 'smoke' is used to describe a type of aerosol that is produced by smoking articles, such as cigarettes, or by combusting an aerosol forming material.

In one embodiment, there is also provided cured material from the mutant, transgenic and non-naturally occurring plants described herein. Processes of curing green tobacco leaves are known by those having skills in the art and include without limitation air-curing, fire-curing, flue-curing and sun-curing. The process of curing green tobacco leaves depends on the type of tobacco harvested. For example, Virginia flue (bright) tobacco is typically flue-cured, Burley and certain dark strains are usually air-cured, and pipe tobacco, chewing tobacco, and snuff are usually fire-cured.

In another embodiment, there is described tobacco products including tobacco-containing aerosol forming materials comprising leaves, preferably cured leaves, from the mutant tobacco plants, transgenic tobacco plants or non-naturally occurring tobacco plants described herein. The tobacco products described herein can be a blended tobacco product which may further comprise unmodified tobacco.

The % sucrose esters in these aerosol forming materials or tobacco compositions may be at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, and 100%, 150%, or 200% or higher, when compared to aerosol forming materials or tobacco compositions derived from non-mutant, non-naturally occurring or non-transgenic counterpart plants.

The % sucrose esters in these aerosol forming materials or tobacco compositions may be at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, and 100% lower, when compared to aerosol forming materials or tobacco compositions derived from non-mutant, non-naturally occurring or non-transgenic counterpart plants.

The mutant, non-naturally occurring or transgenic plants may have other uses in, for example, agriculture. For example, mutant, non-naturally occurring or transgenic plants described herein can be used to make animal feed and human food products.

The disclosure also provides methods for producing seeds comprising cultivating the mutant plant, non-naturally occurring plant, or transgenic plant described herein, and collecting seeds from the cultivated plants. Seeds from plants described herein can be conditioned and bagged in packaging material by means known in the art to form an article of manufacture. Packaging material such as paper and cloth are well known in the art. A package of seed can have a label, for example, a tag or label secured to the packaging material, a label printed on the packaging material, or a label inserted within the package, that describes the nature of the seeds therein. A further aspect relates to a method for producing a composition comprising sucrose esters comprising the steps of: (a) providing part of a mutant, non-naturally occurring or transgenic plant; biomass, seed or leaves; or the tobacco product as described herein; and (b) extracting the sucrose esters therefrom; and (c) optionally purifying the sucrose esters.

A further aspect relates to a method for producing beta-methylvaleric acid comprising the steps of: (a) providing part of a mutant, non-naturally occurring or transgenic plant; biomass, or leaves; or the aerosol forming material as described herein; (b) hydrolysing the material obtained in step (a) or an extract thereof; and (c) optionally collecting the beta-methylvaleric acid. Beta-methylvaleric acid can be used in the production of polyhydroxyalkanoates and the like which can give materials, including plastics, beneficial properties. The plastics that can be produced can be biodegradable and can therefore be used in the production of bioplastics. A bacterium—such as $E.\ coli$ or $Pseudomonas$—can be engineered to express the isopropylmalate synthase described herein. Suitably, the bacterium that is used may also be engineered to also produce polyhydroxyalkanoates. Methods for the production of polyhydroxyalkanotes using microbial systems are described in, for example, U.S. Pat. Nos. 5,750,848 and 6,492,134. Thus, one aspect relates to a bacterium comprising isopropylmalate synthase and optionally one or more genes for producing a polyhydroxyalkanoate. A further aspect relates to a method for producing polyhydroxyalkanoate comprising the use of the bacterium.

In one embodiment, there is also provided cured material from the mutant, transgenic and non-naturally occurring plants described herein. For example, processes of curing green tobacco leaves are known by those having skills in the field and include without limitation air-curing, fire-curing, flue-curing and sun-curing. The process of curing green tobacco leaves depends on the type of tobacco harvested. For example, Virginia flue (bright) tobacco is typically flue-cured, Burley and certain dark strains are usually air-cured, and pipe tobacco, chewing tobacco, and snuff are usually fire-cured.

In another embodiment, there is described tobacco products including tobacco products comprising leaves, for example cured leaves, from the mutant, transgenic and non-naturally occurring plants described herein or which are produced by the methods described herein. The tobacco products described herein may further comprise unmodified tobacco.

In another embodiment, there is described tobacco products comprising plant material, preferably leaves—such as cured leaves, from the mutant, transgenic and non-naturally occurring plants described herein. For example, the plant material may be added to the inside or outside of the tobacco product and so upon burning a desirable aroma is released. The tobacco product according to this embodiment may even be an unmodified tobacco or a modified tobacco. The tobacco product according to this embodiment may even be derived from a mutant, transgenic or non-naturally occurring plant which has modifications in one or more genes other than the genes disclosed herein.

A further aspect relates to an (isolated) sucrose ester composition comprising, consisting or consisting essentially of one or more of the sucrose esters described herein. The sucrose ester may be a sucrose ester in which the total number of carbons in the acyl chains at R1, R2 and R4 is 14; a sucrose ester in which the total number of carbons in the acyl chains at R1, R2 and R4 is 15; a sucrose ester in which the total number of carbons in the acyl chains at R1, R2 and R4 is 16; a sucrose ester in which the total number of carbons in the acyl chains at R1, R2 and R4 is 17; and a sucrose ester in which the total number of carbons in the acyl chains at R1, R2 and R4 is 18. Provided that this total number of carbons is present then the constituent acyl chains may be selected from any of those set forth in FIG. 6. Suitably, the sucrose ester has an acetyl at R3 and an acetyl or hydrogen at R5. Suitably, the sucrose ester has an acetyl at R3 and a hydrogen at R5. Suitably, one or more, two or more or three of more of the acyl chains will be beta-methylvaleryl. Thus, by way of example, the sucrose ester can be a sucrose ester as shown in FIG. 5 wherein R3=acetyl, R1=propionyl or an isomer thereof, R2=propionyl or an isomer thereof, R4=hexanoyl or an isomer thereof and R5 is hydrogen or acetyl; or a sucrose ester as shown in FIG. 5 wherein R3=acetyl, R1=propionyl or an isomer thereof, R2=valeryl or an isomer thereof, R4=valeryl or an isomer thereof and R5 is hydrogen or acetyl; or a sucrose ester as shown in FIG. 5 wherein R3=acetyl, R1=butyryl, R2=valeryl or an isomer thereof, R4=hexanoyl or an isomer thereof and R5 is hydrogen or acetyl (C2C14:0); a sucrose ester as shown in FIG. 5 wherein R3=acetyl, R1=propionyl or an isomer thereof, R2=valeryl or an isomer thereof, R4=hexanoyl or an isomer thereof and R5 is hydrogen or acetyl; or a sucrose ester as shown in FIG. 5 wherein R3=acetyl, R1=valeryl or an isomer thereof, R2=valeryl or an isomer thereof, R4=valeryl or an isomer thereof and R5 is hydrogen or acetyl; or a sucrose ester as shown in FIG. 5 wherein R3=acetyl, R1=butyrl, R2=hexanoyl or an isomer thereof, R4=hexanoyl or an isomer thereof and R5 is hydrogen or acetyl (C2C15:0); a sucrose ester that has the general structure shown in FIG. 5 and wherein R3 is acetyl, R1 is valeryl or an isomer thereof, R2 is valeryl or an isomer thereof, R4 is hexanoyl or an isomer thereof and R5 is either a hydrogen atom or an acetyl moiety (C2C16:0); or wherein the sucrose ester has the general structure shown in FIG. 5 and wherein R3 is acetyl, R1 is propionyl or an isomer thereof, R2 is hexanoyl or an isomer thereof, R4 is hexanoyl or an isomer thereof and R5 is either a hydrogen atom or an acetyl moiety (C2C16:0); a sucrose ester as shown in FIG. 5 wherein R3 is acetyl, R1 is valeryl or an isomer thereof, R2 is hexanoyl or an isomer thereof, R4 is hexanoyl or an isomer thereof and R5 is either a hydrogen atom or an acetyl moiety (C2C17:0); and a sucrose ester as shown in FIG. 5 wherein R3 is acetyl, R1 is hexanoyl or an isomer thereof, R2 is hexanoyl or an isomer thereof, R4 is hexanoyl or an isomer thereof and R5 is either a hydrogen atom or an acetyl moiety (C2C18:0).

Alternatively, the sucrose ester may be a sucrose ester in which the total number of carbons in the acyl chains at R1, R2 and R4 is 14; a sucrose ester in which the total number of carbons in the acyl chains at R1, R2 and R4 is 15; a sucrose ester in which the total number of carbons in the acyl chains at R1, R2 and R4 is 16; a sucrose ester in which the total number of carbons in the acyl chains at R1, R2 and R4 is 17; and a sucrose ester in which the total number of carbons in the acyl chains at R1, R2 and R4 is 18 is not present, is not substantially present or is not present at detectable levels (C2C18:0). Provided that this total number of carbons is present then the constituent acyl chains may be selected from any of those set forth in FIG. 6. Suitably, the sucrose ester has an acetyl at R3 and an acetyl or hydrogen at R5. Suitably, the sucrose ester has an acetyl at R3 and a hydrogen at R5. Suitably, one or more, two or more or three of more of the acyl chains will be beta-methylvaleryl. Thus, by way of example, the sucrose ester can be a sucrose ester as shown in FIG. 5 wherein R3=acetyl, R1=propionyl or an isomer thereof, R2=propionyl or an isomer thereof, R4=hexanoyl or an isomer thereof and R5 is hydrogen or acetyl; or a sucrose ester as shown in FIG. 5 wherein R3=acetyl, R1=propionyl or an isomer thereof, R2=valeryl or an isomer thereof, R4=valeryl or an isomer thereof and R5 is hydrogen or acetyl; or a sucrose ester as shown in FIG. 5 wherein R3=acetyl, R1=butyryl, R2=valeryl or an isomer thereof, R4=hexanoyl or an isomer thereof and R5 is hydrogen or acetyl (C2C14:0); a sucrose ester as shown in FIG. 5 wherein R3=acetyl, R1=propionyl or an isomer thereof, R2=valeryl or an isomer thereof, R4=hexanoyl or an isomer thereof and R5 is hydrogen or acetyl; or a sucrose ester as shown in FIG. 5 wherein R3=acetyl, R1=valeryl or an isomer thereof, R2=valeryl or an isomer thereof, R4=valeryl or an isomer thereof and R5 is hydrogen or acetyl; or a sucrose ester as shown in FIG. 5 wherein R3=acetyl, R1=butyrl, R2=hexanoyl or an isomer thereof, R4=hexanoyl or an isomer thereof and R5 is hydrogen or acetyl (C2C15:0); a sucrose ester that has the general structure shown in FIG. 5 and wherein R3 is acetyl, R1 is valeryl or an isomer thereof, R2 is valeryl or an isomer thereof, R4 is hexanoyl or an isomer thereof and R5 is either a hydrogen atom or an acetyl moiety (C2C16:0); or wherein the sucrose ester has the general structure shown in FIG. 5 and wherein R3 is acetyl, R1 is propionyl or an isomer thereof, R2 is hexanoyl or an isomer thereof, R4 is hexanoyl or an isomer thereof and R5 is either a hydrogen atom or an acetyl moiety (C2C16:0); a sucrose ester as shown in FIG. 5 wherein R3 is acetyl, R1 is valeryl or an isomer thereof, R2 is hexanoyl or an isomer thereof, R4 is hexanoyl or an isomer thereof and R5 is either a hydrogen atom or an acetyl moiety (C2C17:0); and wherein a sucrose ester as shown in FIG. 5 wherein R3 is acetyl, R1 is hexanoyl or an isomer thereof, R2 is hexanoyl or an isomer thereof, R4 is hexanoyl or an isomer thereof and R5 is either a hydrogen atom or an acetyl moiety is not present, is not substantially present or is not present at detectable levels (C2C18:0).

Alternatively, the sucrose ester may be a sucrose ester in which the total number of carbons in the acyl chains at R1, R2 and R4 is 14; a sucrose ester in which the total number of carbons in the acyl chains at R1, R2 and R4 is 15; a sucrose ester in which the total number of carbons in the acyl chains at R1, R2 and R4 is 16; a sucrose ester in which the total number of carbons in the acyl chains at R1, R2 and R4 is 17 is not present, is not substantially present or is not present at detectable levels; and a sucrose ester in which the total number of carbons in the acyl chains at R1, R2 and R4 is 18 is not present, is not substantially present or is not present at detectable levels. Provided that this total number of carbons is present then the constituent acyl chains may be selected from any of those set forth in FIG. 6. Suitably, the sucrose ester has an acetyl at R3 and an acetyl or hydrogen at R5. Suitably, the sucrose ester has an acetyl at R3 and a hydrogen at R5. Suitably, one or more, two or more or three of more of the acyl chains will be beta-methylvaleryl. Thus, by way of example, the sucrose ester can be a sucrose. ester as shown in FIG. 5 wherein R3=acetyl, R1=propionyl or an isomer thereof, R2=propionyl or an isomer thereof, R4=hexanoyl or an isomer thereof and R5 is hydrogen or acetyl; or a sucrose ester as shown in FIG. 5 wherein R3=acetyl, R1=propionyl or an isomer thereof, R2=valeryl or an isomer thereof, R4=valeryl or an isomer thereof and R5 is hydrogen or acetyl; or a sucrose ester as shown in FIG. 5 wherein R3=acetyl, R1=butyryl, R2=valeryl or an isomer thereof, R4=hexanoyl or an isomer thereof and R5 is hydrogen or acetyl (C2C14:0); a sucrose ester as shown in FIG. 5 wherein R3=acetyl, R1=propionyl or an isomer thereof, R2=valeryl or an isomer thereof, R4=hexanoyl or an isomer thereof and R5 is hydrogen or acetyl; or a sucrose ester as shown in FIG. 5 wherein R3=acetyl, R1=valeryl or an isomer thereof, R2=valeryl or an isomer thereof, R4=valeryl or an isomer thereof and R5 is hydrogen or acetyl; or a sucrose ester as shown in FIG. 5 wherein R3=acetyl, R1=butyrl, R2=hexanoyl or an isomer thereof, R4=hexanoyl or an isomer thereof and R5 is hydrogen or acetyl (C2C15:0); a sucrose ester that has the general structure shown in FIG. 5 and wherein R3 is acetyl, R1 is valeryl or an isomer thereof, R2 is valeryl or an isomer thereof, R4 is hexanoyl or an isomer thereof and R5 is either a hydrogen atom or an acetyl moiety (C2C16:0); or wherein the sucrose ester has the general structure shown in FIG. 5 and wherein R3 is acetyl, R1 is propionyl or an isomer thereof, R2 is hexanoyl or an isomer thereof, R4 is hexanoyl or an isomer thereof and R5 is either a hydrogen atom or an acetyl moiety (C2C16:0); a sucrose ester as shown in FIG. 5 wherein R3 is acetyl, R1 is valeryl or an isomer thereof, R2 is hexanoyl or an isomer thereof, R4 is hexanoyl or an isomer thereof and R5 is either a hydrogen atom or an acetyl moiety is not present, is not substantially present or is not present at detectable levels (C2C17:0); and wherein a sucrose ester as shown in FIG. 5 wherein R3 is acetyl, R1 is hexanoyl or an isomer thereof, R2 is hexanoyl or an isomer thereof, R4 is hexanoyl or an isomer thereof and R5 is either a hydrogen atom or an acetyl moiety is not present, is not substantially present or is not present at detectable levels (C2C18:0).

Alternatively, the sucrose ester may be a sucrose ester in which the total number of carbons in the acyl chains at R1, R2 and R4 is 14; a sucrose ester in which the total number of carbons in the acyl chains at R1, R2 and R4 is 15; a sucrose ester in which the total number of carbons in the acyl chains at R1, R2 and R4 is 16 is not present, is not substantially present or is not present at detectable levels; a sucrose ester in which the total number of carbons in the acyl chains at R1, R2 and R4 is 17 is not present, is not substantially present or is not present at detectable levels; and a sucrose ester in which the total number of carbons in the acyl chains at R1, R2 and R4 is 18 is not present, is not substantially present or is not present at detectable levels. Provided that this total number of carbons is present then the constituent acyl chains may be selected from any of those set forth in FIG. 6. Suitably, the sucrose ester has an acetyl at R3 and an acetyl or hydrogen at R5. Suitably, the sucrose ester has an acetyl at R3 and a hydrogen at R5. Suitably, one or more, two or more or three of more of the acyl chains will be beta-methylvaleryl. Thus, by way of example, the sucrose ester can be a sucrose ester as shown in FIG. 5 wherein R3=acetyl, R1=propionyl or an isomer thereof, R2=propionyl or an isomer thereof, R4=hexanoyl or an isomer thereof and R5 is hydrogen or acetyl; or a sucrose ester as shown in FIG. 5 wherein R3=acetyl, R1=propionyl or an isomer thereof, R2=valeryl or an isomer thereof, R4=valeryl or an isomer thereof and R5 is hydrogen or acetyl; or a sucrose ester as shown in FIG. 5 wherein R3=acetyl, R1=butyryl, R2=valeryl or an isomer thereof, R4=hexanoyl or an isomer thereof and R5 is hydrogen or acetyl (C2C14:0); a sucrose ester as shown in FIG. 5 wherein R3=acetyl, R1=propionyl or an isomer thereof, R2=valeryl or an isomer thereof, R4=hexanoyl or an isomer thereof and R5 is hydrogen or acetyl; or a sucrose ester as shown in FIG. 5 wherein R3=acetyl, R1=valeryl or an isomer thereof, R2=valeryl or an isomer thereof, R4=valeryl or an isomer thereof and R5 is hydrogen or acetyl; or a sucrose ester as shown in FIG. 5 wherein R3=acetyl, R1=butyrl, R2=hexanoyl or an isomer thereof, R4=hexanoyl or an isomer thereof and R5 is hydrogen or acetyl (C2C15:0); a sucrose ester that has the general structure shown in FIG. 5 and wherein R3 is acetyl, R1 is valeryl or an isomer thereof, R2 is valeryl or an isomer thereof, R4 is hexanoyl or an isomer thereof and R5 is either a hydrogen atom or an acetyl moiety is not present, is not substantially present or is not present at detectable levels (C2C16:0); or wherein the sucrose ester has the general structure shown in FIG. 5 and wherein R3 is acetyl, R1 is propionyl or an isomer thereof, R2 is hexanoyl or an isomer thereof, R4 is hexanoyl or an isomer thereof and R5 is either a hydrogen atom or an acetyl moiety is not present, is not substantially present or is not present at detectable levels (C2C16:0); a sucrose ester as shown in FIG. 5 wherein R3 is acetyl, R1 is valeryl or an isomer thereof, R2 is hexanoyl or an isomer thereof, R4 is hexanoyl or an isomer thereof and R5 is either a hydrogen atom or an acetyl moiety is not present, is not substantially present or is not present at detectable levels (C2C17:0); and wherein a sucrose ester as shown in FIG. 5 wherein R3 is acetyl, R1 is hexanoyl or an isomer thereof, R2 is hexanoyl or an isomer thereof, R4 is hexanoyl or an isomer thereof and R5 is either a hydrogen atom or an acetyl moiety is not present, is not substantially present or is not present at detectable levels (C2C18:0).

A further aspect relates to a mutant, non-naturally occurring or transgenic plant (suitably, a tobacco plant), wherein expression of isopropylmalate synthase as described herein or the activity of the protein encoded thereby is increased as compared to a control plant in which the expression of isopropylmalate synthase or the activity of the protein encoded thereby has not been increased and wherein said plant produces beta-methylvaleryl containing sucrose esters therein at levels higher than said control plant. A further aspect relates to a mutant, non-naturally occurring or transgenic plant (suitably, a tobacco plant), wherein expression of isopropylmalate synthase as described herein or the activity of the protein encoded thereby is decreased as compared to a control plant in which the expression of isopropylmalate synthase or the activity of the protein encoded thereby has not been decreased and wherein production of beta-methylvaleryl containing sucrose esters is lower than said control plant.

A further aspect relates to a mutant, non-naturally occurring or transgenic flue cured tobacco plant, wherein expression of isopropylmalate synthase as described herein or the activity of the protein encoded thereby is increased as compared to a control plant in which the expression of isopropylmalate synthase or the activity of the protein encoded thereby has not been increased and wherein production of beta-methylvaleryl containing sucrose esters is higher than said control plant.

A further aspect relates to a mutant, non-naturally occurring or transgenic oriental tobacco plant, wherein expression of isopropylmalate synthase as described herein or the activity of the protein encoded thereby is decreased as compared to a control plant in which the expression of isopropylmalate synthase or the activity of the protein encoded thereby has not been decreased and wherein production of beta-methylvaleryl containing sucrose esters is lower than said control plant.

The mutant, non-naturally occurring or transgenic tobacco plants described herein can be harvested and the tobacco derived therefrom can be treated or cured using practices known for the chosen tobacco type. The leaf surface compounds can be collected, using for example water or organic solvent washes and subsequently dried out. The resulting powder can then be used to enhance the flavour properties of smoking material. The tobacco material remaining after the washes could then be used as material for expanded tobacco for example.

In a further aspect, there is provided a method for modulating the pest resistance in at least a part of a plant, comprising the steps of: (i) modulating the expression or activity of isopropylmalate synthase in the plant, preferably, wherein the isopropylmalate synthase comprises the polynucleotide sequence or the polypeptide sequence described herein; (ii) optionally measuring the quantity of beta-methylvaleryl sucrose esters in at least a part of the mutant, non-naturally occurring or transgenic plant obtained in step (i); (iii) identifying a mutant, non-naturally occurring or transgenic plant in which the quantity of beta-methylvaleryl containing sucrose esters therein has changed in comparison to a control plant in which the expression or activity of isopropylmalate synthase has not been modulated and, preferably, wherein the visual appearance of said mutant, non-naturally occurring or transgenic plant is substantially the same as the control plant; and (iv) obtaining a plant in which the pest resistance thereof has been modulated.

Suitably, there is provided a method for increasing the pest resistance in at least a part of a plant, comprising the steps of: (i) increasing the expression or activity of isopropylmalate synthase in the plant, preferably, wherein the isopropylmalate synthase comprises the polynucleotide sequence or the polypeptide sequence described herein; (ii) optionally measuring the quantity of beta-methylvaleryl containing sucrose esters in at least a part of the mutant, non-naturally occurring or transgenic plant obtained in step (i); (iii) identifying a mutant, non-naturally occurring or transgenic plant in which the quantity of beta-methylvaleryl containing sucrose esters therein has increased in comparison to a control plant in which the expression or activity of isopropylmalate synthase has not been increased and, preferably, wherein the visual appearance of said mutant, non-naturally occurring or transgenic plant is substantially the same as the control plant; and (iv) obtaining a plant in which the pest resistance thereof has been increased.

A plant or plant material obtained or obtainable by said method is also provided.

A further aspect relates to a mutant, non-naturally occurring or transgenic plant, wherein expression of isopropylmalate synthase or the activity of the protein encoded thereby is modulated and at least a part of the plant has a change in the composition of beta-methylvaleryl containing sucrose esters as compared to a control plant in which the expression or the activity of isopropylmalate synthase has not been modulated and wherein the visual appearance of said plant is substantially the same as the control plant and wherein the pest resistance thereof is also modulated.

Suitably, a mutant, non-naturally occurring or transgenic plant is provided, wherein expression of isopropylmalate synthase or the activity of the protein encoded thereby is increased and at least a part of the plant has a change in the composition of beta-methylvaleryl containing sucrose ester(s) as compared to a control plant in which the expression or the activity of isopropylmalate synthase has not been increased and wherein the visual appearance of said plant is substantially the same as the control plant and wherein the pest resistance thereof is also increased.

Compositions, methods and kits for genotyping plants for identification, selection, or breeding are encompassed and can comprise a means of detecting the presence of a isopropylmalate synthase polynucleotide in a sample. Accordingly, a composition is described comprising one of more primers for specifically amplifying at least a portion of isopropylmalate synthase polynucleotide and optionally one or more probes and optionally one or more reagents for conducting the amplification or detection. Gene specific oligonucleotide primers or probes comprising about 10 or more contiguous polynucleotides corresponding to the isopropylmalate synthase polynucleotide are disclosed. Said primers or probes may comprise or consist of about 15, 20, 25, 30, 40, 45 or 50 more contiguous polynucleotides that hybridise (for example, specifically hybridise under, for example, stringent hybridisation conditions) to the isopropylmalate synthase polynucleotide. In some embodiments, the primers or probes may comprise or consist of about 10 to 50 contiguous nucleotides, about 10 to 40 contiguous nucleotides, about 10 to 30 contiguous nucleotides or about 15 to 30 contiguous nucleotides that may be used in sequence-dependent methods of gene identification (for example, Southern hybridization) or isolation (for example, in situ hybridization of bacterial colonies or bacteriophage plaques) or gene detection (for example, as one or more amplification primers in nucleic acid amplification or detection). The one or more specific primers or probes can be designed and used to amplify or detect a part or all of the isopropylmalate synthase polynucleotide. By way of specific example, two primers may be used in a polymerase chain reaction protocol to amplify a nucleic acid fragment encoding isopropylmalate synthase nucleic acid—such as DNA or RNA. The polymerase chain reaction may also be performed using one primer that is derived from the isopropylmalate synthase nucleic acid sequence and a second primer that hybridises to a sequence upstream or downstream of the isopropylmalate synthase nucleic acid sequence—such as a isopropylmalate synthase promoter sequence, the 3' end of the mRNA precursor or a sequence derived from a vector and the like. Examples of thermal and isothermal techniques useful for in vitro amplification of polynucleotides are well known in the art. The sample may be or may be derived from a plant, a plant cell or plant material or a tobacco product made or derived from the plant, the plant cell or the plant material as described herein.

Thus, in a further aspect, there is also provided a method of detecting an isopropylmalate synthase polynucleotide in a sample comprising the step of: (a) providing a sample comprising, or suspected of comprising, a polynucleotide; (b) contacting said sample with one of more primers or one or more probes for specifically detecting at least a portion of the isopropylmalate synthase polynucleotide; and (c) detecting the presence of an amplification product, wherein the presence of an amplification product is indicative of the presence of the isopropylmalate synthase polynucleotide in the sample. In a further aspect, there is also provided the use of one of more primers or probes for specifically detecting at least a portion of isopropylmalate synthase polynucleotide. Kits for detecting at least a portion of the isopropylmalate synthase polynucleotide are also provided which comprise one of more primers or probes for specifically detecting at least a portion of isopropylmalate synthase polynucleotide. The kit may comprise reagents for polynucleotide amplification—such as polymerase chain reaction (PCR)— or reagents for nucleic acid probe hybridization-detection technology—such as Southern Blots, Northern Blots, in-situ hybridization, or microarray. The kit may comprise reagents for antibody binding-detection technology such as Western Blots, ELISAs, SELDI mass spectrometry or test strips. The kit may comprise reagents for nucleic acid sequencing. The kit may comprise reagents and/or instructions for determining sucrose ester content. In some embodiments, a kit may comprise instructions for one or more of the methods described. The kits described may be useful for genetic identity determination, phylogenetic studies, genotyping, haplotyping, pedigree analysis or plant breeding particularly with co-dominant scoring.

The present invention also provides a method of genotyping a plant, a plant cell or plant material comprising a isopropylmalate synthase polynucleotide. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. The specific method of genotyping may employ any number of molecular marker analytic techniques including amplification fragment length polymorphisms (AFLPs). AFLPs are the product of allelic differences between amplification fragments caused by nucleotide sequence variability. Thus, the present invention further provides a means to follow segregation of a isopropylmalate synthase gene or nucleic acid as well as chromosomal sequences genetically linked to these genes or nucleic acids using such techniques as AFLP analysis.

The disclosure is further described in the Examples below, which are provided to describe the disclosure in further detail. These examples, which set forth a preferred mode presently contemplated for carrying out the disclosure, are intended to illustrate and not to limit the disclosure.

EXAMPLES

Example 1: Sucrose Ester Analysis in the *Nicotinia tabacum* Varieties of Flue Cured Hicks Broadleaf (HBL) and Primitive Red Russian (RR)

To study sucrose ester synthesis in tobacco, two model varieties are chosen: the flue cured Hicks Broadleaf (HBL) and the primitive Red Russian (RR). Initial data available from the National Genetic Resources Program (Germplasm Resources Information Network—(GRIN), National Germplasm Resources Laboratory, Beltsville, Md.) catalogue suggests a different content in beta-methylvaleryl containing sucrose ester content between these two lines.

Figure 1:
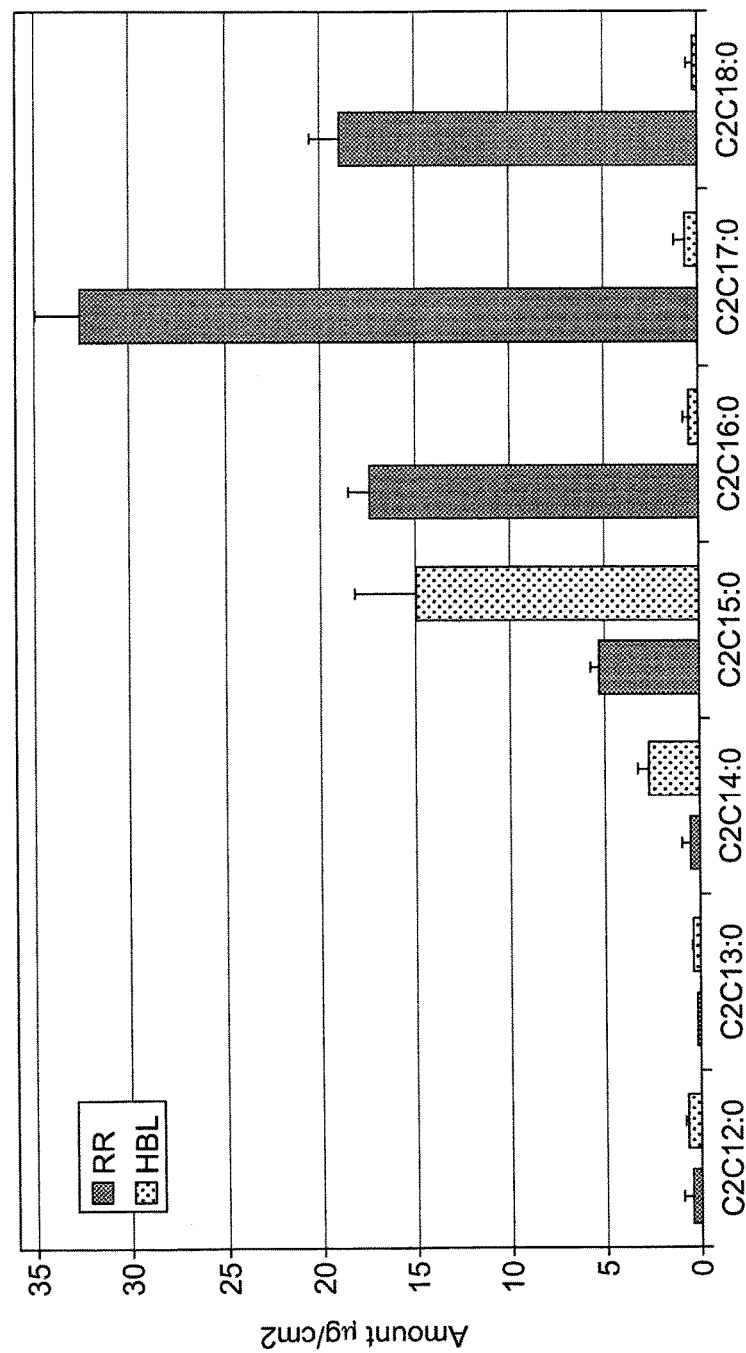
FIG. 1 illustrates the estimated quantity of sucrose ester isomers measured on leaf exudates. The measurement is performed in acetone/methanol washes of green leaf discs from a bmvse tobacco variety Hicks Broadleaf (HBL) and from a BMVSE tobacco variety Red Russian (RR). The quantity is estimated from the addition of sucrose octaacetate as an external standard. n=4 for each variety. C2C12:0 includes a (saturated) sucrose ester as shown in FIG. 5 wherein R3=acetyl, R1=butyryl, R2=propionyl or an isomer thereof, R4=valeryl or an isomer thereof and R5 is hydrogen or acetyl; or a sucrose ester as shown in FIG. 5 wherein R3=acetyl, R1=acetyl, R2=valeryl or an isomer thereof, R4=valeryl or an isomer thereof and R5 is hydrogen or acetyl. C2C13:0 includes a (saturated) sucrose ester as shown in FIG. 5 wherein R3=acetyl, R1=butyryl, R2=butyryl, R4=valeryl or an isomer thereof and R5 is hydrogen or acetyl; or a sucrose ester as shown in FIG. 5 wherein R3=acetyl, R1=butyryl, R2=propionyl or an isomer thereof, R4=hexanoyl or an isomer thereof and R5 is hydrogen or acetyl; or a sucrose ester as shown in FIG. 5 wherein R3=acetyl, R1=butyryl, R2=propionyl or an isomer thereof, R4=valeryl or an isomer thereof and R5 is hydrogen or acetyl. C2C14:0 includes a (saturated) sucrose ester as shown in FIG. 5 wherein R3=acetyl, R1=propionyl or an isomer thereof, R2=propionyl or an isomer thereof, R4=hexanoyl or an isomer thereof and R5 is hydrogen or acetyl; or a sucrose ester as shown in FIG. 5 wherein R3=acetyl, R1=propionyl or an isomer thereof, R2=valeryl or an isomer thereof, R4=valeryl or an isomer thereof and R5 is hydrogen or acetyl; or a sucrose ester as shown in FIG.

The composition of HBL and RR leaf exudates in sucrose esters is analysed and the results are presented in FIG. 1. RR sucrose ester composition differs from HBL sucrose ester composition. In HBL, sucrose esters are mainly composed of C2C15:0 whereas in RR the presence of higher molecular weight species—such as C2C16:0, C2C17:0 and C2C18:0—are observed. As shown in FIG. 2, the differences between RR and HBL are accounted for by the presence or absence of methylvaleryl esters in the molecules. Thus it is concluded that RR is a BMVSE variety and HBL a bmvse variety.

Example 2: Quantitative Tract Locus Analysis

The composition of sucrose esters in leaf exudates is analyzed in 136 populations of 8 F3 plants descending respectively from 136 selfed F2 genotyped plants that were resulting from the cross of HBL and RR parents. A quantitative trait locus study is performed to correlate microsatellites markers and the beta-methylvaleryl containing sucrose ester phenotype. Data is analyzed using Quantitative trait locus cartographer. The beta-methylvaleryl containing sucrose ester trait is linked to one single locus in the tobacco genome. This locus is located on the linkage group 15 (chromosome A) of tobacco.

Example 3: Identification of the Beta-Methylvaleryl Containing Sucrose Ester Related Gene The transcription level of tobacco exons in trichomes is studied to select the preferential gene target among all the potential genes encoding for the functions described in FIG. 3. The expression was studied in several varieties selected for their beta-methylvaleryl containing sucrose ester production profile using microarrays.

The results identify isopropylmalate synthase related exon probes since their expression correlates with the estimated amounts of beta-methylvaleryl containing sucrose esters measured in each of the extracts of each variety (R>0.95).

Four tobacco sequences are identified encoding for homologs of the tomato isopropylmalate synthases IPMSA and IPMSB. They are named NtIPMS1A (SEQ ID NO: 10), NtIPMS1Bv1 (SEQ ID NO: 12), NtIPMS1Bv2 (SEQ ID NO:14) and NtIPMS2 (SEQ ID NO:1). According to EST databases, SEQ ID NO:1 was the choice candidate since most of its expression can be observed in trichomes.

A BAC library constructed from *N. tabacum* var. HBL is screened using the NtIPMS2 cDNA as PCR bait, identifying a BAC named PISOGE. This BAC is shotgun sequenced. The assembly produces several contigs of which pisoge1 and pisoge2 contain sequences related to NtIPMS2.

The intron-exon structure is conserved among isopropylmalate synthases from tobacco and tomato. For NtIPMS1Bv1, NtIPMS1Bv2, SlIPMSB and SlIPMSA it is observed that the genes are separated into twelve exons. NtIPMS2 is also expected to be composed of twelve exons but since the SlIPMSA first exon corresponds to two exons on pisoge1 it is postulated that NtIPMS2 contains thirteen exons.

The reliability of the genomic sequence prediction is tested by PCR. Globally the predicted sequence from the pisoge assembly is verified using the purified PISOGE BAC or genomic DNA isolated from either Hicks Broadleaf or Red Russian plants. One full length genomic structure corresponding to NtIPMS2 is identified. In addition, two other gene like structures are observed and are likely to represent pseudogene duplicates. The structure proposed by the PISOGE BAC is partially verified but some discrepancies between the BAC structure and the HBL genomic DNA are observed.

PCR is used as a genetic marker to distinguish between RR and HBL alleles of NtIPMS2. The IPMS2 marker is used in PCR amplification on genomic DNA of all the F2 plants used in the quantitative trait locus mapping. The sucrose ester quantitative trait locus is recalculated with this additional marker. The quantitative trait locus peak identifies the location where the probability of association between the trait and the marker is maximal. The IPMS2 marker, together with the simple sequence repeat marker PT30172 are the markers where the probability of effect on the beta-methylvaleryl containing sucrose ester trait is the highest.

Example 4: Demonstration of the Activity of NtIPMS2 as the Key Factor in the Synthesis of Beta-Methylvaleryl Containing Sucrose Esters The express sequence tags corresponding to NtIPMS2 are isolated from trichome EST libraries in the form of: GT09L09 (origin: Galpao [TI1068] trichomes) and OT05C20 (origin Orinocco [TI81] trichomes). Both molecules are identical in nucleotide sequence and thus only the OT05C20 cDNA is used for expression experiments. An RNAi construct is generated using the first exon and the first intron of NtIPMS2 based on consensus sequence. Both constructs are transferred into a binary vector comprising either the CPS2p promoter (CPS2 refers to the copalyl synthase 2 involved in cis-abienol synthesis which occurs in trichomes only) specific to trichomes or the MMVp viral promoter (MMV refers to the mirabilis mosaic virus). Stable transformations using *Agrobacterium tumefaciens* AGL1 carrying respective binary vectors are performed in the oriental tobacco variety *Basma xanthi* and the flue cured variety K326.

Leaves are collected from one month old regenerating plants resulting from independent transformation events. Internal standard (sucrose octaacetate) is added at the rate of 2.5 ng/mg fresh weight. The area of the signal recorded for the ion specific to each sucrose ester is measured and plotted as ratio of internal standard area. The signal response varies from molecule to molecule so the comparison is valid only between each molecule. The ratio to internal standard signal area allows the normalisation of signals on leaf fresh weight. FIG. 2 describes the sucrose ester nomenclature presented here. Referring to FIG. 4: (A) composition of leaf exudates of the parental variety K326 (Flue cured, n=3) and the transformants expressing NtIPMS2 under a trichome specific promoter; (B) composition of leaf exudates of the parental variety K326 and the transformants expressing NtIPMS2 under a viral promoter; (C) composition of leaf exudates of the parental variety Basma (Oriental, n=4) and the transformants expressing NtIPMS2-RNAi construct under a trichome specific promoter; (D): composition of leaf exudates of the parental variety Basma and the transformants expressing NtIPMS2-RNAi construct under a viral promoter.

The data presented are sufficient to demonstrate that NtIPMS2 is the key gene in beta methlyvaleric acid containing sucrose ester production. Suppression of IPMS2 in a beta methlyvaleric acid containing sucrose ester variety (oriental) reduces or abolishes production of beta methlyvaleric acid containing sucrose ester (see C and D) thus proving that IPMS2 is a key component of the biosynthetic pathway. The constitutive and trichome specific expression of an RNA interference construct results in the loss of accumulation of the sucrose esters C2C16:0, C2C17:0 and C2C18:0 which are the esters which can contain beta methlyvaleric acid.

The introduction of NtIPMS2 in a bmvse variety (flue cured) can induce the production of sucrose esters (see A and B). This proves that NtIPMS2 cDNA expression alone is sufficient to restore the production of the sucrose esters. Here the constitutive and trichome specific expression of NtIPMS2 cDNA results in the de novo accumulation of the sucrose esters C2C16:0, C2C17:0 and C2C18:0 which are the esters that can contain beta methlyvaleric acid. Interestingly, the constitutive expression of the cDNA (B) did not result in a high accumulation of the sucrose esters whereas the trichome specific expression resulted in the accumulation of the sucrose esters to levels that are comparable to what can be observed in, for example, the beta methlyvaleric acid containing sucrose ester variety.

Example 5: Search Protocol for the Selection of Zinc Finger Nuclease Target Sites This example illustrates how to search the isopropylmalate synthase gene to screen for the occurrence of unique target sites within the given gene sequence compared to a given genome database to develop tools for modifying the expression of the gene. The target sites identified by methods of the disclosure, the sequence motifs, and use of any of the sites or motifs in modifying the corresponding gene sequence in a plant, such as tobacco, are encompassed in the disclosure.

Search Algorithm.

A computer program is developed that allows one to screen an input query (target) nucleotide sequence for the occurrence of two fixed-length substring DNA motifs separated by a given spacer size using a suffix array within a DNA database. The suffix array construction and the search use the open source libdivsufsort library-2.0.0 (http://code.google.com/p/libdivsufsort/) which converts any input string directly into a Burrows-Wheeler transformed string. The program scans the full input (target) nucleotide sequence and returns all the substring combinations occurring less than a selected number of times in the selected DNA database.

Selection of Target Site for Zinc Finger Nuclease-Mediated Mutagenesis of a Query Sequence.

A zinc finger DNA binding domain recognizes a three basepair nucleotide sequence. A zinc finger nuclease comprises a zinc finger protein comprising one, two, three, four, five, six or more zinc finger DNA binding domains, and the non-specific nuclease of a Type IIS restriction enzyme. Zinc finger nucleases can be used to introduce a double-stranded break into a target sequence. To introduce a double-stranded break, a pair of zinc finger nucleases, one of which binds to the plus (upper) strand of the target sequence and the other to the minus (lower) strand of the same target sequence separated by 0, 1, 2, 3, 4, 5, 6 or more nucleotides is required. By using plurals of 3 for each of the two fixed-length substring DNA motifs, the program can be used to identify two zinc finger protein target sites separated by a given spacer length.

Program Inputs:
1. The target query DNA sequence
2. The DNA database to be searched
3. The fixed size of the first substring DNA motif
4. The fixed size of the spacer
5. The fixed size of the second substring DNA motif
6. The threshold number of occurrences of the combination of program inputs 3 and 5 separated by program input 4 in the chosen DNA database of program input 2

Program Output:

A list of nucleotide sequences with for each sequence the number of times the sequence occurs in the DNA database with a maximum of the program input 6 threshold.

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference. Various modifications and variations of the disclosure will be apparent to those skilled in the art without departing from the scope and spirit of the disclosure. Although the disclosure has been described in connection with specific preferred embodiments, it should be understood that the invention as claimed should not be unduly limited to such specific embodiments. Indeed, various modifications of the described modes for carrying out the invention which are obvious to those skilled in cellular, molecular and plant biology or related fields are intended to be within the scope of the following claims.

Sequences

SEQ ID NO:1 (NtIPMS2 nucleotide sequence)

```
ATGGCTTCTCTCTCTGTAAATTCTATAATTTCCCTGAGCAC
TTCCCTTTCATTACATTCTAAAAACCCACTTATTCACAGTG
TCTTCAGTTTCACGCCTTCAACCACAAGGCATTCAGCTATA
TGCTGCTCAAATATTCGTCGGCGGCCGGAGTATAAACATGG
AAAATTCTCTGACCCTGATTATGTTGGTATTTTTGACACCA
GTCTTCGCGATGGCGAACAGGCCGCTGGTGCTACCATGACT
AGTAAAGAAAAACTGGACATTGCACGTCAGTTGGCTAAGCT
TGGTGTTGATGTTATTGAGGCCGGTTTTCCTTTTGCCTCTG
AAGCTGAGTTCGAGCTTGTAAAGTTGATAGCACAGGAAATT
GGTAATAACGTAGACAAAGAAGGATACGTGCCGATGATATG
TGCCTTAGCTAGGTCTAGTAAGAAGGATATTGAAAGAGCTT
GGGATGCTTTAAAGTATGCAAAGAAACCAATGCTTCATATG
TTTATTGCGACGAGTGATATACATATGAAGTACAAGTTAAA
GATGAGTAGAGAAGAAATTGTGGAGACAGCTAGGAGTACGG
TGGCTTATGCAAAAACCCTATTTGAGGATGTTCGGTTTAGC
GCTGAAGATGCTGCAAGATCTGATAGGGAGTTCCTTTATCA
TATTATTGGAGAAGTTATCAAAGCTGGTGCAACAGTGATTG
GCCTCCCTGATACAGTTGGATGCAATTTGCCCAGTGAATAT
GCACAACTGATTTCTGATATAAAAGCCAATACCCCAGGAAT
ACAAGATGCAAACATTTCAACACACTGTCACAACGATCTTG
GGCTTGCTACTGCCAACTCCTTAGCTGGAATTTGCGCAGGC
GCAAGACTAGTAGATGTTACCATCARTGGAATTGGTGAAAG
AGCTGGAAATGCTTCTCTGGAGGAGATTGTAATGGCCTTAA
AATATCGTGGAGAGCAAGTACTAGGTGGTATCTATACTGGG
ATTAATACAAAGCATATATTCATGACGAGCAAAATGGTAGA
AGAGTACAGTGGGCTTAAGCTGCAGCCACATAAGGCCATTG
TTGGAGCTAATGCATTTTCTCATGAGAGTGGCATCCATCAG
GATGGAGTGTTAAAGAACAGAGATACATATGAGTTTGTATC
TCATGAAGATGTTGGGTATCGTCGTGCTAATGAAAACGGTA
TTAGTCTGGGAAAGCTCAGTGGCCGCCATGCATTGAAAGCC
AAAATGGCTGAGCTTGGATATGACTTTGATGGAAAAGAACT
TGATGACCTCTTTCGTCGATTCAAGTCACTAGCTGAGAGGA
AAAAGAAAATTACAGATGATGACTTGAGAGCACTTGTATCA
GATGACGTTTTCCAGCCTCAAGTTTCCTGGCAACTTGGAGA
TGTACAGATTACTTGTGGAAATGTTGGCCGCTCTACAGCAA
ATGTTAAGCTTATTGACAGCGATGGTCAAGAGCACACTGCC
TTTTCTGTTGGAACAGGACCTGTTGATGCAGCTTACAAGGC
```

```
AGTTGACCTCATTGTAAAGGTACCTGTAACACTCGTTGAAT

ATTCGGTTAATGCAATCACAAAACGTATAAATTCCACAGCT

TCAACCAGAGTGTTAGTTCGTGGGAATGATGACTATGCATC

GTTTAATACTTCAAACGGGCAAACTGTTAATCGTACAGTTA

GTGGAACAGGAGCGCATATGGACATTGTCGTTTCAAGTGTC

CAAGCCTATGTTGAGGCGTTGAACAAAATATTCAGTTACAA

AAAAACAGGTCTCGTGAACAAATTTGAAGGCAGTGCGCAAT

CGTAA
```

SEQ ID NO:2 (NtIPMS2 amino acid sequence)

```
MASLSVNSIISLSTSLSLHSKNPLIHSVFSFTPSTTRHSAIC

CSNIRRRPEYKHGKFSDPDYVGIFDTSLRDGEQAAGATMTSK

EKLDIARQLAKLGVDVIEAGFPFASEAEFELVKLIAQEIGNN

VDKEGYVEMICALARSSKKDIERAWDALKYAKKPMLHMFIAT

SDIHMKYKLKMSREEIVETARSTVAYAKTLFEDVRFSAEDAA

RSDREFLYHIIGEVIKAGATIGLPDTVGCNLPSEYAQLISDI

KANTPGIQDANISTHCHNDLGLATANSLAGICAGARLVDVTI

NGIGERAGNASLEEIVMALKYRGEQVLGGIYTGINTKHIFMT

SKMVEEYSGLKLQPHKAIVGANAFSHESGIHQDGVLKNRDTY

EFVSHEDVGYRRANENGISLGKLSGRHALKAKMAELGYDEDG

KELDDLFRRFKSLAERKKKITDDDLRALVSDDVFQPQVSWQL

GDVQITCGNVGRSTANVKLIDSDGQEHTAFSVGTGPVDAAYK

AVDLIVKVPVTLVEYSVNAITKRINSTASTRVLVRGNDDYAS

FNTSNGQTVNRTVSGTGAHMDIVVSSVQAYVEALNKIFSYKK

TGLVNKFEGSAQS
```

SEQ ID NO:3 (NtIPMS2 cDNA sequence used for complementation)

```
ctcttttcttagggaaaagaataatggcttctctctctgtaaattct ataatttccctgagcacttcccttcattacattctaaaaacccact tattcacagtgtcttcagtttcacgccttcaaccacaaggcattcag ctatatgctgctcaaatattcgtcggcggccggagtataaacatgga aaattctctgacctgattatgttggtattttttgacaccagtcttcg cgatggcgaacaggccgctggtgctaccatgactagtaaagaaaaac tggacattgcacgtcagttggctaagcttggtgttgatgttattgag gccggttttccttttgcctctgaagctgagttcgagcttgtaaagtt gatagcacaggaaattggtaataacgtagacaaagaaggatacgtgc cgatgatatgtgccttagctaggtctagtaagaaggatattgaaaga gcttgggatgctttaaagtatgcaaagaaaccaatgcttcatatgtt tattgcgacgagtgatatacatatgaagtacaagttaaagatgagta gagaagaaattgtggagacagctaggagtacggtggcttatgcaaaa accctatttgaggatgttcggtttagcgctgaagatgctgcaagatc tgatagggagttccttatcatattattggagaagttatcaaagctg gtgcaacagtgattggcctccctgatacagttggatgcaatttgccc agtgaatatgcacaactgatttctgatataaaagccaataccccagg aatacaagatgcaaacatttcaacacactgtcacaacgatcttgggc ttgctactgccaactccttagctggaatttgcgcaggcgcaagacta gtagatgttaccatcaatggaattggtgaaagagctggaaatgcttc tctggaggagattgtaatggccttaaaatatcgtggagagcaagtac taggtggtatctatactgggattaatacaaagcatatattcatgacg agcaaaatggtagaagagtacagtgggcttaagctgcagccacataa ggccattgttggagctaatgcattttctcatgagagtggcatccatc aggatggagtgttaaagaacagagatacatatgagtttgtatctcat gaagatgttgggtatcgtcgtgctaatgaaaacggtattagtctggg aaagctcagtggccgccatgcattgaaagccaaaatggctgagcttg gatatgactttgatggaaaagaacttgatgacctcttcgtcgattc aagtcactagctgagaggaaaaagaaaattacagatgatgacttgag agcacttgtatcagatgacgttttccagcctcaagtttcctggcaac ttggagatgtacagattacttgtggaaatgttggccgctctacagca aatgttaagcttattgacagcgatggtcaagagcacactgcctttc tgttggaacaggacctgttgatgcagcttacaaggcagttgacctca ttgtaaaggtacctgtaacactcgttgaatattcggttaatgcaatc acaaaacgtataaattccacagcttcaaccagagtgttagttcgtgg gaatgatgactatgcatcgtttaatacttcaaacgggcaaactgtta atcgtacagttagtggaacaggagcgcatatggacattgtcgtttca agtgtccaagcctatgttgaggcgttgaacaaaatattcagttacaa aaaaacaggtctcgtgaacaaatttgaaggcagtgcgcaatcgtaaa agtgatggtgtgtgctccagaaacaaaagcttaaatgctgcttagtg ctcgatgatcataaatttatgctctattcatgcatgcattactgaag ttaattaagaagtaatcttaattgtataagatgtaaacatgtttcta ttcatgcattactatgaaattaattacaatttctgagccaaaaaaaa aaaaaaaaaaaaaaa
```

SEQ ID NO:4 (Genomic DNA sequence of NtIPMS2 region covering exons XI, XII and XIII as observed in Red Russian. cDNA matching regions are underlined. Bold shows conserved DNA regions between Red Russian and Hicks Broadleaf DNA sequence)

<u>AGCAAGATGTCAAGAAGCACACTTGCCTTTTCCTGTTGGAACAGGAC</u>

<u>CTGTTGATGCAGCTTACAAGGCAGTTGACCTCATTGTAAAGGTTTAT</u>

AATGAAACTGAAAACTCTCATAATGTTTGTATCTTGTCACACTAGTA

GGATAGGTAATTTAGGTTTTATATACGCTGAAGGTATAAAAATATTT

ACTCAATCAGAGCGCTTACAAGACAATTGCAGGTAACTCTATGAGTA

GCTTAGACTAAAAGATAAACGTAGTAATTTCAATGTAAATAGTTTAG

GAGACATGCGAATCTTTCCTTGACAAAGAAACTAAAAAACTTGCGAA
GCACGCACCTCAATCACCCCGTCTGTGTGAATTGAACGAACTTAAAA
GTACAACCAGCTTAAACTGATTTTTTACCTATTTTTTAGTGTTCAGA
CGGATCTGCAGCAACCATGATTTGATTCACCGGTCGACAAATATCCT
CACCGTGCATTCGAACTCCCTTTCTCCACATCCTAAAAATCCTCTTC
TAAGATGTCTTTGTTTGCAAACTCTAGCCGTCATATCTTGGTGGAAA
ACATGTCTCTTCTAATATGTGTATTTATATGTTATAAATAGTATTTA
GGAGAATGGCAAGTTAACAGACTAATTAACACCTATTATGAATGGAT
CCAACCGAATAGAAATATTCCAACATTTAGCTAAGTAAGCTGCCAAG
TCAAATAAGACTGATAGAGTAAAAACTCTTTCATATAGCAATGAATA
TAACCTAAATCCTTTAGTTACTGCTAGCAATTTTGTAGGTATAATTG
CTTTGTTTGGTAAAAACATCTATGTAACTTTTGTTTTATAAGTAATG
TTCTTTGTCATTATGCAG<u>GTACCTGTAACACTCGTTGAATATTCGGT</u>
<u>TAATGCAATCACAAAACGTATAAATTCCACAG</u>CTTCAACCAGAGTGT
<u>TAGTTCGTGGGAATGATGACTATGCATCCGTTTAATACTTCAAACGG</u>
<u>GCAAACTGTTAATCGTACAGTTAGG</u>TATGAAATATACATGAAGTACT
GTTTCCCTTTAATTTATCCTTATTTCCCTTAATAATATTCTTTCATG
CATAATGTGGGAACATGAAGATGACAGAGAAGAATTAAAACGATTTT
TTCCTAAAGGAGAAATAATATGTGAAGGAATGAAATGTTGTCAGTT
TTATATTAGTTCTCAAATTTTATGGTACTACGGGTATCTAGAGCCAA
CCTGAGAATAGAAAGTATCATATAAGAAATATACACAGCAGTTAGAT
AGAGTACATTTTTAATTATTTAATTATATTTATGCATGCCTCAACAC
GTTTACTCACCTCTTAGCCTAATTTTTGTTACATGGGATCGTTCTAC
ATTTTGAGTAGCTGAGAGATTTGAACTTAGGACCTTTATTTTCTCTA
ACACTATGTTATATTGCCAGT<u>GGAACAGGAGCGCATATGGACATTGT</u>
<u>CGTTTCAAGTGTCCAAGCCTATGTTGAGGCGTTGAACAAAATATTCA</u>
<u>GTTACAAAAAAACAG</u>NTCTCGTGAACAAATTTGAAGGCAGTGCGCAA
TCGTAAAAGTGATGGTGTGTGCTNCNNCTANAAG

SEQ ID NO:5 (Genomic DNA sequence of NtIPMS2 region covering exons XI and XIII as observed in Hicks Broadleaf. cDNA matching regions are underlined. Bold shows conserved DNA regions between Red Russian and Hicks Broadleaf DNA sequence.)

<u>GTCAAGAGCACACTGCCTTTTCTGTTGGAACAGGACCTGTTGATGCAGC</u>
<u>TTACAAGGCAGTTGACCTCATTGTAAAGGTTTATAATGAAACTGAAAAC</u>
TCTCATAATGTTTGTATCTTGTCACACTAGTAGGATAGGTAATTTAAGT
TTTATATACGCTGAAGGTATAAAAATATTTACTCAATCAGAGCGCTTAC
AAGACAATTGCAGGTAACTCTATGAGTAGCTTAGACTAAAAGTTTTAAT
TATTTAATTATATTTATGCATGCCTCAACACGTTTACTCACCTCTTAGC
CTAATTTTTGTTACATGGGATCGTTCTACATTTTGAGTAGCTGAGAGAT
TTGAACTTAGGACCTTTATTTTCTCTAACACTATGTTATATTGCCAGT<u>TG</u>
<u>GAACAGGAGCGCATATGGACATTGTCGTTTCAAGTGTCCAAGCCTATGT</u>
TGAGGCGTTGAACAAAATATTCAGTTACAAAAAAACAGGTCTCGTGAAC
<u>AAATTTGAAGGCAGTGCGCAATCGTAAAAGTGATGGTGTGTGCTATCTG</u>
CNAAAAACTCGA

SEQ ID NO:6 (NtIPMS2 corresponding BAC contig sequence (total BAC length is 76832 bp. Only 14232 bp are shown)

TGATGATTTCTCATTATAATTGTAACTAGTGGTGGCAAAATGGTAAAAAGAAAACAGTTATCCATCCATATTATTCA
TTAAAAAATGGGTTGTATAATGAACTTTTTAAAAAAGGATCAATTATGGATAAGAACCATATTATCCGCTTAGAAAA
TGGATAACCAATAAGTTAACTTCTACACTTGTAAAGCTTCAAATTGGGGGTTCCTCAAGTTTGTGAGAAGAAGAATT
CTCCCAAAGTGATCATATTCAAGAAGTCTTGGATAAATGAATATCCATATTATCCGCCGATTATCTCGTTTTAATCC
GTATTAAATATGAGTCGGTTCGAATAATTTATCTGTTTTTGTATTATCTACTTTGGACATGTCCATACCCGACCCGA
CCCCGCTCGTTTGTCACCCCTAGTTGTAACATATACTGTTTGCTTACCTAACGGGTTGAGTTAAGTACCATCACGAC
TTGGTGGGATTTTGGCTCTTACAAAACTACAATTGAGCCTGATTATAATATTTTATTATAAAATTGAGGTTCGGTAT
AATTTATTTTGCTGATCAAATCTTGGTGATTCAAAGTTCAACTGAAATATGCAATACTAAATTATTTTCTTATTTAA
TAAATTTTATGATGAGCTAATATTTATAATTTGAATAAAAAAAAATTCATAATACTAGTATTTTTGAGTTGAATAGA
AATTGTCAGTACAGTTGAATATAACAACTGTAATTATTCATAAAATATTTTAGTTTGATATAATAATAATCTTTCAA
AAAACATTCTTACAGAACTTGACTGAAACCATAATAAAGTATCTCACTACTTTTGTGCGACAAGGTTTCTTCCTAAA
TGAGATCAACAATCATTCTTTTAAGGATTTTTATTTTTATTTTTATCACAAATATATTACTCAATATCTAAGTAATC
TTTAAAAATCTGTATACTCATTACTATAAAGCATACATGCAAAACGCGTACAATAAAAACTAATTTTTAAAAAATAG
GGGGAAGGAGAAGGGATGAACAGAACCCTCATTAATAAAGCAAAAATTTAAATATCCAACAAATTGAACTGTTAAGA
TTATAAAAAAAAGAAAAAAGAACTTCATTGTCGAAGTAAGTCAAAGTATCACTAGCCGTAAAAATTTCGGCACCTT
TTAAAAGAATGATAAATATACTAGGGAAAGCCTAAAACCTCTTGGTATTAATAACTATAGTTTAGAAATTAGGCAAA

-continued

```
GCCGCTACTAGGGTAGTTAATTATTGGTTCTGTTTATATTTATATCATTCGTTTTGTTGATAATGATGAGCAACGTT
CCATTACATGAAGAAACCACGTCAATGTTTATTCCCTCATTCGTTTTCTAAATTTATTCGAGATGTGAGTAAACCTC
CCCCCACCCCCACACACCCCCTTTTTTTTTTGCTGTTAAAGTTTCGACAATAAGAACGTTCAGAGTTTCTTGAACTT
CTGTTTTATCTGCAGAAATTATAAATTGGAGTCAACCACTGCATCCCAAATTGATGCAGACTTTATCTGAATAATTA
ATCAGTATATAATTATAATATCTATTTTCTATGTTTCTAATTTATGTGACACATTTCTTATCCGTTAGTTTAAAAAA
AATGATAAATTTATATATTTCAGAATAATTTAACTTTAAATTTTTTATTTTATCCATTTTACCTTTAATGAGAAAC
TTTTGTAACCATACAAATGTTATAGAATATATTTAGAACAACAAGTTTCAAATATTTTATAGTCACATAAATTTAAC
ACACAAATATTAGAGCAAATTTCAAACTACTTCACATAAATTGAAACAGAGGGAAAAATAATACTCCCTCCGTTCCC
TTTTACTTGGCACGTTTTGACTTTTTACGCCCCTTAAGAAATAATAAATGAAGTGCATAATTTACCATGATACCCAT
ATTAATTGATGTATATTTTATTGGATTTGAAAAATGATTTGAAATGAGTAATAAATATCGTGGGTATAACAAAAAAA
AAATTATCTTCTCTTGATATGCGTAAAGTGACAAGCAAAAATGAAATCTATTTTTAGTATACATGCCAAATAAAAG
TGAACGGTAAAAATGAACGGAGGGAGTATATATTATTACTACTAAAACGGGAAACTGGGCATGCTAAGTTTTTCATT
GCTATTTCAAGTTCCGATTAATAGCCATAATATAATGTTTTCTAGAAACAAAGAACAACGCCAAGATAAATTTTCCC
AAAAAGTAGCACAAATGTAACAAATTCTTACCTCAAATTTTAATCTAAACACATAAATTTTCTTTATAATTGTTTCT
TAAAAACTTAAACTAAATTCAAATGCCAACAAGTTTAAATGAGCAAGGAAGTATTTTCAGTTTCTATTTCTTGAATT
TAATAAGAATGGAAATATTTTCCGTTTGTTTACTGGGTTCTGTCTAGTCTAGCTTAAGACGAAAATTGTCTTGTTTT
AAGTTTTACAAACCGTAAGGGGTGGTAATTCAATTTTCAATTGTAGTATGAGCAATTAATTCCAACACAAAATCTCA
CGTGAAATAATATACTCTAGTGTTTGTTTGGCGTACGAAAAAGAAAGTCTACATAATTAATGCAGCGTTCCATAGTT
GATATTAAATAATACCCGTAATAAATTATATAAAACTTTATGTGTTATTCTTTTGATAAAACAGCAACCAGACACA
CCAGGGGCTACTTTGGTCATTTTCTCTCCAATAAAAACCCTTGTTTCACCAGCTTTGTAGGTGTTCGAATTCACCAA
AGCGAACATTCCATTAACTCCGATCCACTCTCTTTTCTTAGGGAAAAGAATAATGGCTTCTCTCTGTAAATTCTA
TAATTTCCCTGAGCACTTCCCTTTCATTACATTCTAAAAACCCACTTATTCACAGTGTCTTCAGTTTCACGCCTTCA
ACCACAAGGCATTCAGCTATATGCTGCTCAAATATTCGTCGGCGGCCGGAGTATAAACATGGAAAATTCTCTGACCC
TGATTATGTTGGTATTTTTGACACCAGTCTTCGCGATGGCGAACAGGCCGCTGGTGCTACCATGACTAGTAAAGAAA
AACTGGACATTGCACGTCAGTTGGCTAAGCTTGGTGTTGATGTTATTGAGGCCGGTTTTCCTTTTGCCTCTGAAGCT
GAGTTCGAGCTTGTAAAGTTGATAGCACAGGAAATTGGTAACCTTTAATGTTTAACCGTTCACATTTCTAATATTTA
CTTATTTGTAACATGTCGTCACGTGTTAGTTTCATTCTTTTTATGAACCAAACATGCATGCAAAGATATTTTAGAT
ATTTGGACGGCGAGTGAGATTTGAAACTAGGACCGTTTGCCTGATACAATATTAAAATATGTAACCATTTTATGTAC
AAGTTTAAACTGTTGATAGTAGCATATTTTTTACTTTTATTTAAGTATACTATATTCCAACAGGTAATAACGTAGAC
AAAGAAGGATACGTGCCGATGATATGTGCCTTAGCTAGGTCTAGTAAGAAGGATATTGAAAGAGCTTGGGATGCTTT
AAAGTATGCAAAGAAACCAATGCTTCATAGTAAGAAAATATTTCAAGATCGAATTAGGTCAAAAGTGTAATCGTAAA
AAGTAAAAGAGAGAATCTAAAGGTACTTATTTGTTCTGGTCTTTTCTTTTTTAATATAAGCGGCCTTGAGATTATA
GGAGGTTTGATATAGACCTCTACCATGTAAATTCTTATTTATTTGCTTTTTGTTTAGCTTTTAACCTTTTCCCTGTA
CTGAAATAGATTGTAATGGCCTTAAAATATCGTGGAGAGCAAGTACTAGGTGGTATCTATACTGGGATTAATACAAA
GCATATATTCATGACGAGCAAAATGGTACTCTCATCTTATTCTTCTAGTTAGAGATATATTTTACCAGTTTTAAAGC
TGCTTAATTTTTTGTGCCTTTCTGTTGACACAATTGTTGCTATGTAGGTAGAAGAGTACAGTGGGCTTAAGCTGCAG
CCACATAAGGCCATTGTCGGAGCTAATGCTATTTCTCATGAGAGTGGCATCCATCAGGTTTTGCGTTATTTTCTCT
AAAAGTTTTACTTCTACATACACTAGATTTGTTGAAAGATTACTGAATTGGCGACCTTCTACACTAGGTTAAATTGC
AATAAACATTTCATACCACTACCGGTTGATATAAAATAAATCCTTTCTCGTTAAGATAAGATGGGTAAAATGAAGAA
TTCAAAGTTGAATTATTTTCAATTATAGAAATGTATCATTCTTTTTGTAACAGACTAATAAGGAAATTGTGTCATCT
```

-continued
```
AAATAACACATGAAGTATTTGGATTCAGCCCATTGCCCCTTCCTCTTTCATTATCGCCTTAATCAGGATTCTCTACT
TCCATAGTATCATTCAGTTTTCATTCTTCCTTTTTAAATTTTTTTTAATGTGGTTTAGGATGGAGTGTTAAAGAACA
GAGATACATATGAATTTGTATCTCTTGAAGATGTTGGGTATCGTCGTGCTAATGAAAACGGTATTAGTCTGGGAAAG
CTCAGGTATGATTTGATTTTCAGAGTGATCGATTTGTTATGTTGATGGTTTGATAGAGATTATTGTTTCAAATTCTT
TGGTCTTTCCCCCATATTTTTGGATGAGTCAAAATAATTCGACTAATATATAGTCCTACCAATTTGGTGTCAACATA
TGTACGAATTGAATATAGTCATCAATCAACTATGTCCAACTATCCATACTGTAAGGTATACTCCCTTTACATTAAAA
AATACAAGTGAACTGAAAAAAAAAAGACATTTTTTAATTAAAGTGTGCTATCTCTAACCGTTTAAATTTTTAGATTA
GATTATCATACAGTTCAAACACTTTAAAACTCGTACTATCCCCTAGAATTTCAGTACCTCCGTTGTATTGAATCAAC
CCCAACCCTTCATTTTTCTCATTTACATTAGGCACATTGATGTACCTCTTTCCTTTAAGGAATACATTTTGTAACAT
GGTAGAATATTTTGTGCAGTGGCCGCCATGCATTGAAAGCCAAAATGGCTGAGGTAAGATACATAATCTATAGTACG
ATATACTACAAATATTATAGTATATGGAAATGGATCAAATCATTTTATTTTTGTTACAGCTTGGATATGACTTTGAT
GGAAAAGAACTTGATGACCTCTTTCGTCGATTCAAGTCACTGGCTGAGAGGAAAAAGGTGATTACGTTGCTGATATT
TCATAGTGCAACAGTCAAATTTGTGATCGCACCTTTTCGTTCCTAGTGTTTGTCCATATTTTTTGAGTTAATTTCAA
ATATGATCACTAATTTCTACTATAACAATAAAATTTAAATTTTTTTATTCGCATTAAAGTGACTGAACTAACAATTA
AAAATATTTGAAAAATATATGAAAAATTACGGCCAAAGAAAAACTCTTTTGACTCTCGACATCCGAGCATCACCACA
TAGTAATAAATGAGAAAATTATTTTTTATCAAATTAAAGTAACTGAATTTTACTTATTATTCATAATAAAAGAAAAT
CACTAAACTATACGCACTATAGTGGCAAAACCTATCCATATTCAAGGTGACTTTAAGTACCGGTCTAGTAGGTAGAT
TTTTGTGATTTTACTGTTATAGTGGATAAAATTAAAGTCACTTTTTTTGATAAATTGGAAGAATAGCCTGACAGACA
TCTCACTTATTCGGCTTTGACATCCCGGTCCCCCTACTCCATATAATTTCAACCAAACACTTAAACTTGTATAAAAC
ATTAGTCTTAAACACCTCTGATACTGTGTGTGTTGTTCACTCGTGCTGATATAAAGGACACATCAGATCCACCTCAG
ATATATTAATGCCACATCATTATCTATTTTTACAAAAAATATTTTTTAATAAAAATATCAAACTCATCCCTTTCTTC
TCCAAAAAAAAAACAAACCTTATTCCTCTCTCCACCATTCCATCTCTGCCTCTTCCACCCGTCACCGCCACTACCA
AACACTGCACCCTTCCTCTTCCATGAGAAAACACTCAATCAAACCTACTTCATCTTTTATTTTTGTCCTAAACTTCT
CCATTACTACAATCTATTCAACCACCCATGGTAGTCTTGTTGCCACCATCGCCAGCAACCACTCCAAAACCACCACT
ATATCTCCTCTTCTCTTCATATTCATGTCACTCTTTCAAAACCTAGACATTGAACGAGTTTAATAAAATCTATCCTT
AAATTTTCTTTCTAGCCAAATACCCAAAGCAAAACCAAAAAAATTGAAAAAGAAAGAGAAGAAATTTTTACTCAAAA
TTCTTATTGACCCCTCCAGCAACGATAAAATTTATAAAACTAACAAAATCAAGCTTCGGCGTTTTCAACAACCGATG
ACGATCCAATTTCTGGCTTAAACACTATTTTCAAGCTTCAATGTCTCTTAATTCTCCGGCGTCTTCATTGTCTTCTT
CAGTTATTTTGAGAAAAACAAAAATTAAATAACTTTGTTCCTTGACTAGCTGCTCTGCTAAACTCTATTAGTTTGGT
CTTGTTATACTGCTTCTTTTTTTATTTTTATCATAGTCCAGTTGATTGCTAAAATTGTAAGAGAAATAATGTAATGC
TGTTTGAGAAAACTCTACTTGAGAAACAAAAATTTAATATAGAGGGTGTGGAGCGTGTCAATTTCAATGGCGTTTTT
AAGAGATTTGGGGGTAAGAAGAAGCGGCTGGGATAGAGAGGGGCGAGATAATGGCTAGCATTGTTTTTAATTTTTTT
TTCTTTTCATTTTTCTCTTTTATTATTTTCTAATCAAATTTTGTATAGTTACTCGCTTTTAGGAGCGTGCAATCACT
TATTTTGTTTGACTCACAAAACAAAGGCTACATAAGTTTGGTCAATGGTTAGATGAGTTTAAAACTAATGTCTTATA
CAAGTTCAAGTGCCTGATTGAAACTATGTGGAGTAGGGTGATCGGAATGTCAAAGCCGAATAAGTCGAGGCAGTGGC
GAAGCCAAGAAATTCAACAAGGGTATTCAAACCTTTGCCAGTGGGCTATGTAAGGGTGTTCAAAGCCTATTTTAAT
CAATAACAAGTAATATTTTACCTTATACGGAGTATAATTTTCTGGCGAAGGGTAGTCAGTTGACCACCCTTGATTGC
ACGTAGCTTCGCCCCTGAGTCGAGGTGTCTCTTAGGCTAAAATAGCGTGATAAATTTTATAATAAAATTTATTTTAT
ATGAGTAAAGTTAATAAAATTTATTTTATATGAGTAAAGTTAAGTAAATTATAATACTTAAAGAAAATTGAAAGCTT
ACATATGCAGAGGTCCGGTCCTCGACCCACTTATCTTGATCCCCCTCTTTCTTCTTCTTCACAATATGCGTCTCCTT
GAATAGCTCATCATGACTCATTGGACGCCCATACTTCTTTTCCTGAAAATAAATTAATTTAGTTAATAAATAAAATA
```

-continued

```
GATATACTTAGAAAAGTAAAATAATTTAAGCAATTACGTACCAATCTTCTTTTTATTGTCCCTAGGCTGATCGCACC

TCTAGTGTGCAAGGAGCCTCCCTTCTCGGATGCGCGAGCTTTCTTTCCTTTTTCGCTCCTCTCTAAGAACTTTGCGG

TAAGCCATTGCCTTTGCAAATCATTCCACAAATTCTCAAGTAACCAGCCAGGCCTCTTGTTCTTCTTTCTAGCATCC

GAGAAAGCATCCGCCAATCTCTTACTAGCTTTGTGATGAAAATTTGCAGCCACTTCCGCGCTATAGCGGTCTTTCCA

TACACACTTGCTCTGTATTTTAAAATTTAATTATTAGATGGAAACATCATAAATATAAATTATTAAACTGTTTAAAA

AAATATTTATACCTTAAATTGATTGAAAATTTGCTCTTTCAGTGAGAATGGACAATCAGTCCAAGTCGTATAAGGGC

CATCATAAAGCTTTCTGATGGCATTAGTGATTATCTTCGTAGTCTTATTACCCGGCCTGAACCTACAATTTAATAAT

AAAAACACATTAATATCTTAGTAAAAATGTTACAAATCAATAGACGGAAAAATAATGAATAACACTTACCCATCACC

CTTAGGGACTATGATGATCCTGCCATATCGATCATAATGCACTACCTCGTCATCACTATTCGAAGCATGTGTATCAG

AGGCATGTGAAGACGGTGTAGGCGGGTCAGAGCTACTGCCTCGTAGGCGAAGGCCTGCAATAGATGGAGTCGATAAT

GAAGATGGTTGTGATCCCTTGACTACAACATAGCTGGATGTGACCCAAGTGGATGTGATAATGCTGGCTGTGACCC

GAGTGGCTGTGACATGGATGGATGCGATCCATGTGGCTGTGATATGTAGGGATGTGATCCATATGGATGTGATGTAG

ATGGCTGCGATGCAGATGGCTGTGAGGCAGCTGGACTGTATGTCGAACATATAGTCCTATGGCCCTGTGATGGAAGA

CCTGGTGTCTGAACGAAGGTGTATGATTCGTGATGCTGTGGAAACTCAGTATAGCCGTGTGGTGGAGGATAAGACAT

AGGCATCTCTGAAAAGGGTGGACAAGAGGGACTATTATTTTCTACCCTCCTCTTTCCCTTCCTACCCTTTTCTCGAC

CCTGAGAACTAGTAGGGTCATTGTTACCTTGACCCTTGCCTGCCATCTGTATGATATAATGCACATTTAGATTGAAA

CATATAAGAAACTAGCTATAAAACAAGAGTGCTTTAAAAAACCAACTTTTTAATCCTCATCGACGTATTGTTCCTCG

TCCGAGAATTCTTCGTCCTCATTTGTTTGAGCTTCATCAGTTGATTCTTCGTCCTCATTTTCTTTAATTGTTACTTC

ATTTATATCACCTTCTTCCAATATGCATTCAGGATGTTCCAAATCATTTTCTAACTGATCGTCCACTATTTGGTGAA

TATTAGAAATATCATTTTGATATGCAATATTTAACACATTCTCGACTTCCACCCTACCTACATGCTTAGTTTTTATT

ACAACCCACCAATCGGACTTATTCCGCCGCAATGGATAAGGAGCATAATACACTTGCCTAACGTTATGTGCAATTAT

GAAAGGATCATAGCGATCATACTCCCTCGTATGATTAACCTCAATTATGTTGTATTGGTGGTGTACACTTGTACCTC

TTGTTGGATTTGGGTCAAACCACTTGCATATAAAGAGTATCAATTTCTTATATGGCCAACCTGTATATTCTAGTTGT

AATATTTCTTTGACCACACCATAATAATCAATATCTCCAACTTGGTTGCCATCACCACCTTGAACCCACACCCCGCT

GTTGTTACTATTTTTATTTTTAGAGCCATCCTTTGTATGAAACTTATAACCATTCACTACGTACTTAGACATTGTTG

TGACCTGAAGCCCAGGTCCCCAAGATATATCTTTCAAAAATTGATTTACACCATTATTTGGATTATTTACCTACATA

GTGTTAAAAATATTCATAAGTTAGCATAACTTATAAATCAATTTTTATACATTCATTACATATATATATATATATAT

ATATAACTAGTGTATATATATATACAAACTGTTTGAACACGTATCAAATCTCGTATATACAACATCATGGCCAAATT

GACCTACGAAGTGACTGTGACACATCAAATATTTTTAGTAGTTGCATCAATATGTAGTCACAGTAAATTTTACATTT

TGATAACTAATAAATCAATACTTACTTGAGAAATGGTACAACTTCGGAACAATTTAGCAACACATGAAGTGTAGCTG

ACTTGTACTCCATATCACTCAAACTTCTCTTTCTAACATCCTTAGAACATCGGCCTGGTTGATTGAATATAGATATT

GGTGGATATAATGGATCATTCACATATTCGACCGTGTGCCTATTGGGCCTATTCCTAGAACATGGCACGTTATTCTC

AAAATAATAAGAACAAAAATATGCAGTTTTCTTTGCAAGATAGGCTTCGCATATAGATCCTTCAATCCTATTCCCTG

CTTAACAAATTGTTTGCATTTGCCAATTGTCCTACATAATGTCATGTTAGCCAAGAACATTCAAATAAAATAGAATA

TTACATCAAACTTATAATATTACCTCTCAAAGGGATACATCCATCTGCATTGAACATGCCCTCCAAGTCGTGCCTCG

TGTACAAGGTGTATTGGAAGGTGTTCCATTACATCAAAGAAACCACATGGGAATATTTTTCCATCTTACTAGAAAT

TACACGAATGTTCTGGTCCATCCGAAGTAGGTTTTCTTCCCTTAATGTGGTAGAACACAAGCCTTTGAAAAACAAAT

TAATCTTTATGATGGGTTTCCAGATTCTTTCAGGCAAACCACAAAATGCAATAGGTACTAAGGTCTCCATGAAAACA

TGGCAGTCATGACTTTTCAAATGGCTCAACTTCCCTACCTCCATATCTATTTTTTTCAAGATTCGACGCATAACCCT

CAGGCATCTTCAATTTCGTAACCCAATCACAAATTTGTCGTCTTTCCTCCAAAATGAATGTGTAACTTGCTTTGGAC
```

-continued

```
TTGAACACCTTACCATTGTTTGCTGTCTGCAAGTATAATTCAGGCCGCCTGCAATATTCTTGTAAGTCCATTCTAGC
CTTCGGGGTATCTTTTGTCTTACCTTTAACATCCATCACTATGTTGAACAAATTGTCAAAATAATTCTTCTCTATAT
GCATGACATCAAGGTTGTGTCGGAGAAGATTATCCTTCCAATAAGGCAACTCCCAAAATATACTTTGTTTCGTCCAA
TTATGATTAACACCATATCCGAGGAATCTATAAGGTGGAGCCTCAGTAACTTTACTGAAGTTCTGGACCCTCTLCCA
AATTTTCTCACCTGAAAGTATCGGAGGTGGAGAATCATATTCCACTTTATTCTTTTTGAATGCATTTTTCATCCTTC
TAAACTCATGATCATCAGGCAAGAATTGACGGTGACAATCAAACCATGATTACTTTCGGCCATGTTTCAAAGTGAAC
GCTTTACTATTTTTCATACAGTAAGGATAAGCTAGCTTTCCAGCAGTCATCCACCCAGACAACATTCCATACGCAGG
AAAATCGTTAATAGTCCACATTAAATTAGGACGCAAATTGAAATTCTGCTTGGTTGATATGTCATATGTTTCAACAC
CATCATACCACAATTGTTTTAGCTCATCAATCAAAGGTTACAAATATAAATAAATCAAACCTTTTGGATTACGTGGA
CTGAGGATAATATAATTTCAGAATATATATGGACTAGTCATATACAACTAAGGTGGTAGATTATAAGGTATAAGAAA
GACAGGCTAACATGAGTATGGTGTCGCAGATATAGAAAAAGGCGTGAAGCCATCCGCACACAGACCTAACCGAATGT
TCCTTGATTCACTAGCAAAATCTGGATATGTCCTATCAAAGTGTTTCCAAGCTTCTCCATCTGAAAGATGACACATA
ACACCGGGTGGTCTTCTATTTTCAAAGTGCCATCTCATATGAGGAGCAGAACTCATCGACGCATATAACCTTTTTAA
CCTAGGTATAAGAAGTAAATAATGCATCGCCTTGACAACGGCCATATTCCCACTGGAAAGCCTCTTGAAACGAGGAT
TTTCGCAAAATTTACAACTGTCTAAAGTTGCATCATCTTTATAATATAACATGCAACCATCTTCACAACAATCAATT
CTCATTGACGAAAGTCCTAACTTAGAAACCAATCTCTTTGCCTCATAGAAATCACCAGGTAAGTTGATATTAGGGTC
AACTAGTTCACTCATAAGGTCAATGAAAGAGTCCATGGCTGCTTGAGAAATATTCCAATCAGATTTGATACTTAGTA
ATCTAACTGCAACAGACAGCTCAGAGTGCAGACTTCCTTCACGTAGTAGATGACTAGCTTCCTCTAGTGTTCATAAA
AACATTTTGCGTCTTCATTAGGAGTTTGTTCAATATTTTCATTGGGCTCACCCCGAAGTGCATCCCAAAAGCATCC
GCAACCATATCCTGAATTCTAGAATCAAGATTTGTATTCTCCACCGACCTACTACTTTCACCAACAACCATGTTACG
AAATATCCCACGGCTACCATCGATCTCTCCATGATTACTCCACACAAAGTAATTCTCTATAAACCCCTTCCTATAAA
GATGAAGCTTAATTTCCTCCGATTTTTTAAATTTCATACAATCGCACCTGATACAAGGTCACCAAATTACTCCTTCA
CTTTGGTATGGTGGAAGTGACATTGCATGTCTAATAAAGTCATCAACCCCTTCTACAAAATCCTCCCGCAATCCCCG
CCGATTAGGATAATTCCTATTGTACATCCAAGTACATGTTCCATCTATACAAATAAAACAAGAACAAATTATTTTAT
TCTACAATTATAAATTAATTATATCTTTTTTAGTTAATTCAAGATAATTATTGTTTCCTAATTATACCAATTTATAT
CCTAAAAGTTCAATTCACACCCAAAAGGTCCAATTCATATCTTAAAAGTTTAATTCATATCCTAAAAGTTTAATTCA
CAAGAACAAATCCTAAAAACTAAAATTTCAATTCATATCCTACGAGTTTAACCATAAACGAACTAAACTAAAGAAAT
TCAACCCATACCCTAAAAGTTCGATTCACAAGAACAAATTAATTTATTCTACAATTATAAATTAATTATATTTTTTT
TAGTTAATTCAAGATAATTATTTTTTTCTAATTACACCAATTTATATCCTAAAAGTTCAATTCATATCCAAAAGGTC
CAATTCATATCTTAAAAGTTCAATTCATATCCTAAAAGTTCAATTCACTAGAACAAATCCTAAAAACTAAAATTTCA
ATTCATATCCTACGAGTTTAAACATAAACTAACTAAACTAAAAAATTTCAACCCATACCCTAAAAGTTTGATTCACA
AGAACAAATCATAAACCCTAGATTCTAACTAAACTATTCAAGAAAATACAAAGTTAATAATTCAATTCTAACTAGAC
TATTCAAGACAATACAAACTCAAAATTGAAATACTCATCAATTAAAACTAATTCATAACTAATTGACTAACTAACAA
AACTAATTACTTAATAAAACTAATTAACAAAACTATTTAAAACAAGACCTAAACCCTATTCCTCAATAAAATGCAAT
GTTCAAATAATTGAAATACTAATCAATTGAAACTAATTCATAACTAATTAACAAAACCTAGAAATAATAAATAAATG
GGTTGTAATTCAAACGTAGAATTTTTAGGAGATGGAGAAGGAGAGGGCGGCAGTGGCAGTGGCAGTGGCAGTGGCA
GCGGCGATGGCGATGGCGACGGCGCGGCGACGGTGATGGCTGGGCAGTGGCGACGCGGGGTGGGGAATGAGATTTAT
GTGAGGGAAATATAGAAGGAGAGGGGAAGGTTTTGAGTGAGAAAAATAGAGAAGGAGAGGGAAGATAAGAGAGAAA
TGGGGGTTCCCCCGTTTTTCAATTCTGATTTCAGAATTACCGACCAAAGTTGGTCAGTAATTTTGGTCGGTACATTA
AGTGTTGACCGTTTGACCAAAAACCGACCAACTTCGGTCGGTTTTTTTTTTAAAATTAAACTTTTTTTTTGGTGT
GTTTTTTTCTTAAAATATTATAAACTATAAAAAATATATTATAAACTACAAGCATTTATTTTATTTAACAATACAAT
```

-continued

```
TATTATAAATAATTATAAACTATAAGTATAATATTTACAAATAATTATATTAACTATTTATTTTTAATAAATTATAA

TAGCATCTATCTAAGTAAATTTTCTAAGTTATAATTAAGTATGTGAGTAATTTCTCACATACACACATACACTATAT

TGTAATTGATGCTAATTACTTCTTTTTTCATTCGTTCATCACTAATAATGCATGACATAGATTAATCGATATATAGG

TCGAGACGTTTTGATGAATCATCGATTAATATTCATCGATACATCTAAGTAAGTTATAAGTCGATGAATCAATTTAC

AAATAGATATATTTGATGATAAAGTATATATACTAATTAGTATCTTCCCAAGTCTATCCCTAAAAGAACCCGACCCT

ATGGTCCTAGCGCTTCGTGTTCTTATATATATACGGCTATACCTATATATATATACACACACACACACACACACAAA

TACACTTCACTGTAATACTTTAACTATATATATATATATATATATATATATATATATATATA
```

SEQ ID NO:7 (NtIPMS2 corresponding BAC contig sequence (total BAC length is 10082 bp))

```
TAAAACACGCTTCGTTGTACTACTTTAACTACATATATACCATATTATATATAGTATATGTTAGTGTATTCATTATT

TGTATTACAAAAGTGTTAACGAATTACATTTATATTATTTAGATAGTAAATATAAAAGTAATTCGAAAGTTTGACCA

ATGTTGACGTAATAACCGACCAACTTTGGTCGGTTATTTTACAGAAAATATCAATTACCGACCAAAGTTGGTCGGTA

AATACTTTCCCTGCATTAACCGACCAACGTTGGTCGATAATTTTAAATATAAATTCTTAAATATTATAAAATATTTT

AAATAATAAAATAATTATTAAAATTTTAAAAATTGGGTCCAGATTACCGACCAACGTTGGTCGGTAATCCAAAATTT

TCTTGTCTGACCAGCTAGGTCAATTCGTTGACCAATTTTGCCGACCAACGTTGGTCGGTATTTAGTTCAAAAAAAT

GTAAATTTTTTGTTTCCAGTTTTCGTCCAAGCTGGACGGTTTTTGGTCGCTTTTTTTTTACCGACCAACGTTGGT

CGGAAATATTTGGTCAGTTTTTATCAGATTTTTAGTAGTGTCAAACACTTTAAAACTCGTTTTATCCCTTAGAATTT

CAGTACCTCCATTGTATTGAATCAACCCCAACCCTCCATTTTTCTCATTTACATTAGGCGCATTGATGTACCTCTTT

CCTTTTAAGGAATATATTTTGTAACATGGTGAATATTTTGTCCAGTGGCCACCATGCATTGAAAGCCAAATGGCTG

AGGTAAGATACATAATCTATAGTACGATATACTACAAATATTATAGTATATGGACTTGGATCAAATCATTTTATTTT

TGTTACAGCTTGGATATGACTTTGATGGAAAAGAACTTGATGACCTCTTTCGTCGATTCAAGTCACTGGCTGAGAGG

AAAAAGGTGATTAAGTTGCTGATCTTTCATAGTGCAATGGTCAAACTTGTGATCGCACCTTTTCGTTCCTAGTGTTT

GTTCATATTTTTTGAGTTAATTTTAAGTATGATCACTAATTTCTATTATAATAATAAAATTTAATTTTATTTATTCA

CATTAAAATGACTGAACTAACAATTAAAAATATTTGAAAAACATATGAAAAATTACGGCCAAAGAAAAATTTCTTTG

ACTCTCAAACATCCAAGCATCACCACATAGTAATAAATGAAAAAATTATTTTTTATCACATTAAAGTAACTGAATTT

TACTTACTATTCATAATAAAAGAAAACCACTAAACTTTACGCACTATAGTGGGAAAACCTATCCATATTCAAGGTGA

CTTTAAGTACTGGTCTAATAGGTAGATTTTTGTGATTTTACTGTTATAGTGGATAAAATTAAGTAACTTTTTTTGAT

AAATTAGCAGAATAGCCTGAGTGACATCTCACTAATTCGGCTTTGACATCTCGGTCCCCTTACTCCACAGTTTCAAC

CAAACACTTGAACTTGTATAAAATATTAGTTTTAAACACCTCTGATACTGTGTGTTGTCCACTCGCGCTGATATAAA

TGACACATCAGAGTCACCTCAGATACATTTAATGCCACGTCATTATCTATTTTTACAAAAAATATTTTTTAATAAA

AATATCAAACTCATCCCTTTTTCTCCAAAAAAGAAAACAAACCTTAGTTCTCTCTCCACCGTTCCATATCTGCCTC

TTCCACCCATCACCGCCACTACCAAACACTGCACCCTTCCTCTTCCATGAGAAAACACTCAATCAAACCACTTTATC

TTTTTTTTGTCCTAAATTTCTCCATTACTACAATCTATTCAACCACCCATGGAAGTTCTGTTGCCACCATCGCCAG

CAACCACTCCAAAACCACCACTATATCTCCTCTTCTCTTCATATTCATGTCACCCTTTCAAAACCTAGACATTGAAC

GAGTTTAAGAAAATTTATCCTTCAATTTTCTTTCTAGCCAAACACCCAAAGAAAAACCCAAAAATTGAAAAGAAAG

AGAAGAAATTTTTACTTAATATTTGGTACCTCAAAATTCTTATTAACCCCTCTAGCTACGGCAAAATTTATAAAACT

AACAAAATCAAGCTTCGACGTCTTCAACAACCGATGACGACCCAATTTTTGGCTTAAACACTATTTTCAAGCTTCAA

TGTCTCTTAATTCTCCGACGTCTTTATTGTCTTCTTCAGTTATTTTGAGAAAAAACAAAAATTAAACAACTTTGTTC

CTTGACTAGCTGCTCTGCTAAGCTCTATTAGTTTGATGTTGTTATGCTACACCTTTTTGTTTTTTATCATAGTCCAG
```

-continued

```
TTGATTGCTAAGATTGTAAGAGAAATAATGTAATGTTATTTGAGAAAACTCTACTTGAGAAACAAAAATTTAATATT
AGAGGGTGTGGAGCGTGCCAATTTCAATGGCGTTTTTAAGGGATTTGGCGGTAAGAAGAAGCGGATGGGATAGAGGG
GCGAGATAATGGCTAGCATTGTTTTTAATTTTTTAATTTTTTATTTTTCTCTTATATTATTTTCTAATCAAATTTTG
TATAGTTACTTGCTTTTAGGAGTGTGCAATCACTTATTTTGCTTGACTCAACAAAACAAAGGCCGTATAAGCTTGGT
CAATGGTCATATGGGTTTAAAACTAATGTCTTATACAAGTTCAAGTACCTGATTGAAACTATGTGGAGTAGGGGGAT
CGTAATAGCAAAGCCGAATAAGTCGAGGTGTCTCTTAGTCTAAAGTAGCCTTATTTTATAGTGAGTAAAGTTATGTC
ATTATATTTATATATGAAATTAACCCTATAGGTTTTCCAGTTCTTTGGTGAAGCTTACCTAATTAAAATTTTACCTG
TGTCGGTATAATGAATATGTATGTCCGCCTATTTATCTTCCCTACATCTATTTTTCAGAAAATTACAGATGATGACT
TGAGAGCACTTGTATCAGATGACGTTTTCCAGCCTCAAGTTTCCTGGCAACTTGGAGATGTACAGGTACATGTAAAT
ACTATTTCATGTGTTTTTGCCTAAGTTGCTCTGACACGGCAGTTTAGGTGACACGCCCGTGTCGGCAAGACACTAGT
ATGAGTGTGGATGTGAGATCCGTACCGGATCTGGTCAAATAATTTTGGGTACTTTGACCGCAGCGTACGAAAAAATT
AGAGATAAGATACAATTTGATTCCCGAAATCAGAACCAAAGCTAGGGTGAATTTGAACAAAATAGCATACATTATCT
AGGAAATCAATCCTTTACTTATCTACAACTCGAGAATAAAAAATAAATCCACACATTACAAGTTATACGTAAGTATT
CCACAAAATTTCTCGTAATTTAGATATATTTTTATATTTTTATTTAATTGAATTATTTTTAGTCGGATCCCCGCACC
CGTATCCGTATTAGGATCAGTATCCCAAAATCTTAGAATTTACATCTCGAAGGATCCGACCTCTAGATCTGCACCTG
TATCGGATACCCGTACCCGTATCTGAGCAACTTAGGTTTTTGCTAGTCTCACTTAGTTGTGGATTGAAAAGGAATTA
ATGTTCACCTAAATCTAATGATTTGCTGTTTATTGTACAGATTACTTGTGGAAATGTTGGCCGCTCTACAGCAAATG
TTAAGCTTATTGACAGCGATGGTCAAGAGCACACTGCCTTTTCTGTTGGAACAGGACCTGTTGATGCAGCTTACAAG
GCAGTTGACCTCATTGTAAAGGTTTATAATGAAACTGAAAACTCTCATAATGTTTGTATCTTGTCACACTAGTAGGA
TAGGTAATTTAAGTTTTATATACGCTGAAGGTATAAAAATATTTACTCAATCAGAGCGCTTACAAGACAATTGCAGG
TAACTCTATGAGTAGCTTAGACTAAAAGTTTTAATTATTTAATTATATTTATGCATGCCTCAACACGTTTACTCACC
TCTTAGCCTAATTTTTGTTACATGGGATCGTTCTACATTTTGAGTAGCTGAGAGATTTGAACTTAGGACCTTTATTT
TCTCTAACACTATGTTATATTGCCAGTGGAACAGGAGCGCATATGGACATTGTCGTTTCAAGTGTCCAAGCCTATGT
TGAGGCGTTGAACAAAATATTCAGTTACAAAAAAACAGGTCTCGTGAACAAATTTGAAGGCAGTGCGCAATCGTAAA
AGTGATGGTGTGTGCTCCAGAAACAAAAGCTTAAATGCTGCVTAGTGCTCGATGATCATAAATTTATGCTCTATTCA
TGCATGCATTACTGAAGTTAATTAAGAAGTAATCTTAATTGTATAAGATGTAAACATGTTTCTATTCATGCATTACT
ATGAAATTAATTACAATTTCTGAGCCAATTTTTTTATTTGGTTCTTAAAATTTATACAAATCTCTTTATTTGTATTT
GACTAACAGATTTTCGGGAATTAGGGCAAGTAGTCCAATCAGAATCACATTAAGCTTGGAGAGTAAAATCAAAATCT
GCACTCCTGAACAAACCTTGACTCAAAGTACCTTTAACATATTTTAAAACATGAAAAGGAGCAGCCATATGAGAAGC
AGCCATATGAGAAGCAGCCATGTGCGGTCCTCACATTGCTTGAGCCTGCAGGTATTCTGTAGCTGCACAATTTGATC
TGCAGCTGCACTTCAGCTTCTACGATCGCACAATTCATGTGCAGTCCGCACTTCTGGCAAGGCTTCAGTCTTGTTCA
TTTTGCACGCTCTCTGAACTTTTTGTATTCTTTTCAGTGCAACTATGTTCTGCGGCCACACAAATTGTGTGCGGTCT
GCAATTCTCTTCAATCACTTCTAGGCTTCTACATTAGATCTATGGCCGTAGAGAGAATTATATGGTCCGCACTTTCC
TCTACGGCCACAGAAATACTTTTGCGGACCGCACTTCTGCTCTACTGCGCTCCTTCTTGCCTTGTGAGCCGGAACAC
TCCTTTTTGAGTTGAATTTCTTCATTAGAGTACAAATTTCCAACATTCCTGTAATTTGCAGACTTTTATTAGTTTTG
GGAACATAAATCAATACTTTTGGACTAAAACTAAAGCAAGAAGGTACTAATAAGTGGTCAAAATCCACACTTATCAC
CAATCCATACCCAAAATAACATCAAAATCTACCATATTAAGTAACAAAAGATTAACCCTAGTCTCGTAGCCCCAATA
GTGACAAAACAAGAACAATAGACACAGTCTACCACAATAGAATCCCCAACGGGTGTAGACACATAAGTAGGAGTATT
GAGAGAATCATGAGACATATCCAAATATGAAGAAAAGTAGGATGACACATACGAATATGTAGAACCCAGATCAAATC
AAACTAATGCCTCTCTATGACAGATCAGAATGATACCTGTGATAACTGCATCTGAAGCAACTGCCTCAGTCCTACCA
AGGAAAGAATAACAACGAGCTCGGCCTCCTCCTCTATGATGACCTCTACCCGCCTGTCCTCCACCTCCAGCTAGCTG
```

-continued

```
TGCAGGTGAAGTAGCAACTGGAGCGGGAACTGTAGCCTTAGTACCTTGCTGAGGTCCATCCATCTTAAGTCTGGGAC

AATCTCTCACCTTGTCCCTAGTATCATCACACTCTAAATAACCTCTATGCGAGCGTTGCTGCTGGTACTGAGTTTGC

CCGTGACGATTGGAATGACCACTCTAGGAACCTCATGCAGAAGGCACACTGAAATATGTCCGGTACGAGTGCTCTAA

GATCCATGGCTAGCTGGAGCACCACAGGAAATGTGAGGTGCATACTGAACTAGTCGACTGACAAAGCCTCTGCCATA

AAGGGTCTAAGCTGTATAGTAAAAACCACTAAATCCTCCAGAACCACGAGGCTTCTTATCCTCCCTATCCTCCCTCT

CCTGACAGCGGATACGCTCTAACATCCTAGCAATCTCCACAACCTGATGAAATGCAATCTCAGTCTCTAACTCCCGT

GCCATACCATATCTGAGGCTAAAGGCGAGTCCCTCAATAAATCTACGAACTCTCTCTATCAGTGGAAACCAAGGA

AGGTGCATGACGAGATAACTCCGTAAACCTCATAGCACTCGGACACAGTCATGCTCCCCTGGCGCAACTGCTCAA

ACTCATTGCACAACTCATCCCTGCAGGTCTAAGCTCCATCAAGAAAAGATCAGAGAATAGGGACCATGTAAATGGTG

TTGCGCCAACTATCATACTCGCCTCATAAATCTACCACCATATGTATGCCGAACCCGTCAACTGGAAAAGTAGTAAG

GTTGACCCCCTCGACTCCACCAAACCTATGGTACGTAGAATGCGATGATACTAATCCAATAAACTTTGTGCATCCT

CAGAAGTCCCTCCACTAAACTAGGGAGGATGAAACTTCAGTAACCTCTCCAAACACCTCTGTCCCTCAGCCGAGACA

ACTGGCCCTACCTCGGGCTGAACTGCCGTTATTGGCTGCACCAACACAACACCCAGTGTCTGGTAAGCATGAGTCGG

CTACTCTGGTGTGCGGGCTGCGTGAGTTTGAGCTCCTCCCCCAGTATATGAAGTAGCTGGTGCAACCAGAATCAACT

CTTCCTCGGCCAAACTCACAAACATACTCATGAAGTATGCCAAGGTCTCCTAGAGCGCCAGTGTAGGAATAGGCTGC

TCAGGTGCACGCTCAACCTGCTCGGGCTCCTAATCCTCAACTGGATCTGTTGGAGATCCACCGTTGCTACTCTAGCT

ATAGCATGTGCCCCTCCTCGGCCTCTACCTCGGCCCTGGCCTCTTGCGACTCTAATAGCGGGCACTTGTGCCTGCTT

AGCTAATTTGGTAGAGCGTGTCTTCGCCATCTATGGGAGAATAGAAGAGTAAAGGTTCAAACTTTGGAATAACAAAT

CGACATGATAAAGAATGAAGGAAGGTGATGTTTCCTAACAGTTCGGTAGCCTCTCAAAGATAAGTACAAATGTCTTT

GTACCGATCGGCAAGATTATACTAAACCTGCTCATGACAACTCGTAGAACTTATGAACCTAGAGCTATAATACCAAC

TTGTCATGATCCAAATCTCACCATAGGGGTCTTGATGGAACCTAGTCTATAAAACTAGGTAAGTCGACCACTTAACA

ATATTTAAATCAGCAAAACATGATATAATAAGGCAGAGTTTAATATGAAAGCAGAAAATAGAGTTAACATCAGCCAA

AATGGCAATACTCAAATATTTCCCCAGAATTAGGTAGTACAAAGTCATGAGCTCTGATAGAATACATAAGGATGTCT

TAAATTACAATACTGTTTGAATATGAAAATAACAATATAAATATAGGGAAGGGACTCCAAGGGAATGCGGCGGTCAT

GCAGGTCTACCTTGAATCCTTGCGGTCAATCTAAGCCTCCTCCCTTTCCTCCCCTGCCTCCAACACCTAAATCTACA

CAAAATATGTAGAATTATAGTATGAGTACACTACTATCGATACCAGTAAGTATCAAGACTAACCTCGGTGAAGTAGT

GATGAGGTTCAAGTCATTTGATACTCACTAGTCAAATAAGCTGTACAATATATCAAAGACTAGAAATAGAATGTATA

ATAGAAAATAATATCAACAATCTCTTTGGAACATATGATAACAACTCAATGCAAGTAAAGGTTCATCTTGACAAAAA

GTTATCAAATAGAAACACAAACGTATGATACCTCGTAACACAATAACAATATCCATCTGCATCACTCAGCCCTGACA

AAATAACAATACCTAAACTTATCTCTTCGTCCTGACACAATAACAATATCCATCTGTATCGCTCTGCCCTGATATAA

TAACAATATCCATCTGTATTACTCCGCCCTGACATAACAACAATATCCACCCGTGTCGTTCCACCCTGACACAATAA

CAATATCCATCTGTTTCGCTCGGCCTTGACACAATAACAATATCCATATGTATCGCTCAGAACTGTCACAATAACAA

TCACAATCGTACGACAGAAACCTCGTGCCAACACCCAAACAATCCGCCAACATGTCCATATGTGTCACAATTATAAC

AAAACAATAATGTCAAGTTTCATCAAATACTAGCTCACAATTTATCAACAAGGTGCACAAGGACATGATAACAATAA

AAATGTGGATGGGTATTCAACATATAAAGCATGACTACGACTAATTCAATTGAAAAGATTATGTTCATGTAGTCACA

AAGTGATTAAGTATGTTTCATGTAGAGGACATTTCCAAATTAAGGCATATTAATAGCCTAAGGTCTAATCTAGTCAT

AAGCCGTATATAACGCCCATGTACACGCTCGTCACCTCATGTACACGTCGCTTTTCACATAACACGAATAATAATTA

AGGACAAATCATAAGGGGTATTCCCCCACCCCACAAGATTAGGCAAGATACTTACCTCAAATAAGGCAAATCAATAC

TTTAAAAAGCCCTTGCCTATCGAATCGGCCTCCGAAAGGGTCAAATATAGCCTAAAAACAACTCAATAATATCAAAT

ACGACTATAGAAATTGATTTCAAGTAAGAAAGCTCTGATCTTTATCAAATATCAAAAATTCACTCCGAACTCGCCTC
```

-continued

```
CCGGAACCCGATAAAATTTACAAATCTCGAGTACCCATTCGAATACGAGTTCAAATGTGCAAGTTTTATCCAAATTG
GACTCCGAATCGGGGTTCAAATCTCTATTTTTTATTTTAGAATAGTTTTTTCCAAAATTCCCAATTTTCTCACTTTG
ATTAACCAATAAAAAGCCAAATTCAAGATGGAATCATGAACAATAATCAAATCCGAGTAAAGAACACTTACCCAATC
CAAGTGGGTGAAAATCGCCTAAAGGATTTCCTCAATTCGAGCTTTAAATCTCAAAATATGATAAAATAAGTCAAACC
TTCAATTAAAATACTCTACTCAGTGATTTTCGCTTCTGCGTACCATCCCATCGCATCTGCAATGCCGCTTTTGTGAG
CCCACTCTCGCATATGCGAAGTTCAGTGGCTCCCCGATCCTCTGCTTCTCTGATACTATTCTCGCTTCTACGGAGTC
GCTTCTGCACCCAAACTAGCATACCTGCGCCCAAAGTTCCGTACCTACGGACAATGCTGCCTTCCTCTTCCCTTCGC
ATCTGTAGCCCTTTTGTCTGCATCTGCAGACTCAAACTCGCTAGTGCGAGAACACTAGAATCTGAAGTGCTACCATA
ATATCAAATAATCCAAACACACCCGAGGCCTCGGGACCCCATGTAATCATACCAATCAATCCAAAATATAACAC
GGACCTACTCGAGTCCGCAAATCACATAGAATAACATCAAAACCATAAATCACACATCAATTCAAGTTTAATGAACT
AACTAACTTCCAAACTTTCAACACTCACGCCAAAACATATCTAAACTACTTAGAATGACCTTAAATTTCACACACAA
GTCTCAAATTACATAATTAACCTATTCCAACTTTCAGAATAACAATCCAGACCCGACAGCCTCAATGTCAACTCCCG
GTAAAACCTATGAACCTTCCAAACCTTTAAATTTCCAACATTCGCCAAATAGAGCCAAATAAACCTAGGAACCTCCA
AATCTAAATCCGGACATACGCCTAAGTCTAAAATCACAATACAAATCTATTGGAACCATCAAAATACCATTCCAGAA
TCATTTTATATAAAAGTCAAACATCGGTCAACTCCTATAACTTAAGCTTGCATGCCTGCAGGTCGACTCTAGAGGAT
CCCCGGGTACCGAGCTCGAATTCGCCCTATAGTGAGTCGTATTACAATTCACTGGCCGTCGTTTTACAACGTCGTGA
CTGGGAAAACCCTGGCGTTACCCAACTTAATCGCCTTGCAGCACATCCCCCTTTCGCCAGCTGGCGTAATAGCGAAG
AGGCCCGCACCGATCGCCCTTCCCAACAGTTGCGCAGCTGAATGGCGAATGGCGCCTGATGCGGTATTTTCTCCTTA
CGCATCTGTGTGGTATTTCACACCGCATATGGTGCACTCTCAGTACAATCTGCTCTGATGCCGCATAGTTAAGCCAG
CCCCCGACACCCGCCAACACCCGCTGACGCGAACCCCTTGCGGCCGCATCGAATATAACTTCGTATAATGT
```

SEQ ID NO:8 (Promoter sequence used to drive trichome specific expression. This promoter was isolated from *Nicotinia tabacum* and is located 1.5 kb upstream of the gene encoding for the copalyl-synthase involved in the synthesis of cis-abienol.)

```
agcttctgcaaatctcccaacattatcaccttctgccgcct
ctgaaagcaagtagctaagcattaattaagaatgaccacac
aaaataaatagtagtagtaaagtagccgaactacatataat
tagacccatcatataggttttctagccaatacttttccaat
taagattaggtttccttttaaaaatttgcacaattcttag
agagatatctaatagtgcaaaacacagaaatatatatccaa
actacctttctctctccttaaacattttatttaactaaca
cggcactagttgaaacaatcagggatatttgtaaaggtaa
taaatgactggttgattttaaacgttagatatgttgaaat
aaattcaatttgaaaaaacgactaataattaaagctggaac
gctacgtattcaacactaagaaaatataatgtgctatttga
caatatgaagtcaagaaataagaactggcattatatatg
tttcaagtaggtttaggctatggcaaaatactaataagca
agcacttaattttgcggtacaaaataaagttttgtattgtt
aaataagaagatatatcacgtaacaaaatagagagtattgc
ctatagttaatttgcatcgctcgtcctttgtgagcatttca
ataggcttatgatcacacataaatttgtgtgtgaattgctt
tagaaaaattacataatttgaatttgaggtcttaatatgtg
ttcaatccagaggagtaggcaccttagctcgagcgatatcg
cgtgacaccgcttcgacaacatatttcataaatatgtatgt
ataaatattaagaaaaataaaaatattgagtataaatataa
aagatgacattgcacttctttaaatattgataccgcttaca
aaacttctttgcgcgcacgccattgattcaatctatcatag
ttcttgtaaatgttatttcagatctttaatttaaaatattt
taataaagtcaatcattttttaacatctagatttctcgtttt
tactttttgtttattatatcacattttggacatagcactaa
gtcggtataactaattgtgacttgtgcaagttaagaaaata
caatgcaatgctgctgaaacaacagagcaactcgtttccag
taaaaatctaaagtttactactttcacaaaaactaataaaa
gttttagagtgcgtttgacaatttatttcatgcaaagattc
gagaacaatcaacacagaattaggctgaagtgtctaagaga
atttaatatttgcccttcatcaagaggcaatatataaataa
gcctgcgccattgcaacaactcaaaccatttccaatattgc
ctcacaagtcagtagtgcctttcctctctcaaacgttcatt
```

-continued
```
gtctttatctcccttccccaattctcattggaagaataaaa caaaaattaaattagaaaatg
```

SEQ ID NO:9 (Synthetic construct used to trigger the suppression of NtIPMS2 gene expression via the RNAi mechanism. Composed of a fragment of NtIPMS2 first intron plus the first exon, the fragment of first intron is repeated invertedly after the exon. Translation and splicing of this construct theoretically results in a double stranded RNA in hairpin structure.)

```
gctaagcttgtcgaccatgg<u>aaattctctgaccctgattatgt</u>

<u>tggtatttttgacaccagtcttcgcgatggcgaacaggccgct</u>

<u>ggtgctaccatgactagtaaagaaaaactggacattgcacgtc</u>

<u>agttggctaagcttggtgttgatgttattgaggccggttttcc</u>

<u>ttttgcctctgaagctgagttcgagcttgtaaagttgatagca</u>

<u>caggaaattggtaa</u>cctttaatgtttaaccgttcacatttcta atatttacttatttgtaacatgtcgtcacgtgttagtttcatt cttttatgaaccaaacatgcatgcaaagatattntagatatt tggacggcgagtgagatttgaaactaggaccgtttgcctgata caatattaaaatatgtaaccattttatgtacaagtttaaactg ttgatagtagcatattttttacttttatttaagtatactatat tccaacaggtaaGTTAACcaatttcctgtgctatcaactttac aagctcgaactcagcttcagaggcaaaaggaaaaccggcctca ataacatcaacaccaagcttagccaactgacgtgcaatgtcca gttttctttactagtcatggtagcaccagcggcctgttcgcc atcgcgaagactggtgtcaaaaataccaacataatcagggtca <u>gagaattt</u>ggcgcgccaattgacc
```

Bold and underlined: exon 1, 21-229
Bold: splicing border
Italic: splicing site
Italic and underlined: intron 1

SEQ ID NO:10 (NtIPMS1A nucleotide sequence)

```
ATGTCTTCTCTCTGTTCAAACTCTGCAACTTCTCTTAGTTGTAATA
ACTCCTTCCAATCCAAAAATCCTCTTCTTCACACCATCTTTAACTT
CTTTCCTTCAATCAAACCACACTCTTGTTTCCCATATACAGTTATC
CGGTGCTCAATTCAAAAGCGACCTGAATATATACCGAGTAAAATCT
CCGACCACAAATACGTACGCATTTTCGACACGACTCTCCGCGATGG
AGAGCAATCCCCGGGCGCTACGATGACTACGAAAGAAAAATTAGAT
GTTGCCCGTAAATTAGCGAAACTCGGAGTTGACATAATCGAAGCTG
GGTTTCCAGCTTCATCTGAAGCTGATTTTGAAGCTGTGAGATTAAT
AGCAGAGGAAATTGGTAATAATAGCGACGGTGATTATGTGCCGGTG
ATTTGTGGATTAGCGAGGTGCAATAAGAGGGATATTGATAAAGCGT
GGGAAGCTGTGAAGTGTGCGAAGAGACCTAGGGTTCATACGTTTAT
```

```
AGCGACGAGTGAGATACATATGAAGTATAAGTTGAAGATGAGTAAA
GAAGAAGTAGTGGAGAAAGCGCGGAGTATGGTTGCTTATGCGAGGA
GTTTGGGATGTGAGGATGTTGAATTTAGCCCTGAAGATGCTGGAAG
GTCTGAGCGTGAGTTCCTTTACCATATCCTTGGAGAAGTTATCAAA
GCTGGTGCAACAACCCTTAACATACCTGATACTGTTGGATACACTG
TGCCCACTGAATTTGGACAATTAATTGCtgacataaaagccaatac
cccaggaattgaaaatgtgatcatttctacacactgccagaatgat
cttggactttctactgccaacactttagctggagattgtgcagggg
caagacaagtagaagtgaccatcaatggcattggtgaaagagctgg
aaatgcttctctggaggaggttgtaatggccttaaaatgtcgtgga
gagcaagtactaggtggcctgtatacaggaattaatacacaacata
tactcatgtcaagcaagatggtagaggagtacaccgggcttcatgt
gcagccacacaaggccattgttggagctaatgctttgctcatgaa
agtggcatccatcagGATGGAATGTTAAAACACAAAGATACATATG
AGATTATATCTCCTGAAGATATTGGGCTTAGTCGTGCTAATGAAGC
CGGTATTGTCCTTGGGAAGCTCAGTGGGCGCCATGCATTGAAATCC
AAAATGCTTGAGCTTGGATATGACATTGAGGGAAAAGAACTGGAGG
ACCTCTTCTGGCGATTTAAGTCGGTGGCTGAGAAGAAAAAGAAAAT
TACAGATGATGACATAATAGCACTGATGTCAGATGAAGTTTTCCAG
CCTCAAGTTGTTTGGCAACTTGCAGATGTACAGATTGCCTGTGGAA
GTCTTGGCCTCTCTACAGCAACTGTTAAGCTTATTGACAGTGATGG
TCAAGAGCATGTTGCTTGTTCTGTTGGAACCGGACCAGTTGATGCA
GCTTATAAGGCAGTTGACCTCATTGTAAAGGTACCTATAACACTCC
TCGAGTATTCCATGAATGCAGTCACAGAAGGTATAGATGCCATAGC
CTCAACCAGAGTATTAATCCGCGGGGAGGATGACCATGCTATAACC
AATGGTTCAATTGGACCGACTCATCACCGTATATTTAGTGGAACTG
GAGCTGATATGGACGTTGTCATCTCTAGTGTCCGAGCCTATATTGG
TGCATTGAACAAAATGTTGAGTTTCGGGAAGCTGGTTTCGAGGTAC
AAGAAGCCTGAAGGTAGTGTGGTAGTATAA
```

SEQ ID NO:11 (NtIPMS1A amino acid sequence)

```
MSSLCSNSATSLSCNNSFQSKNPLLHTIFNFFPSIKPHSCFPYT
VIRCSIQKRPEYIPSKISDHKYVRIFDTTLRDGEQSPGATMTTK
EKLDVARKLAKLGVDIIEAGFPASSEADFEAVRLIAEEIGNNSD
GDYVPVICGLARCNKRDIDKAWEAVKCAKRPRVHTFIATSEIHM
KYKLKMSKEEVVEKARSMVAYARSLGCEDVEFSPEDAGRSEREF
LYHILGEVIKAGATTLNIPDTVGYTVPTEFGQLIADIKANTPGI
ENVIISTHCQNDLGLSTANTLAGACAGARQVEVTINGIGERAGN
ASLEEVVMALKCRGEQVLGGLYTGINTQHILMSSKMVEEYTGLH
VQPHKAIVGANAFAHESGIHQDGMLKKKDTYEIISPEDIGLSRA
NEAGIVLGKLSGRHALKSKMLELGYDIEGKELEDLFWRFKSVAE
```

KKKKITDDDIIALMSDEVFQPQVVWQLADVQIACGSLGLSTATV

KLIDSDGQEHVACSVGTGPVDAAYKAVDLIVKVPITLLEYSMNA

VTEGIDAIASTRVLIRGEDDHAITNGSIGPTHHRIFSGTGADMD

VVISSVRAYIGALNKMLSFGKLVSRYKKPEGSVVV

SEQ ID NO:12 (NtIPMS1Bv1 nucleotide sequence)

ATGGCGTCTATCACCATAAACCATTCATTTTCCCGTAACCCTAAC
ATCTCATTCCATCCCCAAAATCCTCTCATTCAAACCCAAGCTCTC
TTCAATTTCAAACCATCAATCTCCAAATGTTCCCCTATTATCCAC
TGCGCAATCCGCCGTCGACCCGAATATACCCCGAGCCACATTCCC
GACCCGAACTACATTCGCATCTTCGACACCACTCTCCGCGACGGC
GAACAATCCCCAGGCGCCACAATGACCACAAAAGAAAAACTCGAC
GTTGCGCGTCAGTTAGCTAAGCTTGGTGTTGACATAATTGAAGCC
GGTTTTCCTGCTTCTTCTGAAGCTGATCTCGAAGCTGTGAAATTA
ATAGCGAAGGAAGTTGGAAATGGTGTGAATGAAGAGGGACATGTT
CCGGTAATTTGTGGACTTGCGAGGTGTAATAAGAGGGATATTGAT
AAGGCTTGGGAGGCTGTGAAGTATGCGAAAAAACCGAGGATTCAT
ACGTTTATTGCGACTAGTGAGATACATATGAAGTTTAAGTTGAAG
ATGAGTAGAGATGAAGTTGTGGAGAAAGCTAGGAGTATGGTTGCT
TATGCTAGGAGTATTGGTTGTGAGGATGTTGAATTTAGCCCAGAA
GATGCTGGAAGATCCGATCCAGAGTTCCTCTATCATATCCTTGGA
GAGGTCATCAAAGCTGGGGCAACAACCCTTAACATCCCTGATACT
GTTGGATACACTGTTCCCAGCGAATTTGGAAAATTGATTGCTGAT
ATAAAGGCCTUTACCCCAGGAATTGGAGATGTGATCATCTCAACA
CACTGCCAGAACGATCTTGGGCTTTCTACTGCCAACACCTTAGCT
GGAGCATGCGCAGGTGCAAGACAAGTAGAAGTGACCATCAACGGA
ATCGGTAAAGAGCTGGAAATGCTTCTTTGGAGGAGGTTGTAATG
GCCTTAAAATGTCGTGGAGAGCAAGTACTAGGTGGCCTGTATACA
GGAATTAATACACAACATATACTCATGTCAAGCAAGATGGTAGAG
GAGTACACCGGGCTTCATGTGCAGCCACACAAGGCCATTGTTGGA
GCTAATGCGTTTGCTCATGAAAGTGGCATCCATCAGGATGGAATG
TTAAAACACAAAGATACATATGAGATTATATCTCCTGAAGATATT
GGGCTTAACCGAGTTAATGAATCTGGCATCGTCCTTGGGAAACTC
AGTGGGCGTCATGCTTTGCAAGCCAAAATGCTCGAGCTTGGATAC
GATATTGAGGGAAAGAACTTGAGGACCTCTTTTGGCGATTCAAA
TCTGTGGCCGAGAAGAAAAGAAAATTACAGATGATGACCTGATA
GCATTAATGTCAGATGAAGTTTTCCAGCCTCAATTTGTTTGGCAA
CTTGAAAATGTACAGGTTACATGTGGAAGTCTTGGCCTTTCTACG
GCAACTGTTAAGCTCATTGACGCTGATGGTCAAGAGCATGTTTCT
TGTTCTGTTGGAACGGGGCCAGTTGATGCGGCTTATAAGGCAGTT

GATCTCATTGTAAAGGTACCTGTAGCACTCCTTGAATATTCCTTG
AATGCAGTCACGGAAGGTATAGATGCCATAGCTTCAACCAGAGTT
TTAATTCGTGGGGAGAATGGCCATACATCAACCCATGCTTTAACT
GGAGAGACTGTACACCGTTCTTTTAGTGGAACCGGAGCAGATATG
GATATTGTTATCTCCAGTGTCCGAGCCTATATTGGTGCATTGAAT
AAGATGTTGAGTTTCAGAAAGCTGGTATCGAAACACAGCAAACCT
GAAGGCAGTGCAGTCGTATAG

SEQ ID NO:13 (NtIPMS1Bv1 amino acid sequence)

MASITINHSESRNPNISFHPQNPLIQTQALFNEKPSISKCSPIIH

CAIRRRPEYTPSHIPDPNYIRIFDTTLRDGEQSPGATMTTKEKLD

VARQLAKLGVDIIEAGERASSEADLEAVKLIAKEVGNGVNEEGHV

PVICGLARCNKRDIDKAWEAVKYAKKPRIHTFIATSEIHMKFKLK

MSRDEVVEKARSMVAYARSIGCEDVEFSPEDAGRSDREELYHILG

EVIKAGATTLNIPDTVGYTVPSEFGKLIADIKANTPGIGDVIIST

HCQNDLGLSTANTLAGACAGARQVEVTINGIGERAGNASLEEVVM

ALKORGEQVLGGLYTGINTQHILMSSKMVEEYTGLHVQPHKAIVG

ANAFAHESGIHQDGMLKHKDTYEIISPEDIGLNRVNESGIVLGKL

SGRHALQAKMLELGYDIEGKELEDLEWREKSVAEKKKKITDDDLI

ALMSDEVEQPQFVWQLENVQVTCGSLGLSTATVKLIDADGQEHVS

CSVGTGPVDAAYKAVDLIVKVPVALLEYSLNAVTEGIDAIASTRV

LIRGENGHTSTHALTGETVHRSFSGTGADMDIVISSVRAYIGALN

KMLSFRKLVSKHSKPEGSAVV

SEQ ID NO:14 (NtIPMS1Bv2 nucleotide sequence)

ATGGCGTCTATCACCGCAAACCATACATTTTCCCGTAACCCT
AACATCTCATTGCATCCCCAAAATCCTCTCATTCAAACCCAA
GCTCTCTTCAACTTCAAATCATCAATCCCCAAATGTTCCCCT
ATTATCTGCTGCGCAATCCGCCGTCGACCCGACTATACCCCG
AGCCACATTCCCGACCCGAAATACATCCGCATCTTCGACACC
ACTCTCCGCGACGGCGAACAATCTCCAGGCGCCACAATGACC
ACAAAAGAAAAACTCGACGTTGCGCGTCAGTTAGCTAAGCTT
GGTGTTGACATAATTGAAGCCGGTTTTCCTGCTTCTTCTGAA
GCTGATCTCGAAGCTGTGAAATTAATAGCGAAGGAAGTTGGA
AATGGTGTGTATGAAGAGGGACATGTTCCGGTAATCTGTGGA
CTTGCGAGGTGTAATAAGAGGGATATTGATAAGGCTTGGGAG
GCTGTGAAGTATGCGAAAAAACCGAGGATTCATACGTTTATT
GCGACTAGTGAGATACATATGAAGTTTAAGTTGAAGATGAGT
AGAGATGAAGTTGTGGAGAAAGCTAGAAGTATGGTTGCTTAT
GCTAGGAGTATTGGTTGTGAGGATGTTGAATTTAGCCCTGAA
GATGCTGGAAGATCTGATCCTGAGTTCCTCTATCATATCCTT

```
-continued
GGAGAGGTCATCAAAGCTGGGGCAACAACCCTTAACATCCCT

GATACTGTTGGATACACTGTTCCCAGTGAATTTGGAAAATTG

ATCGCTGATATAAAGGCCAATACCCCAGGAATTGGAGATGTG

ATCATCTCAACGCACTGCCAGAACGATCTTGGGCTTTCTACT

GCCAACACCTTAGCTGGAGCATGTGCAGGTGCAAGACAAGTA

GAAGTGACCATCAATGGAATCGGTGAAAGAGCTGGAAATGCT

TCTTTGGAGGAGGTTGTAATGGCCTTAAAATGTCGTGGAGAG

CAAGTACTAGGTGGCCTGTATACAGGAATTAATACACAACAT

ATACTCATGTCAAGCAAGATGGTAGAGGAGTACACCGGGCTT

CATGTGCAGCCACACAAGGCCATTGTTGGAGCTAATGCTTTT

GCTCATGAAAGTGGCATCCATCAGGATGGAATGTTAAAACAC

AAAGATACATATGAGATTATATCTCCTGAAGATATTGGGCTT

AACCGAGCTAATGAATCTGGTATCGTCCTCGGGAAACTCAGT

GGGCGTCATGCTTTGCAAGCCAAAATGCTCGAGCTTGGATAC

GATATTGAGGGAAAAGAACTTGAGGACCTCTTTTGGCGATTC

AAATCTGTGGCTGAGAAGAAAAAGAAAATTACAGATGATGAC

CTGATAGCATTGATGTCAGATGAAGTTTTCCAGCCTCAATTT

GTTTGGCAACTCGAAAATGTACAGGTTACATGTGGAAGTCTT

GGCCTTTCTACGGCAACTGTTAAGCTCATTGACGCTGATGGT

CAAGAGCATGTTTCTTGTTCTGTTGGAACGGGGCCAGTTGAT

GCGGCTTACAAGGCAGTTGATCTCATTGTAAAGGTACCTGTA

GCACTACTTGAATATTCCTTGAATGCAGTCACGGAAGGTATA

GATGCCATAGCTTCAACCAGAGTTTTAATTCGTGGGGAGAAT

GGACATACATCAACCCATGCTTTAACTGGAGAGACTGTACAC

CGTTCGTTTAGTGGAACCGGAGCAGATATGGATATTGTTATC

TCTAGTGTCCGAGCCTATATTGGAGCATTGAATAAGATGCTG

AGTTTCAGAAAGCTGGTGTCGAAACACAGCAGACCTGAAGGC

AGTGCAGTCGTATAG
```

SEQ ID NO 15 (NtIPMS1Bv2 amino acid sequence)

```
MASITANHTFSRNPNISLHPQNPLIQTQALENFKSSIPKCSP

IICCAIRRRPDYTPSHIPDPKYIRIFDTTLRDGEQSPGATMT

TKEKLDVARQLAKLGVDIIEAGFPASSEADLEAVKLIAKEVG

NGVYEEGHVRVICGLARCNKRDIDKAWEAVKYAKKPRIHTFI

ATSEIHMKFKLKMSRDEVVEKARSMVAYARSIGCEDVEFSPE

DAGRSDPEFLYHILGEVIKAGATTLNIPDTVGYTVPSEFGKL

IADIKANTPGIGDVIISTHCQNDLGLSTANTLAGACAGARQV

EVTINGIGERAGNASLEEVVMALKCRGEQVLGGLYTGINTQH

ILMSSKMVEEYTGLHVQPHKAIVGANAFAHESGIHQDGMLKH

KDTYEIISPEDIGLERANESGIVLGKLSGRHALQAKMLELGY

DIEGKELEDLEWREKSVAEKKKKITDDDLIALMSDEVFQPQF

VWQLENVQVTCGSLGLSTATVKLIDADGQEHVSCSVGTGPVD

RAAYKAVDLIVKVPVALLEYSLNAVTEGIDAIASTVLIRGEN

GHTSTHALTGETVHRSFSGTGADMDIVISSVRAYIGALNKML

SFRKLVSKHSRPEGSAVV
```

TABLE 1

Structure of sucrose esters. The general structure of the sucrose ester is shown in FIG. 5 and the various combinations of R1, R2, R3, R4 and R5 groups are described.

| R5 | R3 | R1 | R2 | R4 | Name |
|---|---|---|---|---|---|
| — | C2 | C4i | C4i | C4i | C2C12 |
| — | C2 | C4i | C4i | C5ai | C2C13 |
| — | C2 | C4i | C4i | C5i | C2C13 |
| — | C2 | C4i | C4i | C6ai | C2C14 |
| — | C2 | C4i | C4i | C6i | C2C14 |
| — | C2 | C4i | C5ai | C4i | C2C13 |
| — | C2 | C4i | C5ai | C5ai | C2C14 |
| — | C2 | C4i | C5ai | C5i | C2C14 |
| — | C2 | C4i | C5ai | C6ai | C2C15 |
| — | C2 | C4i | C5ai | C6i | C2C15 |
| — | C2 | C4i | C5i | C4i | C2C13 |
| — | C2 | C4i | C5i | C5ai | C2C14 |
| — | C2 | C4i | C5i | C5i | C2C14 |
| — | C2 | C4i | C5i | C6ai | C2C15 |
| — | C2 | C4i | C5i | C6i | C2C15 |
| — | C2 | C4i | C6ai | C4i | C2C14 |
| — | C2 | C4i | C6ai | C5ai | C2C15 |
| — | C2 | C4i | C6ai | C5i | C2C15 |
| — | C2 | C4i | C6ai | C6ai | C2C16 |
| — | C2 | C4i | C6ai | C6i | C2C16 |
| — | C2 | C4i | C6i | C4i | C2C14 |
| — | C2 | C4i | C6i | C5ai | C2C15 |
| — | C2 | C4i | C6i | C5i | C2C15 |
| — | C2 | C4i | C6i | C6ai | C2C16 |
| — | C2 | C4i | C6i | C6i | C2C16 |
| — | — | C4i | C4i | C4i | C12 |
| — | — | C4i | C4i | C5ai | C13 |
| — | — | C4i | C4i | C5i | C13 |
| — | — | C4i | C4i | C6ai | C14 |
| — | — | C4i | C4i | C6i | C14 |
| — | — | C4i | C5ai | C4i | C13 |
| — | — | C4i | C5ai | C5ai | C14 |
| — | — | C4i | C5ai | C5i | C14 |
| — | — | C4i | C5ai | C6ai | C15 |
| — | — | C4i | C5ai | C6i | C15 |
| — | — | C4i | C5i | C4i | C13 |
| — | — | C4i | C5i | C5ai | C14 |
| — | — | C4i | C5i | C5i | C14 |
| — | — | C4i | C5i | C6ai | C15 |
| — | — | C4i | C5i | C6i | C15 |
| — | — | C4i | C6ai | C4i | C14 |
| — | — | C4i | C6ai | C5ai | C15 |
| — | — | C4i | C6ai | C5i | C15 |
| — | — | C4i | C6ai | C6ai | C16 |
| — | — | C4i | C6ai | C6i | C16 |
| — | — | C4i | C6i | C4i | C14 |
| — | — | C4i | C6i | C5ai | C15 |
| — | — | C4i | C6i | C5i | C15 |
| — | — | C4i | C6i | C6ai | C16 |
| — | — | C4i | C6i | C6i | C16 |
| C2 | — | C4i | C4i | C4i | C12C2 |
| C2 | — | C4i | C4i | C5ai | C13C2 |
| C2 | — | C4i | C4i | C5i | C13C2 |
| C2 | — | C4i | C4i | C6ai | C14C2 |
| C2 | — | C4i | C4i | C6i | C14C2 |
| C2 | — | C4i | C5ai | C4i | C13C2 |
| C2 | — | C4i | C5ai | C5ai | C14C2 |
| C2 | — | C4i | C5ai | C5i | C14C2 |
| C2 | — | C4i | C5ai | C6ai | C15C2 |
| C2 | — | C4i | C5ai | C6i | C15C2 |
| C2 | — | C4i | C5i | C4i | C13C2 |

TABLE 1-continued

Structure of sucrose esters. The general structure of the sucrose ester is shown in FIG. 5 and the various combinations of R1, R2, R3, R4 and R5 groups are described.

| R5 | R3 | R1 | R2 | R4 | Name |
|---|---|---|---|---|---|
| C2 | — | C4i | C5i | C5ai | C14C2 |
| C2 | — | C4i | C5i | C5i | C14C2 |
| C2 | — | C4i | C5i | C6ai | C15C2 |
| C2 | — | C4i | C5i | C6i | C15C2 |
| C2 | — | C4i | C6ai | C4i | C14C2 |
| C2 | — | C4i | C6ai | C5ai | C15C2 |
| C2 | — | C4i | C6ai | C5i | C15C2 |
| C2 | — | C4i | C6ai | C6ai | C16C2 |
| C2 | — | C4i | C6ai | C6i | C16C2 |
| C2 | — | C4i | C6i | C4i | C14C2 |
| C2 | — | C4i | C6i | C5ai | C15C2 |
| C2 | — | C4i | C6i | C5i | C15C2 |
| C2 | — | C4i | C6i | C6ai | C16C2 |
| C2 | — | C4i | C6i | C6i | C16C2 |
| C2 | C2 | C4i | C4i | C4i | C2C12C2 |
| C2 | C2 | C4i | C4i | C5ai | C2C13C2 |
| C2 | C2 | C4i | C4i | C5i | C2C13C2 |
| C2 | C2 | C4i | C4i | C6ai | C2C14C2 |
| C2 | C2 | C4i | C4i | C6i | C2C14C2 |
| C2 | C2 | C4i | C5ai | C4i | C2C13C2 |
| C2 | C2 | C4i | C5ai | C5ai | C2C14C2 |
| C2 | C2 | C4i | C5ai | C5i | C2C14C2 |
| C2 | C2 | C4i | C5ai | C6ai | C2C15C2 |
| C2 | C2 | C4i | C5ai | C6i | C2C15C2 |
| C2 | C2 | C4i | C5i | C4i | C2C13C2 |
| C2 | C2 | C4i | C5i | C5ai | C2C14C2 |
| C2 | C2 | C4i | C5i | C5i | C2C14C2 |
| C2 | C2 | C4i | C5i | C6ai | C2C15C2 |
| C2 | C2 | C4i | C5i | C6i | C2C15C2 |
| C2 | C2 | C4i | C6ai | C4i | C2C14C2 |
| C2 | C2 | C4i | C6ai | C5ai | C2C15C2 |
| C2 | C2 | C4i | C6ai | C5i | C2C15C2 |
| C2 | C2 | C4i | C6ai | C6ai | C2C16C2 |
| C2 | C2 | C4i | C6ai | C61 | C2C16C2 |
| C2 | C2 | C4i | C6i | C4i | C2C14C2 |
| C2 | C2 | C4i | C6i | C5ai | C2C15C2 |
| C2 | C2 | C4i | C6i | C5i | C2C15C2 |
| C2 | C2 | C4i | C6i | C6ai | C2C16C2 |
| C2 | C2 | C4i | C6i | C6i | C2C16C2 |
| — | C2 | C5ai | C4i | C4i | C2C13 |
| — | C2 | C5ai | C4i | C5ai | C2C14 |
| — | C2 | C5ai | C4i | C5i | C2C14 |
| — | C2 | C5ai | C4i | C6ai | C2C15 |
| — | C2 | C5ai | C4i | C6i | C2C15 |
| — | C2 | C5ai | C5ai | C4i | C2C14 |
| — | C2 | C5ai | C5ai | C5ai | C2C15 |
| — | C2 | C5ai | C5ai | C5i | C2C15 |
| — | C2 | C5ai | C5ai | C6ai | C2C16 |
| — | C2 | C5ai | C5ai | C6i | C2C16 |
| — | C2 | C5ai | C5i | C4i | C2C14 |
| — | C2 | C5ai | C5i | C5ai | C2C15 |
| — | C2 | C5ai | C5i | C5i | C2C15 |
| — | C2 | C5ai | C5i | C6ai | C2C16 |
| — | C2 | C5ai | C5i | C6i | C2C16 |
| — | C2 | C5ai | C6ai | C4i | C2C15 |
| — | C2 | C5ai | C6ai | C5ai | C2C16 |
| — | C2 | C5ai | C6ai | C5i | C2C16 |
| — | C2 | C5ai | C6ai | C6ai | C2C17 |
| — | C2 | C5ai | C6ai | C6i | C2C17 |
| — | C2 | C5ai | C6i | C4i | C2C15 |
| — | C2 | C5ai | C6i | C5ai | C2C16 |
| — | C2 | C5ai | C6i | C5i | C2C16 |
| — | C2 | C5ai | C6i | C6ai | C2C17 |
| — | C2 | C5ai | C6i | C6i | C2C17 |
| — | — | C5ai | C4i | C4i | C13 |
| — | — | C5ai | C4i | C5ai | C14 |
| — | — | C5ai | C4i | C5i | C14 |
| — | — | C5ai | C4i | C6ai | C15 |
| — | — | C5ai | C4i | C6i | C15 |
| — | — | C5ai | C5ai | C4i | C14 |
| — | — | C5ai | C5ai | C5ai | C15 |
| — | — | C5ai | C5ai | C5i | C15 |
| — | — | C5ai | C5ai | C6ai | C16 |
| — | — | C5ai | C5i | C4i | C14 |
| — | — | C5ai | C5i | C5ai | C15 |
| — | — | C5ai | C5i | C5i | C15 |
| — | — | C5ai | C5i | C6ai | C16 |
| — | — | C5ai | C5i | C6i | C16 |
| — | — | C5ai | C6ai | C4i | C15 |
| — | — | C5ai | C6ai | C5ai | C16 |
| — | — | C5ai | C6ai | C5i | C16 |
| — | — | C5ai | C6ai | C6ai | C17 |
| — | — | C5ai | C6ai | C6i | C17 |
| — | — | C5ai | C6i | C4i | C15 |
| — | — | C5ai | C6i | C5ai | C16 |
| — | — | C5ai | C6i | C5i | C16 |
| — | — | C5ai | C6i | C6ai | C17 |
| — | — | C5ai | C6i | C6i | C17 |
| C2 | — | C5ai | C4i | C4i | C13C2 |
| C2 | — | C5ai | C4i | C5ai | C14C2 |
| C2 | — | C5ai | C4i | C5i | C14C2 |
| C2 | — | C5ai | C4i | C6ai | C15C2 |
| C2 | — | C5ai | C4i | C6i | C15C2 |
| C2 | — | C5ai | C5ai | C4i | C14C2 |
| C2 | — | C5ai | C5ai | C5ai | C15C2 |
| C2 | — | C5ai | C5ai | C5i | C15C2 |
| C2 | — | C5ai | C5ai | C6ai | C16C2 |
| C2 | — | C5ai | C5ai | C6i | C16C2 |
| C2 | — | C5ai | C5i | C4i | C14C2 |
| C2 | — | C5ai | C5i | C5ai | C15C2 |
| C2 | — | C5ai | C5i | C5i | C15C2 |
| C2 | — | C5ai | C5i | C6ai | C16C2 |
| C2 | — | C5ai | C5i | C6i | C16C2 |
| C2 | — | C5ai | C6ai | C4i | C15C2 |
| C2 | — | C5ai | C6ai | C5ai | C16C2 |
| C2 | — | C5ai | C6ai | C5i | C16C2 |
| C2 | — | C5ai | C6ai | C6ai | C17C2 |
| C2 | — | C5ai | C6ai | C6i | C17C2 |
| C2 | — | C5ai | C6i | C4i | C15C2 |
| C2 | — | C5ai | C6i | C5ai | C16C2 |
| C2 | — | C5ai | C6i | C5i | C16C2 |
| C2 | — | C5ai | C6i | C6ai | C17C2 |
| C2 | — | C5ai | C6i | C6i | C17C2 |
| C2 | C2 | C5ai | C4i | C4i | C2C13C2 |
| C2 | C2 | C5ai | C4i | C5ai | C2C14C2 |
| C2 | C2 | C5ai | C4i | C5i | C2C14C2 |
| C2 | C2 | C5ai | C4i | C6ai | C2C15C2 |
| C2 | C2 | C5ai | C4i | C6i | C2C15C2 |
| C2 | C2 | C5ai | C5ai | C4i | C2C14C2 |
| C2 | C2 | C5ai | C5ai | C5ai | C2C15C2 |
| C2 | C2 | C5ai | C5ai | C5i | C2C15C2 |
| C2 | C2 | C5ai | C5ai | C6ai | C2C16C2 |
| C2 | C2 | C5ai | C5ai | C6i | C2C16C2 |
| C2 | C2 | C5ai | C5i | C4i | C2C14C2 |
| C2 | C2 | C5ai | C5i | C5ai | C2C15C2 |
| C2 | C2 | C5ai | C5i | C5i | C2C15C2 |
| C2 | C2 | C5ai | C5i | C6ai | C2C16C2 |
| C2 | C2 | C5ai | C5i | C6i | C2C16C2 |
| C2 | C2 | C5ai | C6ai | C4i | C2C15C2 |
| C2 | C2 | C5ai | C6ai | C5ai | C2C16C2 |
| C2 | C2 | C5ai | C6ai | C5i | C2C16C2 |
| C2 | C2 | C5ai | C6ai | C6ai | C2C17C2 |
| C2 | C2 | C5ai | C6ai | C6i | C2C17C2 |
| C2 | C2 | C5ai | C6i | C4i | C2C15C2 |
| C2 | C2 | C5ai | C6i | C5ai | C2C16C2 |
| C2 | C2 | C5ai | C6i | C5i | C2C16C2 |
| C2 | C2 | C5ai | C6i | C6ai | C2C17C2 |
| C2 | C2 | C5ai | C6i | C6i | C2C17C2 |
| — | C2 | C5i | C4i | C4i | C2C13 |
| — | C2 | C5i | C4i | C5ai | C2C14 |
| — | C2 | C5i | C4i | C5i | C2C14 |
| — | C2 | C5i | C4i | C6ai | C2C15 |
| — | C2 | C5i | C4i | C6i | C2C15 |
| — | C2 | C5i | C5ai | C4i | C2C14 |
| — | C2 | C5i | C5ai | C5ai | C2C15 |

TABLE 1-continued

Structure of sucrose esters. The general structure of the sucrose ester is shown in FIG. 5 and the various combinations of R1, R2, R3, R4 and R5 groups are described.

| R5 | R3 | R1 | R2 | R4 | Name |
|---|---|---|---|---|---|
| — | C2 | C5i | C5ai | C5i | C2C15 |
| — | C2 | C5i | C5ai | C6ai | C2C16 |
| — | C2 | C5i | C5ai | C6i | C2C16 |
| — | C2 | C5i | C5i | C4i | C2C14 |
| — | C2 | C5i | C5i | C5ai | C2C15 |
| — | C2 | C5i | C5i | C5i | C2C15 |
| — | C2 | C5i | C5i | C6ai | C2C16 |
| — | C2 | C5i | C5i | C6i | C2C16 |
| — | C2 | C5i | C6ai | C4i | C2C15 |
| — | C2 | C5i | C6ai | C5ai | C2C16 |
| — | C2 | C5i | C6ai | C5i | C2C16 |
| — | C2 | C5i | C6ai | C6ai | C2C17 |
| — | C2 | C51 | C6ai | C6i | C2C17 |
| — | C2 | C5i | C6i | C4i | C2C15 |
| — | C2 | C5i | C6i | C5ai | C2C16 |
| — | C2 | C5i | C6i | C5i | C2C16 |
| — | C2 | C5i | C6i | C6ai | C2C17 |
| — | C2 | C5i | C6i | C6i | C2C17 |
| — | — | C5i | C4i | C4i | C13 |
| — | — | C5i | C4i | C5ai | C14 |
| — | — | C5i | C4i | C5i | C14 |
| — | — | C5i | C4i | C6ai | C15 |
| — | — | C5i | C4i | C6i | C15 |
| — | — | C5i | C5ai | C4i | C14 |
| — | — | C5i | C5ai | C5ai | C15 |
| — | — | C5i | C5ai | C5i | C15 |
| — | — | C5i | C5ai | C6ai | C16 |
| — | — | C5i | C5ai | C6i | C16 |
| — | — | C5i | C5i | C4i | C14 |
| — | — | C5i | C5i | C5ai | C15 |
| — | — | C5i | C5i | C5i | C15 |
| — | — | C5i | C5i | C6ai | C16 |
| — | — | C5i | C5i | C6i | C16 |
| — | — | C5i | C6ai | C4i | C15 |
| — | — | C5i | C6ai | C5ai | C16 |
| — | — | C5i | C6ai | C5i | C16 |
| — | — | C5i | C6ai | C6ai | C17 |
| — | — | C5i | C6ai | C6i | C17 |
| — | — | C5i | C6i | C4i | C15 |
| — | — | C5i | C6i | C5ai | C16 |
| — | — | C5i | C6i | C5i | C16 |
| — | — | C5i | C6i | C6ai | C17 |
| — | — | C5i | C6i | C6i | C17 |
| C2 | — | C5i | C4i | C4i | C13C2 |
| C2 | — | C5i | C4i | C5ai | C14C2 |
| C2 | — | C5i | C4i | C5i | C14C2 |
| C2 | — | C5i | C4i | C6ai | C15C2 |
| C2 | — | C5i | C4i | C6i | C15C2 |
| C2 | — | C5i | C5ai | C4i | C14C2 |
| C2 | — | C5i | C5ai | C5ai | C15C2 |
| C2 | — | C5i | C5ai | C5i | C15C2 |
| C2 | — | C5i | C5ai | C6ai | C16C2 |
| C2 | — | C5i | C5ai | C6i | C16C2 |
| C2 | — | C5i | C5i | C4i | C14C2 |
| C2 | — | C5i | C5i | C5ai | C15C2 |
| C2 | — | C5i | C5i | C5i | C15C2 |
| C2 | — | C5i | C5i | C6ai | C16C2 |
| C2 | — | C5i | C5i | C6i | C16C2 |
| C2 | — | C5i | C6ai | C4i | C15C2 |
| C2 | — | C5i | C6ai | C5ai | C16C2 |
| C2 | — | C5i | C6ai | C5i | C16C2 |
| C2 | — | C5i | C6ai | C6ai | C17C2 |
| C2 | — | C5i | C6ai | C6i | C17C2 |
| C2 | — | C5i | C6i | C4i | C15C2 |
| C2 | — | C5i | C6i | C5ai | C16C2 |
| C2 | — | C5i | C6i | C5i | C16C2 |
| C2 | — | C5i | C6i | C6ai | C17C2 |
| C2 | — | C5i | C6i | C6i | C17C2 |
| C2 | C2 | C5i | C4i | C4i | C2C13C2 |
| C2 | C2 | C5i | C4i | C5ai | C2C14C2 |
| C2 | C2 | C5i | C4i | C5i | C2C14C2 |
| C2 | C2 | C5i | C4i | C6ai | C2C15C2 |
| C2 | C2 | C5i | C4i | C6i | C2C15C2 |
| C2 | C2 | C5i | C5ai | C4i | C2C14C2 |
| C2 | C2 | C5i | C5ai | C5ai | C2C15C2 |
| C2 | C2 | C5i | C5ai | C5i | C2C15C2 |
| C2 | C2 | C5i | C5ai | C6ai | C2C16C2 |
| C2 | C2 | C5i | C5ai | C6i | C2C16C2 |
| C2 | C2 | C5i | C5i | C4i | C2C14C2 |
| C2 | C2 | C5i | C5i | C5ai | C2C15C2 |
| C2 | C2 | C5i | C5i | C5i | C2C15C2 |
| C2 | C2 | C5i | C5i | C6ai | C2C16C2 |
| C2 | C2 | C5i | C5i | C6i | C2C16C2 |
| C2 | C2 | C5i | C6ai | C4i | C2C15C2 |
| C2 | C2 | C5i | C6ai | C5ai | C2C16C2 |
| C2 | C2 | C5i | C6ai | C5i | C2C16C2 |
| C2 | C2 | C5i | C6ai | C6ai | C2C17C2 |
| C2 | C2 | C5i | C6ai | C6i | C2C17C2 |
| C2 | C2 | C5i | C6i | C4i | C2C15C2 |
| C2 | C2 | C5i | C6i | C5ai | C2C16C2 |
| C2 | C2 | C5i | C6i | C5i | C2C16C2 |
| C2 | C2 | C5i | C6i | C6ai | C2C17C2 |
| C2 | C2 | C5i | C6i | C6i | C2C17C2 |
| — | C2 | C6ai | C4i | C4i | C2C14 |
| — | C2 | C6ai | C4i | C5ai | C2C15 |
| — | C2 | C6ai | C4i | C5i | C2C15 |
| — | C2 | C6ai | C4i | C6ai | C2C16 |
| — | C2 | C6ai | C4i | C6i | C2C16 |
| — | C2 | C6ai | C5ai | C4i | C2C15 |
| — | C2 | C6ai | C5ai | C5ai | C2C16 |
| — | C2 | C6ai | C5ai | C5i | C2C16 |
| — | C2 | C6ai | C5ai | C6ai | C2C17 |
| — | C2 | C6ai | C5ai | C6i | C2C17 |
| — | C2 | C6ai | C5i | C4i | C2C15 |
| — | C2 | C6ai | C5i | C5ai | C2C16 |
| — | C2 | C6ai | C5i | C5i | C2C16 |
| — | C2 | C6ai | C5i | C6ai | C2C17 |
| — | C2 | C6ai | C5i | C6i | C2C17 |
| — | C2 | C6ai | C6ai | C4i | C2C16 |
| — | C2 | C6ai | C6ai | C5ai | C2C17 |
| — | C2 | C6ai | C6ai | C5i | C2C17 |
| — | C2 | C6ai | C6ai | C6ai | C2C18 |
| — | C2 | C6ai | C6ai | C6i | C2C18 |
| — | C2 | C6ai | C6i | C4i | C2C16 |
| — | C2 | C6ai | C6i | C5ai | C2C17 |
| — | C2 | C6ai | C6i | C5i | C2C17 |
| — | C2 | C6ai | C6i | C6ai | C2C18 |
| — | C2 | C6ai | C6i | C6i | C2C18 |
| — | — | C6ai | C4i | C4i | C14 |
| — | — | C6ai | C4i | C5ai | C15 |
| — | — | C6ai | C4i | C5i | C15 |
| — | — | C6ai | C4i | C6ai | C16 |
| — | — | C6ai | C4i | C6i | C16 |
| — | — | C6ai | C5ai | C4i | C15 |
| — | — | C6ai | C5ai | C5ai | C16 |
| — | — | C6ai | C5ai | C5i | C16 |
| — | — | C6ai | C5ai | C6ai | C17 |
| — | — | C6ai | C5ai | C6i | C17 |
| — | — | C6ai | C5i | C4i | C15 |
| — | — | C6ai | C5i | C5ai | C16 |
| — | — | C6ai | C5i | C5i | C16 |
| — | — | C6ai | C5i | C6ai | C17 |
| — | — | C6ai | C5i | C6i | C17 |
| — | — | C6ai | C6ai | C4i | C16 |
| — | — | C6ai | C6ai | C5ai | C17 |
| — | — | C6ai | C6ai | C5i | C17 |
| — | — | C6ai | C6ai | C6ai | C18 |
| — | — | C6ai | C6ai | C6i | C18 |
| — | — | C6ai | C6i | C4i | C16 |
| — | — | C6ai | C6i | C5ai | C17 |
| — | — | C6ai | C6i | C5i | C17 |
| — | — | C6ai | C6i | C6ai | C18 |
| — | — | C6ai | C6i | C6i | C18 |
| C2 | — | C6ai | C4i | C4i | C14C2 |
| C2 | — | C6ai | C4i | C5ai | C15C2 |
| C2 | — | C6ai | C4i | C5i | C15C2 |

TABLE 1-continued

Structure of sucrose esters. The general structure of the sucrose ester is shown in FIG. 5 and the various combinations of R1, R2, R3, R4 and R5 groups are described.

| R5 | R3 | R1 | R2 | R4 | Name |
|----|----|----|----|----|------|
| C2 | — | C6ai | C4i | C6ai | C16C2 |
| C2 | — | C6ai | C4i | C6i | C16C2 |
| C2 | — | C6ai | C5ai | C4i | C15C2 |
| C2 | — | C6ai | C5ai | C5ai | C16C2 |
| C2 | — | C6ai | C5ai | C5i | C16C2 |
| C2 | — | C6ai | C5ai | C6ai | C17C2 |
| C2 | — | C6ai | C5ai | C6i | C17C2 |
| C2 | — | C6ai | C5i | C4i | C15C2 |
| C2 | — | C6ai | C5i | C5ai | C16C2 |
| C2 | — | C6ai | C5i | C5i | C16C2 |
| C2 | — | C6ai | C5i | C6ai | C17C2 |
| C2 | — | C6ai | C5i | C6i | C17C2 |
| C2 | — | C6ai | C6ai | C4i | C16C2 |
| C2 | — | C6ai | C6ai | C5ai | C17C2 |
| C2 | — | C6ai | C6ai | C5i | C17C2 |
| C2 | — | C6ai | C6ai | C6ai | C18C2 |
| C2 | — | C6ai | C6ai | C6i | C18C2 |
| C2 | — | C6ai | C6i | C4i | C16C2 |
| C2 | — | C6ai | C6i | C5ai | C17C2 |
| C2 | — | C6ai | C6i | C5i | C17C2 |
| C2 | — | C6ai | C6i | C6ai | C18C2 |
| C2 | — | C6ai | C6i | C6i | C18C2 |
| C2 | C2 | C6ai | C4i | C4i | C2C14C2 |
| C2 | C2 | C6ai | C4i | C5ai | C2C15C2 |
| C2 | C2 | C6ai | C4i | C5i | C2C15C2 |
| C2 | C2 | C6ai | C4i | C6ai | C2C16C2 |
| C2 | C2 | C6ai | C4i | C6i | C2C16C2 |
| C2 | C2 | C6ai | C5ai | C4i | C2C15C2 |
| C2 | C2 | C6ai | C5ai | C5ai | C2C16C2 |
| C2 | C2 | C6ai | C5ai | C5i | C2C16C2 |
| C2 | C2 | C6ai | C5ai | C6ai | C2C17C2 |
| C2 | C2 | C6ai | C5ai | C6i | C2C17C2 |
| C2 | C2 | C6ai | C5i | C4i | C2C15C2 |
| C2 | C2 | C6ai | C5i | C5ai | C2C16C2 |
| C2 | C2 | C6ai | C5i | C5i | C2C16C2 |
| C2 | C2 | C6ai | C5i | C6ai | C2C17C2 |
| C2 | C2 | C6ai | C5i | C6i | C2C17C2 |
| C2 | C2 | C6ai | C6ai | C4i | C2C16C2 |
| C2 | C2 | C6ai | C6ai | C5ai | C2C17C2 |
| C2 | C2 | C6ai | C6ai | C5i | C2C17C2 |
| C2 | C2 | C6ai | C6ai | C6ai | C2C18C2 |
| C2 | C2 | C6ai | C6ai | C6i | C2C18C2 |
| C2 | C2 | C6ai | C6i | C4i | C2C16C2 |
| C2 | C2 | C6ai | C6i | C5ai | C2C17C2 |
| C2 | C2 | C6ai | C6i | C5i | C2C17C2 |
| C2 | C2 | C6ai | C6i | C6ai | C2C18C2 |
| C2 | C2 | C6ai | C6i | C6i | C2C18C2 |
| — | C2 | C6i | C4i | C4i | C2C14 |
| — | C2 | C6i | C4i | C5ai | C2C15 |
| — | C2 | C6i | C4i | C5i | C2C15 |
| — | C2 | C6i | C4i | C6ai | C2C16 |
| — | C2 | C6i | C4i | C6i | C2C16 |
| — | C2 | C6i | C5ai | C4i | C2C15 |
| — | C2 | C6i | C5ai | C5ai | C2C16 |
| — | C2 | C6i | C5ai | C5i | C2C16 |
| — | C2 | C6i | C5ai | C6ai | C2C17 |
| — | C2 | C6i | C5ai | C6i | C2C17 |
| — | C2 | C6i | C5i | C4i | C2C15 |
| — | C2 | C6i | C5i | C5ai | C2C16 |
| — | C2 | C61 | C5i | C5i | C2C16 |
| — | C2 | C6i | C5i | C6ai | C2C17 |
| — | C2 | C6i | C5i | C6i | C2C17 |
| — | C2 | C6i | C6ai | C4i | C2C16 |
| — | C2 | C6i | C6ai | C5ai | C2C17 |
| — | C2 | C6i | C6ai | C5i | C2C17 |
| — | C2 | C6i | C6ai | C6ai | C2C18 |
| — | C2 | C6i | C6ai | C6i | C2C18 |
| — | C2 | C6i | C6i | C4i | C2C16 |
| — | C2 | C6i | C6i | C5ai | C2C17 |
| — | C2 | C6i | C6i | C5i | C2C17 |
| — | C2 | C6i | C6i | C6ai | C2C18 |
| — | C2 | C6i | C6i | C6i | C2C18 |
| — | — | C6i | C4i | C4i | C14 |
| — | — | C6i | C4i | C5ai | C15 |
| — | — | C6i | C4i | C5i | C15 |
| — | — | C6i | C4i | C6ai | C16 |
| — | — | C6i | C4i | C6i | C16 |
| — | — | C6i | C5ai | C4i | C15 |
| — | — | C6i | C5ai | C5ai | C16 |
| — | — | C6i | C5ai | C5i | C16 |
| — | — | C6i | C5ai | C6ai | C17 |
| — | — | C6i | C5ai | C6i | C17 |
| — | — | C6i | C5i | C4i | C15 |
| — | — | C6i | C5i | C5ai | C16 |
| — | — | C6i | C5i | C5i | C16 |
| — | — | C6i | C5i | C6ai | C17 |
| — | — | C6i | C5i | C6i | C17 |
| — | — | C6i | C6ai | C4i | C16 |
| — | — | C6i | C6ai | C5ai | C17 |
| — | — | C6i | C6ai | C5i | C17 |
| — | — | C6i | C6ai | C6ai | C18 |
| — | — | C6i | C6ai | C6i | C18 |
| — | — | C6i | C6i | C4i | C16 |
| — | — | C6i | C6i | C5ai | C17 |
| — | — | C6i | C6i | C5i | C17 |
| — | — | C6i | C6i | C6ai | C18 |
| — | — | C6i | C6i | C6i | C18 |
| C2 | — | C6i | C4i | C4i | C14C2 |
| C2 | — | C6i | C4i | C5ai | C15C2 |
| C2 | — | C6i | C4i | C5i | C15C2 |
| C2 | — | C6i | C4i | C6ai | C16C2 |
| C2 | — | C6i | C4i | C6i | C16C2 |
| C2 | — | C6i | C5ai | C4i | C15C2 |
| C2 | — | C6i | C5ai | C5ai | C16C2 |
| C2 | — | C6i | C5ai | C5i | C16C2 |
| C2 | — | C6i | C5ai | C6ai | C17C2 |
| C2 | — | C6i | C5ai | C6i | C17C2 |
| C2 | — | C6i | C5i | C4i | C15C2 |
| C2 | — | C6i | C5i | C5ai | C16C2 |
| C2 | — | C6i | C5i | C5i | C16C2 |
| C2 | — | C6i | C5i | C6ai | C17C2 |
| C2 | — | C6i | C5i | C6i | C17C2 |
| C2 | — | C6i | C6ai | C4i | C16C2 |
| C2 | — | C6i | C6ai | C5ai | C17C2 |
| C2 | — | C6i | C6ai | C5i | C17C2 |
| C2 | — | C6i | C6ai | C6ai | C18C2 |
| C2 | — | C6i | C6ai | C6i | C18C2 |
| C2 | — | C6i | C61 | C4i | C16C2 |
| C2 | — | C6i | C6i | C5ai | C17C2 |
| C2 | — | C6i | C6i | C5i | C17C2 |
| C2 | — | C6i | C6i | C6ai | C18C2 |
| C2 | — | C6i | C6i | C6i | C18C2 |
| C2 | C2 | C6i | C4i | C4i | C2C14C2 |
| C2 | C2 | C6i | C4i | C5ai | C2C15C2 |
| C2 | C2 | C6i | C4i | C5i | C2C15C2 |
| C2 | C2 | C6i | C4i | C6ai | C2C16C2 |
| C2 | C2 | C6i | C4i | C6i | C2C16C2 |
| C2 | C2 | C6i | C5ai | C4i | C2C15C2 |
| C2 | C2 | C6i | C5ai | C5ai | C2C16C2 |
| C2 | C2 | C6i | C5ai | C5i | C2C16C2 |
| C2 | C2 | C6i | C5ai | C6ai | C2C17C2 |
| C2 | C2 | C6i | C5ai | C6i | C2C17C2 |
| C2 | C2 | C6i | C5i | C4i | C2C15C2 |
| C2 | C2 | C6i | C5i | C5ai | C2C16C2 |
| C2 | C2 | C6i | C5i | C5i | C2C16C2 |
| C2 | C2 | C6i | C5i | C6ai | C2C17C2 |
| C2 | C2 | C6i | C5i | C6i | C2C17C2 |
| C2 | C2 | C6i | C6ai | C4i | C2C16C2 |
| C2 | C2 | C6i | C6ai | C5ai | C2C17C2 |
| C2 | C2 | C6i | C6ai | C5i | C2C17C2 |
| C2 | C2 | C6i | C6ai | C6ai | C2C18C2 |
| C2 | C2 | C6i | C6ai | C6i | C2C18C2 |
| C2 | C2 | C6i | C6i | C4i | C2C16C2 |
| C2 | C2 | C6i | C6i | C5ai | C2C17C2 |
| C2 | C2 | C6i | C6i | C5i | C2C17C2 |

TABLE 1-continued

Structure of sucrose esters. The general structure of the sucrose ester is shown in FIG. 5 and the various combinations of R1, R2, R3, R4 and R5 groups are described.

| R5 | R3 | R1 | R2 | R4 | Name |
|---|---|---|---|---|---|
| C2 | C2 | C6i | C6i | C6ai | C2C18C2 |
| C2 | C2 | C6i | C6i | C6i | C2C18C2 |

C2 denotes acetyl; C3 denotes butyryl; C4 denotes propionyl; C4i denotes isobutyryl; C5 denotes valeryl (pentanoyl); C5ai denotes 2-methyl-butyryl; C5i denotes isovaleryl; C5:1i denotes isopentenoyl; C5:1 denotes pentenoyl; C6 denotes hexanoyl; C6(2) denotes 2-methylvaleryl; C6ai denotes beta-methylvaleryl; C6i denotes 4-methylvaleryl; —is typically hydrogen.

The invention claimed is:

1. A mutant tobacco plant cell, a non-naturally occurring tobacco plant cell or a transgenic tobacco plant cell comprising a recombinant construct comprising:
  (a) a polynucleotide encoding an isopropylmalate synthase, operably linked to a trichome-specific promoter, wherein
     (i) the polynucleotide encoding an isopropylmalate synthase has at least 95% sequence identity to SEQ ID NO:1; or
     (ii) the isopropylmalate synthase comprises a polypeptide having at least 95% sequence identity to SEQ ID NO:2; or
  (b) a polynucleotide that reduces or inhibits expression of an isopropylmalate synthase gene having at least 95% sequence identity to SEQ ID NO:2, operably linked to a trichome-specific promoter; wherein said promoter in (a) or (b) comprises the sequence set forth in SEQ ID NO:8 or a variant thereof with at least 95% identity thereto.

2. A mutant tobacco plant, a non-naturally occurring tobacco plant or a transgenic tobacco plant comprising the plant cell according to claim 1.

3. A method for modulating the quantity or type of sucrose esters in at least a part of a tobacco plant, comprising the steps of:
  (i) modulating the expression or activity of isopropylmalate synthase in the plant, by transforming the plant with a recombinant construct:
     (a) comprising a polynucleotide encoding an isopropylmate synthase, operably linked to a trichome-specific promoter,
        wherein the polynucleotide encoding the isopropylmalate synthase has at least 95% sequence identity to SEQ ID NO:1 or wherein the isopropylmalate synthase comprises a polypeptide having at least 90% sequence identity to SEQ ID NO:2; or
     (b) containing a polynucleotide that reduces or inhibits expression of an isopropylmalate synthase gene having at least 95% sequence identity to SEQ ID NO:2, operably linked to a trichome-specific promoter;
        wherein said promoter in (a) and (b) comprises the sequence set forth in SEQ ID NO:8 or a variant thereof with at least 95% identity thereto;
  (ii) measuring the quantity or determining the type of one or more sucrose esters in at least a part of the mutant tobacco plant, the non-naturally occurring tobacco plant or the transgenic tobacco plant obtained in step (i); and
  (iii) identifying a mutant tobacco plant, a non-naturally occurring tobacco plant or a transgenic tobacco plant in which the quantity or type of the one or more sucrose esters therein has changed in comparison to a control plant in which the expression or activity of isopropylmalate synthase has not been modulated.

4. Plant material including biomass, seed or leaves comprising cells or tissue from the tobacco plant according to claim 2.

5. A tobacco product comprising a part of the tobacco plant according to claim 2.

6. A method for producing a composition comprising one or more sucrose esters comprising the steps of:
  (i) providing at least part of a mutant tobacco plant, a non-naturally occurring tobacco plant or a transgenic tobacco plant according to claim 2;
  (ii) extracting the sucrose ester(s) therefrom; and
  (iii) optionally, isolating or purifying the extracted sucrose ester(s).

7. The method according to claim 3, wherein one or more of the sucrose esters has the structure:

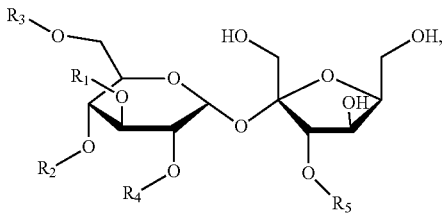

wherein R3 is acetyl or hydrogen, preferably acetyl; one or more of R1, R2 and R4 comprise an acyl chain with 6 carbons, preferably beta-methylvaleryl; and R5 is an acetyl or hydrogen, preferably, hydrogen.

8. A method for modulating the flavour of tobacco or a tobacco product comprising: (i) adding to tobacco or a tobacco product, a part of a plant from a mutant tobacco plant, a non-naturally occurring tobacco plant or a transgenic tobacco plant according to claim 2.

9. A method for producing beta-methylvaleric acid comprising the steps of:
  (i) providing at least part of a mutant tobacco plant, a non-naturally occurring tobacco plant or a transgenic tobacco plant according to claim 2;
  (ii) hydrolysing the material or an extract thereof provided in step (i); and
  (iii) optionally isolating or purifying the beta-methylvaleric acid.

10. A method according to claim 8, wherein the part of the plant is a leaf of the plant.

* * * * *